US010959953B2

(12) United States Patent
Heartlein et al.

(10) Patent No.: US 10,959,953 B2
(45) Date of Patent: *Mar. 30, 2021

(54) LIPID FORMULATIONS FOR DELIVERY OF MESSENGER RNA

(71) Applicants: Translate Bio, Inc., Lexington, MA (US); Massachusetts Institute of Technology, Cambridge, MA (US)

(72) Inventors: Michael Heartlein, Lexington, MA (US); Daniel Anderson, Cambridge, MA (US); Yizhou Dong, Cambridge, MA (US); Frank DeRosa, Lexington, MA (US)

(73) Assignees: Translate Bio, Inc., Lexington, MA (US); Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/685,287

(22) Filed: Nov. 15, 2019

(65) Prior Publication Data

US 2020/0078299 A1    Mar. 12, 2020

Related U.S. Application Data

(60) Continuation of application No. 16/026,577, filed on Jul. 3, 2018, now Pat. No. 10,493,031, which is a continuation of application No. 15/451,312, filed on Mar. 6, 2017, now Pat. No. 10,052,284, which is a division of application No. 14/521,161, filed on Oct. 22, 2014, now Pat. No. 9,629,804.

(60) Provisional application No. 61/953,516, filed on Mar. 14, 2014, provisional application No. 61/894,299, filed on Oct. 22, 2013.

(51) Int. Cl.

| A61K 9/127 | (2006.01) |
| A61K 48/00 | (2006.01) |
| A61K 38/17 | (2006.01) |
| A61K 38/48 | (2006.01) |
| A61K 38/53 | (2006.01) |

(52) U.S. Cl.
CPC .......... *A61K 9/1272* (2013.01); *A61K 38/177* (2013.01); *A61K 38/1709* (2013.01); *A61K 38/4846* (2013.01); *A61K 38/53* (2013.01); *A61K 48/005* (2013.01); *A61K 48/0033* (2013.01); *A61K 48/00* (2013.01)

(58) Field of Classification Search
CPC .................................................. A61K 9/1272
See application file for complete search history.

(56) References Cited

U.S. PATENT DOCUMENTS

| 2,647,121 A | 7/1953 | Jacoby |
| 2,717,909 A | 9/1955 | Kosmin |
| 2,819,718 A | 1/1958 | Goldman |
| 2,844,629 A | 7/1958 | William et al. |
| 3,096,560 A | 7/1963 | Liebig |
| 3,535,289 A | 10/1970 | Yoshihara et al. |
| 3,614,954 A | 10/1971 | Mirowski et al. |
| 3,614,955 A | 10/1971 | Mirowski |
| 3,656,185 A | 4/1972 | Carpentier |
| 3,805,301 A | 4/1974 | Liebig |
| 3,945,052 A | 3/1976 | Liebig |
| 3,995,623 A | 12/1976 | Blake et al. |
| 4,013,507 A | 3/1977 | Rembaum |
| 4,072,146 A | 2/1978 | Howes |
| 4,096,860 A | 6/1978 | McLaughlin |
| 4,099,528 A | 7/1978 | Sorenson et al. |
| 4,106,129 A | 8/1978 | Carpentier et al. |
| 4,134,402 A | 1/1979 | Mahurkar |
| 4,140,126 A | 2/1979 | Choudhury |

(Continued)

FOREIGN PATENT DOCUMENTS

| CA | 2518132 A1 | 3/2006 |
| CA | 2807552 | 9/2012 |

(Continued)

OTHER PUBLICATIONS

U.S. Appl. No. 61/494,714, filed Jun. 8, 2011, Guild.

(Continued)

*Primary Examiner* — Rei Tsang Shiao

(74) *Attorney, Agent, or Firm* — Proskauer Rose LLP; Fangli Chen

(57) ABSTRACT

The present invention provides, among other things, methods of delivering mRNA in vivo, including administering to a subject in need of delivery a composition comprising an mRNA encoding a protein, encapsulated within a liposome such that the administering of the composition results in the expression of the protein encoded by the mRNA in vivo, wherein the liposome comprises a cationic lipid of formula I-c:

or a pharmaceutically acceptable salt thereof.

24 Claims, 17 Drawing Sheets

Specification includes a Sequence Listing.

(56) References Cited

U.S. PATENT DOCUMENTS

| | | |
|---|---|---|
| 4,180,068 A | 12/1979 | Jacobsen et al. |
| 4,182,833 A | 1/1980 | Hicks |
| 4,227,533 A | 10/1980 | Godfrey |
| 4,284,459 A | 8/1981 | Patel et al. |
| 4,308,085 A | 12/1981 | Horhold et al. |
| 4,323,525 A | 4/1982 | Bornat |
| 4,335,723 A | 6/1982 | Patel |
| 4,339,369 A | 7/1982 | Hicks et al. |
| 4,355,426 A | 10/1982 | MacGregor |
| 4,373,071 A | 2/1983 | Itakura |
| 4,375,817 A | 3/1983 | Engle et al. |
| 4,385,631 A | 5/1983 | Uthmann |
| 4,401,472 A | 8/1983 | Gerber |
| 4,401,796 A | 8/1983 | Itakura |
| 4,406,656 A | 9/1983 | Hattler et al. |
| 4,458,066 A | 7/1984 | Caruthers et al. |
| 4,475,972 A | 10/1984 | Wong |
| 4,530,113 A | 7/1985 | Matterson |
| 4,550,447 A | 11/1985 | Seiler, Jr. et al. |
| 4,562,596 A | 1/1986 | Kornberg |
| 4,568,329 A | 2/1986 | Mahurkar |
| 4,571,241 A | 2/1986 | Christopher |
| 4,601,718 A | 7/1986 | Possis et al. |
| 4,647,416 A | 3/1987 | Seiler, Jr. et al. |
| 4,662,382 A | 5/1987 | Sluetz et al. |
| 4,701,162 A | 10/1987 | Rosenberg |
| 4,710,169 A | 12/1987 | Christopher |
| 4,720,517 A | 1/1988 | Ravichandran et al. |
| 4,737,323 A | 4/1988 | Martin et al. |
| 4,762,915 A | 8/1988 | Kung et al. |
| 4,782,836 A | 11/1988 | Alt |
| 4,856,521 A | 8/1989 | Irnich |
| 4,860,751 A | 8/1989 | Callaghan |
| 4,878,908 A | 11/1989 | Martin et al. |
| 4,892,540 A | 1/1990 | Vallana |
| 4,897,355 A | 1/1990 | Eppstein et al. |
| 4,946,857 A | 8/1990 | Kanehira et al. |
| 4,960,409 A | 10/1990 | Catalano |
| 4,966,945 A | 10/1990 | Drawert et al. |
| 5,024,671 A | 6/1991 | Tu et al. |
| 5,025,005 A | 6/1991 | Nomura et al. |
| 5,047,540 A | 9/1991 | Kamata et al. |
| 5,101,824 A | 4/1992 | Lekholm |
| 5,104,399 A | 4/1992 | Lazarus |
| 5,116,360 A | 5/1992 | Pinchuk et al. |
| 5,138,067 A | 8/1992 | Kamata et al. |
| 5,151,105 A | 9/1992 | Kwan-Gett |
| 5,153,319 A | 10/1992 | Caruthers et al. |
| 5,171,678 A | 12/1992 | Behr et al. |
| 5,176,661 A | 1/1993 | Evard et al. |
| 5,200,395 A | 4/1993 | Eto et al. |
| 5,261,419 A | 11/1993 | Osypka |
| 5,282,824 A | 2/1994 | Gianturco |
| 5,284,491 A | 2/1994 | Sutton et al. |
| 5,300,022 A | 4/1994 | Klapper et al. |
| 5,314,430 A | 5/1994 | Bardy |
| 5,330,768 A | 7/1994 | Park et al. |
| 5,334,761 A | 8/1994 | Gebeyehu et al. |
| 5,395,619 A | 3/1995 | Zalipsky et al. |
| 5,405,363 A | 4/1995 | Kroll et al. |
| 5,405,379 A | 4/1995 | Lane |
| 5,455,352 A | 10/1995 | Huellmann et al. |
| 5,464,924 A | 11/1995 | Silvis et al. |
| 5,503,852 A | 4/1996 | Steiner et al. |
| 5,528,023 A | 6/1996 | Butturini et al. |
| 5,607,385 A | 3/1997 | Francischelli et al. |
| 5,609,624 A | 3/1997 | Kalis |
| 5,614,548 A | 3/1997 | Piantadosi et al. |
| 5,626,869 A | 5/1997 | Nyqvist et al. |
| 5,631,018 A | 5/1997 | Zalipsky et al. |
| 5,693,088 A | 12/1997 | Lazarus |
| 5,697,953 A | 12/1997 | Kroll et al. |
| 5,700,437 A | 12/1997 | Fujii et al. |
| 5,700,642 A | 12/1997 | Monforte et al. |
| 5,705,188 A | 1/1998 | Junichi et al. |
| 5,705,385 A | 1/1998 | Bally et al. |
| 5,736,573 A | 4/1998 | Galat |
| 5,744,335 A | 4/1998 | Wolff et al. |
| 5,772,694 A | 6/1998 | Bokros et al. |
| 5,776,165 A | 7/1998 | Ripart |
| 5,776,747 A | 7/1998 | Schinstine et al. |
| 5,874,105 A | 2/1999 | Watkins et al. |
| 5,885,613 A | 3/1999 | Holland et al. |
| 5,910,168 A | 6/1999 | Myers et al. |
| 5,916,208 A | 6/1999 | Luther et al. |
| 5,965,434 A | 10/1999 | Wolff et al. |
| 5,976,567 A | 11/1999 | Wheeler |
| 5,976,569 A | 11/1999 | Milstein |
| 5,981,501 A | 11/1999 | Wheeler et al. |
| 6,055,454 A | 4/2000 | Heemels |
| 6,067,471 A | 5/2000 | Warren |
| 6,090,384 A | 7/2000 | Ra et al. |
| 6,096,070 A | 8/2000 | Ragheb et al. |
| 6,096,075 A | 8/2000 | Bokros et al. |
| 6,120,799 A | 9/2000 | McDonald et al. |
| 6,152,955 A | 11/2000 | KenKnight et al. |
| 6,169,923 B1 | 1/2001 | Kroll |
| 6,176,877 B1 | 1/2001 | Buchanan et al. |
| 6,204,297 B1 | 3/2001 | Tracy et al. |
| 6,271,209 B1 | 8/2001 | Smith et al. |
| 6,299,604 B1 | 10/2001 | Ragheb et al. |
| 6,335,199 B1 | 1/2002 | Bischoff et al. |
| 6,358,278 B1 | 3/2002 | Brendzel et al. |
| 6,370,434 B1 | 4/2002 | Zhang et al. |
| 6,371,983 B1 | 4/2002 | Lane |
| 6,534,484 B1 | 3/2003 | Wheeler et al. |
| 6,696,424 B1 | 2/2004 | Wheeler |
| 6,756,055 B2 | 6/2004 | McDonald et al. |
| 6,815,432 B2 | 11/2004 | Wheeler et al. |
| 6,821,530 B2 | 11/2004 | Koob et al. |
| 6,887,665 B2 | 5/2005 | Trulson et al. |
| 6,998,115 B2 | 2/2006 | Langer et al. |
| 7,022,214 B2 | 4/2006 | Olech |
| 7,084,303 B2 | 8/2006 | Watanabe et al. |
| 7,422,902 B1 | 9/2008 | Wheeler et al. |
| 7,427,394 B2 | 9/2008 | Anderson et al. |
| 7,507,859 B2 | 3/2009 | Grinstaff et al. |
| 7,556,684 B2 | 7/2009 | Bury et al. |
| 7,745,651 B2 | 6/2010 | Heyes et al. |
| 7,799,565 B2 | 9/2010 | MacLachlan et al. |
| 7,799,782 B2 | 9/2010 | Munson et al. |
| 7,803,397 B2 | 9/2010 | Heyes et al. |
| 7,901,708 B2 | 3/2011 | MacLachlan et al. |
| 7,972,435 B2 | 7/2011 | Bury et al. |
| 8,071,082 B2 | 12/2011 | Zugates et al. |
| 8,093,367 B2 | 1/2012 | Kore et al. |
| 8,101,741 B2 | 1/2012 | MacLachlan et al. |
| 8,188,263 B2 | 5/2012 | MacLachlan et al. |
| RE43,612 E | 8/2012 | Anderson et al. |
| 8,236,943 B2 | 8/2012 | Lee et al. |
| 8,278,036 B2 | 10/2012 | Kariko et al. |
| 8,287,849 B2 | 10/2012 | Langer et al. |
| 8,304,529 B2 | 11/2012 | Kore et al. |
| 8,329,070 B2 | 12/2012 | MacLachlan et al. |
| 8,450,298 B2 | 5/2013 | Mahon et al. |
| 8,513,403 B2 | 8/2013 | MacLachlan et al. |
| 8,557,231 B2 | 10/2013 | Langer et al. |
| 8,562,966 B2 | 10/2013 | Zugates et al. |
| 8,569,256 B2 | 10/2013 | Heyes et al. |
| 8,710,200 B2 | 4/2014 | Schrum et al. |
| 8,808,681 B2 | 8/2014 | Anderson et al. |
| 8,822,663 B2 | 9/2014 | Schrum et al. |
| 8,853,377 B2 | 10/2014 | Guild et al. |
| 8,883,202 B2 | 11/2014 | Manoharan et al. |
| 8,936,942 B2 | 1/2015 | Heyes et al. |
| 8,969,353 B2 | 3/2015 | Mahon et al. |
| 8,980,864 B2 | 3/2015 | Hoge et al. |
| 8,999,351 B2 | 4/2015 | Manoharan et al. |
| 8,999,950 B2 | 4/2015 | MacLachlan et al. |
| 9,018,187 B2 | 4/2015 | Heyes et al. |
| 9,051,567 B2 | 6/2015 | Fitzgerald et al. |
| 9,061,059 B2 | 6/2015 | Chakraborty et al. |
| 9,074,208 B2 | 7/2015 | MacLachlan et al. |
| 9,089,604 B2 | 7/2015 | Chakraborty et al. |

(56) References Cited

U.S. PATENT DOCUMENTS

| | | |
|---|---|---|
| 9,095,552 B2 | 8/2015 | Chakraborty et al. |
| 9,107,886 B2 | 8/2015 | Chakraborty et al. |
| 9,114,113 B2 | 8/2015 | Chakraborty et al. |
| 9,181,319 B2 | 11/2015 | Schrum et al. |
| 9,186,325 B2 | 11/2015 | Manoharan et al. |
| 9,186,372 B2 | 11/2015 | de Fougerolles et al. |
| 9,187,748 B2 | 11/2015 | Geisbert et al. |
| 9,192,651 B2 | 11/2015 | Chakraborty et al. |
| 9,220,755 B2 | 12/2015 | Chakraborty et al. |
| 9,220,792 B2 | 12/2015 | Chakraborty et al. |
| 9,233,141 B2 | 1/2016 | Chakraborty et al. |
| 9,254,311 B2 | 2/2016 | Bancel et al. |
| 9,295,689 B2 | 3/2016 | de Fougerolles et al. |
| 9,301,993 B2 | 4/2016 | Chakraborty et al. |
| 9,303,079 B2 | 4/2016 | Chakraborty et al. |
| 9,308,281 B2 * | 4/2016 | Guild ................ A61K 38/4846 |
| 9,334,328 B2 | 5/2016 | Schrum et al. |
| 9,345,780 B2 | 5/2016 | Manoharan et al. |
| 9,352,042 B2 | 5/2016 | Heyes et al. |
| 9,352,048 B2 | 5/2016 | Manoharan et al. |
| 9,364,435 B2 | 6/2016 | Yaworski et al. |
| 9,522,176 B2 * | 12/2016 | DeRosa ................ A61K 48/005 |
| 9,629,804 B2 * | 4/2017 | Heartlein ............. A61K 48/005 |
| 9,943,595 B2 * | 4/2018 | DeRosa ................ C07K 16/00 |
| 10,052,284 B2 * | 8/2018 | Heartlein ............. A61K 48/005 |
| 10,493,031 B2 * | 12/2019 | Heartlein ............. A61K 38/177 |
| 2002/0022721 A1 | 2/2002 | Trulson et al. |
| 2002/0094528 A1 | 7/2002 | Salafsky |
| 2002/0192651 A1 | 12/2002 | Wheeler et al. |
| 2002/0192721 A1 | 12/2002 | Rizzuto et al. |
| 2002/0193622 A1 | 12/2002 | Watanabe et al. |
| 2003/0082154 A1 | 5/2003 | Leamon |
| 2003/0181410 A1 | 9/2003 | Wheeler et al. |
| 2003/0215395 A1 | 11/2003 | Yu et al. |
| 2004/0142025 A1 | 7/2004 | MacLachlan et al. |
| 2004/0235982 A1 | 11/2004 | Rabasco et al. |
| 2005/0059005 A1 | 3/2005 | Tuschl et al. |
| 2005/0069590 A1 | 3/2005 | Buehler et al. |
| 2005/0143332 A1 | 6/2005 | Monahan et al. |
| 2005/0148786 A1 | 7/2005 | Ikeda et al. |
| 2005/0244961 A1 | 11/2005 | Short et al. |
| 2006/0008910 A1 | 1/2006 | MacLachlan et al. |
| 2006/0069225 A1 | 3/2006 | Wintermantel et al. |
| 2006/0083780 A1 | 4/2006 | Heyes et al. |
| 2006/0223939 A1 | 10/2006 | Lange et al. |
| 2006/0228404 A1 | 10/2006 | Anderson et al. |
| 2007/0135372 A1 | 6/2007 | MacLachlan et al. |
| 2007/0275923 A1 | 11/2007 | Chen et al. |
| 2008/0145338 A1 | 6/2008 | Anderson et al. |
| 2008/0242626 A1 | 10/2008 | Zugates et al. |
| 2009/0023673 A1 | 1/2009 | Manoharan et al. |
| 2009/0221684 A1 | 9/2009 | Grinstaff et al. |
| 2009/0263407 A1 | 10/2009 | Dande et al. |
| 2009/0270481 A1 | 10/2009 | MacLachlan et al. |
| 2010/0036084 A1 | 2/2010 | Langer et al. |
| 2010/0041152 A1 | 2/2010 | Wheeler et al. |
| 2010/0178699 A1 | 7/2010 | Gao et al. |
| 2010/0331234 A1 | 12/2010 | Mahon et al. |
| 2011/0009641 A1 | 1/2011 | Anderson et al. |
| 2011/0092739 A1 | 4/2011 | Chen et al. |
| 2011/0200582 A1 | 8/2011 | Baryza et al. |
| 2011/0256175 A1 | 10/2011 | Hope et al. |
| 2011/0293703 A1 | 12/2011 | Mahon et al. |
| 2011/0311583 A1 | 12/2011 | Manoharan et al. |
| 2012/0009222 A1 | 1/2012 | Nguyen et al. |
| 2012/0065252 A1 | 3/2012 | Schrum et al. |
| 2012/0065358 A1 | 3/2012 | Langer et al. |
| 2012/0128760 A1 | 5/2012 | Manoharan et al. |
| 2012/0142756 A1 | 6/2012 | Guild et al. |
| 2012/0195936 A1 | 8/2012 | Rudolph et al. |
| 2012/0202871 A1 | 8/2012 | Heyes et al. |
| 2012/0237975 A1 | 9/2012 | Schrum et al. |
| 2012/0251560 A1 | 10/2012 | Dahlman et al. |
| 2012/0251618 A1 | 10/2012 | Schrum et al. |
| 2012/0328668 A1 | 12/2012 | MacLachlan et al. |
| 2013/0158021 A1 | 6/2013 | Dong et al. |
| 2013/0195967 A1 | 8/2013 | Guild et al. |
| 2013/0237594 A1 | 9/2013 | de Fougerolles et al. |
| 2013/0259923 A1 | 10/2013 | Bancel et al. |
| 2013/0259924 A1 | 10/2013 | Bancel et al. |
| 2013/0266640 A1 | 10/2013 | de Fougerolles et al. |
| 2013/0302401 A1 | 11/2013 | Ma et al. |
| 2014/0010861 A1 | 1/2014 | Bancel et al. |
| 2014/0044772 A1 | 2/2014 | MacLachlan et al. |
| 2014/0094399 A1 | 4/2014 | Langer et al. |
| 2014/0105964 A1 | 4/2014 | Bancel et al. |
| 2014/0105965 A1 | 4/2014 | Bancel et al. |
| 2014/0147432 A1 | 5/2014 | Bancel et al. |
| 2014/0147454 A1 | 5/2014 | Chakraborty et al. |
| 2014/0148502 A1 | 5/2014 | Bancel et al. |
| 2014/0155472 A1 | 6/2014 | Bancel et al. |
| 2014/0155473 A1 | 6/2014 | Bancel et al. |
| 2014/0155474 A1 | 6/2014 | Bancel et al. |
| 2014/0155475 A1 | 6/2014 | Bancel et al. |
| 2014/0161830 A1 | 6/2014 | Anderson et al. |
| 2014/0171485 A1 | 6/2014 | Bancel et al. |
| 2014/0179756 A1 | 6/2014 | MacLachlan et al. |
| 2014/0179771 A1 | 6/2014 | Bancel et al. |
| 2014/0186432 A1 | 7/2014 | Bancel et al. |
| 2014/0193482 A1 | 7/2014 | Bancel et al. |
| 2014/0194494 A1 | 7/2014 | Bancel et al. |
| 2014/0199371 A1 | 7/2014 | Bancel et al. |
| 2014/0200261 A1 | 7/2014 | Hoge et al. |
| 2014/0200262 A1 | 7/2014 | Bancel et al. |
| 2014/0200263 A1 | 7/2014 | Bancel et al. |
| 2014/0200264 A1 | 7/2014 | Bancel et al. |
| 2014/0206752 A1 | 7/2014 | Afeyan et al. |
| 2014/0206753 A1 | 7/2014 | Guild et al. |
| 2014/0206755 A1 | 7/2014 | Bancel et al. |
| 2014/0206852 A1 | 7/2014 | Hoge et al. |
| 2014/0221465 A1 | 8/2014 | Bancel et al. |
| 2014/0243399 A1 | 8/2014 | Schrum et al. |
| 2014/0249208 A1 | 9/2014 | Bancel et al. |
| 2014/0255467 A1 | 9/2014 | Bancel et al. |
| 2014/0255468 A1 | 9/2014 | Bancel et al. |
| 2014/0275227 A1 | 9/2014 | Hoge et al. |
| 2014/0275229 A1 | 9/2014 | Bancel et al. |
| 2014/0288160 A1 | 9/2014 | Guild et al. |
| 2014/0294937 A1 | 10/2014 | MacLachlan et al. |
| 2014/0329884 A1 | 11/2014 | Dong et al. |
| 2014/0343129 A1 | 11/2014 | de Fougerolles et al. |
| 2015/0005372 A1 | 1/2015 | Hoge et al. |
| 2015/0017211 A1 | 1/2015 | de Fougerolles et al. |
| 2015/0044277 A1 | 2/2015 | Bancel et al. |
| 2015/0050354 A1 | 2/2015 | Bouchon et al. |
| 2015/0051268 A1 | 2/2015 | Bancel et al. |
| 2015/0056253 A1 | 2/2015 | Bancel et al. |
| 2015/0064235 A1 | 3/2015 | Bancel et al. |
| 2015/0064236 A1 | 3/2015 | Bancel et al. |
| 2015/0064242 A1 | 3/2015 | Heyes et al. |
| 2015/0064725 A1 | 3/2015 | Schrum et al. |
| 2015/0086614 A1 | 3/2015 | Bancel et al. |
| 2015/0111248 A1 | 4/2015 | Bancel et al. |
| 2015/0111945 A1 | 4/2015 | Geisbert et al. |
| 2015/0166465 A1 | 6/2015 | Chen et al. |
| 2015/0190515 A1 | 7/2015 | Manoharan et al. |
| 2015/0265708 A1 | 9/2015 | Manoharan et al. |
| 2015/0315541 A1 | 11/2015 | Bancel et al. |
| 2015/0315584 A1 | 11/2015 | MacDonald et al. |
| 2015/0366997 A1 | 12/2015 | Guild et al. |
| 2016/0095924 A1 | 4/2016 | Hope et al. |
| 2016/0114011 A1 | 4/2016 | Bancel et al. |
| 2016/0115477 A1 | 4/2016 | MacLachlan et al. |
| 2016/0115483 A1 | 4/2016 | MacLachlan et al. |
| 2016/0136236 A1 | 5/2016 | Hoge et al. |
| 2016/0151284 A1 | 6/2016 | Heyes et al. |
| 2016/0158385 A1 | 6/2016 | Bancel et al. |
| 2016/0193299 A1 | 7/2016 | de Fougerolles et al. |
| 2016/0194368 A1 | 7/2016 | Hoge et al. |
| 2016/0194625 A1 | 7/2016 | Hoge et al. |
| 2016/0213785 A1 | 7/2016 | Manoharan et al. |

(56) References Cited

U.S. PATENT DOCUMENTS

| | | |
|---|---|---|
| 2016/0237108 A1 | 8/2016 | Fraley et al. |
| 2016/0237134 A1 | 8/2016 | Hoge et al. |

FOREIGN PATENT DOCUMENTS

| | | |
|---|---|---|
| CN | 1399561 | 2/2003 |
| CN | 100569877 C | 12/2009 |
| CN | 101863544 A | 10/2010 |
| DE | 24 30 998 A1 | 1/1975 |
| DE | 2520814 A1 | 11/1976 |
| DE | 3728917 A1 | 3/1989 |
| EP | 673637 A1 | 9/1995 |
| EP | 0959092 A1 | 11/1999 |
| EP | 2045251 A1 | 4/2009 |
| EP | 1519714 | 10/2010 |
| EP | 2338520 A1 | 6/2011 |
| EP | 2449106 | 5/2012 |
| EP | 2532649 A1 | 12/2012 |
| EP | 2338478 | 6/2013 |
| EP | 2823809 | 1/2015 |
| FR | 1 378 382 A | 11/1964 |
| FR | 2 235 112 A1 | 1/1975 |
| GB | 1072118 A | 6/1967 |
| GB | 1602085 A | 11/1981 |
| JP | H07-053535 | 2/1955 |
| JP | S48-022365 | 3/1973 |
| JP | S49-127908 | 12/1974 |
| JP | S51-023537 | 2/1976 |
| JP | 51-125144 | 11/1976 |
| JP | S52-010847 | 1/1977 |
| JP | S63125144 A | 5/1988 |
| JP | 63-154788 | 6/1988 |
| JP | H09-505593 A | 6/1997 |
| JP | H10-197978 A | 7/1998 |
| JP | 11-005786 A | 1/1999 |
| JP | 11-080142 | 3/1999 |
| JP | 2001-523215 A | 11/2001 |
| JP | 2002-167368 A | 6/2002 |
| JP | 2003-519199 | 6/2003 |
| JP | 4-108173 B2 | 6/2008 |
| JP | 2008-247749 A | 10/2008 |
| JP | 50-24216 B2 | 9/2012 |
| WO | WO-93/18229 A1 | 9/1993 |
| WO | WO-93/18754 A1 | 9/1993 |
| WO | WO-95/11004 A1 | 4/1995 |
| WO | WO-95/14651 A1 | 6/1995 |
| WO | WO-96/26179 A1 | 8/1996 |
| WO | WO-98/16202 A2 | 4/1998 |
| WO | WO-99/14346 | 3/1999 |
| WO | WO-00/03044 A1 | 1/2000 |
| WO | WO-00/64484 A2 | 11/2000 |
| WO | WO-01/05375 A1 | 1/2001 |
| WO | WO-02/00870 A2 | 1/2002 |
| WO | WO-02/22709 | 3/2002 |
| WO | WO-02/31025 A2 | 4/2002 |
| WO | WO-03/070735 A2 | 8/2003 |
| WO | WO-03/040288 | 12/2003 |
| WO | WO-2004/043588 A2 | 5/2004 |
| WO | WO-2004/048345 A2 | 6/2004 |
| WO | WO-2004/106411 A2 | 12/2004 |
| WO | WO-2005/026372 | 3/2005 |
| WO | WO-2005/028619 A2 | 3/2005 |
| WO | WO-2005/121348 A1 | 12/2005 |
| WO | WO-2006/082088 A1 | 8/2006 |
| WO | WO-2006/105043 A2 | 10/2006 |
| WO | WO-2009/127060 | 10/2006 |
| WO | WO-2006/138380 A2 | 12/2006 |
| WO | WO-2007/024708 | 3/2007 |
| WO | WO-2007/031091 A2 | 3/2007 |
| WO | WO-2007/143659 A2 | 12/2007 |
| WO | WO-2008/011561 A2 | 1/2008 |
| WO | WO-2008/113364 A2 | 9/2008 |
| WO | WO-2009/046220 A2 | 4/2009 |
| WO | WO-2009/127230 A1 | 10/2009 |
| WO | WO-2010/037408 A1 | 4/2010 |
| WO | WO-2010/042877 A1 | 4/2010 |
| WO | WO-2010/045512 A2 | 4/2010 |
| WO | WO-2010/053572 A2 | 5/2010 |
| WO | WO-2010/099387 A1 | 9/2010 |
| WO | WO-2010/114789 A1 | 10/2010 |
| WO | WO-2010/129709 A1 | 11/2010 |
| WO | WO-2011/012316 A2 | 2/2011 |
| WO | WO-2011/012746 A2 | 2/2011 |
| WO | WO-2011/039144 A1 | 4/2011 |
| WO | WO-2011/068810 A1 | 6/2011 |
| WO | WO-2011/141705 A1 | 11/2011 |
| WO | WO-2012/019168 | 2/2012 |
| WO | WO-2012/027675 A2 | 3/2012 |
| WO | WO-2012/133737 A1 | 10/2012 |
| WO | WO-2012/135025 A2 | 10/2012 |
| WO | WO-2012/135805 | 10/2012 |
| WO | WO-2012/170889 A1 | 12/2012 |
| WO | WO-2012/170930 A1 | 12/2012 |
| WO | WO-2013/039857 | 3/2013 |
| WO | WO-2013/039861 | 3/2013 |
| WO | WO-2013/063468 A1 | 5/2013 |
| WO | WO-2013/090186 | 6/2013 |
| WO | WO-2013/101690 | 7/2013 |
| WO | WO-2013/126803 | 8/2013 |
| WO | WO-2013/130161 A1 | 9/2013 |
| WO | WO-2013/151663 A1 | 10/2013 |
| WO | WO-2013/151664 A1 | 10/2013 |
| WO | WO-2013/151666 A2 | 10/2013 |
| WO | WO-2013/151667 A1 | 10/2013 |
| WO | WO-2013/151668 A2 | 10/2013 |
| WO | WO-2013/151670 A2 | 10/2013 |
| WO | WO-2013/151671 A1 | 10/2013 |
| WO | WO-2013/151672 A2 | 10/2013 |
| WO | WO-2013/151736 A2 | 10/2013 |
| WO | WO-2014/028487 A1 | 2/2014 |
| WO | WO-2014/113089 A2 | 7/2014 |
| WO | WO-2014/144039 | 9/2014 |
| WO | WO-2014/144711 | 9/2014 |
| WO | WO-2014/144767 | 9/2014 |
| WO | WO-2014/152027 | 9/2014 |
| WO | WO-2014/152030 | 9/2014 |
| WO | WO-2014/152031 | 9/2014 |
| WO | WO-2014/152211 | 9/2014 |
| WO | WO-2014/152540 | 9/2014 |
| WO | WO-2014/152774 | 9/2014 |
| WO | WO-2014/153052 | 9/2014 |
| WO | WO-2014/158795 | 10/2014 |
| WO | WO-2014/159813 | 10/2014 |
| WO | WO-2014/179562 A1 | 11/2014 |
| WO | WO-2014/210356 A1 | 12/2014 |
| WO | WO-2015/006747 A2 | 1/2015 |
| WO | WO-2015/048744 A2 | 4/2015 |
| WO | WO-2015/051169 A2 | 4/2015 |
| WO | WO-2015/051173 A2 | 4/2015 |
| WO | WO-2015/058069 A1 | 4/2015 |
| WO | WO-2015/011633 | 1/2016 |
| WO | WO-2016/054421 | 4/2016 |
| WO | WO-2016/071857 | 5/2016 |
| WO | WO-2016/077123 | 5/2016 |
| WO | WO-2016/077125 | 5/2016 |
| WO | WO-2016/118724 | 7/2016 |
| WO | WO-2016/118725 | 7/2016 |
| WO | WO-2019/207060 | 10/2019 |

OTHER PUBLICATIONS

U.S. Appl. No. 61/494,745.
U.S. Appl. No. 61/494,881.
U.S. Appl. No. 61/494,882.
Adami, R.C. et al., An amino acid-based amphoteric liposomal delivery system for systemic administration of siRNA. Molecular Therapy 19(6):1141-1151 (2011).
Akinc, A. et al., A combinatorial library of lipid-like materials for delivery of RNAi therapeutics. Nature Biotechnology 26(5):561-569 (2008).
Akinc, A. et al., Development of lipidoid-siRNA formulations for systemic delivery to the liver. Molecular Therapy 17(5):872-879 (2009).

(56) References Cited

OTHER PUBLICATIONS

Alton et al., "A randomised, double-blind, placebo-controlled trial of repeated nebulisation of non-viral cystic fibrosis transmembrane conductance regulator (CFTR) gene therapy in patients with cystic fibrosis", National Institute for Health Research, vol. 3, Issue 5 (2016).
Anderson, D.G. et al., Structure/property studies of polymeric gene delivery using a library of poly(beta-amino esters). Molecular Therapy 11(3):426-434 (2005).
Anderson, J. Biological Responses to Materials. Annual Review of Materials Research 31:81-110 (2001).
Anderson, W. French, Human gene therapy, Nature, 392, 25-30 (1998).
Bajaj, A. et al., Synthesis and gene transfection efficacies of PEI-cholesterol-based lipopolymers. Bioconjugate Chemistry 19(8):1640-516511 (2008).
Behr, J.P. et al., Efficient gene transfer into mammalian primary endocrine cells with lipopolyamine-coated DNA, Proceedings of the National Academy of Sciences USA, 86(18):6982-6986 (1989).
Bloomfield, VA, Quasi-elastic light scattering applications in biochemistry and biology, Annual Review of Biophysics and Bioengineering, 10:421-450 (1981).
Boussif, O. et al., A versatile vector for gene and oligonucleotide transfer into cells in culture and in vivo: polyethylenimine. Proceedings of the National Academy of Sciences of the USA. 92(16):7297-7301 (1995).
Braun, C.S. et al., Structure/function relationships of polyamidoamine/DNA dendrimers as gene delivery vehicles. Journal of Pharmaceutical Sciences 94(2):423-436 (2005).
Breunig, M. et al., Breaking up the correlation between efficacy and toxicity for nonviral gene delivery. Proceedings of the National Academy of Sciences of the U S A. 104(36):14454-14459 (2007).
Breunig, M. et al., Mechanistic investigation of poly(ethylene imine)-based siRNA delivery: disulfide bonds boost intracellular release of the cargo. Journal of Controlled Release 130(1):57-63 (2008).
Brey, D.M. et al., Controlling poly(beta-amino ester) network properties through macromer branching. Acta Biomaterialia 4(2):207-217 (2008).
Brey, D.M. et al., Influence of macromer molecular weight and chemistry on poly(beta-amino ester) network properties and initial cell interactions. Journal of Biomedical Materials Research Part A 85(3):731-741 (2007).
Budker, V. et al., Protein/Amphipathic Polyamine Complexes Enable Highly Efficient Transfection with Minimal Toxicity, BioTechniques, 23:139-147 (1997).
Burnett, J.C. et al., Current progress of siRNA/shRNA therapeutics in clinical trials. Biotechnology Journal 6(9):1130-1146 (2011).
Byk, G. et al., Synthesis, activity, and structure—activity relationship studies of novel cationic lipids for DNA transfer. Journal of Medical Chemistry 41(2):224-235 (1998).
Caplen, N.J. et al., In vitro liposome-mediated DNA transfection of epithelial cell lines using the cationic liposome DC-Chol/DOPE, Gene Therapy, 2:603-613 (1995).
Castanotto, D. et al., The promises and pitfalls of RNA-interference-based therapeutics. Nature 457(7228):426-433 (2009).
Chakraborty, C. Potentiality of Small Interfering RNAs (siRNA) as Recent Therapeutic Targets for Gene-Silencing. Current Drug Targets 8(3):469-82 (2007).
Chau, Y. et al., Investigation of targeting mechanism of new dextran-peptide-methotrexate conjugates using biodistribution study in matrix-metalloproteinase-overexpressing tumor xenograft model, J. Pharm. Sci., 95(3): 542-551 (2006).
Chen, D. et al., Rapid discovery of potent siRNA-containing lipid nanoparticles enabled by controlled microfluidic formulation. Journal of the American Chemical Society 134(16):6948-6951 (2012).
Chen, Y. and Huang, L., Tumor-targeted delivery of siRNA by non-viral vector: safe and effective cancer therapy. Expert Opinion on Drug Delivery 5(12):1301-1311 (2008).

Christensen, U.B. et al., Intercalating nucleic acids containing insertions of 1-O-(1-pyrenylmethyl)glycerol: stabilisation of dsDNA and discrimination of DNA over RNA, Nucl. Acids. Res., 30(22): 4918-4925 (2002).
Cotton, M. et al., Receptor-mediated transport of DNA into eukaryotic cells. Methods in Enzymology 217 (H):618-644 (1993).
Creusat, G. et al., Proton sponge trick for pH-sensitive disassembly of polyethylenimine-based siRNA delivery systems. Bioconjugate Chemistry 21(5):994-1002 (2010).
Crooke, S.T. Molecular mechanisms of action of antisense drugs. Biochimica et Biophysica Acta 1489(1):31-44. Review (1999).
Crystal, R.G. Transfer of genes to humans: early lessons and obstacles to success. Science 270(5235):404-410. Review (1995).
Damen, M. et al., Delivery of DNA and siRNA by novel gemini-like amphiphilic peptides. Journal of Controlled Release 145(1):33-39 (2010).
Davis, M. E., The first targeted delivery of siRNA in humans via a self-assembling, cyclodextrin polymer-based nanoparticle: from concept to clinic. Molecular Pharmacuetics 6(3):659-668 (2009).
Davis, M.E. et al., Evidence of RNAi in humans from systemically administered siRNA via targeted nanoparticles. Nature 464(7291):1067-1070 (2010).
Decher, G. Fuzzy Nanoassemblies: Toward Layered Polymeric Multicomposites. Science 277: 1232-1237 (1997).
Denardo, S.J. et al., Enhanced Therapeutic Index of Radioimmunotherapy (RIT) in Prostate Cancer Patients Comparison of Radiation Dosimetry for 1,4,7,10-Tetraazacyclododecane-N,N',N'',N'41-Tetraacetic Acid (DOTA)-Peptide versus 2IT-DOTA Monoclonal Antibody Linkage for RIT1, Clin. Cancer Res., 9: 3665s (2003).
Dern, R.J. et al., Toxicity studies of pyrimethamine (daraprim). The American Journal of Tropical Medicine and Hygiene 4(2):217-220 (1955).
Deshmukh, H. M and Huang, L., Liposome and polylysine mediated gene therapy. New Journal of Chemistry 21:113-124 (1997).
Discher, B.M. et al., Polymersomes: tough vesicles made from diblock copolymers. Science 284(5417):1143-1146 (1999).
Discher, D.E. and Eisenberg, A., Polymer vesicles. Science 297(5583):967-973. Review (2002).
Dong, Y. et al., Lipopeptide nanoparticles for potent and selective siRNA delivery in rodents and nonhuman primates, Proceedings of the National Academy of Sciences, 111(11): 3955-3960 (2014).
Elbashir, S.M. et al., RNA interference is mediated by 21- and 22-nucleotide RNAs. Genes & Development 15: 188-200 (2001).
Ewert, K. et al., Cationic lipid-DNA complexes for gene therapy: understanding the relationship between complex structure and gene delivery pathways at the molecular level. Current Medicinal Chemistry 11(2): 133-149 (2004).
Fechter, P. and Brownlee, G.G., Recognition of mRNA cap structures by viral and cellular proteins, Journal of General Virology, 86(Pt 5):1239-1249 (2005).
Felgner, P.L. et al., Lipofection: a highly efficient, lipid-mediated DNA-transfection procedure, Proceedings of the National Academy of Sciences USA, 84(21):7413-7417 (1987).
Fenske, D.B. and Cullis, P., Liposomal nanomedicines. Expert Opinion on Drug Delivery 5(1):25-44 (2008).
Ferruti, P.F. and Barbucci, R. , Linear amino polymers: Synthesis, protonation and complex formation. Advances in Polymer Science 58:55-92 (1984).
Ferruti, P.F. et al., A novel modification of poly(l-lysine) leading to a soluble cationic polymer with reduced toxicity and with potential as a transfection agent. Macromolecular Chemistry and Physics 199:2565-2575 (1998).
Fire, A. et al., Potent and specific genetic interference by double-stranded RNA in Caenorhabditis elegans. Nature 391(6669):806-811 (1998).
Furgeson, D.Y. et al., Modified linear polyethylenimine-cholesterol conjugates for DNA complexation. Bioconjugate Chemistry 14(4):840-847 (2003).
Furgeson, D.Y. et al., Novel water insoluble lipoparticulates for gene delivery. Pharmaceutical Research 19(4): 382-390 (2002).
Gao, X. and Huang, L., A novel cationic liposome reagent for efficient transfection of mammalian cells, Biochemical and Biophysical Research Communications, 179(1):280-285 (1991).

(56) References Cited

OTHER PUBLICATIONS

Godbey, W.T. et al., Size matters: molecular weight affects the efficiency of poly(ethylenimine) as a gene delivery vehicle. Journal of Biomedical Materials Research 45(3):268-275 (1998).
Gonzalez, H. et al., New class of polymers for the delivery of macromolecular therapeutics. Bioconjugate Chemistry 10(6):1068-1074 (1999).
Grayson, A.C.R. et al., Biophysical and structural characterization of polyethylenimine-mediated siRNA delivery in vitro. Pharmaceutical Research 23(8): 1868-1876 (2006).
Grudzien, E. et al., Novel cap analogs for in vitro synthesis of mRNAs with high translational efficiency, RNA, 10(9):1479-1487 (2004).
Grudzien-Nogalska, E. et al., Phosphorothioate cap analogs stabilize mRNA and increase translational efficiency in mammalian cells, RNA, 13(10):1745-1755 (2007).
Grunlan, M.A. et al., Synthesis of 1,9-bis[glycidyloxypropyl]penta(1'H, 1'H, 2'H, 2'H-perfluoroalkylmethylsiloxane)s and copolymerization with piperazine. Polymer 45:2517-2523 (2004).
Gupta, U. et al., A review of in vitro-in vivo investigations on dendrimers: the novel nanoscopic drug carriers. Nanomedicine: Nanotechnology, Biology, and Medicine 2(2):66-73 (2006).
Gust, T.C. et al., RNA-containing adenovirus/polyethylenimine transfer complexes effectively transduce dendritic cells and induce antigen-specific T cell responses, The Journal of Gene Medicine, 6(4): 464-470 (2004).
Guttman, M. et al., Chromatin signature reveals over a thousand highly conserved large non-coding RNAs in mammals, Nature, 458:223-227 (2009).
Haensler, J. and Szoka, F., Polyamidoamine cascade polymers mediate efficient transfection of cells in culture. Bioconjugate Chemistry 4(5):372-379 (1993).
Heidenreich, O. et al., High Activity and Stability of Hammerhead Ribozymes Containing 2'-Modified Pyrimidine Nucleosides and Phosphorothioates, The Journal of Biological Chemistry, 269(3):2131-2138 (1994).
Heyes, J. et al., Cationic lipid saturation influences intracellular delivery of encapsulated nucleic acids, Journal of Controlled Release, 107(2):276-287 (2005).
Hill, I.R.C. et al., In vitro cytotoxicity of poly(amidoamine)s: relevance to DNA delivery. Biochimica et Biophysica Acta 1427: 161-174 (1999).
Hill, J.G. et al., Enantioselective Epoxidation of Allylic Alcohols: (2S,3S)-3-Propyloxiranemethanol. Organic Syntheses Collection 7: 461 (1990) and 63: 66 (1985) (8 pages).
Hofland, H.E.J et al., Formation of stable cationic lipid/DNA complexes for gene transfer. Proceedings of the National Academy of Sciences of the USA 93 (14): 7305-7309 (1996).
Hope, M.J. et al., Cationic Lipids, Phosphatidylethanolamine and the Intracellular Delivery of Polymeric, Nucleic Acid-Based Drugs. Molecular Membrane Technology 15:1-14 (1998).
Hornung, V. et al., Quantitative expression of toll-like receptor 1-10 mRNA in cellular subsets of human peripheral blood mononuclear cells and sensitivity to CpG oligodeoxynucleotides. The Journal of Immunology 168: 4531-4537 (2002).
Howard, K.A. Delivery of RNA interference therapeutics using polycation-based nanoparticles. Advanced Drug Delivery Reviews 61: 710-720 (2009).
Huang, Z. et al., Thiocholesterol-Based Lipids for Ordered Assembly of Bioresponsive Gene Carriers, Molecular Therapy, 11(3):409-417 (2005).
Incani, V. et al., Lipid and hydrophobic modification of cationic carriers on route to superior gene vectors. Soft Matter 6: 2124-2138 (2010).
International Search Report for PCT/US2012/041663, 4 pages (dated Oct. 8, 2012).
International Search Report for PCT/US2013/034604, 4 pages (dated Jun. 17, 2013).
International Search Report for PCT/US2014/061793, 4 pages (dated Feb. 6, 2015).

Jemiety, J. et al., Novel "anti-reverse" cap analogs with superior translational properties, RNA, 9(9):1108-1122 (2003).
Jiang, G. et al., Hyaluronic acid-polyethyleneimine conjugate for target specific intracellular delivery of siRNA. Biopolymers 89 (7): 635-642 (2008).
Jiang, M. et al., Electrochemically controlled release of lipid/DNA complexes: a new tool for synthetic gene delivery system. Electrochemistry Communications (6): 576-582 (2004).
Jiang, S. and Cao, Z., Ultralow-fouling, functionalizable, and hydrolyzable zwitterionic materials and their derivatives for biological applications. Advanced Materials 22(9):920-932 (2010).
Jolck, R.I. et al., Solid-phase synthesis of PEGylated lipopeptides using click chemistry. Bioconjugate Chemistry 21(5):807-810 (2010).
Jon, S. et al., Degradable poly(amino alcohol esters) as potential DNA vectors with low cytotoxicity. Biomacromolecules 4(6):1759-1762 (2003).
Kabanov, A.V. and Kabanov, V.A., DNA complexes with polycations for the delivery of genetic material into cells. Bioconjugate Chemistry 6(1): 7-20 (1995).
Kamath, S. et al., Surface chemistry influences implant-mediated host tissue responses. Journal of Biomedical Materials Research A 86(3):617-626 (2007).
Kariko, K. et al., Incorporation of Pseudouridine Into mRNA Yields Superior Nonimmunogenic Vector With Increased Translational Capacity and Biological Stability, Molecular Therapy, 16(11): 1833-1840 (2008).
Kaur, N. et al., A delineation of diketopiperazine self-assembly processes: understanding the molecular events involved in Nepsilon-(fumaroyl)diketopiperazine of L-Lys (FDKP) interactions. Molecular Pharmaceutics 5(2):294-315 (2007).
Kim, S.H. et al., Comparative evaluation of target-specific GFP gene silencing efficiencies for antisense ODN, synthetic siRNA, and siRNA plasmid complexed with PEI-PEG-FOL conjugate. Bioconjugate Chemistry 17(1): 241-244 (2006).
Kim, T. et al., Synthesis of biodegradable cross-linked poly(beta-amino ester) for gene delivery and its modification, inducing enhanced transfection efficiency and stepwise degradation. Bioconjugate Chemistry 16(5):1140-1148 (2005).
Klibanov, A.L. et al., Amphipathic polyethylenglycols effectively prolong the circulation time of liposomes, FEBS Letters, 268(1):235-237 (1990).
Kozak, M. An analysis of 5'-noncoding sequences from 699 vertebrate messenger RNAs, Nucleic Acid Research, 15(20):8125-8148 (1987).
Lasic, D.D. et al., Gelation of liposome interior. A novel method for drug encapsulation, FEBS Letters, 312(2-3):255-258 (1992).
Lee, S. et al., Stability and cellular uptake of polymerized siRNA (poly-siRNA)/polyethylenimine (PEI) complexes for efficient gene silencing. Journal of Controlled Release 141: 339-346 (2010).
Li, S. et al., In vivo gene transfer via intravenous administration of cationic lipid-protamine-DNA (LPD) complexes, Gene Therapy, 4:891-900 (1997).
Li, W. et al., Lipid-based Nanoparticles for Nucleic Acid Delivery, Pharmaceutical Research, 24(3):438-449 (2007).
Lim, Y. et al., A self-destroying polycationic polymer: biodegradable poly(4-hydroxy-l-proline ester). Journal of American Chemical Society 121: 5633-5639 (1999).
Love, K.T. et al., Lipid-like materials for low-dose in vivo gene silencing, Proceedings of the National Academy of Sciences USA, 107(5):1864-1869 (2010).
Lubke, T. et al., Proteomics of the Lysosome, Biochimica et Biophysica Acta, 1793(4):625-635 (2009).
Lukyanov, A.N. and Torchilin, V.P., Micelles from lipid derivatives of water-soluble polymers as delivery systems for poorly soluble drugs. Advanced Drug Delivery Reviews 56: 1273-1289 (2004).
Luo, D. and Saltzman, M., Synthetic DNA delivery systems. Nature Biotechnology 18: 33-37. Review (2000).
Lynn, D.M. et al., Accelerated discovery of synthetic transfection vectors: parallel synthesis and screening of a degradable polymer library. Journal of American Chemical Society 123(33): 8155-8156 (2001).

(56) References Cited

OTHER PUBLICATIONS

Lynn, D.M. et al., Degradable Poly(β-amino esters): Synthesis, Characterization, and Self-Assembly with Plasmid DNA. Journal of American Chemical Society 122(44): 10761-10768 (2000).
Lynn, D.M. et al., pH-Responsive Polymer Microspheres: Rapid Release of Encapsulated Material within the Range of Intracellular pH. Angewandte Chemie International Edition 40(9): 1707-1710 (2001).
Ma, M. et al., Development of Cationic Polymer Coatings to Regulate Foreign Body Responses. Advanced Healthcare Materials 23: H189-H194. Reviews (2011).
Margus, H. et al., Cell-penetrating peptides as versatile vehicles for oligonucleotide delivery. Molecular Therapy 20 (3): 525-533 (2012).
Martell, A.E. and Chaberek, S., The Preparation and the Properties of Some N,N'-Disubstituted-ethylenediaminedipropionic Acids. Journal of the American Chemical Society 72: 5357-5361 (1950).
Mathiowitz, E. and Langer, R., Polyanhydride microspheres as drug carriers I. Hot-melt microencapsulation. Journal of Controlled Release 5: 13-22 (1987).
Mathiowitz, E. et al., Novel microcapsules for delivery systems. Reactive Polymers 6: 275-283 (1987).
Mathiowitz, E. et al., Polyanhydride microspheres as drug carriers II. Microencapsulation by solvent removal. Journal of Applied Polymer Sciences 35: 755-774 (1988).
Mendelsohn, J.D. et al., Rational design of cytophilic and cytophobic polyelectrolyte multilayer thin films. Biomacromolecules 4(1): 96-106 (2003).
Miller, A. Cationic Liposomes for Gene Therapy. Angewandte Chemie International Edition 37: 1768-1785 (1998).
Morrissey, D. et al., Potent and persistent in vivo anti-HBV activity of chemically modified siRNAs, Nature Biotechnology, 23(8):1002-1007 (2005).
Narang, A.S. et al., Cationic lipids with increased DNA binding affinity for nonviral gene transfer in dividing and nondividing cells. Bioconjugate Chemistry 16(1): 156-168 (2005).
Navarro, G. et al., Phospholipid—polyethylenimine conjugate-based micelle-like nanoparticles for siRNA delivery. Drug Delivery and Translational Research 1: 25-33 (2011).
Neamnark, A. et al., Aliphatic lipid substitution on 2 kDa polyethylenimine improves plasmid delivery and transgene expression. Molecular Pharmaceutics 6(6): 1798-1815 (2009).
Ng, J. et al., LincRNAs join the pluripotency alliance, Nature Genetics, 42:1035-1036 (2010).
Nguyen, D.N. et al., A novel high-throughput cell-based method for integrated quantification of type I interferons and in vitro screening of immunostimulatory RNA drug delivery. Biotechnology and Bioengineering 103(4): 664-675 (2009).
Nguyen, D.N. et al., Drug delivery-mediated control of RNA immunostimulation. Molecular Therapy 17(9): 1555-1562 (2009).
Nori, A. et al., Tat-conjugated synthetic macromolecules facilitate cytoplasmic drug delivery to human ovarian carcinoma cells, Bioconj. Chem., 14(1): 44-50 (2003).
Parrish, D.A. and Mathias, L.J., Five- and six-membered ring opening of pyroglutamic diketopiperazine. Journal of Organic Chemistry 67(6): 1820-1826 (2002).
Peppas, N.A. et al., Hydrogels in Biology and Medicine: From Molecular Principles to Bionanotechnology. Advanced Materials 18: 1345-1360 (2006).
Philipp, A. et al., Hydrophobically modified oligoethylenimines as highly efficient transfection agents for siRNA delivery. Bioconjugate Chemistry 20(11): 2055-2061 (2009).
Pons, M. et al., Liposomes obtained by the ethanol injection method, International Journal of Pharmacology, 95:51-56 (1993).
Prata, C.A. et al., Lipophilic peptides for gene delivery. Bioconjugate Chemistry 19(2): 418-420 (2008).
Putnam, D. Polymers for gene delivery across length scales. Nature Materials 5: 439-451 (2006).
Putnam, D. and Langer, R., Poly(4-hydroxy-l-proline ester): Low-Temperature Polycondensation and Plasmid DNA Complexation. Macromolecules 32(11): 3658-3662 (1999).

Ratner, B.D. and Bryant, S., Biomaterials: where we have been and where we are going. Annual Review of Biomedical Engineering 6: 41-75 (2004).
Ryng, S. et al., Synthesis and structure elucidation of 5-aminomethinimino-3-methyl-4-isoxazolecarboxylic acid phenylamides and their immunological activity. Arch. Pharm. Pharm. Med. Chem 330(11):319-26 (1997).
Sahay, G. et al., Endocytosis of nanomedicines. Journal of Controlled Release 145: 182-195 (2010).
Sakiyama-Elbert, S.E. and Hubbell, J.A., Functional Biomaterials: Design of Novel Biomaterials. Annual Review of Materials Research 31: 183-201 (2001).
Semple,S.C. et al., Rational Design of Cationic Lipids for siRNA Delivery, Nature Biotechnology, 28(2):172-176 (2010).
Shchori E., Poly(secondary Amine)s from Diacrylates and Diamines. Journal of Polymer Science 21(6):413-15 (1983).
Sherwood, R.F. Advanced drug delivery reviews: enzyme prodrug therapy, Adv. Drug Del. Rev., 22: 269-288 (1996).
Siegwart, D.J. et al., Combinatorial synthesis of chemically diverse core-shell nanoparticles for intracellular delivery. Proceedings of the National Academy of the Sciences of the USA 108(32):12996-123001 (2011).
Stern, L. et al., A novel antitumor prodrug platform designed to be cleaved by the endoprotease legumain, Bioconj. Chem., 20: 500-510 (2009).
Szoka, F. and Papahadjopoulos, D., Comparative properties and methods of preparation of lipid vesicles (liposomes). Annual Review of Biophysics Bioengineering 9: 467-508 (1980).
Tan, S. et al., Engineering Nanocarriers for siRNA Delivery. Small 7(7): 841-856 (2011).
Tang, F. and Hughes, J. et al., Introduction of a Disulfide Bond into a Cationic Lipid Enhances Transgene Expression of Plasmid DNA, Biochemical and Biophysical Research Communications, 242(1):141-145 (1998).
Tang, M.X. et al., In vitro gene delivery by degraded polyamidoamine dendrimers. Bioconjugate Chemistry 7(6): 703-714 (1996).
Tarcha, P.J. et al., Synthesis and characterization of chemically condensed oligoethylenimine containing beta-aminopropionamide linkages for siRNA delivery. Biomaterials 28: 3731-3740 (2007).
Thompson, P.E. et al., Antiamebic action of 5-chloro-7-diethylaminomethyl-8-quinolinol and of other substituted 8-quinolinols in vitro and in experimental animals. American Journal of Tropical Medicine and Hygiene 2(4): 224-248 (1955).
Toki, B.E. et al., Protease-mediated fragmentation of p-amidobenzyl ethers: a new strategy for the activation of anticancer prodrugs, J. Org. Chem., 67(6): 1866-1872 (2002).
Tran M. A. et al., Use of liposomes as drug delivery vehicles for treatment of melanoma. Pigment Cell Melanoma Res., 22(4): 388-399 (2009).
Tranchant, I. et al., Physicochemical optimisation of plasmid delivery by cationic lipids. Journal of Gene Medicine 6: S24-S35 (2004).
Tsvetkov, D.E. et al., Neoglycoconjugates based on dendrimeric poly(aminoamides). Russian Journal of Bioorganic Chemistry 28(6): 470-486 (2002).
Urban-Klein, B. et al., RNAi-mediated gene-targeting through systemic application of polyethylenimine (PEI)-complexed siRNA in vivo. Gene Therapy 12(5): 461-466 (2005).
Van Balen, G.P. et al., Liposome/water lipophilicity: methods, information content, and pharmaceutical applications. Medicinal Research Reviews 24(3): 299-324 (2004).
Van De Wetering, P. et al., Structure-activity relationships of water-soluble cationic methacrylate/methacrylamide polymers for nonviral gene delivery. Bioconjugate Chemistry 10(4): 589-597 (1999).
Vandenbroucke, R.E. et al., Prolonged gene silencing in hepatoma cells and primary hepatocytes after small interfering RNA delivery with biodegradable poly(beta-amino esters). Journal of Gene Medicine 10: 783-794 (2008).
Veronese, F.M. et al., PEG-doxorubicin conjugates: influence of polymer structure on drug release, in vitro cytotoxicity, biodistribution, and antitumor activity, Bioconj. Chem., 16(4): 775-784 (2005).
Von Harpe et al., Characterization of commercially available and synthesized polyethylenimines for gene delivery. Journal of Controlled Release 69(2):309-322 (2000).

(56) References Cited

OTHER PUBLICATIONS

Walde, P. et al., Preparation of Vesicles (Liposomes). Encyclopedia of Nanoscience and Nanotechnology. Nalwa, ed. American Scientific Publishers, Los Angeles 9:43-79 (2004).

Werth, S. et al., A low molecular weight fraction of polyethylenimine (PEI) displays increased transfection efficiency of DNA and siRNA in fresh or lyophilized complexes. Journal of Controlled Release 112: 257-270 (2006).

Wetzer, B. et al., Reducible cationic lipids for gene transfer, Biochem. J., 356:747-756 (2001).

White, J.E. et al., Poly(hydroxyaminoethers): A New Family of Epoxy-Based Thermoplastics. Advanced Materials 12(23): 1791-1800 (2000).

White, J.E. et al., Step-growth polymerization of 10,11-epoxyundecanoic acid. Synthesis and properties of a new hydroxy-functionalized thermopastic polyester. Advanced Materials 48: 3990-3998 (2007).

Whitehead, K.A. et al., Knocking down barriers: advances in siRNA delivery. Nature Reviews Drug Discovery 8(2): 129-139 (2009).

Written Opinion for PCT/US2013/034604, 9 pages (dated Jun. 17, 2013).

Written Opinion for PCT/US2014/061793, 4 pages (dated Feb. 6, 2015).

Wu, J. et al., Cationic lipid polymerization as a novel approach for constructing new DNA delivery agents. Bioconjugate Chemistry 12(2): 251-257 (2001).

Yokoe, H. and Meyer, T., Spatial Dynamics of GFP-tagged proteins investigated by local fluorescence enhancement, Nature Biotechnology, 14(10):1252-1256 (1996).

Yoneda et al., A cell-penetrating peptidic GRP78 ligand for tumor cell-specific prodrug therapy, Bioorg. Med. Chern. Lett., 18(5): 1632-1636 (2008).

Yoshioka, Y. and Calvert, P., Epoxy-based Electroactive Polymer Gels. Experimental Mechanics 42(4): 404-408 (2002).

Zagridullin, P.H. et al., Monobasic amines. II. Cycloalkylation and hydroxyalkylation of cyclic and acyclic di- and polyamines. Journal of Organic Chemistry 26(1):184-88. Russian (1990).

Zaugg, H.E. et al., 3-Carboxy-2,5-piperazinedione and Derivatives. Journal of American Chemical Society 78(11):2626-2631 (1956).

Zauner, W. et al., Polylysine-based transfection systems utilizing receptor-mediated delivery. Advanced Drug Delivery Reviews 30(1-3):97-113(1998).

Zintchenko, A. et al., Simple modifications of branched PEI lead to highly efficient siRNA carriers with low toxicity. Bioconjugate Chemistry 19(7):1448-1455 (2008).

\* cited by examiner

Detection of hSMN-1 mRNA in Spinal Tissue

Detection of hSMN-1 mRNA in Spinal Tissue

*In Vivo* Delivery of CFTR mRNA to CFTR

A    Saline

B    cKK-E12

SEQUENCE LISTING

```
<160> NUMBER OF SEQ ID NOS: 15

<210> SEQ ID NO 1
<211> LENGTH: 1632
<212> TYPE: RNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1527)..(1527)
<223> OTHER INFORMATION: May or may not be present
<220> FEATURE:
<221> NAME/KEY: modified_base
<222> LOCATION: (1627)..(1627)
<223> OTHER INFORMATION: May or may not be present

<400> SEQUENCE: 1
ggacagaucg  ccuggagacg  ccauccacgc  uguuuugacc  uccauagaag  acaccgggac      60
cgauccagcc  uccgcggccg  ggaacggugc  auuggaacgc  ggauccccg   ugccaagagu     120 gacucaccgu  ccuugacacg  augcagcgcg  ugaacaugau  cauggcagaa  ucaccaggcc    180
ucaucaccau  cugccuuuua  ggauaucuac  ucagugcuga  auguacaguu  uuucuugauc    240
augaaaacgc  caacaaaauu  cugaggcgga  gaaggaggua  uaauucaggu  aaauuggaag    300
aguuuguuca  agggaaccuu  gagagagaau  guauggaaga  aagucuagu   uuugaagaag    360 cacgagaagu  uuuugaaaac  acugaaagaa  caacugaauu  uuggaagcag  uauguugaug    420
gagaucagug  ugaguccaau  ccauguuuaa  auggcggcag  uugcaaggau  gacauuaauu    480
ccuaugaaug  uuggugucc   uuuggauuug  aaggaaagaa  cugugaauua  gauguaacau    540
guaacauuaa  gaauggcaga  ugcgagcagu  uuugaaaaa   uagugcugau  aacaaggugg    600
uuugcuccug  uacugaggga  uaucgacuug  cagaaaacca  gaaguccugu  gaaccagcag    660
ugccauuucc  augugggaaga guuucuguuu  cacaaacuuc  uaagcucacc  cgucugagg    720 cuguuuuucc  ugauguggac  uauguaaauu  cuacugaagc  ugaaaccauu  uggauaaca    780 ucacucaaag  cacccaauca  uuuaaugacu  ucacucgggu  uguuggugga  gaagaugcca    840
aaccagguca  auucccuugg  cagguuguuu  ugaauggua   aguugaugca  uucuguggag    900
gcucuaucgu  uaaugaaaaa  uggauuguaa  cugcugccca  cuguguugaa  acuggugua    960 aaauuacagu  ugucgcaggu  gaacauaaua  uugaggagac  agaacauaca  gagcaaaagc   1020
gaaaugugau  ucgaauuauu  ccucaccaca  acuacaaugc  agcauuaau   aaguacaacc   1080 augacauugc  ccuucuggaa  cuggacgaac  ccuuagugcu  aaacagcuac  guuacaccua   1140
uuugcauugc  ugacaaggaa  uacacgaaca  ucuuccucaa  auuggaucu   ggcuauguaa   1200 guggcugggg  aagagucuuc  cacaaaggga  gaucagcuuu  aguucuucag  uaccuuagag   1260
```

| | |
|---|---:|
| uuccacuugu ugaccgagcc acaugucuuc gaucuacaaa guucaccauc uauaacaaca | 1320 |
| uguucugugc uggcuuccau gaaggaggua gagauucaug ucaaggagau agugggggac | 1380 |
| cccauguuac ugaaguggaa gggaccaguu ucuuaacugg aauuauuagc uggggugaag | 1440 |
| agugugcaau gaaaggcaaa uauggaauau auaccaaggu aucccgguau gucaacugga | 1500 |
| uuaaggaaaa aacaaagcuc acuuaacggg uggcaucccu ugaccccuc cccagugccu | 1560 |
| cuccuggccc uggaaguugc cacuccagug cccaccagcc uuguccuaau aaaauuaagu | 1620 |
| ugcaucaaag cu | 1632 |

<210> SEQ ID NO 2
<211> LENGTH: 1485
<212> TYPE: RNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1380)..(1380)
<223> OTHER INFORMATION: May or may not be present
<220> FEATURE:
<221> NAME/KEY: modified_base
<222> LOCATION: (1480)..(1480)
<223> OTHER INFORMATION: May or may not be present

<400> SEQUENCE: 2

| | |
|---|---:|
| ggacagaucg ccuggagacg ccauccacgc uguuugacc uccauagaag acaccgggac | 60 |
| cgauccagcc uccgcggccg ggaacggugc auuggaacgc ggauucccg ugccaagagu | 120 |
| gacucaccgu ccuugacacg augagcagca agggcagcgu ggugcuggcc uacagcggcg | 180 |
| gccuggacac cagcugcauc cuggugugge ugaaggagca gggcuacgac gugaucgccu | 240 |
| accuggccaa caucggccag aaggaggacu cgaggaggcc ccgcaagaag gcccugaagc | 300 |
| ugggcgccaa gaagguguuc aucgaggacg ugagccgcga guucguggag gaguucaucu | 360 |
| ggcccgccau ccagagcagc gcccuguacg aggaccgcua ccugcugggc ccagccugg | 420 |
| cccgcccug caucgcccgc aagcaggugg agaucgccca gcgcgagggc gccaaguacg | 480 |
| ugagccacgg cgccaccggc aagggcaacg accaggugcg cuucgagcug agcugcuaca | 540 |
| gccuggcccc ccagaucaag gugaucgccc ccuggcgcau gcccgaguuc uacaaccgcu | 600 |
| ucaagggccg caacgaccug auggaguacg ccaagcagca cggcauccc auccccguga | 660 |
| cccccaagaa cccccuggag auggacgaga accugaugca caucagcuac gaggccggca | 720 |
| uccuggagaa ccccaagaac caggcccccc ccggccugua caccaagacc caggaccccg | 780 |
| ccaaggcccc caacacccc gacauccugg agaucgaguu caagaagggc gugcccguga | 840 |
| aggugaccaa cgugaaggac ggcaccaccc accagaccag ccuggagcug uucauguacc | 900 |
| ugaacgaggu ggccggcaag cacggcgugg gccgcaucga caucguggag aaccgcuuca | 960 |
| ucggcaugaa gagccgcggc aucuacgaga ccccgccgg caccauccug uaccacgccc | 1020 |
| accuggacau cgaggccuuc accauggacc gcgaggugcg caagaucaag cagggccugg | 1080 |
| gccugaaguu cgccgagcug guguacaccg gcuucuggca cagccccgag ugcgaguucg | 1140 |
| ugcgccacug caucgccaag agccaggagc gcguggaggg caaggugcag gugagcgugc | 1200 |
| ugaagggcca ggguacauc cugggccgcg agagccccu gagccuguac aacgaggagc | 1260 |
| uggugagcau gaacgugcag ggcgacuacg agcccaccga cgccaccggc uucaucaaca | 1320 |
| ucaacagccu cgccugaag gaguaccacc gccugcagag caaggugacc gccaagugac | 1380 |
| ggguggcauc ccugugaccc cuccccagug ccucuccugg cccuggaagu ugccacucca | 1440 |

```
gugcccacca gccuuguccu aauaaaauua aguugcauca aagcu            1485
```

<210> SEQ ID NO 3
<211> LENGTH: 1899
<212> TYPE: RNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1794)..(1794)
<223> OTHER INFORMATION: May or may not be present
<220> FEATURE:
<221> NAME/KEY: modified_base
<222> LOCATION: (1894)..(1894)
<223> OTHER INFORMATION: May or may not be present

<400> SEQUENCE: 3

```
ggacagaucg ccuggagacg ccauccacgc uguuugacc uccauagaag acaccgggac      60
cgauccagcc uccgcggccg ggaacggugc auuggaacgc ggauucccg ugccaagagu     120
gacucaccgu ccuugacacg auggaagaug ccaaaaacau uagaagggc ccagcgccau     180
ucuacccacu cgaagacggg accgccggcg agcagcugca caaagccaug aagcgcuacg     240
cccuggugcc cggcaccauc gccuuuaccg acgcacauau cgaggugac auuaccuacg     300
ccgaguacuu cgagaugagc guucggcugg cagaagcuau gaagcgcuau ggcugaaua     360
caaaccaucg gaucgguggu gcagcgaga auagcuugca guucuucaug cccguguugg     420
gugcccuguu caucggugug gcugugggcc cagcuaacga caucuacaac gagcgcgagc     480
ugcugaacag caugggcauc agccagccca ccgucguauu cgugagcaag aaagggcugc     540
aaaagauccu caacgugcaa aagaagcuac cgaucauaca aaagaucauc aucauggaua     600
gcaagaccga cuaccagggc uuccaaagca uguacaccuu cgugacuucc cauuugccac     660
ccggcuucaa cgaguacgac uucgugcccc agagcuucga ccgggacaaa accaucgccc     720
ugaucaugaa caguagugcc aguaccggau ugcccaaggg cguagcccua ccgcaccgca     780
ccgcuugugu ccgauucagu caugcccgcg accccaucuu cggcaaccag aucauccccg     840
acaccgcuau ccucagcgug gugccauuuc accacgcuu cggcauguuc accacgcugg     900
gcuacuugau cugcggcuuu cgggucgugc caugccg cuucgaggag agcuauucu     960
ugcgcagcuu gcaagacuau aagauucaau cugcccugcu ggugcccaca cuauuuagcu    1020
ucuucgcuaa gagcacucuc aucgacaagu acgaccuaag caacuugcac gagaucgcca    1080
gcggcggggc gccgcucagc aaggagguag gugaggccgu ggccaaacgc uuccaccuac    1140
caggcauccg ccagggcuac ggccugacag aaacaaccag cgccauucug aucacccccg    1200
aaggggacga caagccuggc gcaguaggca agguggugcc cuucuucgag gcuaagguug    1260
uggacuugga caccgguaag acacuggugu gaaccagcg cggcgagcug ugcguccgug    1320
gccccaugau caugacgggc uacguuaaca cccccgaggc ucaaaacgcu cucaucgaca    1380
aggacggcug gcugcacagc ggcgacaucg ccuacuggga cgaggacgag cacuucuuca    1440
ucguggaccg gcugaagagc cugaucaaau acaagggcua ccaguagcc ccagccgaac    1500
uggagagcau ccugcugcaa cacccccaaca ucuucgacgc cggggucgcc ggccugcccg    1560
acgacgaugc cggcgagcug cccgccgcag ucgucgugcu ggaacacggu aaaaccauga    1620
ccgagaagga gaucguggac uauguggcca gccagguuac aaccgccaag aagcugcgcg    1680
guguguugu guucguggac gaggugccua aaggacugac cggcaaguug gacgccgca    1740
```

| | |
|---|---|
| agauccgcga gauucucauu aaggccaaga agggcggcaa gaucgccgug uaacggguqg | 1800 |
| caucccugug accccucccc agugccucuc cuggcccugg aaguugccac uccagugccc | 1860 |
| accagccuug uccuaauaaa auuaaguugc aucaaagcu | 1899 |

<210> SEQ ID NO 4
<211> LENGTH: 1131
<212> TYPE: RNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1026)..(1026)
<223> OTHER INFORMATION: May or may not be present
<220> FEATURE:
<221> NAME/KEY: modified_base
<222> LOCATION: (1126)..(1126)
<223> OTHER INFORMATION: May or may not be present

<400> SEQUENCE: 4

| | |
|---|---|
| ggacagaucg ccuggagacg ccauccacgc uguuuugacc uccauagaag acaccgggac | 60 |
| cgauccagcc uccgcggccg ggaacggugc auuggaacgc ggauuccccg ugccaagagu | 120 |
| gacucaccgu ccuugacacg auggccauga gcagcggagc cagcggcgga ggagugcccg | 180 |
| agcaggagga cagcgugcug uucaggagag gcaccggcca gagcgaugac agcgauaucu | 240 |
| gggacgauac cgcucugauc aaggccuacg acaaggccgu ggccagcuuc aagcacgccc | 300 |
| ugaaaaacgg cgacaucugc gagaccagcg gcaagcccaa gacaaccccc aagagaaagc | 360 |
| ccgccaagaa gaauaagagc cagaaaaaga acaccgccgc cagccugcag caguggaagg | 420 |
| uggcgacaa gugcagcgcc aucggagcg aggacggcug caucuacccc gccaccaucg | 480 |
| ccagcaucga cuucaagaga gagaccgccg uggucguqua caccggcuac ggcaacagag | 540 |
| aggagcagaa ccugagcgac cugcugagcc cauuguqa ggugqccaau aacaucgaac | 600 |
| agaacgccca ggagaacgag aaugaaagcc aggugagcac cgacgagagc gagaacagca | 660 |
| gaucuccuqg caacaagagc gacaacauca agccuaaquc ugcccuugg aacagcuucc | 720 |
| ugcccccucc uccacccaug cccggaccca gacugggacc cggaaaaccu ggccugaagu | 780 |
| ucaacggacc accuccccu ccaccuccuc ccccaccuca ucuccugagc ugcuggcuqc | 840 |
| cacccuuccc cagcggaccc ccuaucaucc caccaccccc ucccaucuqc ccgacagcc | 900 |
| uggacgacgc cgaugcccug ggcagcaugc ugaucagcug guacaugagc ggcuaccaca | 960 |
| caggauacua caugggcuuc agacagaacc agaaggaggg cagagucucc cacucccuga | 1020 |
| acugacgggu ggcaucccug ugaccccucc ccagugccuc uccuggcccu ggaaguugcc | 1080 |
| acuccagugc ccaccagccu uguccuaaua aauuaaguu gcaucaaagc u | 1131 |

<210> SEQ ID NO 5
<211> LENGTH: 140
<212> TYPE: RNA
<213> ORGANISM: Artificial Sequence
<220> FEATURE:
<223> OTHER INFORMATION: Synthetic polynucleotide

<400> SEQUENCE: 5

| | |
|---|---|
| ggacagaucg ccuggagacg ccauccacgc uguuuugacc uccauagaag acaccgggac | 60 |
| cgauccagcc uccgcggccg ggaacggugc auuggaacgc ggauuccccg ugccaagagu | 120 |
| gacucaccgu ccuugacacg | 140 |

<210> SEQ ID NO 6
<211> LENGTH: 105
<212> TYPE: RNA
<213> ORGANISM: Artificial Sequence
<220> FEATURE:
<223> OTHER INFORMATION: Synthetic polynucleotide

<400> SEQUENCE: 6

```
cggguggcau cccugugacc cucccccagu gccucuccug gcccuggaag uugccacucc      60
agugcccacc agccuugucc uaauaaaauu aaguugcauc aagcu                     105
```

<210> SEQ ID NO 7
<211> LENGTH: 105
<212> TYPE: RNA
<213> ORGANISM: Artificial Sequence
<220> FEATURE:
<223> OTHER INFORMATION: Synthetic polynucleotide

<400> SEQUENCE: 7

```
ggguggcauc ccugugaccc ucccccagug ccucuccugg cccuggaagu ugccacucca      60
gugcccacca gccuuguccu aauaaaauua aguugcauca aagcu                     105
```

<210> SEQ ID NO 8
<211> LENGTH: 4719
<212> TYPE: RNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (4614)..(4614)
<223> OTHER INFORMATION: May or may not be present
<220> FEATURE:
<221> NAME/KEY: modified_base
<222> LOCATION: (4714)..(4714)
<223> OTHER INFORMATION: May or may not be present

<400> SEQUENCE: 8

```
ggacagaucg ccuggagacg ccauccacgc uguuuugacc uccauagaag acaccgggac        60
cgauccagcc uccgcggccg ggaacggugc auuggaacgc ggauuccccg ugccaagagu       120
gacucaccgu ccuugacacg augcagcggu ccccgcucga aaaggccagu gucgugucca       180
aacucuucuu cucauggacu cggccuaucc uuagaaaggg guaucggcag aggcuugagu       240
ugucugacau cuaccagauc cccucgguag auucggcgga uaaccucucg gagaagcucg       300
aacgggaaug ggaccgcgaa cucgcgucua agaaaacccc gaagcucauc aacgcacuga       360
gaaggugcuu cuucuggcgg uucauguucu acgguaucuu cuuguaucuc ggggagguca       420
caaaagcagu ccaaccccug uguuggguc gcauuaucgc cucguacgac cccgauaaca       480
aagaagaacg gagcaucgcg aucuaccucg ggaucggacu uguuugcuu ucaucguca        540
gaacacuuuu guugcaucca gcaaucuucg gccuccauca caucgguaug cagaugcgaa       600
ucgcuauguu uagcuugauc uacaaaaaga cacugaaacu cucgucgcgg guguggauu        660
agauuuccau cggucaguug guguccccugc uuaguaauaa ccaacaaa uucgaugagg       720
gacuggcgcu ggcacauuuc guguggauu ccccguugca agucgcccuu ugauggggcc       780
uuauuuggga gcuguugcag gcaucugccu uuuguggccu gggauuucug auuguguugg       840
cauuguuuca ggcugggcuu gggcggauga ugaugaagua ucgcgaccag agagcgggua       900
aaaucucgga aagacucguc aucacuucg aaaugaucga aaacauccag ucggucaaag       960
ccuauugcug ggaagaagcu auggagaaga ugauugaaaa ccuccgccaa acugagcuga      1020
```

-continued

```
aacugacccg caaggcggcg uaugaccggu auuucaauuc gucagcguuc uucuuuuccg    1080
gguucuucgu ugucuuucuc ucgguuuugc cuuaugccuu gauuaagggg auuauccucc    1140
gcaagauuuu caccacgauu ucguucugca uuguauugcg cauggcagug acacggcaau    1200
uuccgugggc cgugcagaca ugguaugacu cgcuuggagc gaucaacaaa auccaagacu    1260
ucuugcaaaa gcaagaguac aagacccugg aguacaaucu acuacuacg gagguaguaa    1320
uggagaaugu gacggcuuuu ugggaagagg guuuuggaga acuguuugag aaagcaaagc    1380
agaauaacaa caaccgcaag accucaaaug gggacgauuc ccuguuuuuc ucgaacuucu    1440
cccugcucgg aacacccgug uugaaggaca ucaauuucaa gauugagagg ggacagcuuc    1500
ucgcgguagc gggaagcacu ggugcgggaa aaacuagccu cuugauggug auuauggggg    1560
agcuugagcc cagcgagggg aagauuaaac acuccgggcg uaucauuc uguagccagu      1620
uuucauggau caugcccgga accauuaaag agaacaucau uuucggagua uccuaugaug    1680
aguaccgaua cagaucggu auuaaggcgu gccaguugga agaggacauu ucuaaguucg     1740
ccgagaagga uaacaucguc uugggagaag ggguauuac auugucggga gggcagcgag     1800
cgcggaucag ccucgcgaga gcgguauaca aagaugcaga uuuguaucg cuugauucac      1860
cguuggaua cccgacgua uugacagaaa aagaaaucuu cgagucggc guguguaaac         1920
uuauggcuaa uaagacgaga auccgguga caucaaaaau ggaacaccuu aagaaggcgg     1980
acaagauccu gauccuccac gaaggaucgu ccuacuuuua cggcacuuuc ucagaguugc    2040
aaaacuugca gccggacuuc ucaagcaaac ucauggggug ugacucauuc gaccaguuca    2100
gcgcggaacg gcgaaacgcg aucuugacg aaacgcugca ccgauucucg cuugagggug      2160
augccccggu aucguggacc gagacaaaga agcagucguu uaagcagaca ggagaauuug    2220
gugagaaaag aaagaacagu aucuugaauc cuauuaacuc aauucgcaag uucucaaucg    2280
uccagaaaac uccacugcag augaauggaa uugaagagga uucggacgaa ccccuggagc    2340
gcaggcuuag ccucgugccg gauucagagc aaggggaggc cauucuuccc cggauuucgg    2400
ugauuucaac cggaccuaca cuucaggcga ggcgaaggca auccgugcuc aaccucauga    2460
cgcauucggu aaaccagggg caaaacauuc accgcaaaac gacggccuca acgagaaaag    2520
ugucacuugc accccaggcg aauuugacug aacucgacau cuacagccgu aggcuuucgc    2580
aagaaaccgg acuugagauc agcgaagaaa ucaaugaaga agauugaaa gaguguuucu     2640
uugaugacau ggaaucaauc ccagcgguga caacguggaa cacauacuug cguuacauca    2700
cggugcacaa guccuugauu ucguccuca ucuggugucu cgugaucuuu ucgcugaggg     2760
ucgcagcguc acuuggguc cucuggcugc uugguaauac gcccuugcaa gacaaaggca    2820
auucuacaca cucaagaaac aauuccuaug ccgugauuau cacuucuaca agcucgauuu    2880
acguguuuua caucuacgua ggaguggccg acacucugcc cgcgaugggu ucuuccgag     2940
gacucccacu cguucacacg cuuaucacug ucuccaagau ucuccaccau aagaugcuuc    3000
auagcguacu gcaggcuccc augucaccu ugaauacgcu caaggcggga gguauuuga      3060
aucgcuucuc aaaagauauu gcaauuuugg augaccuucu gccccugacg aucuucgacu    3120
ucauccaguu guugcugauc gugauugggg cuauugcagu agcgcuguc cuccagccuu     3180
acauuuuugu cgcgaccguu ccggugaucg uggcguuuau caugcugcgg gccuauuucu    3240
ugcagacguc acagcagcuu aagcaacugg agcugaagg gaggucgccu aucuuuacgc    3300
aucuugugac caguuugaag ggauuggga cguugcgcgc cuuggcagg cagcccuacu     3360
uugaaacacu guuccacaaa gcgcugaauc uccauacggc aaauugguu uuguauuuga    3420
```

| | |
|---|---|
| guacccuccg augguuucag augcgcauug agaugauuuu ugugaucuuc uuuaucgcgg | 3480 |
| ugacuuuuau cuccaucuug accacgggag agggcgaggg acggucggu auuauccuga | 3540 |
| cacucgccau gaacauuaug agcacuuugc agugggcagu gaacagcucg auugaugugg | 3600 |
| auagccugau gagguccguu ucgagggucu uuaaguucau cgacaugccg acggagggaa | 3660 |
| agcccacaaa aaguacgaaa cccuauaaga augggcaauu gaguaaggua augaucaucg | 3720 |
| agaacaguca cgugaagaag gaugacaucu ggccuagcgg gggucagaug accgugaagg | 3780 |
| accugacggc aaaauacacc gagggaggga acgcaauccu ugaaaacauc cguucagca | 3840 |
| uuagccccgg ucagcgugug ggguugcucg ggaggaccgg gucaggaaaa ucgacguugc | 3900 |
| ugucggccuu cuugagacuu cugaauacag agggugagau ccagaucgac ggcguuucgu | 3960 |
| gggauagcau caccuugcag cagugggcgga aagcguuugg aguaauccc caaaaggucu | 4020 |
| uuaucuuuag cggaaccuuc cgaaagaauc ucgauccuua ugaacagugg ucagaucaag | 4080 |
| agauuuggaa agucgcggac gagguuggcc uucggagugu aaucgagcag uuccgggaa | 4140 |
| aacucgacuu uguccuugua gauggggau gcguccuguc gcaugggcac aagcagcuca | 4200 |
| ugugccuggc gcgauccguc cucucuaaag cgaaaauucu ucucuuggau gaaccuucgg | 4260 |
| cccaucugga cccgguaacg uaucagauca ucagaaggac acuuaagcag gcguuugccg | 4320 |
| acugcacggu gauucucugu gagcaucgua ucgaggccau gcucgaaugc cagcaauuuc | 4380 |
| uugucaucga agagaauaag guccgccagu acgacuccau ccagaagcug cuuaaugaga | 4440 |
| gaucauuguu ccggcaggcg auuucaccau ccgauagggu gaaacuuuuu ccacacagaa | 4500 |
| auucgucgaa gugcaagucc aaaccgcaga ucgcggccuu gaaagaagag acugaagaag | 4560 |
| aaguucaaga cacgcgucuu caccaucacc aucaccauca ccaucaccau uaacgggugg | 4620 |
| caucccgugu accccucccc agugccucuc cuggcccugg aaguugccac uccagugccc | 4680 |
| accagccuug uccuaauaaa auuaaguugc aucaaagcu | 4719 |

<210> SEQ ID NO 9
<211> LENGTH: 4689
<212> TYPE: RNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (4584)..(4584)
<223> OTHER INFORMATION: May or may not be present
<220> FEATURE:
<221> NAME/KEY: modified_base
<222> LOCATION: (4684)..(4684)
<223> OTHER INFORMATION: May or may not be present

<400> SEQUENCE: 9

| | |
|---|---|
| ggacagaucg ccuggagacg ccauccacgc uguuugacc uccauagaag acaccgggac | 60 |
| cgauccagcc uccgcggccg ggaacggugc auuggaacgc ggauuccccg ugccaagagu | 120 |
| gacucaccgu ccuugacacg augcagcggu ccccgcucga aaaggccagu gucgugucca | 180 |
| aacucuucuu cucaauggacu cggccuaucc uuagaaaggg guaucggcag aggcuugagu | 240 |
| ugucugacau cuaccagauc cccucgguag auucggcgga uaaccucucg gagaagcucg | 300 |
| aacgggaaug ggaccgcgaa cucgcgucua agaaaaaccc gaagcucauc aacgcacuga | 360 |
| gaaggugcuu cuucuggcgg uucauguucu acgguaucuu cuuguaucuc ggggagguca | 420 |
| caaaagcagu ccaacccccug uuguggguc gcauuaucgc cucguacgac cccgauaaca | 480 |

```
aagaagaacg gagcaucgcg aucuaccucg ggaucggacu guguuugcuu uucaucguca    540
gaacacuuuu guugcaucca gcaaucuucg gccuccauca caucgguaug cagaugcgaa    600
ucgcuauguu uagcuugauc uacaaaaaga cacugaaacu cucgucgcgg guguuggaua    660
agauuuccau cggucaguug gugucccugc uuaguaauaa ccuaacaaa uucgaugagg     720 gacuggcgcu ggcacauuuc guguggauug ccccguugca agucgcccuu uugaugggcc    780
uuauuuggga gcuguugcag gcaucugccu uuuguggccu gggauuucug auuguguugg    840
cauuguuuca ggcugggcuu gggcggauga ugaugaagua ucgcgaccag agagcgggua    900
aaaucucgga aagacucguc aucacuucgg aaaugaucga aaacauccag ucggucaaag    960
ccuauugcug gaagaagcu auggagaaga ugauugaaaa ccuccgccaa acugagcuga    1020
aacugacccg caaggcggcg uaguccggu auuucaauuc gucagcguuc uucuuuuccg    1080
gguucuucgu ugucuuucuc ucgguuuugc cuuaugccuu gauuaagggg auuauccucc    1140
gcaagauuuu caccacgauu ucguucugca uguauugcg caugcagug acacggcaau     1200 uccgugggc cgugcagaca ugguaugacu cgcuuggagc gaucaacaaa uccaagacu      1260 ucuugcaaaa gcaagaguac aagacccugg aguacaaucu uacuacuacg gagguaguaa    1320
uggagaaugu gacggcuuuu ugggaagagg guuuggaga acuguuugag aaagcaaagc     1380
agaauaacaa caaccgcaag accucaaaug gggacgauuc ccuguuuuuc ucgaacuucu    1440
cccugcucgg aacacccgug uugaaggaca ucaauuucaa gauugagagg ggacagcuuc    1500
ucgcgguagc gggaagcacu ggugcgggaa aaacuagccu cuugaugugug auuauggggg   1560 agcuugagcc cagcgagggg aagauuaaac acucccgggcg uaucucauuc guagccagu    1620 uuucauggau caugcccgga accauuaaag agaacaucau uucggaagua uccuaugaug    1680
aguaccgaua cagaucgguc auuaaggcgu gccaguggaa agaggacauu ucuaaguucg    1740
ccgagaagga uaacaucguc uggggagaag ggguauuac auugucggga gggcagcgag     1800
cgcggaucag ccucgcgaga gcgguauaca aagaugcaga uuuguaucug cuugauucac    1860
cguuuggaua cccucgacgua uugacagaaa aagaaaucuu cgagucgugc guguguaaac    1920
uuauggcuaa uaagacgaga auccggugu caucaaaaau ggaacaccuu aagaaggcgg     1980
acaagauccu gauccuccac gaaggaucgu ccuacuuuua cggcacuuuc ucagaguugc    2040
aaaacuugca gccggacuuc ucaagcaaac ucauggggug ugacucauuc gaccaguuca    2100
gcgcggaacg gcggaacucg aucuugacgg aaacgcugca ccgauucucg cuugagggug    2160 augcccccggu aucguggacc gagacaaaga agcagucguu uaagcagaca ggagaauuug    2220
gugagaaaag aaagaacagu aucuugaauc cuauuaacuc aauucgcaag uucucaaucg    2280
uccagaaaac uccacugcag augaauggaa uugaagagga uucggacgaa ccccuggagc    2340
gcaggcuuag ccucgugccg gauucagagc aaggggaggc cauucuuccc cggauuucgg    2400
ugauuucaac cggaccuaca cuucaggcga ggcgaaggca auccgugcuc aaccucauga    2460
cgcauucggu aaaccagggg caaaacauuc accgcaaaac gacggccuca acgagaaaag    2520
ugucacuugc accccaggcg aauuugacug aacucgacau cuacagccgu aggcuuucgc    2580
aagaaaccgg acuugagauc agcgaagaaa ucaaugaaga agauugaaa gaguguuucu    2640 uugaugacau ggaaucaauc ccagcgguga caacguggaa cacauacuug cguuacauca    2700
cggugcacaa guccuugauu uucguccuca ucuggugucu cgugaucuuu ucgcugagg    2760 ucgcagcguc acuugggguc cucggcugc uuggaauac gcccuugcaa gacaaaggca    2820
auucuacaca cucaagaaac aauuccuaug ccgugauuau cacuucuaca agcucguauu    2880
```

```
acguguuuua caucuacgua ggagugcccg acacucugcu cgcgaugggu uucuuccgag    2940
gacucccacu cguucacacg cuuaucacug ucuccaagau ucuccaccau aagaugcuuc    3000
auagcguacu gcaggcuccc auguccaccu ugaauacgcu caaggcggga gguauuuuga    3060
aucgcuucuc aaaagauauu gcaauuuugg augaccuucu gccccugacg aucuucgacu    3120
ucauccaguu guugcugauc gugauuggg cuauugcagu agucgcuguc cuccagccuu    3180 acauuuugu cgcgaccguu ccggugaucg uggcguuuau caugcugcgg gccuauuucu    3240
ugcagacguc acagcagcuu aagcaacugg agucugaagg gaggucgccu aucuuuacgc    3300
aucuugugac caguuugaag ggauugugga cgugcgcgc cuuuggcagg cagcccuacu    3360
uugaaacacu guuccacaaa gcgcugaauc uccauacggc aaauugguuu uuguauuuga    3420
guaccuuccg augguuucag augcgcauug agaugauuuu ugugaucuuc uuuaucgcgg    3480
ugacuuuuau cuccaucuug accacgggag agggcgaggg acggucggu auuauccuga     3540 cacucgccau gaacauuaug agcacuuugc aguggcagu gaacagcucg auugaugugg    3600
auagccugau gaggucgcuu ucgagggucu uuaaguucau cgacaugccg acggagggaa    3660
agcccacaaa aaguacgaaa cccuauaaga augggcaauu gaguaaggua augaucaucg    3720
agaacaguca cgugaagaag gaugacaucu ggccuagcgg gggucagaug accgugaagg    3780 accgacggc aaaauacacc gagggaggga acgcaauccu ugaaaacauc cguucagca     3840 uuagccccgg ucagcgugug ggguugcucg ggaggaccgg ucaggaaaaa ucgacguugc    3900
ugucggccuu cuugagacuu cugaauacag agggugagau ccagaucgac ggcguuucgu    3960
gggauagcau caccuugcag caguggcgga aagcguuugg aguaaucccc caaaaggucu    4020
uuaucuuuag cggaaccuuc cgaaagaauc ucgauccuua ugaacaguigg ucagaucaag    4080 agauuuggaa agucgcggac gagguuggcc uucggagugu aaucgagcag uuccgggaa     4140 aacucgacuu uguccuugua gauggggau gcguccuguc gcaugggcac aagcagcuca    4200
ugugccuggc gcgauccguc cucucuaaag cgaaaauucu ucucuuggau gaaccuucgg    4260
cccaucugga cccgguaacg uaucagauca ucagaaggac acuuaagcag gcguuugccg    4320
acugcacggu gauucucugu gagcaucgua ucgaggccau gcucgaaugc cagcaauuuc    4380
uugucaucga agagaauaag guccgccagu acgacuccau ccagaagcug cuuaaugaga    4440
gaucauuguu ccgcaggcg auuucaccau ccgauagggu gaaacuuuuu ccacacagaa     4500
auucgucgaa gugcaagucc aaaccgcaga ucgcggccuu gaaagaagag acugaagaag    4560
aaguucaaga cacgcgucuu uaacggugg cauccccugu accccucccc agugccucuc     4620
cuggcccugg aaguugccac uccagugccc accagccuug uccuaauaaa auuaaguugc    4680
aucaaagcu                                                            4689
```

<210> SEQ ID NO 10
<211> LENGTH: 4542
<212> TYPE: RNA
<213> ORGANISM: Artificial Sequence
<220> FEATURE:
<223> OTHER INFORMATION: Synthetic polynucleotide

<400> SEQUENCE: 10

```
auggccacug gaucaagaac cucacugcug cucgcuuuug gacugcuuug ccugcccugg      60
uugcaagaag gaucggcuuu cccgaccauc ccacucucca ugcagcgguc cccgcucgaa     120
aaggccagug ucguguccaa acucuucuuc ucauggacuc ggccuauccu uagaaagggg     180
```

```
uaucggcaga ggcuugaguu gucugacauc uaccagaucc ccucgguaga uucggcggau    240
aaccucucgg agaagcucga acgggaaugg gaccgcgaac ucgcgucuaa gaaaaacccg    300
aagcucauca acgcacugag aaggugcuuc uucuggcggu ucauguucua cgguaucuuc    360
uuguaucucg gggaggucac aaaagcaguc aaccccugu uguugggucg cauuaucgcc    420
ucguacgacc ccgauaacaa agaagaacgg agcaucgcga ucuaccucgg gaucggacug    480
uguuugcuuu ucaucgucag aacacuuuug uugcauccag caaucuucgg ccuccaucac    540
aucgguaugc agaugcgaau cgcuauguuu agcuugaucu acaaaaagac acugaaacuc    600
ucgucgcggg guuggauaa gauuuccauc ggucaguugg ugcccugcu aaguaauaac    660 cucaacaaau ucgaugaggg acuggcgcug gcacauuucg uguggauugc cccguugcaa    720
gucgcccuuu ugaugggccu uauuuggag cuguugcagg caucugccuu uguggccug    780 ggauuucuga uuguguugc auuguucag gcugggcuug ggcggaugau gaugaaguau    840
cgcgaccaga gagcgggaa aucucgaa agacucguca ucacuucgga auugaucgaa    900
aacauccagu cggucaaagc cuauugcugg gaagaagcua uggagaagau gauugaaaac    960
cuccgccaaa cugagcugaa acugacccgc aaggcggcgu augccggua uuucaauucg   1020 ucagcguucu cuuuuccgg guucuucguu gucuuucucu cgguuuugcc uuaugccuug   1080
auuaagggga uuauccuccg caagauuuuc accacgauuu cguucugcau uguauugcgc   1140
auggcaguga cacggcaauu uccgguggcc gugcagacau gguagacuc gcuuggagcg   1200 aucaacaaaa uccaagacuu cuugcaaaag caagaguaca agacccugga guacaaucuu   1260
acuacuacgg agguaguaau ggagaaugug acggcuuuu gggaagaggg uuuggagaa   1320 cuguuugaga aagcaaagca gaauaacaac aaccgcaaga ccucaaaugg ggacgauucc   1380
cuguuuuucu cgaacuucuc ccugcucgga acacccgugu ugaaggacau caauuucaag   1440
auugagaggg gacagcuucu cgcgguagcg ggaagcacug gugcgggaaa aacuagccuc   1500 uugauggua uauggggga gcuugagccc agcgagggga agauuaaaca cuccgggcgu   1560
aucucauucu guagccaguu ucauggauc augcccggaa ccauaaaga gaacaucauu   1620 uucggaguau ccuaugauga guaccgauac agacgguca uuaaggcgug ccaguuggaa   1680
gaggacauuu cuaaguucgc cgagaaggau aacaucgucu ugggagaagg ggguauuaca   1740
uugucgggag ggcagcgagc gcggaucagc cucgcgagag cgguauacaa agaugcagau   1800
uuguaucugc uugauucacc guuuggauac cucgacguau ugacagaaaa agaaaucuuc   1860
gagucgugcg uguguaaacu uauggcuaau aagacgagaa uccggugac aucaaaaaug   1920 gaacaccuua gaaggcggga caagauccug auccuccacg aaggaucguc cuacuuuuac   1980
ggcacuuucu cagaguugca aaacuugcag ccggacuucu caagcaaacu cauggggugu   2040
gacucauucg accaguucag cgcggaacgg cggaacucga ucuugacgga aacgcugcac   2100
cgauucucgc uugaggguga ugccccggua ucgggaccg agacaaagaa gcagucguuu   2160
aagcagacag gagaauuugg ugagaaaaga aagaacagua ucuugaaucc uauuaacuca   2220
auucgcaagu ucucaaucgu ccagaaaacu ccacugcaga ugaauggaau ugaagaggau   2280
ucggacgaac cccuggagcg caggcuuagc cucgugccgg auucagagca aggggaggcc   2340 auucuuccc ggauuucggu gauuucaacc ggaccuacac uucaggcgag gcgaaggcaa   2400
uccgugcuca accucaugac gcaucggua aaccagggc aaaacauuca ccgcaaaacg   2460
acggccucaa cgagaaaagu gucacuugca ccccaggcga auuugacuga acucgacauc   2520
uacagccgua ggcuuucgca agaaaccgga cuugagauca gcgaagaaau caaugaagaa   2580
```

```
gauuugaaag aguguuucuu ugaugacaug gaaucaauucc cagcggugac aacguggaac    2640
acauacuugc guuacaucac ggugcacaag uccuugauuu ucguccucau cuggugucuc    2700
gugaucuuuc ucgcugaggu cgcagcguca cuugguggucc ucuggcugcu ugguaauacg   2760
cccuugcaag acaaaggcaa uucuacacac ucaagaaaca auuccauagc cgugauuauc    2820
acuucuacaa gcucguauua cguguuuuac aucuacguag gaguggccga cacucugcuc    2880 gcgaugggguu ucuuccgagg acucccacuc guucacacgc uuaucacugu uccaagauu    2940 cuccaccaua agaugcuuca uagcguacug caggcuccca uguccaccuu gaauacgcuc    3000
aaggcgggag guauuuugaa ucgcuucuca aaagauauug caauuuugga ugaccuucg    3060 ccccugacga ucuucgacuu cauccaguug uugcugaucg ugauuggggc uauugcagua    3120
gucgcugucc uccagccuua cauuuuuguc gcgaccguuc cggugaucgu ggcguuuauc     3180
augcugcggg ccuauuucuu gcagacguca cagcagcuua agcaacugga gucugaaggg    3240
aggucgccua ucuuuacgca ucuugugacc aguuugaagg gauuguggac guugcgcgcc   3300
uuuggcaggc agcccuacuu ugaaacacug uuccacaaag cgcugaaucu ccauacggca    3360
aauugguuuu uguauuugag uacccuccga ugguuucaga ugcgcauuga gaugauuuuu    3420
gugaucuucu uuaucgcggu gacuuuuauc uccaucuuga ccacgggaga gggcgaggga   3480
cgggucggua uuauccugac acucgccaug aacauuauga gcacuuugca gugggcagug    3540
aacagcucga uugaugugga uagccugaug aagguccguuu cgagggucuu uaaguucauc   3600
gacaugccga cggagggaaa gcccacaaaa aguacgaaac ccuauaagaa ugggcaauug    3660
aguaagguaa ugaucaucga aacagucac gugaagaagg augacaucug gccuagcggg     3720
ggucagauga ccgugaagga ccugacggca aaauacaccg aggagggaa cgcaauccuu    3780 gaaaacaucu cguucagcau uagccccggu cagcgugugg gguugcucgg gaggaccggg   3840
ucaggaaaau cgacguugcu gucggccuuc uugagacuuc ugaauacaga gggugagauc   3900
cagaucgacg gcguuucgug ggauagcauc accuugcagc aguggcggaa agcguuugga    3960 guaaucccc aaaaggucuu uaucuuuagc ggaaccuucc gaaagaaucu cgauccuuau     4020
gaacaguggu cagaucaaga gauuggaaa gucgcggacg agguuggccu ucggagugua    4080
aucgagcagu uccgggaaaa acucgacuuu guccuuguag augggggaug cguccugucg   4140 cauggcaca agcagcucau gugccuggcg cgauccgucc ucucuaaagc gaaaauucuu    4200
cucuuggaug aaccuucggc ccaucuggac ccgguaacgu aucagaucau cagaaggaca   4260
cuuaagcagg cguugccga cugcacggug auucucugug agcaucguau cgaggccaug     4320
cucgaaugcc agcaauuucu ugucaucgaa gagaauaagg uccgccagua cgacuccauc    4380
cagaagcugc uuaaugagag aucauuguuc cggcaggcga uuucaccauc cgauagggug   4440
aaacuuuuuc cacacagaaa uucgucgaag ugcaagucca aaccgcagau cgcggccuug    4500
aaagaagaga cugaagaaga aguucaagac acgcgucuuu aa                     4542
```

<210> SEQ ID NO 11
<211> LENGTH: 10
<212> TYPE: PRT
<213> ORGANISM: Artificial Sequence
<220> FEATURE:
<223> OTHER INFORMATION: Synthetic 10xHis tag

<400> SEQUENCE: 11

```
His His His His His His His His His His
1               5                   10
```

```
<210> SEQ ID NO 12
<211> LENGTH: 500
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(500)
<223> OTHER INFORMATION: This sequence may encompass 10-500 nucleotides

<400> SEQUENCE: 12
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa aaaaaaaaaa aaaaaaaaaa aaaaaaaaaa aaaaaaaaaa aaaaaaaaaa     300
aaaaaaaaaa aaaaaaaaaa aaaaaaaaaa aaaaaaaaaa aaaaaaaaaa aaaaaaaaaa     360
aaaaaaaaaa aaaaaaaaaa aaaaaaaaaa aaaaaaaaaa aaaaaaaaaa aaaaaaaaaa     420
aaaaaaaaaa aaaaaaaaaa aaaaaaaaaa aaaaaaaaaa aaaaaaaaaa aaaaaaaaaa     480
aaaaaaaaaa aaaaaaaaaa                                                 500

<210> SEQ ID NO 13
<211> LENGTH: 300
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(300)
<223> OTHER INFORMATION: This sequence may encompass 10-300 nucleotides

<400> SEQUENCE: 13
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa aaaaaaaaaa aaaaaaaaaa aaaaaaaaaa aaaaaaaaaa aaaaaaaaaa     300

<210> SEQ ID NO 14
<211> LENGTH: 200
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(200)
<223> OTHER INFORMATION: This sequence may encompass 10-200 nucleotides

<400> SEQUENCE: 14
cccccccccc cccccccccc cccccccccc cccccccccc cccccccccc cccccccccc      60
cccccccccc cccccccccc cccccccccc cccccccccc cccccccccc cccccccccc     120
cccccccccc cccccccccc cccccccccc cccccccccc cccccccccc cccccccccc     180
cccccccccc cccccccccc                                                 200
```

```
<210> SEQ ID NO 15
<211> LENGTH: 250
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(250)
<223> OTHER INFORMATION: See specification as filed for detailed
      description of substitutions and preferred embodiments

<400> SEQUENCE: 15
aaaaaaaaaa aaaaaaaaaa aaaaaaaaaa aaaaaaaaaa aaaaaaaaaa aaaaaaaaaa        60
aaaaaaaaaa aaaaaaaaaa aaaaaaaaaa aaaaaaaaaa aaaaaaaaaa aaaaaaaaaa       120
aaaaaaaaaa aaaaaaaaaa aaaaaaaaaa aaaaaaaaaa aaaaaaaaaa aaaaaaaaaa       180
aaaaaaaaaa aaaaaaaaaa aaaaaaaaaa aaaaaaaaaa aaaaaaaaaa aaaaaaaaaa       240
aaaaaaaaaa                                                              250
```

LIPID FORMULATIONS FOR DELIVERY OF MESSENGER RNA

RELATED APPLICATIONS

This application is a continuation of U.S. application Ser. No. 16/026,577, filed Jul. 3, 2018; which is continuation application of U.S. application Ser. No. 15/451,312, filed Mar. 6, 2017; which is a divisional application of U.S. application Ser. No. 14/521,161, filed Oct. 22, 2014; which claims priority to U.S. Provisional Application Ser. No. 61/894,299, filed Oct. 22, 2013 and U.S. Provisional Application Ser. No. 61/953,516, filed Mar. 14, 2014, the disclosures of which are hereby incorporated by reference.

SEQUENCE LISTING

The present specification makes reference to a Sequence Listing (submitted electronically as .txt file named "MRT-1121US4 MIT17255 SL.txt" on Nov. 14, 2019). The .txt file was generated on Nov. 14, 2019 and is 32,585 bytes in size. The entire contents of the Sequence Listing are herein incorporated by reference.

BACKGROUND

Delivery of nucleic acids has been explored extensively as a potential therapeutic option for certain disease states. In particular, RNA interference (RNAi) has been the subject of significant research and clinical development. While RNAi, such as short interfering RNA (siRNA), may have therapeutic potential, it is of little use in treating diseases involving deficiency of one or more proteins. messenger RNA (mRNA) therapy has become an increasingly important option for treatment of various diseases, in particular, for those associated with deficiency of one or more proteins.

SUMMARY OF THE INVENTION

The present invention provides improved methods and compositions for highly efficient delivery and expression of mRNA and encoded protein in vivo. The invention is based, in part, on the surprising discovery that liposomes based on a particular class of cationic lipids, such as, those having a structure of formula I-c described herein, are unexpectedly effective in delivering mRNA and producing encoded protein in vivo, more effective even as compared to those cationic lipids that were considered to be among the best in delivering mRNA in the prior art. Indeed, prior to the present invention, cationic lipids have been extensively explored as an important component of liposomes typically used to encapsulate nucleic acids including mRNA for in vivo delivery. Due to the uniquely fragile and long structure of mRNA and the complicated in vivo translation process, cationic lipids used in the liposomes typically play two roles. First, cationic lipids promote interaction with negatively charged mRNA during encapsulation, circulation and endocytosis, thereby capturing and protecting the mRNA. Then, once inside cytosol, cationic lipids need to be able to release the mRNA so that the mRNA can be translated to produce encoded protein. Some cationic lipids, in particular, those known as titratable cationic lipids are particularly effective in delivering mRNA. One example of such cationic lipids known to be capable of efficient delivery of mRNA is C12-200. Surprisingly, the present inventors found that cationic lipids described herein can be even more effective in delivering various mRNA in vivo, than those best known in the prior art including C12-200. For example, as shown in the Examples below, liposome particles incorporating a cationic lipid described herein (e.g., cKK-E12) resulted in close to 50% higher protein expression of human Factor IX protein detected in the plasma of administered mice, as compared to C12-200-based liposome particles. Furthermore, the plasma residence time of different proteins expressed from mRNA delivered by cKK-E12 based liposomes is sustained up to 7 days or longer post a single administration. Thus, the present inventors have demonstrated that this class of cationic lipids having a structure of formula I-c described herein (e.g., cKK-E12) can be uniquely useful in delivering mRNA for highly efficient and sustained production of protein (e.g., therapeutic protein) in vivo. The present invention therefore permits an improved mRNA therapy that can significantly reduce required amount of mRNA and associated lipids, administration frequency, and possible side effects, providing more potent, safer, and patient friendly mRNA therapy for various diseases.

In one aspect, the present invention provides methods of delivering messenger RNA (mRNA) in vivo, including administering to a subject in need of delivery a composition comprising an mRNA encoding a protein, encapsulated within a liposome such that the administering of the composition results in the expression of the protein encoded by the mRNA in vivo, wherein the liposome comprises a cationic lipid of formula I-c:

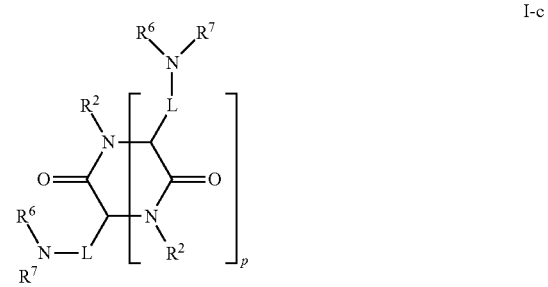

I-c or a pharmaceutically acceptable salt thereof,
wherein:
p is an integer of between 1 and 9, inclusive;
each instance of $R^2$ is independently hydrogen or optionally substituted $C_{1-6}$ alkyl;
each instance of $R^6$ and $R^7$ is independently a group of the formula (i), (ii), or (iii);
Formulae (i), (ii), and (iii) are:

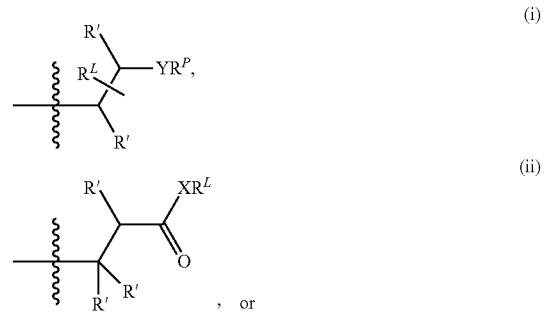

-continued (iii)

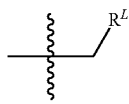

wherein:
each instance of R' is independently hydrogen or optionally substituted alkyl;

X is O, S, or $NR^X$, wherein $R^X$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

Y is O, S, or $NR^Y$, wherein $R^Y$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

$R^P$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to a sulfur atom, or a nitrogen protecting group when attached to a nitrogen atom; and $R^L$ is optionally substituted $C_{1-50}$ alkyl, optionally substituted $C_{2-50}$ alkenyl, optionally substituted $C_{2-50}$ alkynyl, optionally substituted hetero$C_{1-50}$ alkyl, optionally substituted hetero$C_{2-50}$ alkenyl, optionally substituted hetero$C_{2-50}$ alkynyl, or a polymer.

In another aspect, the present invention provides methods of treating a disease or disorder including administering to subject in need of treatment a composition comprising an mRNA encoding a therapeutic protein encapsulated within a liposome such that the administering of the composition results in the expression of the protein encoded by the mRNA in one or more tissues affected by the disease or disorder, wherein the liposome comprises a cationic lipid having a structure of formula I-c.

In another aspect, the present invention provides compositions for delivery of messenger RNA (mRNA) comprising an mRNA encoding a protein encapsulated within a liposome, wherein the liposome comprises a cationic lipid having a structure of formula I-c.

In some embodiments, a suitable cationic lipid is cKK-E12:

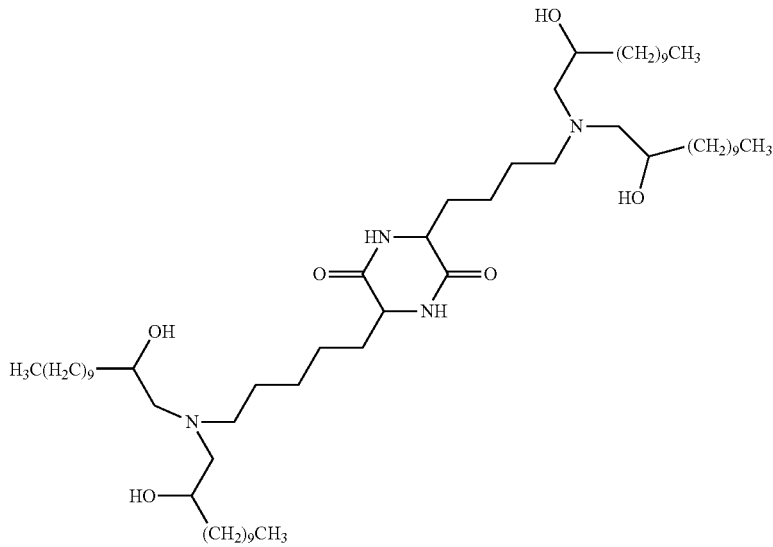

In some embodiments, a suitable liposome further comprises one or more non-cationic lipids, one or more cholesterol-based lipids and/or one or more PEG-modified lipids. In some embodiments, the one or more non-cationic lipids are selected from distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), or a mixture thereof.

In some embodiments, a suitable liposome further comprises one or more cholesterol-based lipids. In some embodiments, the one or more cholesterol-based lipids are selected from cholesterol, PEGylated cholesterol and DC-Chol (N,N-dimethyl-N-ethylcarboxamidocholesterol), 1,4-bis(3-N-oleylamino-propyl)piperazine.

In some embodiments, a suitable liposome further comprises one or more PEG-modified lipids. In some embodiments, the one or more PEG-modified lipids comprise a poly(ethylene) glycol chain of up to 5 kDa in length covalently attached to a lipid with alkyl chain(s) of $C_6$-$C_{20}$ length. In some embodiments, a PEG-modified lipid is a derivatized ceramide such as N-Octanoyl-Sphingosine-1-[Succinyl(Methoxy Polyethylene Glycol)-2000]. In some embodiments, a PEG-modified or PEGylated lipid is PEGylated cholesterol or Dimyristoylglycerol (DMG)-PEG-2K.

In some embodiments, a suitable liposome comprises cKK-E12, DOPE, cholesterol and DMG-PEG2K.

In some embodiments, the cationic lipid (e.g., cKK-E12) constitutes about 30-50% (e.g., about 30-45%, about 30-40%, about 35-50%, about 35-45%, or about 35-40%) of the liposome by molar ratio. In some embodiments, the cationic lipid (e.g., cKK-E12) constitutes about 30%, about 35%, about 40%, about 45%, or about 50% of the liposome by molar ratio.

In particular embodiments, the ratio of cKK-E12:DOPE:cholesterol:DMG-PEG2K is approximately 40:30:20:10 by molar ratio. In particular embodiments, the ratio of cKK-E12:DOPE:cholesterol:DMG-PEG2K is approximately 40:30:25:5 by molar ratio. In particular embodiments, the ratio of cKK-E12:DOPE:cholesterol:DMG-PEG2K is approximately 40:32:25:3 by molar ratio.

In some embodiments, a suitable liposome has a size of or less than about 500 nm, 450 nm, 400 nm, 350 nm, 300 nm, 250 nm, 200 nm, 150 nm, 125 nm, 110 nm, 100 nm, 95 nm, 90 nm, 85 nm, 80 nm, 75 nm, 70 nm, 65 nm, 60 nm, 55 nm, or 50 nm.

In some embodiments, a composition according to the invention is administered intravenously. In some embodiments, a composition according to the invention is administered via pulmonary delivery. In some embodiments, the pulmonary delivery is by aerosolization, inhalation, nebulization or instillation. In some embodiments, a composition according to the invention is administered intrathecally. In some embodiments, the composition is formulated as respirable particles, nebulizable lipid, or inhalable dry powder.

In some embodiments, the expression of the protein encoded by the mRNA is detectable in liver, kidney, heart, spleen, serum, brain, skeletal muscle, lymph nodes, skin, and/or cerebrospinal fluid.

In some embodiments, the expression of the protein encoded by the mRNA is detectable 6, 12, 18, 24, 30, 36, 42, 48, 54, 60, 66, and/or 72 hours after the administration. In some embodiments, the expression of the protein encoded by the mRNA is detectable 1 day, 2 days, 3 days, 4 days, 5 days, 6 days, and/or 7 days after the administration. In some embodiments, the expression of the protein encoded by the mRNA is detectable 1 week, 2 weeks, 3 weeks, and/or 4 weeks after the administration. In some embodiments, the expression of the protein encoded by the mRNA is detectable after a month after the administration.

In some embodiments, the protein encoded by the mRNA is a cytosolic protein. In some embodiments, the protein encoded by the mRNA is a secreted protein. In some embodiments, the protein encoded by the mRNA is an enzyme. In some embodiments, the mRNA has a length of or greater than about 0.5 kb, 1 kb, 1.5 kb, 2 kb, 2.5 kb, 3 kb, 3.5 kb, 4 kb, 4.5 kb, or 5 kb. In some embodiments, the protein encoded by the mRNA is Argininosuccinate Synthetase (ASS1), Factor IX, survival of motor neuron 1, or phenylalanine hydroxylase.

In some embodiments, the mRNA is administered at a dose ranging from about 0.1-5.0 mg/kg body weight, for example about 0.1-4.5, 0.1-4.0, 0.1-3.5, 0.1-3.0, 0.1-2.5, 0.1-2.0, 0.1-1.5, 0.1-1.0, 0.1-0.5, 0.1-0.3, 0.3-5.0, 0.3-4.5, 0.3-4.0, 0.3-3.5, 0.3-3.0, 0.3-2.5, 0.3-2.0, 0.3-1.5, 0.3-1.0, 0.3-0.5, 0.5-5.0, 0.5-4.5, 0.5-4.0, 0.5-3.5, 0.5-3.0, 0.5-2.5, 0.5-2.0, 0.5-1.5, or 0.5-1.0 mg/kg body weight. In some embodiments, the mRNA is administered at a dose of or less than about 5.0, 4.5, 4.0, 3.5, 3.0, 2.5, 2.0, 1.5, 1.0, 0.8, 0.6, 0.5, 0.4, 0.3, 0.2, or 0.1 mg/kg body weight.

In some embodiments, the mRNA comprises one or more modified nucleotides. In some embodiments, the one or more modified nucleotides comprise pseudouridine, N-1-methyl-pseudouridine, 2-aminoadenosine, 2-thiothymidine, inosine, pyrrolo-pyrimidine, 3-methyl adenosine, 5-methyl-cytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and/or 2-thiocytidine. In some embodiments, the mRNA is unmodified.

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF THE DRAWING

The drawings are for illustration purposes only not for limitation.

DEFINITIONS

Figure 1:
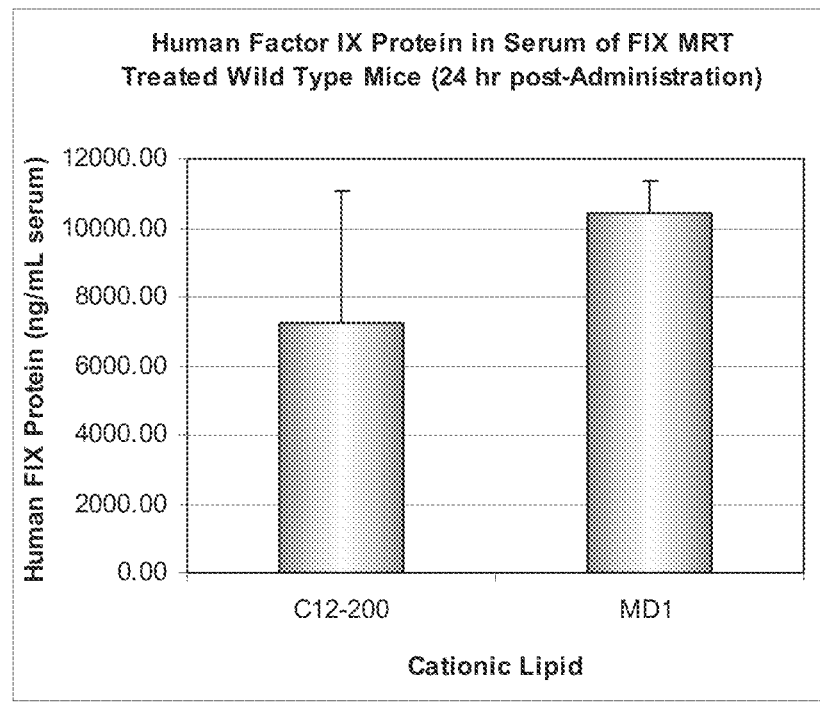
FIG. 1 shows an exemplary graph of the levels of human factor IX (FIX) detected in the serum of treated mice 24 hours after administration of C12-200 or cKK-E12 liposomes containing FIX mRNA.

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

Amino acid: As used herein, term "amino acid," in its broadest sense, refers to any compound and/or substance that can be incorporated into a polypeptide chain. In some embodiments, an amino acid has the general structure $H_2N$—C(H)(R)—COHO. In some embodiments, an amino acid is a naturally occurring amino acid. In some embodiments, an amino acid is a synthetic amino acid; in some embodiments, an amino acid is a d-amino acid; in some embodiments, an amino acid is an 1-amino acid. "Standard amino acid" refers to any of the twenty standard 1-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxyl- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Delivery: As used herein, the term "delivery" encompasses both local and systemic delivery. For example, delivery of mRNA encompasses situations in which an mRNA is delivered to a target tissue and the encoded protein is expressed and retained within the target tissue (aslo referred to as "local distribution" or "local delivery"), and situations in which an mRNA is delivered to a target tissue and the encoded protein is expressed and secreted into patient's circulation system (e.g., serum) and systematically distributed and taken up by other tissues (also referred to as "systemic distribution" or "systemic delivery).

Expression: As used herein, "expression" of a nucleic acid sequence refers to translation of an mRNA into a polypeptide, assemble multiple polypeptides (e.g., heavy chain or light chain of antibody) into an intact protein (e.g., antibody) and/or post-translational modification of a polypeptide or fully assembled protein (e.g., antibody). In this application, the terms "expression" and "production," and grammatical equivalent, are used inter-changeably.

Functional: As used herein, a "functional" biological molecule is a biological molecule in a form in which it exhibits a property and/or activity by which it is characterized.

Half-life: As used herein, the term "half-life" is the time required for a quantity such as nucleic acid or protein concentration or activity to fall to half of its value as measured at the beginning of a time period.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

Local distribution or delivery: As used herein, the terms "local distribution," "local delivery," or grammatical equivalent, refer to tissue specific delivery or distribution. Typically, local distribution or delivery requires a protein (e.g., enzyme) encoded by mRNAs be translated and expressed intracellularly or with limited secretion that avoids entering the patient's circulation system.

messenger RNA (mRNA): As used herein, the term "messenger RNA (mRNA)" refers to a polynucleotide that encodes at least one polypeptide. mRNA as used herein encompasses both modified and unmodified RNA. mRNA may contain one or more coding and non-coding regions. mRNA can be purified from natural sources, produced using recombinant expression systems and optionally purified, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

In some embodiments, the mRNA comprises one or more nonstandard nucleotide residues. The nonstandard nucleotide residues may include, e.g., 5-methyl-cytidine ("5mC"), pseudouridine ("pU"), and/or 2-thio-uridine ("2sU"). See, e.g., U.S. Pat. No. 8,278,036 or WO2011012316 for a discussion of such residues and their incorporation into mRNA. The mRNA may be RNA, which is defined as RNA in which 25% of U residues are 2-thio-uridine and 25% of C residues are 5-methylcytidine. Teachings for the use of RNA are disclosed US Patent Publication US20120195936 and internation publication WO2011012316, both of which are hereby incorporated by reference in their entirety. The presence of nonstandard nucleotide residues may render an mRNA more stable and/or less immunogenic than a control mRNA with the same sequence but containing only standard residues. In further embodiments, the mRNA may comprise one or more nonstandard nucleotide residues chosen from isocytosine, pseudoisocytosine, 5-bromouracil, 5-propynyluracil, 6-aminopurine, 2-aminopurine, inosine, diaminopurine and 2-chloro-6-aminopurine cytosine, as well as combinations of these modifications and other nucleobase modifications. Certain embodiments may further include additional modifications to the furanose ring or nucleobase. Additional modifications may include, for example, sugar modifications or substitutions (e.g., one or more of a 2'-O-alkyl modification, a locked nucleic acid (LNA)). In some embodiments, the RNAs may be complexed or hybridized with additional polynucleotides and/or peptide polynucleotides (PNA). In embodiments where the sugar modification is a 2'-O-alkyl modification, such modification may include, but are not limited to a 2'-deoxy-2'-fluoro modification, a 2'-O-methyl modification, a 2'-O-methoxyethyl modification and a 2'-deoxy modification. In certain embodiments, any of these modifications may be present in 0-100% of the nucleotides—for example, more than 0%, 1%, 10%, 25%, 50%, 75%, 85%, 90%, 95%, or 100% of the constituent nucleotides individually or in combination.

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre and post natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Systemic distribution or delivery: As used herein, the terms "systemic distribution," "systemic delivery," or grammatical equivalent, refer to a delivery or distribution mechanism or approach that affect the entire body or an entire organism. Typically, systemic distribution or delivery is accomplished via body's circulation system, e.g., blood stream. Compared to the definition of "local distribution or delivery."

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Target tissues: As used herein, the term "target tissues" refers to any tissue that is affected by a disease to be treated. In some embodiments, target tissues include those tissues that display disease-associated pathology, symptom, or feature.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION

The present invention provides, among other things, methods and compositions for delivering mRNA in vivo using improved liposomes incorporating cationic lipids described herein.

Liposomes for mRNA Delivery

As used herein, the term "liposome" refers to any lamellar, multilamellar, or solid lipid nanoparticle vesicle. Typically, a liposome as used herein can be formed by mixing one or more lipids or by mixing one or more lipids and polymer(s). Thus, the term "liposome" as used herein encompasses both lipid and polymer based nanoparticles. In particular, a liposome according to the present invention incorporates a cationic lipid described herein. As a non-limiting example, a cationic lipid suitable for the present invention is cKK-E12, or (3,6-bis(4-(bis(2-hydroxydodecyl) amino)butyl)piperazine-2,5-dione), as described in more detail below. A suitable liposome may also contain second or additional cationic lipids, helper lipids (e.g., non-cationic lipids and/or cholesterol-based lipids), PEG-modified lipids, and/or polymers.

In some embodiments, cationic lipid(s) (e.g., cKK-E12) constitute(s) about 30-50% (e.g., about 30-45%, about 30-40%, about 35-50%, about 35-45%, or about 35-40%) of the liposome by molar ratio. In some embodiments, the cationic lipid (e.g., cKK-E12) constitutes about 30%, about 35%, about 40%, about 45%, or about 50% of the liposome by molar ratio.

Cationic Lipids

In some embodiments, provided liposomes or compositions provided comprise a cationic lipid according to formula I:

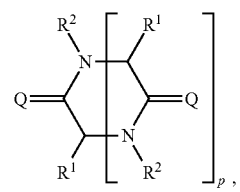

or a pharmaceutically acceptable salt thereof, wherein:

p is an integer of between 1 and 9, inclusive;

each instance of Q is independently O, S, or $NR^Q$;

$R^Q$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of the formula (i), (ii) or (iii);

each instance of $R^1$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, halogen, $-OR^{41}$, $-N(R^{41})_2$, $-SR^{41}$, or a group of formula (iv):

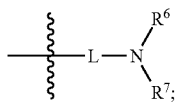
(iv)

L is an optionally substituted,alkylene, optionally substituted alkenylene, optionally substituted alkynylene, optionally substituted heteroalkylene, optionally substituted heteroalkenylene, optionally substituted heteralkynylene, optionally substituted carbocyclylene, optionally substituted heterocyclylene, optionally substituted arylene, or optionally substituted heteroarylene, or combination thereof, and each of $R^6$ and $R^7$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of formula (i), (ii) or (iii);

each occurrence of $R^{41}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to an sulfur atom, a nitrogen protecting group when attached to a nitrogen atom, or two $R^{41}$ groups, together with the nitrogen atom to which they are attached, are joined to form an optionally substituted heterocyclic or optionally substituted heteroaryl ring;

each instance of $R^2$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of the formula (i), (ii), or (iii);

Formulae (i), (ii), and (iii) are:

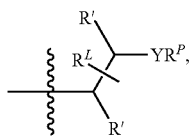
(i)

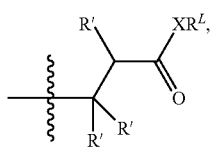
(ii)

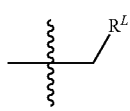
(iii)

each instance of R' is independently hydrogen or optionally substituted alkyl;

X is O, S, or $NR^X$;

$R^X$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

Y is O, S, or $NR^Y$;

$R^Y$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

$R^P$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to a sulfur atom, or a nitrogen protecting group when attached to a nitrogen atom;

$R^L$ is optionally substituted $C_{1\text{-}50}$ alkyl, optionally substituted $C_{2\text{-}50}$ alkenyl, optionally substituted $C_{2\text{-}50}$ alkynyl, optionally substituted hetero$C_{1\text{-}50}$ alkyl, optionally substituted hetero$C_{2\text{-}50}$ alkenyl, optionally substituted hetero$C_{2\text{-}50}$ alkynyl, or a polymer;

provided that at least one instance of $R^Q$, $R^2$, $R^6$, or $R^7$ is a group of the formula (i), (ii), or (iii).

In some embodiments, a cationic lipid in a provided composition or method is a compound of formula I. In some embodiments, a cationic lipid in a provided composition or method is a compound of formula I, wherein the compound comprises one or more basic groups. In some embodiments, a cationic lipid in a provided composition or method is a compound of formula I, wherein the compound comprises one or more amino groups.

In certain embodiments, a group of formula (i) represents a group of formula (i-a) or a group of formula (i-b):

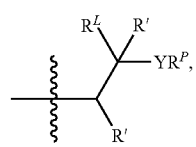
(i-a)

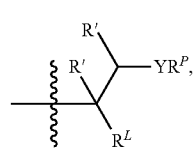
(i-b)

wherein each variable is independently as defined above and described herein. In some embodiments, a group of formula (i) is a group of formula (i-a). In some embodiments, a group of formula (i) is a group of formula (i-b).

In some embodiments, at least one instance of $R^1$ is a group of formula (iv). In some embodiments, at least one instance of $R^1$ is a group of formula (iv), wherein at least one of $R^6$ and $R^7$ is a group of formula (i), (ii) or (iii). In some embodiments, at least one instance of $R^1$ is a group of formula (iv), wherein each of $R^6$ and $R^7$ is independently a group of formula (i), (ii) or (iii).

In some embodiments, each $R^1$ is independently a group of formula (iv). In some embodiments, each $R^1$ is independently a group of formula (iv), wherein at least one of $R^6$ and $R^7$ is a group of formula (i), (ii) or (iii). In some embodiments, each $R^1$ is independently a group of formula (iv), wherein each of $R^6$ and $R^7$ is independently a group of formula (i), (ii) or (iii). In some embodiments, each $R^1$ is independently a group of formula (iv), wherein each of $R^6$ and $R^7$ is independently a group of formula (i). In some embodiments, each $R^1$ is independently a group of formula (iv), wherein each of $R^6$ and $R^7$ is independently a group of formula (ii). In some embodiments, each $R^1$ is independently a group of formula (iv), wherein each of $R^6$ and $R^7$ is independently a group of formula (iii). In some embodiments, each $R^1$ is independently a group of formula (iv), wherein each of $R^6$ and $R^7$ is independently a group of formula (i-a). In some embodiments, each $R^1$ is independently a group of formula (iv), wherein each of $R^6$ and $R^7$ is independently a group of formula (i-b).

In some embodiments, each instance of R' is hydrogen.

In some embodiments, L is an optionally substituted alkylene.

In some embodiments, a group of formula (iv) is of formula

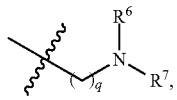

wherein q is an integer between 1 and 50, inclusive, and each of $R^6$ and $R^7$ is independently as defined above and described herein.

As generally defined above, p is an integer of between 1 and 9, inclusive. In certain embodiments, p is 1. In certain embodiments, p is 2. In certain embodiments, p is 3. In certain embodiments, p is 4. In certain embodiments, p is 5. In certain embodiments, p is 6. In certain embodiments, p is 7. In certain embodiments, p is 8. In certain embodiments, p is 9.

In some embodiments, p is 1. In some embodiments, a compound of formula I is a compound of formula (I-a):

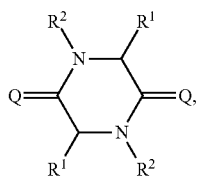

I-a or a pharmaceutically acceptable salt thereof, wherein each variable is independently as defined above and described herein.

In some embodiments, p is 2. In some embodiments, a compound of formula I is a compound of formula (I-p2):

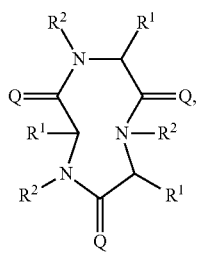

I-p2 or a pharmaceutically acceptable salt thereof, wherein each variable is independently as defined above and described herein.

In some embodiments, p is 3. In some embodiments, a compound of formula I is a compound of formula (I-p3):

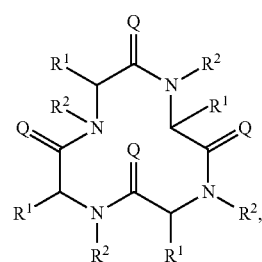

I-p3 or a pharmaceutically acceptable salt thereof, wherein each variable is independently as defined above and described herein.

In some embodiments, p is 4. In some embodiments, a compound of formula I is a compound of formula (I-p4):

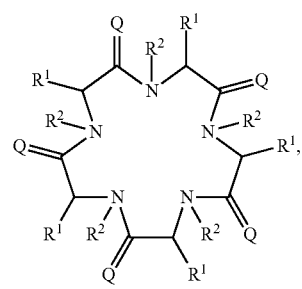

I-p4 or a pharmaceutically acceptable salt thereof, wherein each variable is independently as defined above and described herein.

In some embodiments, p is 5. In some embodiments, a compound of formula I is a compound of formula (I-p5):

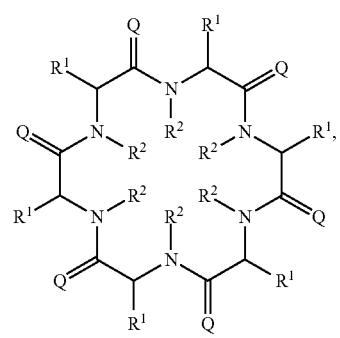

I-p5 or a pharmaceutically acceptable salt thereof, wherein each variable is independently as defined above and described herein.

In some embodiments, p is 6. In some embodiments, a compound of formula I is a compound of formula (I-p6):

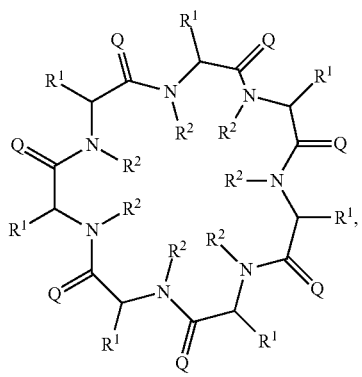

I-p6 or a pharmaceutically acceptable salt thereof, wherein each variable is independently as defined above and described herein.

In some embodiments, p is 7. In some embodiments, a compound of formula I is a compound of formula (I-p7):

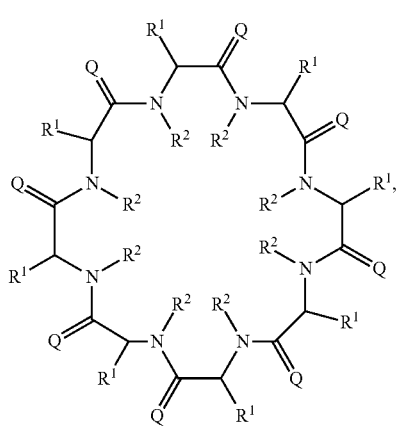

I-p7 or a pharmaceutically acceptable salt thereof, wherein each variable is independently as defined above and described herein.

In some embodiments, p is 8. In some embodiments, a compound of formula I is a compound of formula (I-p8):

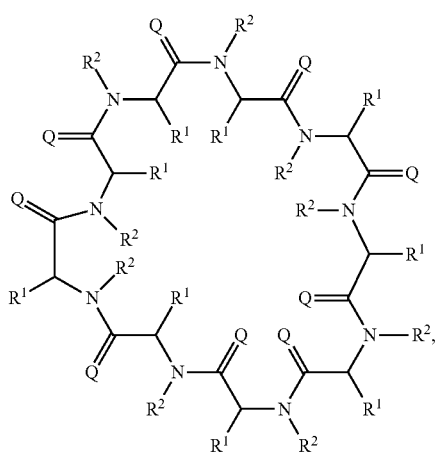

I-p8 or a pharmaceutically acceptable salt thereof, wherein each variable is independently as defined above and described herein.

In some embodiments, p is 9. In some embodiments, a compound of formula I is a compound of formula (I-p9):

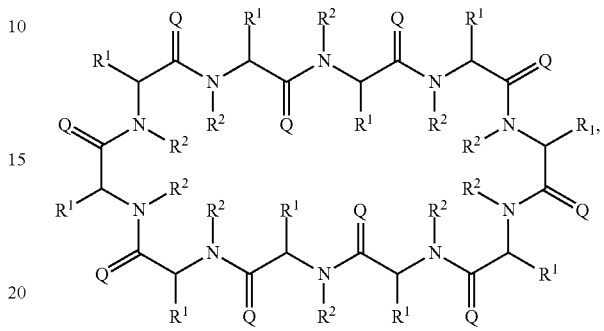

I-p9 or a pharmaceutically acceptable salt thereof, wherein each variable is independently as defined above and described herein.

As generally defined above, each instance of Q is independently O, S, or $NR^Q$, wherein $R^Q$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of the formula (i), (ii), or (iii).

In certain embodiments, at least one instance of Q is O. In certain embodiments, each instance of Q is O. In certain embodiments, at least one instance of Q is S. In certain embodiments, each instance of Q is S. In certain embodiments, at least one instance of Q is $NR^Q$, wherein $R^Q$ is as defined above and described herein. In certain embodiments, each instance of Q is $NR^Q$, wherein each $R^Q$ is independently as defined above and described herein. In certain embodiments, each instance of $R^Q$ is independently hydrogen or a group of the formula (i), (ii), or (iii).

As generally defined above, $R^Q$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of the formula (i), (ii) or (iii).

In some embodiments, $R^Q$ is hydrogen. In some embodiments, $R^Q$ is optionally substituted alkyl. In some embodiments, $R^Q$ is optionally substituted alkenyl. In some embodiments, $R^Q$ is optionally substituted alkynyl. In some embodiments, $R^Q$ is carbocyclyl. In some embodiments, $R^Q$ is optionally substituted heterocyclyl. In some embodiments, $R^Q$ is optionally substituted aryl. In some embodiments, $R^Q$ is optionally substituted heteroaryl. In some embodiments, $R^Q$ is a nitrogen protecting group. In some embodiments, $R^Q$ is a group of formula (i), (ii) or (iii). In some embodiments, $R^Q$ is a group of formula (i). In some embodiments, $R^Q$ is a group of formula (ii). In some embodiments, $R^Q$ is a group of formula (iii).

As generally defined above, each instance of $R^1$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, halogen, —OR$^{A1}$, —N(R$^{A1}$)$_2$, or —SR$^{A1}$, or a group of formula (iv), wherein each of R$^{A1}$ and formula (iv) is independently as defined above and described herein.

In some embodiments, R$^1$ is hydrogen.

In certain embodiments, R$^1$ is optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, at least one instance of R$^1$ is optionally substituted alkyl, optionally substituted alkenyl, optionally substituted alkynyl, optionally substituted carbocyclyl, optionally substituted heterocyclyl, optionally substituted aryl, or optionally substituted heteroaryl.

In certain embodiments, R$^1$ is optionally substituted alkyl; e.g., optionally substituted C$_{1-6}$alkyl, optionally substituted C$_{2-6}$alkyl, optionally substituted C$_{3-6}$alkyl, optionally substituted C$_{4-6}$alkyl, optionally substituted C$_{4-5}$alkyl, or optionally substituted C$_{3-4}$alkyl. In certain embodiments, at least one instance of R$^1$ is optionally substituted alkyl; e.g., optionally substituted C$_{1-6}$alkyl, optionally substituted C$_{2-6}$alkyl, optionally substituted C$_{3-6}$alkyl, optionally substituted C$_{4-6}$alkyl, optionally substituted C$_{4-5}$alkyl, or optionally substituted C$_{3-4}$alkyl.

In certain embodiments, R$^1$ is optionally substituted alkenyl, e.g., optionally substituted C$_{2-6}$alkenyl, optionally substituted C$_{3-6}$alkenyl, optionally substituted C$_{4-6}$alkenyl, optionally substituted C$_{4-5}$alkenyl, or optionally substituted C$_{3-4}$alkenyl. In certain embodiments, at least one instance of R$^1$ is optionally substituted alkenyl, e.g., optionally substituted C$_{2-6}$ alkenyl, optionally substituted C$_{3-6}$alkenyl, optionally substituted C$_{4-6}$alkenyl, optionally substituted C$_{4-5}$alkenyl, or optionally substituted C$_{3-4}$alkenyl.

In certain embodiments, R$^1$ is optionally substituted alkynyl, e.g., optionally substituted C$_{2-6}$alkynyl, optionally substituted C$_{3-6}$alkynyl, optionally substituted C$_{4-6}$alkynyl, optionally substituted C$_{4-5}$alkynyl, or optionally substituted C$_{3-4}$alkynyl. In certain embodiments, at least one instance of R$^1$ is optionally substituted alkynyl, e.g., optionally substituted C$_{2-6}$alkynyl, optionally substituted C$_{3-6}$alkynyl, optionally substituted C$_{4-6}$alkynyl, optionally substituted C$_{4-5}$alkynyl, or optionally substituted C$_{3-4}$alkynyl.

In certain embodiments, R$^1$ is optionally substituted carbocyclyl, e.g., optionally substituted C$_{3-10}$ carbocyclyl, optionally substituted C$_{5-8}$ carbocyclyl, optionally substituted C$_{5-6}$ carbocyclyl, optionally substituted C$_5$ carbocyclyl, or optionally substituted C$_6$ carbocyclyl. In certain embodiments, at least one instance of R$^1$ is optionally substituted carbocyclyl, e.g., optionally substituted C$_{3-10}$ carbocyclyl, optionally substituted C$_{5-8}$ carbocyclyl, optionally substituted C$_{5-6}$ carbocyclyl, optionally substituted C$_5$ carbocyclyl, or optionally substituted C$_6$ carbocyclyl.

In some embodiments, R$^1$ is optionally substituted heterocyclyl, e.g., optionally substituted 3-14 membered heterocyclyl, optionally substituted 3-10 membered heterocyclyl, optionally substituted 5-8 membered heterocyclyl, optionally substituted 5-6 membered heterocyclyl, optionally substituted 5-membered heterocyclyl, or optionally substituted 6-membered heterocyclyl. In certain embodiments, at least one instance of R$^1$ is optionally substituted heterocyclyl, e.g., optionally substituted 3-14 membered heterocyclyl, optionally substituted 3-10 membered heterocyclyl, optionally substituted 5-8 membered heterocyclyl, optionally substituted 5-6 membered heterocyclyl, optionally substituted 5-membered heterocyclyl, or optionally substituted 6-membered heterocyclyl.

In some embodiments, R$^1$ is optionally substituted aryl. In some embodiments, R$^1$ is optionally substituted phenyl. In some embodiments, R$^1$ is phenyl. In some embodiments, R$^1$ is substituted phenyl. In certain embodiments, at least one instance of R$^1$ is optionally substituted aryl, e.g., optionally substituted phenyl.

In some embodiments, R$^1$ is optionally substituted heteroaryl, e.g., optionally substituted 5-14 membered heteroaryl, optionally substituted 5-10 membered heteroaryl, optionally substituted 5-6 membered heteroaryl, optionally substituted 5 membered heteroaryl, or optionally substituted 6 membered heteroaryl. In certain embodiments, at least one instance of R$^1$ is optionally substituted heteroaryl, e.g., optionally substituted 5-14 membered heteroaryl, optionally substituted 5-10 membered heteroaryl, optionally substituted 5-6 membered heteroaryl, optionally substituted 5 membered heteroaryl, or optionally substituted 6 membered heteroaryl.

In some embodiments, R$^1$ is halogen. In some embodiments, R$^1$ is —F. In some embodiments, R$^1$ is —Cl. In some embodiments, R$^1$ is —Br. In some embodiments, R$^1$ is —I.

In some embodiments, R$^1$ is —OR$^{A1}$, wherein R$^{A1}$ is as defined above and described herein. In some embodiments, R$^1$ is —N(R$^{A1}$)$_2$, wherein each R$^{A1}$ is independently as defined above and described herein. In some embodiments, R$^1$ is —SR$^{A1}$, wherein R$^{A1}$ is as defined above and described herein.

In some embodiments, an R$^1$ alkyl, alkenyl, alkynyl, carbocyclyl, heterocyclyl, aryl, or heteroaryl group may be substituted. In some embodiments, an R$^1$ alkyl, alkenyl, alkynyl, carbocyclyl, heterocyclyl, aryl, or heteroaryl group may be substituted with an optionally substituted amino group. In some embodiments, an R$^1$ alkyl, alkenyl, alkynyl, carbocyclyl, heterocyclyl, aryl, or heteroaryl group may be substituted with an optionally substituted hydroxyl group. In some embodiments, an R$^1$ alkyl, alkenyl, alkynyl, carbocyclyl, heterocyclyl, aryl, or heteroaryl group may be substituted with an optionally substituted thiol group. In any of the above embodiments, an R$^1$ alkyl, alkenyl, alkynyl, carbocyclyl, heterocyclyl, aryl, or heteroaryl group may be substituted, for example, with an optionally substituted amino group (e.g., —NR$^6$R$^7$), an optionally substituted hydroxyl group (e.g., —OR$^6$), an optionally substituted thiol group (e.g., —SR$^6$), or with a group of formula (i), (ii), or (iii), wherein each instance of R$^6$ and R$^7$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or a group of formula (i), (ii), or (iii).

In some embodiments, R$^1$ is an optionally substituted natural amino acid side chain. In some embodiments, R$^1$ is a natural amino acid side chain. In some embodiments, R$^1$ is an optionally substituted unnatural amino acid side chain. In some embodiments, R$^1$ is an unnatural amino acid side chain.

In certain embodiments, each instance of R$^1$ is the same. In certain embodiments, at least one R$^1$ group is different. In certain embodiments, each R$^1$ group is different.

In certain embodiments, R$^1$ is an alkyl, alkenyl, alkynyl, carbocyclyl, heterocyclyl, aryl, or heteroaryl group substituted with an amino group of the formula —NR$^6$R$^7$.

In certain embodiments, $R^1$ is a group of formula (iv):

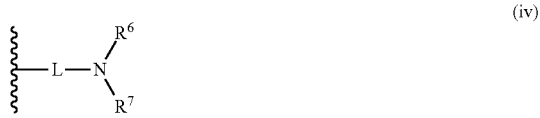

wherein:
L is an optionally substituted alkylene, optionally substituted alkenylene, optionally substituted alkynylene, optionally substituted heteroalkylene, optionally substituted heteroalkenylene, optionally substituted heteralkynylene, optionally substituted carbocyclylene, optionally substituted heterocyclylene, optionally substituted arylene, or optionally substituted heteroarylene, or combination thereof, and
each of $R^6$ and $R^7$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of formula (i), (ii) or (iii):

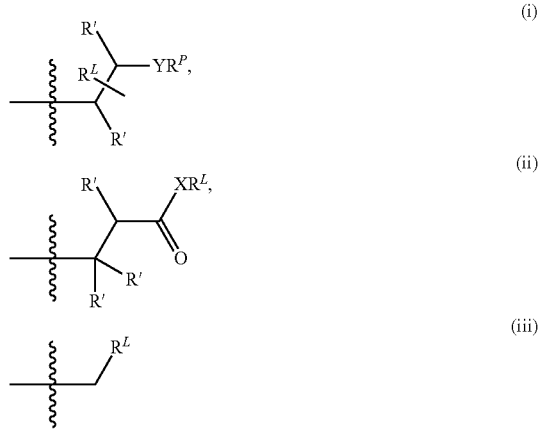

wherein each of R', Y, $R^P$, $R^L$ and X is independently as defined above and described herein.

In some embodiments, at least one instance of $R^1$ is an alkyl, alkenyl, alkynyl, carbocyclyl, heterocyclyl, aryl, or heteroaryl group substituted with an amino group of the formula —$NR^6R^7$. In some embodiments, at least one instance of $R^1$ is a group of formula (iv). In some embodiments, at least one instance of $R^1$ is a group of formula (iv), wherein at least one instance of $R^6$ and $R^7$ is a group of the formula (i), (ii) or (iii). In some embodiments, at least one instance of $R^1$ is a group of formula (iv), wherein each instance of $R^6$ and $R^7$ is a group of the formula (i), (ii) or (iii). In some embodiments, at least one instance of $R^1$ is a group of formula (iv), wherein each instance of $R^6$ and $R^7$ is a group of the formula (i). In some embodiments, at least one instance of $R^1$ is a group of formula (iv), wherein each instance of $R^6$ and $R^7$ is a group of the formula (ii). In some embodiments, at least one instance of $R^1$ is a group of formula (iv), wherein each instance of $R^6$ and $R^7$ is a group of the formula (iii).

In some embodiments, each instance of $R^1$ is a group of formula (iv). In some embodiments, each instance of $R^1$ is a group of formula (iv), wherein each instance of $R^6$ and $R^7$ is a group of the formula (i), (ii) or (iii). In some embodiments, each instance of $R^1$ is a group of formula (iv), wherein each instance of $R^6$ and $R^7$ is a group of the formula (i), (ii) or (iii). In some embodiments, each instance of $R^1$ is a group of formula (iv), wherein each instance of $R^6$ and $R^7$ is a group of the formula (i). In some embodiments, each instance of $R^1$ is a group of formula (iv), wherein each instance of $R^6$ and $R^7$ is a group of the formula (ii). In some embodiments, each instance of $R^1$ is a group of formula (iv), wherein each instance of $R^6$ and $R^7$ is a group of the formula (iii).

In certain embodiments, at least two instances of $R^1$ is a group of formula (iv). In certain embodiments, at least three instances of $R^1$ is a group of formula (iv). In certain embodiments, at least four instances of $R^1$ is a group of formula (iv). In certain embodiments, at least five instances of $R^1$ is a group of formula (iv). In certain embodiments, at least six instances of $R^1$ is a group of formula (iv). In certain embodiments, at least seven instances of $R^1$ is a group of formula (iv). In certain embodiments, at least eight instances of $R^1$ is a group of formula (iv). In certain embodiments, at least nine instances of $R^1$ is a group of formula (iv). In certain embodiments, each instance of $R^1$ is a group of formula (iv).

In certain embodiments, L is an optionally substituted alkylene; e.g., optionally substituted $C_{1-50}$alkylene, optionally substituted $C_{1-40}$alkylene, optionally substituted $C_{1-30}$alkylene, optionally substituted $C_{1-20}$alkylene, optionally substituted $C_{4-20}$alkylene, optionally substituted $C_{6-20}$alkylene, optionally substituted $C_{8-20}$alkylene, optionally substituted $C_{10-20}$ alkylene, optionally substituted $C_{1-6}$alkylene, optionally substituted $C_{2-6}$alkylene, optionally substituted $C_{3-6}$alkylene, optionally substituted $C_{4-6}$alkylene, optionally substituted $C_{4-5}$alkylene, or optionally substituted $C_{3-4}$alkylene. In some embodiments, L is optionally substituted $C_1$ alkylene. In some embodiments, L is optionally substituted $C_2$ alkylene. In some embodiments, L is optionally substituted $C_3$ alkylene. In some embodiments, L is optionally substituted $C_4$ alkylene. In some embodiments, L is optionally substituted $C_5$ alkylene. In some embodiments, L is optionally substituted $C_6$ alkylene. In some embodiments, L is optionally substituted $C_7$ alkylene. In some embodiments, L is optionally substituted $C_8$ alkylene. In some embodiments, L is optionally substituted $C_9$ alkylene. In some embodiments, L is optionally substituted $C_{10}$ alkylene. In some embodiments, L is —$CH_2$—. In some embodiments, L is —$(CH_2)_2$—. In some embodiments, L is —$(CH_2)_3$—. In some embodiments, L is —$(CH_2)_4$—. In some embodiments, L is —$(CH_2)_5$—. In some embodiments, L is —$(CH_2)_6$—. In some embodiments, L is —$(CH_2)_7$—. In some embodiments, L is —$(CH_2)_8$—. In some embodiments, L is —$(CH_2)_9$—. In some embodiments, L is —$(CH_2)_{10}$—.

In certain embodiments, L is an optionally substituted alkenylene, e.g., optionally substituted $C_{2-50}$alkenylene, optionally substituted $C_{2-40}$alkenylene, optionally substituted $C_{2-30}$alkenylene, optionally substituted $C_{2-20}$alkenylene, optionally substituted $C_{4-20}$alkenylene, optionally substituted $C_{6-20}$alkenylene, optionally substituted $C_{8-20}$alkenylene, optionally substituted $C_{1-20}$alkenylene, optionally substituted $C_{2-6}$alkenylene, optionally substituted $C_{3-6}$ alkenylene, optionally substituted $C_{4-6}$alkenylene, optionally substituted $C_{4-5}$alkenylene, or optionally substituted $C_{3-4}$alkenylene.

In certain embodiments, L is an optionally substituted alkynylene, e.g., optionally substituted $C_{2-50}$alkynylene, optionally substituted $C_{2-40}$alkynylene, optionally substituted $C_{2-30}$alkynylene, optionally substituted $C_{2-20}$alkynylene, optionally substituted $C_{4-20}$alkynylene, optionally substituted $C_{6-20}$alkynylene, optionally substituted C$_{8-20}$alkynylene, optionally substituted C$_{10-20}$ alkynylene, optionally substituted C$_{2-6}$alkynylene, optionally substituted C$_{3-6}$ alkynylene, optionally substituted C$_{4-6}$alkynylene, optionally substituted C$_{4-5}$alkynylene, or optionally substituted C$_{3-4}$alkynylene.

In certain embodiments, L is an optionally substituted heteroalkylene; e.g., optionally substituted heteroC$_{1-50}$alkylene, optionally substituted heteroC$_{1-40}$alkylene, optionally substituted heteroC$_{1-30}$alkylene, optionally substituted heteroC$_{1-20}$alkylene, optionally substituted heteroC$_{4-20}$alkylene, optionally substituted heteroC$_{6-20}$alkylene, optionally substituted heteroC$_{3-20}$alkylene, optionally substituted heteroC$_{10-20}$alkylene, optionally substituted heteroC$_{1-6}$alkylene, optionally substituted heteroC$_{2-6}$alkylene, optionally substituted heteroC$_{3-6}$alkylene, optionally substituted heteroC$_{4-6}$alkylene, optionally substituted heteroC$_{4-5}$alkylene, or optionally substituted heteroC$_{3-4}$alkylene. In some embodiments, L is optionally substituted heteroC$_2$alkylene. In some embodiments, L is optionally substituted heteroC$_3$alkylene. In some embodiments, L is optionally substituted heteroC$_4$alkylene. In some embodiments, L is optionally substituted heteroC$_5$alkylene. In some embodiments, L is optionally substituted heteroC$_6$alkylene. In some embodiments, L is optionally substituted heteroC$_7$alkylene. In some embodiments, L is optionally substituted heteroC$_8$alkylene. In some embodiments, L is optionally substituted heteroC$_9$alkylene. In some embodiments, L is optionally substituted heteroC$_{10}$alkylene.

In certain embodiments, L is an optionally substituted heteroalkenylene, e.g., optionally substituted heteroC$_{2-50}$alkenylene, optionally substituted heteroC$_{2-40}$alkenylene, optionally substituted heteroC$_{2-30}$alkenylene, optionally substituted heteroC$_{2-20}$alkenylene, optionally substituted heteroC$_{4-20}$alkenylene, optionally substituted heteroC$_{6-20}$alkenylene, optionally substituted heteroC$_{8-20}$alkenylene, optionally substituted heteroC$_{10-20}$alkenylene, optionally substituted heteroC$_{2-6}$alkenylene, optionally substituted heteroC$_{3-6}$alkenylene, optionally substituted heteroC$_{4-6}$alkenylene, optionally substituted heteroC$_{4-5}$alkenylene, or optionally substituted heteroC$_{3-4}$alkenylene.

In certain embodiments, L is an optionally substituted heteralkynylene, e.g., optionally substituted heteroC$_{2-50}$alkynylene, optionally substituted heteroC$_{2-40}$alkynylene, optionally substituted heteroC$_{2-30}$alkynylene, optionally substituted heteroC$_{2-20}$alkynylene, optionally substituted heteroC$_{4-20}$alkynylene, optionally substituted heteroC$_{6-20}$alkynylene, optionally substituted heteroC$_{8-20}$alkynylene, optionally substituted heteroC$_{10-20}$alkynylene, optionally substituted heteroC$_{2-6}$alkynylene, optionally substituted heteroC$_{3-6}$alkynylene, optionally substituted heteroC$_{4-6}$alkynylene, optionally substituted heteroC$_{4-5}$alkynylene, or optionally substituted heteroC$_{3-4}$alkynylene.

In certain embodiments, L is an optionally substituted carbocyclylene, e.g., optionally substituted C$_{3-10}$carbocyclylene, optionally substituted C$_{5-8}$carbocyclylene, optionally substituted C$_{5-6}$carbocyclylene, optionally substituted C$_5$carbocyclylene, or optionally substituted C$_6$carbocyclylene.

In certain embodiments, L is an optionally substituted heterocyclylene, e.g., optionally substituted 3-14 membered heterocyclylene, optionally substituted 3-10 membered heterocyclylene, optionally substituted 5-8 membered heterocyclylene, optionally substituted 5-6 membered heterocyclylene, optionally substituted 5-membered heterocyclylene, or optionally substituted 6-membered heterocyclylene.

In certain embodiments, L is an optionally substituted arylene, e.g., optionally substituted phenylene. In some embodiments, L is optionally substituted phenylene. In some embodiments, L is substituted phenylene. In some embodiments, L is unsubstituted phenylene.

In certain embodiments, L is an optionally substituted heteroarylene, e.g., optionally substituted 5-14 membered heteroarylene, optionally substituted 5-10 membered heteroarylene, optionally substituted 5-6 membered heteroarylene, optionally substituted 5-membered heteroarylene, or optionally substituted 6-membered heteroarylene.

In certain embodiments, wherein L is an optionally substituted alkylene group, the group of formula (iv) is a group of the formula

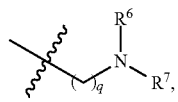

wherein q is an integer between 1 and 50, inclusive, and each of $R^6$ and $R^7$ is independently as defined above and described herein.

In certain embodiments, q is an integer between 1 and 40, inclusive. In certain embodiments, q is an integer between 1 and 30, inclusive. In certain embodiments, q is an integer between 1 and 20, inclusive. In certain embodiments, q is an integer between 1 and 10, inclusive. In certain embodiments, q is an integer between 4 and 20, inclusive. In certain embodiments, q is an integer between 6 and 20, inclusive. In certain embodiments, q is an integer between 2 and 10, inclusive. In certain embodiments, q is an integer between 2 and 9, inclusive. In certain embodiments, q is an integer between 2 and 8, inclusive. In certain embodiments, q is an integer between 2 and 7, inclusive. In certain embodiments, q is an integer between 2 and 6, inclusive. In certain embodiments, q is an integer between 2 and 5, inclusive. In certain embodiments, q is an integer between 2 and 4, inclusive. In certain embodiments, q is an integer between 3 and 10, inclusive. In certain embodiments, q is an integer between 3 and 8, inclusive. In certain embodiments, q is an integer between 3 and 7, inclusive. In certain embodiments, q is an integer between 3 and 6, inclusive. In certain embodiments, q is an integer between 3 and 5, inclusive. In certain embodiments, q is 3 or 4. In certain embodiments, q is an integer between 3 and 9, inclusive. In certain embodiments, q is an integer between 8 and 20, inclusive. In certain embodiments, q is 1. In certain embodiments, q is 2. In certain embodiments, q is 3. In certain embodiments, q is 4. In certain embodiments, q is 5. In certain embodiments, q is 6. In certain embodiments, q is 7. In certain embodiments, q is 8. In certain embodiments, q is 9. In certain embodiments, q is 10.

As generally defined above, each $R^6$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of formula (i), (ii) or (iii).

In some embodiments, $R^6$ is hydrogen.
In some embodiments, $R^6$ is optionally substituted alkyl. In some embodiments, $R^6$ is optionally substituted C$_{2-50}$ alkyl. In some embodiments, $R^6$ is optionally substituted C$_{2-40}$ alkyl. In some embodiments, $R^6$ is optionally substituted C$_{2-30}$ alkyl. In some embodiments, $R^6$ is optionally substituted $C_{2-20}$ alkyl. In some embodiments, $R^6$ is optionally substituted $C_{2-19}$ alkyl. In some embodiments, $R^6$ is optionally substituted $C_{2-18}$ alkyl. In some embodiments, $R^6$ is optionally substituted $C_{2-17}$ alkyl. In some embodiments, $R^6$ is optionally substituted $C_{2-16}$ alkyl. In some embodiments, $R^6$ is optionally substituted $C_{2-15}$ alkyl. In some embodiments, $R^6$ is optionally substituted $C_{2-14}$ alkyl. In some embodiments, $R^6$ is optionally substituted $C_{2-13}$ alkyl. In some embodiments, $R^6$ is optionally substituted $C_{2-12}$ alkyl. In some embodiments, $R^6$ is optionally substituted $C_{2-11}$ alkyl. In some embodiments, $R^6$ is optionally substituted $C_{2-10}$ alkyl. In some embodiments, $R^6$ is optionally substituted $C_{2-9}$ alkyl. In some embodiments, $R^6$ is optionally substituted $C_{2-8}$ alkyl. In some embodiments, $R^6$ is optionally substituted $C_{2-7}$ alkyl. In some embodiments, $R^6$ is optionally substituted $C_{2-6}$ alkyl.

In some embodiments, $R^6$ is optionally substituted $C_{4-50}$ alkyl. In some embodiments, $R^6$ is optionally substituted $C_{4-40}$ alkyl. In some embodiments, $R^6$ is optionally substituted $C_{4-30}$ alkyl. In some embodiments, $R^6$ is optionally substituted $C_{4-20}$ alkyl. In some embodiments, $R^6$ is optionally substituted $C_{4-19}$ alkyl. In some embodiments, $R^6$ is optionally substituted $C_{4-18}$ alkyl. In some embodiments, $R^6$ is optionally substituted $C_{4-17}$ alkyl. In some embodiments, $R^6$ is optionally substituted $C_{4-16}$ alkyl. In some embodiments, $R^6$ is optionally substituted $C_{4-15}$ alkyl. In some embodiments, $R^6$ is optionally substituted $C_{4-14}$ alkyl. In some embodiments, $R^6$ is optionally substituted $C_{4-13}$ alkyl. In some embodiments, $R^6$ is optionally substituted $C_{4-12}$ alkyl. In some embodiments, $R^6$ is optionally substituted $C_{4-11}$ alkyl. In some embodiments, $R^6$ is optionally substituted $C_{4-10}$ alkyl. In some embodiments, $R^6$ is optionally substituted $C_{4-9}$ alkyl. In some embodiments, $R^6$ is optionally substituted $C_{4-8}$ alkyl. In some embodiments, $R^6$ is optionally substituted $C_{4-7}$ alkyl. In some embodiments, $R^6$ is optionally substituted $C_{4-6}$ alkyl.

In some embodiments, $R^6$ is optionally substituted $C_{6-50}$ alkyl. In some embodiments, $R^6$ is optionally substituted $C_{6-40}$ alkyl. In some embodiments, $R^6$ is optionally substituted $C_{6-30}$ alkyl. In some embodiments, $R^6$ is optionally substituted $C_{6-20}$ alkyl. In some embodiments, $R^6$ is optionally substituted $C_{6-19}$ alkyl. In some embodiments, $R^6$ is optionally substituted $C_{6-18}$ alkyl. In some embodiments, $R^6$ is optionally substituted $C_{6-17}$ alkyl. In some embodiments, $R^6$ is optionally substituted $C_{6-16}$ alkyl. In some embodiments, $R^6$ is optionally substituted $C_{6-15}$ alkyl. In some embodiments, $R^6$ is optionally substituted $C_{6-14}$ alkyl. In some embodiments, $R^6$ is optionally substituted $C_{6-13}$ alkyl. In some embodiments, $R^6$ is optionally substituted $C_{6-12}$ alkyl. In some embodiments, $R^6$ is optionally substituted $C_{6-11}$ alkyl. In some embodiments, $R^6$ is optionally substituted $C_{6-10}$ alkyl. In some embodiments, $R^6$ is optionally substituted $C_{6-9}$ alkyl. In some embodiments, $R^6$ is optionally substituted $C_{6-8}$ alkyl. In some embodiments, $R^6$ is optionally substituted $C_{6-7}$ alkyl.

In some embodiments, $R^6$ is optionally substituted $C_{8-50}$ alkyl. In some embodiments, $R^6$ is optionally substituted $C_{8-40}$ alkyl. In some embodiments, $R^6$ is optionally substituted $C_{8-30}$ alkyl. In some embodiments, $R^6$ is optionally substituted $C_{8-20}$ alkyl. In some embodiments, $R^6$ is optionally substituted $C_{8-19}$ alkyl. In some embodiments, $R^6$ is optionally substituted $C_{8-18}$ alkyl. In some embodiments, $R^6$ is optionally substituted $C_{8-17}$ alkyl. In some embodiments, $R^6$ is optionally substituted $C_{8-16}$ alkyl. In some embodiments, $R^6$ is optionally substituted $C_{8-15}$ alkyl. In some embodiments, $R^6$ is optionally substituted $C_{8-14}$ alkyl. In some embodiments, $R^6$ is optionally substituted $C_{8-13}$ alkyl. In some embodiments, $R^6$ is optionally substituted $C_{8-12}$ alkyl. In some embodiments, $R^6$ is optionally substituted $C_{8-11}$ alkyl. In some embodiments, $R^6$ is optionally substituted $C_{8-10}$ alkyl. In some embodiments, $R^6$ is optionally substituted $C_{8-9}$ alkyl.

In some embodiments, $R^6$ is optionally substituted $C_950$ alkyl. In some embodiments, $R^6$ is optionally substituted $C_{9-40}$ alkyl. In some embodiments, $R^6$ is optionally substituted $C_{9-30}$ alkyl. In some embodiments, $R^6$ is optionally substituted $C_{9-20}$ alkyl. In some embodiments, $R^6$ is optionally substituted $C_{9-19}$ alkyl. In some embodiments, $R^6$ is optionally substituted $C_{9-18}$ alkyl. In some embodiments, $R^6$ is optionally substituted $C_{9-17}$ alkyl. In some embodiments, $R^6$ is optionally substituted $C_{9-16}$ alkyl. In some embodiments, $R^6$ is optionally substituted $C_{9-15}$ alkyl. In some embodiments, $R^6$ is optionally substituted $C_{9-14}$ alkyl. In some embodiments, $R^6$ is optionally substituted $C_{9-13}$ alkyl. In some embodiments, $R^6$ is optionally substituted $C_{9-12}$ alkyl. In some embodiments, $R^6$ is optionally substituted $C_{9-11}$ alkyl. In some embodiments, $R^6$ is optionally substituted $C_{9-10}$ alkyl.

In some embodiments, $R^6$ is optionally substituted $C_{10-50}$ alkyl. In some embodiments, $R^6$ is optionally substituted $C_{10-40}$ alkyl. In some embodiments, $R^6$ is optionally substituted $C_{10-30}$ alkyl. In some embodiments, $R^6$ is optionally substituted $C_{10-20}$ alkyl. In some embodiments, $R^6$ is optionally substituted $C_{10-19}$ alkyl. In some embodiments, $R^6$ is optionally substituted $C_{10-18}$ alkyl. In some embodiments, $R^6$ is optionally substituted $C_{10-17}$ alkyl. In some embodiments, $R^6$ is optionally substituted $C_{10-16}$ alkyl. In some embodiments, $R^6$ is optionally substituted $C_{10-15}$ alkyl. In some embodiments, $R^6$ is optionally substituted $C_{10-14}$ alkyl. In some embodiments, $R^6$ is optionally substituted $C_{10-13}$ alkyl. In some embodiments, $R^6$ is optionally substituted $C_{10-12}$ alkyl. In some embodiments, $R^6$ is optionally substituted $C_{10-11}$ alkyl.

In some embodiments, $R^6$ is optionally substituted $C_{11-50}$ alkyl. In some embodiments, $R^6$ is optionally substituted $C_{11-40}$ alkyl. In some embodiments, $R^6$ is optionally substituted $C_{11-30}$ alkyl. In some embodiments, $R^6$ is optionally substituted $C_{11-20}$ alkyl. In some embodiments, $R^6$ is optionally substituted $C_{11-19}$ alkyl. In some embodiments, $R^6$ is optionally substituted $C_{11-18}$ alkyl. In some embodiments, $R^6$ is optionally substituted $C_{11-17}$ alkyl. In some embodiments, $R^6$ is optionally substituted $C_{11-16}$ alkyl. In some embodiments, $R^6$ is optionally substituted $C_{11-15}$ alkyl. In some embodiments, $R^6$ is optionally substituted $C_{11-14}$ alkyl. In some embodiments, $R^6$ is optionally substituted $C_{11-13}$ alkyl. In some embodiments, $R^6$ is optionally substituted $C_{11-12}$ alkyl.

In some embodiments, $R^6$ is optionally substituted $C_{12-50}$ alkyl. In some embodiments, $R^6$ is optionally substituted $C_{12-40}$ alkyl. In some embodiments, $R^6$ is optionally substituted $C_{12-30}$ alkyl. In some embodiments, $R^6$ is optionally substituted $C_{12-20}$ alkyl. In some embodiments, $R^6$ is optionally substituted $C_{12-19}$ alkyl. In some embodiments, $R^6$ is optionally substituted $C_{12-18}$ alkyl. In some embodiments, $R^6$ is optionally substituted $C_{12-17}$ alkyl. In some embodiments, $R^6$ is optionally substituted $C_{12-16}$ alkyl. In some embodiments, $R^6$ is optionally substituted $C_{12-15}$ alkyl. In some embodiments, $R^6$ is optionally substituted $C_{12-14}$ alkyl. In some embodiments, $R^6$ is optionally substituted $C_{12-13}$ alkyl.

In some embodiments, $R^6$ is optionally substituted $C_6$ alkyl. In some embodiments, $R^6$ is optionally substituted $C_7$ alkyl. In some embodiments, $R^6$ is optionally substituted $C_8$ alkyl. In some embodiments, $R^6$ is optionally substituted $C_9$ alkyl. In some embodiments, $R^6$ is optionally substituted $C_{10}$ alkyl. In some embodiments, $R^6$ is optionally substituted $C_{11}$ alkyl. In some embodiments, $R^6$ is optionally substituted $C_{12}$ alkyl. In some embodiments, $R^6$ is optionally substituted $C_{13}$ alkyl. In some embodiments, $R^6$ is optionally substituted $C_{14}$ alkyl. In some embodiments, $R^6$ is optionally substituted $C_{15}$ alkyl. In some embodiments, $R^6$ is optionally substituted $C_{16}$ alkyl. In some embodiments, $R^6$ is optionally substituted $C_{17}$ alkyl. In some embodiments, $R^6$ is optionally substituted $C_{18}$ alkyl. In some embodiments, $R^6$ is optionally substituted $C_{19}$ alkyl. In some embodiments, $R^6$ is optionally substituted $C_{20}$ alkyl.

In some embodiments, for example, in any of the above embodiments, $R^6$ is a substituted alkyl group. In some embodiments, $R^6$ is an unsubstituted alkyl group. In some embodiments, $R^6$ is an optionally substituted straight-chain alkyl group. In some embodiments, $R^6$ is a substituted straight-chain alkyl group. In some embodiments, $R^6$ is an unsubstituted straight-chain alkyl group. In some embodiments, $R^6$ is an optionally substituted branched alkyl group. In some embodiments, $R^6$ is a substituted branched alkyl group. In some embodiments, $R^6$ is an unsubstituted branched alkyl group.

In some embodiments, $R^6$ is optionally substituted alkenyl. In some embodiments, $R^6$ is optionally substituted $C_{2-50}$ alkenyl. In some embodiments, $R^6$ is optionally substituted $C_{2-40}$ alkenyl. In some embodiments, $R^6$ is optionally substituted $C_{2-30}$ alkenyl. In some embodiments, $R^6$ is optionally substituted $C_{2-20}$ alkenyl. In some embodiments, $R^6$ is optionally substituted $C_{2-19}$ alkenyl. In some embodiments, $R^6$ is optionally substituted $C_{2-18}$ alkenyl. In some embodiments, $R^6$ is optionally substituted $C_{2-17}$ alkenyl. In some embodiments, $R^6$ is optionally substituted $C_{2-16}$ alkenyl. In some embodiments, $R^6$ is optionally substituted $C_{2-15}$ alkenyl. In some embodiments, $R^6$ is optionally substituted $C_{2-14}$ alkenyl. In some embodiments, $R^6$ is optionally substituted $C_{2-13}$ alkenyl. In some embodiments, $R^6$ is optionally substituted $C_{2-12}$ alkenyl. In some embodiments, $R^6$ is optionally substituted $C_{2-11}$ alkenyl. In some embodiments, $R^6$ is optionally substituted $C_{2-10}$ alkenyl. In some embodiments, $R^6$ is optionally substituted $C_{2-9}$ alkenyl. In some embodiments, $R^6$ is optionally substituted $C_{2-8}$ alkenyl. In some embodiments, $R^6$ is optionally substituted $C_{2-7}$ alkenyl. In some embodiments, $R^6$ is optionally substituted $C_{2-6}$ alkenyl.

In some embodiments, $R^6$ is optionally substituted $C_{4-50}$ alkenyl. In some embodiments, $R^6$ is optionally substituted $C_{4-40}$ alkenyl. In some embodiments, $R^6$ is optionally substituted $C_{4-30}$ alkenyl. In some embodiments, $R^6$ is optionally substituted $C_{4-20}$ alkenyl. In some embodiments, $R^6$ is optionally substituted $C_{4-19}$ alkenyl. In some embodiments, $R^6$ is optionally substituted $C_{4-11}$ alkenyl. In some embodiments, $R^6$ is optionally substituted $C_{4-17}$ alkenyl. In some embodiments, $R^6$ is optionally substituted $C_{4-16}$ alkenyl. In some embodiments, $R^6$ is optionally substituted $C_{4-15}$ alkenyl. In some embodiments, $R^6$ is optionally substituted $C_{4-14}$ alkenyl. In some embodiments, $R^6$ is optionally substituted $C_{4-13}$ alkenyl. In some embodiments, $R^6$ is optionally substituted $C_{4-12}$ alkenyl. In some embodiments, $R^6$ is optionally substituted $C_{4-11}$ alkenyl. In some embodiments, $R^6$ is optionally substituted $C_{4-10}$ alkenyl. In some embodiments, $R^6$ is optionally substituted $C_{4-9}$ alkenyl. In some embodiments, $R^6$ is optionally substituted $C_{4-8}$ alkenyl. In some embodiments, $R^6$ is optionally substituted $C_{4-7}$ alkenyl. In some embodiments, $R^6$ is optionally substituted $C_{4-6}$ alkenyl.

In some embodiments, $R^6$ is optionally substituted $C_{6-50}$ alkenyl. In some embodiments, $R^6$ is optionally substituted $C_{6-40}$ alkenyl. In some embodiments, $R^6$ is optionally substituted $C_{6-30}$ alkenyl. In some embodiments, $R^6$ is optionally substituted $C_{6-20}$ alkenyl. In some embodiments, $R^6$ is optionally substituted $C_{6-19}$ alkenyl. In some embodiments, $R^6$ is optionally substituted $C_{6-18}$ alkenyl. In some embodiments, $R^6$ is optionally substituted $C_{6-17}$ alkenyl. In some embodiments, $R^6$ is optionally substituted $C_{6-16}$ alkenyl. In some embodiments, $R^6$ is optionally substituted $C_{6-15}$ alkenyl. In some embodiments, $R^6$ is optionally substituted $C_{6-14}$ alkenyl. In some embodiments, $R^6$ is optionally substituted $C_{6-13}$ alkenyl. In some embodiments, $R^6$ is optionally substituted $C_{6-12}$ alkenyl. In some embodiments, $R^6$ is optionally substituted $C_{6-11}$ alkenyl. In some embodiments, $R^6$ is optionally substituted $C_{6-10}$ alkenyl. In some embodiments, $R^6$ is optionally substituted $C_{6-9}$ alkenyl. In some embodiments, $R^6$ is optionally substituted $C_{6-8}$ alkenyl. In some embodiments, $R^6$ is optionally substituted $C_{6-7}$ alkenyl.

In some embodiments, $R^6$ is optionally substituted $C_{8-50}$ alkenyl. In some embodiments, $R^6$ is optionally substituted $C_{8-40}$ alkenyl. In some embodiments, $R^6$ is optionally substituted $C_{8-30}$ alkenyl. In some embodiments, $R^6$ is optionally substituted $C_{8-20}$ alkenyl. In some embodiments, $R^6$ is optionally substituted $C_{8-19}$ alkenyl. In some embodiments, $R^6$ is optionally substituted $C_{8-18}$ alkenyl. In some embodiments, $R^6$ is optionally substituted $C_{8-17}$ alkenyl. In some embodiments, $R^6$ is optionally substituted $C_{8-16}$ alkenyl. In some embodiments, $R^6$ is optionally substituted $C_{8-15}$ alkenyl. In some embodiments, $R^6$ is optionally substituted $C_{8-14}$ alkenyl. In some embodiments, $R^6$ is optionally substituted $C_{8-13}$ alkenyl. In some embodiments, $R^6$ is optionally substituted $C_{8-12}$ alkenyl. In some embodiments, $R^6$ is optionally substituted $C_{8-11}$ alkenyl. In some embodiments, $R^6$ is optionally substituted $C_{8-10}$ alkenyl. In some embodiments, $R^6$ is optionally substituted $C_{8-9}$ alkenyl.

In some embodiments, $R^6$ is optionally substituted $C_{9-50}$ alkenyl. In some embodiments, $R^6$ is optionally substituted $C_{9-40}$ alkenyl. In some embodiments, $R^6$ is optionally substituted $C_{9-30}$ alkenyl. In some embodiments, $R^6$ is optionally substituted $C_{9-20}$ alkenyl. In some embodiments, $R^6$ is optionally substituted $C_{9-19}$ alkenyl. In some embodiments, $R^6$ is optionally substituted $C_{9-18}$ alkenyl. In some embodiments, $R^6$ is optionally substituted $C_{9-17}$ alkenyl. In some embodiments, $R^6$ is optionally substituted $C_{9-16}$ alkenyl. In some embodiments, $R^6$ is optionally substituted $C_{9-15}$ alkenyl. In some embodiments, $R^6$ is optionally substituted $C_{9-14}$ alkenyl. In some embodiments, $R^6$ is optionally substituted $C_{9-13}$ alkenyl. In some embodiments, $R^6$ is optionally substituted $C_{9-12}$ alkenyl. In some embodiments, $R^6$ is optionally substituted $C_{9-11}$ alkenyl. In some embodiments, $R^6$ is optionally substituted $C_{9-10}$ alkenyl.

In some embodiments, $R^6$ is optionally substituted $C_{10-50}$ alkenyl. In some embodiments, $R^6$ is optionally substituted $C_{10-40}$ alkenyl. In some embodiments, $R^6$ is optionally substituted $C_{10-30}$ alkenyl. In some embodiments, $R^6$ is optionally substituted $C_{10-20}$ alkenyl. In some embodiments, $R^6$ is optionally substituted $C_{10-19}$ alkenyl. In some embodiments, $R^6$ is optionally substituted $C_{10-18}$ alkenyl. In some embodiments, $R^6$ is optionally substituted $C_{10-17}$ alkenyl. In some embodiments, $R^6$ is optionally substituted $C_{10-16}$ alkenyl. In some embodiments, $R^6$ is optionally substituted $C_{10-15}$ alkenyl. In some embodiments, $R^6$ is optionally substituted $C_{10-14}$ alkenyl. In some embodiments, $R^6$ is optionally substituted $C_{10-13}$ alkenyl. In some embodiments, $R^6$ is optionally substituted $C_{10-12}$ alkenyl. In some embodiments, $R^6$ is optionally substituted $C_{10-11}$ alkenyl.

In some embodiments, $R^6$ is optionally substituted $C_{11-50}$ alkenyl. In some embodiments, $R^6$ is optionally substituted $C_{11-40}$ alkenyl. In some embodiments, $R^6$ is optionally substituted $C_{11-30}$ alkenyl. In some embodiments, $R^6$ is optionally substituted $C_{11-20}$ alkenyl. In some embodiments, $R^6$ is optionally substituted $C_{11-19}$ alkenyl. In some embodiments, $R^6$ is optionally substituted $C_{1-18}$ alkenyl. In some embodiments, $R^6$ is optionally substituted $C_{1-17}$ alkenyl. In some embodiments, $R^6$ is optionally substituted $C_{11-16}$ alkenyl. In some embodiments, $R^6$ is optionally substituted $C_{11-15}$ alkenyl. In some embodiments, $R^6$ is optionally substituted $C_{1-14}$ alkenyl. In some embodiments, $R^6$ is optionally substituted $C_{11-13}$ alkenyl. In some embodiments, $R^6$ is optionally substituted $C_{11-12}$ alkenyl.

In some embodiments, $R^6$ is optionally substituted $C_{12-50}$ alkenyl. In some embodiments, $R^6$ is optionally substituted $C_{12-40}$ alkenyl. In some embodiments, $R^6$ is optionally substituted $C_{12-30}$ alkenyl. In some embodiments, $R^6$ is optionally substituted $C_{12-20}$ alkenyl. In some embodiments, $R^6$ is optionally substituted $C_{12-19}$ alkenyl. In some embodiments, $R^6$ is optionally substituted $C_{12-18}$ alkenyl. In some embodiments, $R^6$ is optionally substituted $C_{12-17}$ alkenyl. In some embodiments, $R^6$ is optionally substituted $C_{12-16}$ alkenyl. In some embodiments, $R^6$ is optionally substituted $C_{12-15}$ alkenyl. In some embodiments, $R^6$ is optionally substituted $C_{12-14}$ alkenyl. In some embodiments, $R^6$ is optionally substituted $C_{12-13}$ alkenyl.

In some embodiments, $R^6$ is optionally substituted $C_6$ alkenyl. In some embodiments, $R^6$ is optionally substituted $C_7$ alkenyl. In some embodiments, $R^6$ is optionally substituted $C_8$ alkenyl. In some embodiments, $R^6$ is optionally substituted $C_9$ alkenyl. In some embodiments, $R^6$ is optionally substituted $C_{10}$ alkenyl. In some embodiments, $R^6$ is optionally substituted $C_{11}$ alkenyl. In some embodiments, $R^6$ is optionally substituted $C_{12}$ alkenyl. In some embodiments, $R^6$ is optionally substituted $C_{13}$ alkenyl. In some embodiments, $R^6$ is optionally substituted $C_{14}$ alkenyl. In some embodiments, $R^6$ is optionally substituted $C_{15}$ alkenyl. In some embodiments, $R^6$ is optionally substituted $C_{16}$ alkenyl. In some embodiments, $R^6$ is optionally substituted $C_{17}$ alkenyl. In some embodiments, $R^6$ is optionally substituted $C_{18}$ alkenyl. In some embodiments, $R^6$ is optionally substituted $C_{19}$ alkenyl. In some embodiments, $R^6$ is optionally substituted $C_{20}$ alkenyl.

In some embodiments, for example, in any of the above embodiments, $R^6$ is a substituted alkenyl group. In some embodiments, $R^6$ is an unsubstituted alkenyl group. In some embodiments, $R^6$ is an optionally substituted straight-chain alkenyl group. In some embodiments, $R^6$ is a substituted straight-chain alkenyl group. In some embodiments, $R^6$ is an unsubstituted straight-chain alkenyl group. In some embodiments, $R^6$ is an optionally substituted branched alkenyl group. In some embodiments, $R^6$ is a substituted branched alkenyl group. In some embodiments, $R^6$ is an unsubstituted branched alkenyl group.

In some embodiments, $R^6$ is optionally substituted alkynyl. In some embodiments, $R^6$ is optionally substituted $C_{2-50}$ alkynyl. In some embodiments, $R^6$ is optionally substituted $C_{2-40}$ alkynyl. In some embodiments, $R^6$ is optionally substituted $C_{2-30}$ alkynyl. In some embodiments, $R^6$ is optionally substituted $C_{2-20}$ alkynyl. In some embodiments, $R^6$ is optionally substituted $C_{2-19}$ alkynyl. In some embodiments, $R^6$ is optionally substituted $C_{2-18}$ alkynyl. In some embodiments, $R^6$ is optionally substituted $C_{2-17}$ alkynyl. In some embodiments, $R^6$ is optionally substituted $C_{2-16}$ alkynyl. In some embodiments, $R^6$ is optionally substituted $C_{2-15}$ alkynyl. In some embodiments, $R^6$ is optionally substituted $C_{2-14}$ alkynyl. In some embodiments, $R^6$ is optionally substituted $C_{2-13}$ alkynyl. In some embodiments, $R^6$ is optionally substituted $C_{2-12}$ alkynyl. In some embodiments, $R^6$ is optionally substituted $C_{2-11}$ alkynyl. In some embodiments, $R^6$ is optionally substituted $C_{2-10}$ alkynyl. In some embodiments, $R^6$ is optionally substituted $C_{2-9}$ alkynyl. In some embodiments, $R^6$ is optionally substituted $C_{2-8}$ alkynyl. In some embodiments, $R^6$ is optionally substituted $C_{2-7}$ alkynyl. In some embodiments, $R^6$ is optionally substituted $C_{2-6}$ alkynyl.

In some embodiments, $R^6$ is optionally substituted $C_{4-50}$ alkynyl. In some embodiments, $R^6$ is optionally substituted $C_{4-40}$ alkynyl. In some embodiments, $R^6$ is optionally substituted $C_{4-30}$ alkynyl. In some embodiments, $R^6$ is optionally substituted $C_{4-20}$ alkynyl. In some embodiments, $R^6$ is optionally substituted $C_{4-19}$ alkynyl. In some embodiments, $R^6$ is optionally substituted $C_{4-11}$ alkynyl. In some embodiments, $R^6$ is optionally substituted $C_{4-17}$ alkynyl. In some embodiments, $R^6$ is optionally substituted $C_{4-16}$ alkynyl. In some embodiments, $R^6$ is optionally substituted $C_{4-15}$ alkynyl. In some embodiments, $R^6$ is optionally substituted $C_{4-14}$ alkynyl. In some embodiments, $R^6$ is optionally substituted $C_{4-13}$ alkynyl. In some embodiments, $R^6$ is optionally substituted $C_{4-12}$ alkynyl. In some embodiments, $R^6$ is optionally substituted $C_{4-11}$ alkynyl. In some embodiments, $R^6$ is optionally substituted $C_{4-10}$ alkynyl. In some embodiments, $R^6$ is optionally substituted $C_{4-9}$ alkynyl. In some embodiments, $R^6$ is optionally substituted $C_{4-8}$ alkynyl. In some embodiments, $R^6$ is optionally substituted $C_{4-7}$ alkynyl. In some embodiments, $R^6$ is optionally substituted $C_{4-6}$ alkynyl.

In some embodiments, $R^6$ is optionally substituted $C_{6-50}$ alkynyl. In some embodiments, $R^6$ is optionally substituted $C_{6-40}$ alkynyl. In some embodiments, $R^6$ is optionally substituted $C_{6-30}$ alkynyl. In some embodiments, $R^6$ is optionally substituted $C_{6-20}$ alkynyl. In some embodiments, $R^6$ is optionally substituted $C_{6-19}$ alkynyl. In some embodiments, $R^6$ is optionally substituted $C_{6-18}$ alkynyl. In some embodiments, $R^6$ is optionally substituted $C_{6-17}$ alkynyl. In some embodiments, $R^6$ is optionally substituted $C_{6-16}$ alkynyl. In some embodiments, $R^6$ is optionally substituted $C_{6-15}$ alkynyl. In some embodiments, $R^6$ is optionally substituted $C_{6-14}$ alkynyl. In some embodiments, $R^6$ is optionally substituted $C_{6-13}$ alkynyl. In some embodiments, $R^6$ is optionally substituted $C_{6-12}$ alkynyl. In some embodiments, $R^6$ is optionally substituted $C_{6-11}$ alkynyl. In some embodiments, $R^6$ is optionally substituted $C_{6-10}$ alkynyl. In some embodiments, $R^6$ is optionally substituted $C_{6-9}$ alkynyl. In some embodiments, $R^6$ is optionally substituted $C_{6-8}$ alkynyl. In some embodiments, $R^6$ is optionally substituted $C_{6-7}$ alkynyl.

In some embodiments, $R^6$ is optionally substituted $C_{8-50}$ alkynyl. In some embodiments, $R^6$ is optionally substituted $C_{8-40}$ alkynyl. In some embodiments, $R^6$ is optionally substituted $C_{8-30}$ alkynyl. In some embodiments, $R^6$ is optionally substituted $C_{8-20}$ alkynyl. In some embodiments, $R^6$ is optionally substituted $C_{8-19}$ alkynyl. In some embodiments, $R^6$ is optionally substituted $C_{8-18}$ alkynyl. In some embodiments, $R^6$ is optionally substituted $C_{8-17}$ alkynyl. In some embodiments, $R^6$ is optionally substituted $C_{8-16}$ alkynyl. In some embodiments, $R^6$ is optionally substituted $C_{8-15}$ alkynyl. In some embodiments, $R^6$ is optionally substituted $C_{8-14}$ alkynyl. In some embodiments, $R^6$ is optionally substituted $C_{8-13}$ alkynyl. In some embodiments, $R^6$ is optionally substituted $C_{8-12}$ alkynyl. In some embodiments, $R^6$ is optionally substituted $C_{8-11}$ alkynyl. In some embodiments, $R^6$ is optionally substituted $C_{8-10}$ alkynyl. In some embodiments, $R^6$ is optionally substituted $C_{8-9}$ alkynyl.

In some embodiments, $R^6$ is optionally substituted $C_{9-50}$ alkynyl. In some embodiments, $R^6$ is optionally substituted $C_{9-40}$ alkynyl. In some embodiments, $R^6$ is optionally substituted $C_{9-30}$ alkynyl. In some embodiments, $R^6$ is optionally substituted $C_{9-20}$ alkynyl. In some embodiments, $R^6$ is optionally substituted $C_{9-19}$ alkynyl. In some embodiments, $R^6$ is optionally substituted $C_{9-18}$ alkynyl. In some embodiments, $R^6$ is optionally substituted $C_{9-17}$ alkynyl. In some embodiments, $R^6$ is optionally substituted $C_{9-16}$ alkynyl. In some embodiments, $R^6$ is optionally substituted $C_{9-15}$ alkynyl. In some embodiments, $R^6$ is optionally substituted $C_{9-14}$ alkynyl. In some embodiments, $R^6$ is optionally substituted $C_{9-13}$ alkynyl. In some embodiments, $R^6$ is optionally substituted $C_{9-12}$ alkynyl. In some embodiments, $R^6$ is optionally substituted $C_{9-11}$ alkynyl. In some embodiments, $R^6$ is optionally substituted $C_{9-10}$ alkynyl.

In some embodiments, $R^6$ is optionally substituted $C_{10-50}$ alkynyl. In some embodiments, $R^6$ is optionally substituted $C_{10-40}$ alkynyl. In some embodiments, $R^6$ is optionally substituted $C_{10-30}$ alkynyl. In some embodiments, $R^6$ is optionally substituted $C_{10-20}$ alkynyl. In some embodiments, $R^6$ is optionally substituted $C_{10-19}$ alkynyl. In some embodiments, $R^6$ is optionally substituted $C_{10-18}$ alkynyl. In some embodiments, $R^6$ is optionally substituted $C_{10-17}$ alkynyl. In some embodiments, $R^6$ is optionally substituted $C_{10-16}$ alkynyl. In some embodiments, $R^6$ is optionally substituted $C_{10-15}$ alkynyl. In some embodiments, $R^6$ is optionally substituted $C_{10-14}$ alkynyl. In some embodiments, $R^6$ is optionally substituted $C_{10-13}$ alkynyl. In some embodiments, $R^6$ is optionally substituted $C_{10-12}$ alkynyl. In some embodiments, $R^6$ is optionally substituted $C_{10-11}$ alkynyl.

In some embodiments, $R^6$ is optionally substituted $C_{11-50}$ alkynyl. In some embodiments, $R^6$ is optionally substituted $C_{11-40}$ alkynyl. In some embodiments, $R^6$ is optionally substituted $C_{1-30}$ alkynyl. In some embodiments, $R^6$ is optionally substituted $C_{11-20}$ alkynyl. In some embodiments, $R^6$ is optionally substituted $C_{11-19}$ alkynyl. In some embodiments, $R^6$ is optionally substituted $C_{11-18}$ alkynyl. In some embodiments, $R^6$ is optionally substituted $C_{11-17}$ alkynyl. In some embodiments, $R^6$ is optionally substituted $C_{11-16}$ alkynyl. In some embodiments, $R^6$ is optionally substituted $C_{11-15}$ alkynyl. In some embodiments, $R^6$ is optionally substituted $C_{11-14}$ alkynyl. In some embodiments, $R^6$ is optionally substituted $C_{11-13}$ alkynyl. In some embodiments, $R^6$ is optionally substituted $C_{11-12}$ alkynyl.

In some embodiments, $R^6$ is optionally substituted $C_{12-50}$ alkynyl. In some embodiments, $R^6$ is optionally substituted $C_{12-40}$ alkynyl. In some embodiments, $R^6$ is optionally substituted $C_{12-30}$ alkynyl. In some embodiments, $R^6$ is optionally substituted $C_{12-20}$ alkynyl. In some embodiments, $R^6$ is optionally substituted $C_{12-19}$ alkynyl. In some embodiments, $R^6$ is optionally substituted $C_{12-18}$ alkynyl. In some embodiments, $R^6$ is optionally substituted $C_{12-17}$ alkynyl. In some embodiments, $R^6$ is optionally substituted $C_{12-16}$ alkynyl. In some embodiments, $R^6$ is optionally substituted $C_{12-15}$ alkynyl. In some embodiments, $R^6$ is optionally substituted $C_{12-14}$ alkynyl. In some embodiments, $R^6$ is optionally substituted $C_{12-13}$ alkynyl.

In some embodiments, $R^6$ is optionally substituted $C_6$ alkynyl. In some embodiments, $R^6$ is optionally substituted $C_7$ alkynyl. In some embodiments, $R^6$ is optionally substituted $C_8$ alkynyl. In some embodiments, $R^6$ is optionally substituted $C_9$ alkynyl. In some embodiments, $R^6$ is optionally substituted $C_{10}$ alkynyl. In some embodiments, $R^6$ is optionally substituted $C_{11}$ alkynyl. In some embodiments, $R^6$ is optionally substituted $C_{12}$ alkynyl. In some embodiments, $R^6$ is optionally substituted $C_{13}$ alkynyl. In some embodiments, $R^6$ is optionally substituted $C_{14}$ alkynyl. In some embodiments, $R^6$ is optionally substituted $C_{15}$ alkynyl. In some embodiments, $R^6$ is optionally substituted $C_{16}$ alkynyl. In some embodiments, $R^6$ is optionally substituted $C_{17}$ alkynyl. In some embodiments, $R^6$ is optionally substituted $C_{18}$ alkynyl. In some embodiments, $R^6$ is optionally substituted $C_{19}$ alkynyl. In some embodiments, $R^6$ is optionally substituted $C_{20}$ alkynyl.

In some embodiments, for example, in any of the above embodiments, $R^6$ is a substituted alkynyl group. In some embodiments, $R^6$ is an unsubstituted alknyl group. In some embodiments, $R^6$ is an optionally substituted straight-chain alkynyl group. In some embodiments, $R^6$ is a substituted straight-chain alkynyl group. In some embodiments, $R^6$ is an unsubstituted straight-chain alkynyl group. In some embodiments, $R^6$ is an optionally substituted branched alkynyl group. In some embodiments, $R^6$ is a substituted branched alkynyl group. In some embodiments, $R^6$ is an unsubstituted branched alkynyl group.

In some embodiments, $R^6$ is optionally substituted carbocyclyl. In some embodiments, $R^6$ is optionally substituted heterocyclyl. In some embodiments, $R^6$ is optionally substituted aryl. In some embodiments, $R^6$ is optionally substituted heteroaryl. In some embodiments, $R^6$ is a nitrogen protecting group.

In some embodiments, $R^6$ is a group of formula (i). In some embodiments, $R^6$ is a group of formula (i-a). In some embodiments, $R^6$ is a group of formula (i-a1).

(i-a1)

In some embodiments, $R^6$ is a group of formula (i-b). In some embodiments, R is a group of formula (ii). In some embodiments, $R^6$ is a group of formula (iii).

In some embodiments, $R^6$ is substituted with one or more hydroxyl groups. In some embodiments, $R^6$ is substituted with one hydroxyl group. In some embodiments, $R^6$ is substituted with one 2-hydroxyl group (C1 is the carbon atom directly bonded to the nitrogen atom depicted in formula (iv)).

As generally defined above, each $R^7$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of formula (i), (ii) or (iii).

In some embodiments, $R^7$ is hydrogen.

In some embodiments, $R^7$ is optionally substituted alkyl. In some embodiments, $R^7$ is optionally substituted $C_{2-50}$ alkyl. In some embodiments, $R^7$ is optionally substituted $C_{2-40}$ alkyl. In some embodiments, $R^7$ is optionally substituted $C_{2-30}$ alkyl. In some embodiments, $R^7$ is optionally substituted $C_{2-20}$ alkyl. In some embodiments, $R^7$ is optionally substituted $C_{2-19}$ alkyl. In some embodiments, $R^7$ is optionally substituted $C_{2-18}$ alkyl. In some embodiments, $R^7$ is optionally substituted $C_{2-17}$ alkyl. In some embodiments, $R^7$ is optionally substituted $C_{2-16}$ alkyl. In some embodiments, $R^7$ is optionally substituted $C_{2-15}$ alkyl. In some embodiments, $R^7$ is optionally substituted $C_{2-14}$ alkyl. In some embodiments, $R^7$ is optionally substituted $C_{2-13}$ alkyl. In some embodiments, $R^7$ is optionally substituted $C_{2-12}$ alkyl. In some embodiments, $R^7$ is optionally substituted $C_{2-11}$ alkyl. In some embodiments, $R^7$ is optionally substituted $C_{2-10}$ alkyl. In some embodiments, $R^7$ is optionally substituted $C_{2-9}$ alkyl. In some embodiments, $R^7$ is optionally substituted $C_{2-8}$ alkyl. In some embodiments, $R^7$ is optionally substituted $C_{2-7}$ alkyl. In some embodiments, $R^7$ is optionally substituted $C_{2-6}$ alkyl.

In some embodiments, $R^7$ is optionally substituted $C_{4-50}$ alkyl. In some embodiments, $R^7$ is optionally substituted $C_{4-40}$ alkyl. In some embodiments, $R^7$ is optionally substituted $C_{4-30}$ alkyl. In some embodiments, $R^7$ is optionally substituted $C_{4-20}$ alkyl. In some embodiments, $R^7$ is optionally substituted $C_{4-19}$ alkyl. In some embodiments, $R^7$ is optionally substituted $C_{4-18}$ alkyl. In some embodiments, $R^7$ is optionally substituted $C_{4-17}$ alkyl. In some embodiments, $R^7$ is optionally substituted $C_{4-16}$ alkyl. In some embodiments, $R^7$ is optionally substituted $C_{4-15}$ alkyl. In some embodiments, $R^7$ is optionally substituted $C_{4-14}$ alkyl. In some embodiments, $R^7$ is optionally substituted $C_{4-13}$ alkyl. In some embodiments, $R^7$ is optionally substituted $C_{4-12}$ alkyl. In some embodiments, $R^7$ is optionally substituted $C_{4-11}$ alkyl. In some embodiments, $R^7$ is optionally substituted $C_4$-10 alkyl. In some embodiments, $R^7$ is optionally substituted $C_{4-9}$ alkyl. In some embodiments, $R^7$ is optionally substituted $C_{4-8}$ alkyl. In some embodiments, $R^7$ is optionally substituted $C_{4-7}$ alkyl. In some embodiments, $R^7$ is optionally substituted $C_{4-6}$ alkyl.

In some embodiments, $R^7$ is optionally substituted $C_{6-50}$ alkyl. In some embodiments, $R^7$ is optionally substituted $C_{6-40}$ alkyl. In some embodiments, $R^7$ is optionally substituted $C_{6-30}$ alkyl. In some embodiments, $R^7$ is optionally substituted $C_{6-20}$ alkyl. In some embodiments, $R^7$ is optionally substituted $C_{6-19}$ alkyl. In some embodiments, $R^7$ is optionally substituted $C_{6-18}$ alkyl. In some embodiments, $R^7$ is optionally substituted $C_{6-17}$ alkyl. In some embodiments, $R^7$ is optionally substituted $C_{6-16}$ alkyl. In some embodiments, $R^7$ is optionally substituted $C_{6-15}$ alkyl. In some embodiments, $R^7$ is optionally substituted $C_{6-14}$ alkyl. In some embodiments, $R^7$ is optionally substituted $C_{6-13}$ alkyl. In some embodiments, $R^7$ is optionally substituted $C_{6-12}$ alkyl. In some embodiments, $R^7$ is optionally substituted $C_{6-11}$ alkyl. In some embodiments, $R^7$ is optionally substituted $C_{6-10}$ alkyl. In some embodiments, $R^7$ is optionally substituted $C_{6-9}$ alkyl. In some embodiments, $R^7$ is optionally substituted $C_{6-8}$ alkyl. In some embodiments, $R^7$ is optionally substituted $C_{6-7}$ alkyl.

In some embodiments, $R^7$ is optionally substituted $C_{8-50}$ alkyl. In some embodiments, $R^7$ is optionally substituted $C_{8-40}$ alkyl. In some embodiments, $R^7$ is optionally substituted $C_{8-30}$ alkyl. In some embodiments, $R^7$ is optionally substituted $C_{8-20}$ alkyl. In some embodiments, $R^7$ is optionally substituted $C_{8-19}$ alkyl. In some embodiments, $R^7$ is optionally substituted $C_{8-18}$ alkyl. In some embodiments, $R^7$ is optionally substituted $C_{8-17}$ alkyl. In some embodiments, $R^7$ is optionally substituted $C_{8-16}$ alkyl. In some embodiments, $R^7$ is optionally substituted $C_{8-15}$ alkyl. In some embodiments, $R^7$ is optionally substituted $C_{8-14}$ alkyl. In some embodiments, $R^7$ is optionally substituted $C_{8-13}$ alkyl. In some embodiments, $R^7$ is optionally substituted $C_{8-12}$ alkyl. In some embodiments, $R^7$ is optionally substituted $C_{8-11}$ alkyl. In some embodiments, $R^7$ is optionally substituted $C_{8-10}$ alkyl. In some embodiments, $R^7$ is optionally substituted $C_{8-9}$ alkyl.

In some embodiments, $R^7$ is optionally substituted $C_{9-50}$ alkyl. In some embodiments, $R^7$ is optionally substituted $C_{9-40}$ alkyl. In some embodiments, $R^7$ is optionally substituted $C_{9-30}$ alkyl. In some embodiments, $R^7$ is optionally substituted $C_{9-20}$ alkyl. In some embodiments, $R^7$ is optionally substituted $C_{9-19}$ alkyl. In some embodiments, $R^7$ is optionally substituted $C_{9-18}$ alkyl. In some embodiments, $R^7$ is optionally substituted $C_{9-17}$ alkyl. In some embodiments, $R^7$ is optionally substituted $C_{9-16}$ alkyl. In some embodiments, $R^7$ is optionally substituted $C_{9-15}$ alkyl. In some embodiments, $R^7$ is optionally substituted $C_{9-14}$ alkyl. In some embodiments, $R^7$ is optionally substituted $C_{9-13}$ alkyl. In some embodiments, $R^7$ is optionally substituted $C_{9-12}$ alkyl. In some embodiments, $R^7$ is optionally substituted $C_{9-11}$ alkyl. In some embodiments, $R^7$ is optionally substituted $C_{9-10}$ alkyl.

In some embodiments, $R^7$ is optionally substituted $C_{00}$-50 alkyl. In some embodiments, $R^7$ is optionally substituted $C_{10-40}$ alkyl. In some embodiments, $R^7$ is optionally substituted $C_{10-30}$ alkyl. In some embodiments, $R^7$ is optionally substituted $C_{10-20}$ alkyl. In some embodiments, $R^7$ is optionally substituted $C_{10-19}$ alkyl. In some embodiments, $R^7$ is optionally substituted $C_{10-18}$ alkyl. In some embodiments, $R^7$ is optionally substituted $C_{10-17}$ alkyl. In some embodiments, $R^7$ is optionally substituted $C_{10-16}$ alkyl. In some embodiments, $R^7$ is optionally substituted $C_{10-15}$ alkyl. In some embodiments, $R^7$ is optionally substituted $C_{00-14}$ alkyl. In some embodiments, $R^7$ is optionally substituted $C_{10-13}$ alkyl. In some embodiments, $R^7$ is optionally substituted $C_{10-12}$ alkyl. In some embodiments, $R^7$ is optionally substituted $C_{10-11}$ alkyl.

In some embodiments, $R^7$ is optionally substituted $C_{11-50}$ alkyl. In some embodiments, $R^7$ is optionally substituted $C_{11-40}$ alkyl. In some embodiments, $R^7$ is optionally substituted $C_{11-30}$ alkyl. In some embodiments, $R^7$ is optionally substituted $C_{11-20}$ alkyl. In some embodiments, $R^7$ is optionally substituted $C_{11-19}$ alkyl. In some embodiments, $R^7$ is optionally substituted $C_{11-18}$ alkyl. In some embodiments, $R^7$ is optionally substituted $C_{11-17}$ alkyl. In some embodiments, $R^7$ is optionally substituted $C_{11-16}$ alkyl. In some embodiments, $R^7$ is optionally substituted $C_{1-15}$ alkyl. In some embodiments, $R^7$ is optionally substituted $C_{11-14}$ alkyl. In some embodiments, $R^7$ is optionally substituted $C_{11-13}$ alkyl. In some embodiments, $R^7$ is optionally substituted $C_{11-12}$ alkyl.

In some embodiments, $R^7$ is optionally substituted $C_{12-50}$ alkyl. In some embodiments, $R^7$ is optionally substituted $C_{12-40}$ alkyl. In some embodiments, $R^7$ is optionally substituted $C_{12-30}$ alkyl. In some embodiments, $R^7$ is optionally substituted $C_{12-20}$ alkyl. In some embodiments, $R^7$ is optionally substituted $C_{12-19}$ alkyl. In some embodiments, $R^7$ is optionally substituted $C_{12-18}$ alkyl. In some embodiments, $R^7$ is optionally substituted $C_{12-17}$ alkyl. In some embodiments, $R^7$ is optionally substituted $C_{12-16}$ alkyl. In some embodiments, $R^7$ is optionally substituted $C_{12-15}$ alkyl. In some embodiments, $R^7$ is optionally substituted $C_{12-14}$ alkyl. In some embodiments, $R^7$ is optionally substituted $C_{12-13}$ alkyl.

In some embodiments, $R^7$ is optionally substituted $C_6$ alkyl. In some embodiments, $R^7$ is optionally substituted $C_7$ alkyl. In some embodiments, $R^7$ is optionally substituted $C_8$ alkyl. In some embodiments, $R^7$ is optionally substituted $C_9$ alkyl. In some embodiments, $R^7$ is optionally substituted $C_{10}$ alkyl. In some embodiments, $R^7$ is optionally substituted $C_{11}$ alkyl. In some embodiments, $R^7$ is optionally substituted $C_{12}$ alkyl. In some embodiments, $R^7$ is optionally substituted $C_{13}$ alkyl. In some embodiments, $R^7$ is optionally substituted $C_{14}$ alkyl. In some embodiments, $R^7$ is optionally substituted $C_{15}$ alkyl. In some embodiments, $R^7$ is optionally substituted $C_{16}$ alkyl. In some embodiments, $R^7$ is optionally substituted $C_{17}$ alkyl. In some embodiments, $R^7$ is optionally substituted $C_{18}$ alkyl. In some embodiments, $R^7$ is optionally substituted $C_{19}$ alkyl. In some embodiments, $R^7$ is optionally substituted $C_{20}$ alkyl.

In some embodiments, for example, in any of the above embodiments, $R^7$ is a substituted alkyl group. In some embodiments, $R^7$ is an unsubstituted alkyl group. In some embodiments, $R^7$ is an optionally substituted straight-chain alkyl group. In some embodiments, $R^7$ is a substituted straight-chain alkyl group. In some embodiments, $R^7$ is an unsubstituted straight-chain alkyl group. In some embodiments, $R^7$ is an optionally substituted branched alkyl group. In some embodiments, $R^7$ is a substituted branched alkyl group. In some embodiments, $R^7$ is an unsubstituted branched alkyl group.

In some embodiments, $R^7$ is optionally substituted alkenyl. In some embodiments, $R^7$ is optionally substituted $C_{2-50}$ alkenyl. In some embodiments, $R^7$ is optionally substituted $C_{2-40}$ alkenyl. In some embodiments, $R^7$ is optionally substituted $C_{2-30}$ alkenyl. In some embodiments, $R^7$ is optionally substituted $C_{2-20}$ alkenyl. In some embodiments, $R^7$ is optionally substituted $C_{2-19}$ alkenyl. In some embodiments, $R^7$ is optionally substituted $C_{2-18}$ alkenyl. In some embodiments, $R^7$ is optionally substituted $C_{2-17}$ alkenyl. In some embodiments, $R^7$ is optionally substituted $C_{2-16}$ alkenyl. In some embodiments, $R^7$ is optionally substituted $C_{2-15}$ alkenyl. In some embodiments, $R^7$ is optionally substituted $C_{2-14}$ alkenyl. In some embodiments, $R^7$ is optionally substituted $C_{2-13}$ alkenyl. In some embodiments, $R^7$ is optionally substituted $C_{2-12}$ alkenyl. In some embodiments, $R^7$ is optionally substituted $C_{2-11}$ alkenyl. In some embodiments, $R^7$ is optionally substituted $C_{2-10}$ alkenyl. In some embodiments, $R^7$ is optionally substituted $C_{2-9}$ alkenyl. In some embodiments, $R^7$ is optionally substituted $C_{2-8}$ alkenyl. In some embodiments, $R^7$ is optionally substituted $C_{2-7}$ alkenyl. In some embodiments, $R^7$ is optionally substituted $C_{2-6}$ alkenyl.

In some embodiments, $R^7$ is optionally substituted $C_{4-50}$ alkenyl. In some embodiments, $R^7$ is optionally substituted $C_{4-40}$ alkenyl. In some embodiments, $R^7$ is optionally substituted $C_{4-30}$ alkenyl. In some embodiments, $R^7$ is optionally substituted $C_{4-20}$ alkenyl. In some embodiments, $R^7$ is optionally substituted $C_{4-19}$ alkenyl. In some embodiments, $R^7$ is optionally substituted $C_{4-18}$ alkenyl. In some embodiments, $R^7$ is optionally substituted $C_{4-17}$ alkenyl. In some embodiments, $R^7$ is optionally substituted $C_{4-16}$ alkenyl. In some embodiments, $R^7$ is optionally substituted $C_{4-15}$ alkenyl. In some embodiments, $R^7$ is optionally substituted $C_{4-14}$ alkenyl. In some embodiments, $R^7$ is optionally substituted $C_{4-13}$ alkenyl. In some embodiments, $R^7$ is optionally substituted $C_{4-12}$ alkenyl. In some embodiments, $R^7$ is optionally substituted $C_{4-11}$ alkenyl. In some embodiments, $R^7$ is optionally substituted $C_{4-10}$ alkenyl. In some embodiments, $R^7$ is optionally substituted $C_{4-9}$ alkenyl. In some embodiments, $R^7$ is optionally substituted $C_{4-8}$ alkenyl. In some embodiments, $R^7$ is optionally substituted $C_{4-7}$ alkenyl. In some embodiments, $R^7$ is optionally substituted $C_{4-6}$ alkenyl.

In some embodiments, $R^7$ is optionally substituted $C_{6-50}$ alkenyl. In some embodiments, $R^7$ is optionally substituted $C_{6-40}$ alkenyl. In some embodiments, $R^7$ is optionally substituted $C_{6-30}$ alkenyl. In some embodiments, $R^7$ is optionally substituted $C_{6-20}$ alkenyl. In some embodiments, $R^7$ is optionally substituted $C_{6-19}$ alkenyl. In some embodiments, $R^7$ is optionally substituted $C_{6-18}$ alkenyl. In some embodiments, $R^7$ is optionally substituted $C_{6-17}$ alkenyl. In some embodiments, $R^7$ is optionally substituted $C_{6-16}$ alkenyl. In some embodiments, $R^7$ is optionally substituted $C_{6-15}$ alkenyl. In some embodiments, $R^7$ is optionally substituted $C_{6-14}$ alkenyl. In some embodiments, $R^7$ is optionally substituted $C_{6-13}$ alkenyl. In some embodiments, $R^7$ is optionally substituted $C_{6-12}$ alkenyl. In some embodiments, $R^7$ is optionally substituted $C_{6-11}$ alkenyl. In some embodiments, $R^7$ is optionally substituted $C_{6-10}$ alkenyl. In some embodiments, $R^7$ is optionally substituted $C_{6-9}$ alkenyl. In some embodiments, $R^7$ is optionally substituted $C_{6-8}$ alkenyl. In some embodiments, $R^7$ is optionally substituted $C_{6-7}$ alkenyl.

In some embodiments, $R^7$ is optionally substituted $C_{8-50}$ alkenyl. In some embodiments, $R^7$ is optionally substituted $C_{8-40}$ alkenyl. In some embodiments, $R^7$ is optionally substituted $C_{8-30}$ alkenyl. In some embodiments, $R^7$ is optionally substituted $C_{8-20}$ alkenyl. In some embodiments, $R^7$ is optionally substituted $C_{8-19}$ alkenyl. In some embodiments, $R^7$ is optionally substituted $C_{8-18}$ alkenyl. In some embodiments, $R^7$ is optionally substituted $C_{8-17}$ alkenyl. In some embodiments, $R^7$ is optionally substituted $C_{8-16}$ alkenyl. In some embodiments, $R^7$ is optionally substituted $C_{8-15}$ alkenyl. In some embodiments, $R^7$ is optionally substituted $C_{8-14}$ alkenyl. In some embodiments, $R^7$ is optionally substituted $C_{8-13}$ alkenyl. In some embodiments, $R^7$ is optionally substituted $C_{8-12}$ alkenyl. In some embodiments, $R^7$ is optionally substituted $C_{8-11}$ alkenyl. In some embodiments, $R^7$ is optionally substituted $C_{8-10}$ alkenyl. In some embodiments, $R^7$ is optionally substituted $C_{8-9}$ alkenyl.

In some embodiments, $R^7$ is optionally substituted $C_{9-50}$ alkenyl. In some embodiments, $R^7$ is optionally substituted $C_{9-40}$ alkenyl. In some embodiments, $R^7$ is optionally substituted $C_{9-30}$ alkenyl. In some embodiments, $R^7$ is optionally substituted $C_{9-20}$ alkenyl. In some embodiments, $R^7$ is optionally substituted $C_{9-19}$ alkenyl. In some embodiments, $R^7$ is optionally substituted $C_{9-18}$ alkenyl. In some embodiments, $R^7$ is optionally substituted $C_{9-17}$ alkenyl. In some embodiments, $R^7$ is optionally substituted $C_{9-16}$ alkenyl. In some embodiments, $R^7$ is optionally substituted $C_{9-15}$ alkenyl. In some embodiments, $R^7$ is optionally substituted $C_{9-14}$ alkenyl. In some embodiments, $R^7$ is optionally substituted $C_{9-13}$ alkenyl. In some embodiments, $R^7$ is optionally substituted $C_{9-12}$ alkenyl. In some embodiments, $R^7$ is optionally substituted $C_{9-11}$ alkenyl. In some embodiments, $R^7$ is optionally substituted $C_{9-10}$ alkenyl.

In some embodiments, $R^7$ is optionally substituted $C_{10-50}$ alkenyl. In some embodiments, $R^7$ is optionally substituted $C_{10-40}$ alkenyl. In some embodiments, $R^7$ is optionally substituted $C_{10-30}$ alkenyl. In some embodiments, $R^7$ is optionally substituted $C_{10-20}$ alkenyl. In some embodiments, $R^7$ is optionally substituted $C_{10-19}$ alkenyl. In some embodiments, $R^7$ is optionally substituted $C_{10-18}$ alkenyl. In some embodiments, $R^7$ is optionally substituted $C_{10-17}$ alkenyl. In some embodiments, $R^7$ is optionally substituted $C_{10-16}$ alkenyl. In some embodiments, $R^7$ is optionally substituted $C_{10-15}$ alkenyl. In some embodiments, $R^7$ is optionally substituted $C_{10-14}$ alkenyl. In some embodiments, $R^7$ is optionally substituted $C_{10-13}$ alkenyl. In some embodiments, $R^7$ is optionally substituted $C_{10-12}$ alkenyl. In some embodiments, $R^7$ is optionally substituted $C_{10-11}$ alkenyl.

In some embodiments, $R^7$ is optionally substituted $C_{11-50}$ alkenyl. In some embodiments, $R^7$ is optionally substituted $C_{11-40}$ alkenyl. In some embodiments, $R^7$ is optionally substituted $C_{11-30}$ alkenyl. In some embodiments, $R^7$ is optionally substituted $C_{11-20}$ alkenyl. In some embodiments, $R^7$ is optionally substituted $C_{11-19}$ alkenyl. In some embodiments, $R^7$ is optionally substituted $C_{11-18}$ alkenyl. In some embodiments, $R^7$ is optionally substituted $C_{11-17}$ alkenyl. In some embodiments, $R^7$ is optionally substituted $C_{11-16}$ alkenyl. In some embodiments, $R^7$ is optionally substituted $C_{11-15}$ alkenyl. In some embodiments, $R^7$ is optionally substituted $C_{11-14}$ alkenyl. In some embodiments, $R^7$ is optionally substituted $C_{11-13}$ alkenyl. In some embodiments, $R^7$ is optionally substituted $C_{11-12}$ alkenyl.

In some embodiments, $R^7$ is optionally substituted $C_{12-50}$ alkenyl. In some embodiments, $R^7$ is optionally substituted $C_{12-40}$ alkenyl. In some embodiments, $R^7$ is optionally substituted $C_{12-30}$ alkenyl. In some embodiments, $R^7$ is optionally substituted $C_{12-20}$ alkenyl. In some embodiments, $R^7$ is optionally substituted $C_{12-19}$ alkenyl. In some embodiments, $R^7$ is optionally substituted $C_{12-18}$ alkenyl. In some embodiments, $R^7$ is optionally substituted $C_{12-17}$ alkenyl. In some embodiments, $R^7$ is optionally substituted $C_{12-16}$ alkenyl. In some embodiments, $R^7$ is optionally substituted $C_{12-15}$ alkenyl. In some embodiments, $R^7$ is optionally substituted $C_{12-14}$ alkenyl. In some embodiments, $R^7$ is optionally substituted $C_{12-13}$ alkenyl.

In some embodiments, $R^7$ is optionally substituted $C_6$ alkenyl. In some embodiments, $R^7$ is optionally substituted $C_7$ alkenyl. In some embodiments, $R^7$ is optionally substituted $C_8$ alkenyl. In some embodiments, $R^7$ is optionally substituted $C_9$ alkenyl. In some embodiments, $R^7$ is optionally substituted $C_{10}$ alkenyl. In some embodiments, $R^7$ is optionally substituted $C_{11}$ alkenyl. In some embodiments, $R^7$ is optionally substituted $C_{12}$ alkenyl. In some embodiments, $R^7$ is optionally substituted $C_{13}$ alkenyl. In some embodiments, $R^7$ is optionally substituted $C_{14}$ alkenyl. In some embodiments, $R^7$ is optionally substituted $C_{15}$ alkenyl. In some embodiments, $R^7$ is optionally substituted $C_{16}$ alkenyl. In some embodiments, $R^7$ is optionally substituted $C_{17}$ alkenyl. In some embodiments, $R^7$ is optionally substituted $C_{11}$ alkenyl. In some embodiments, $R^7$ is optionally substituted $C_{19}$ alkenyl. In some embodiments, $R^7$ is optionally substituted $C_{20}$ alkenyl.

In some embodiments, for example, in any of the above embodiments, $R^7$ is a substituted alkenyl group. In some embodiments, $R^7$ is an unsubstituted alkenyl group. In some embodiments, $R^7$ is an optionally substituted straight-chain alkenyl group. In some embodiments, $R^7$ is a substituted straight-chain alkenyl group. In some embodiments, $R^7$ is an unsubstituted straight-chain alkenyl group. In some embodiments, $R^7$ is an optionally substituted branched alkenyl group. In some embodiments, $R^7$ is a substituted branched alkenyl group. In some embodiments, $R^7$ is an unsubstituted branched alkenyl group.

In some embodiments, $R^7$ is optionally substituted alkynyl. In some embodiments, $R^7$ is optionally substituted $C_{2-50}$ alkynyl. In some embodiments, $R^7$ is optionally substituted $C_{2-40}$ alkynyl. In some embodiments, $R^7$ is optionally substituted $C_{2-30}$ alkynyl. In some embodiments, $R^7$ is optionally substituted $C_{2-20}$ alkynyl. In some embodiments, $R^7$ is optionally substituted $C_{2-19}$ alkynyl. In some embodiments, $R^7$ is optionally substituted $C_{2-18}$ alkynyl. In some embodiments, $R^7$ is optionally substituted $C_{2-17}$ alkynyl. In some embodiments, $R^7$ is optionally substituted $C_{2-16}$ alkynyl. In some embodiments, $R^7$ is optionally substituted $C_{2-15}$ alkynyl. In some embodiments, $R^7$ is optionally substituted $C_{2-14}$ alkynyl. In some embodiments, $R^7$ is optionally substituted $C_{2-13}$ alkynyl. In some embodiments, $R^7$ is optionally substituted $C_{2-12}$ alkynyl. In some embodiments, $R^7$ is optionally substituted $C_{2-11}$ alkynyl. In some embodiments, $R^7$ is optionally substituted $C_{2-10}$ alkynyl. In some embodiments, $R^7$ is optionally substituted $C_{2-9}$ alkynyl. In some embodiments, $R^7$ is optionally substituted $C_{2-8}$ alkynyl. In some embodiments, $R^7$ is optionally substituted $C_{2-7}$ alkynyl. In some embodiments, $R^7$ is optionally substituted $C_{2-6}$ alkynyl.

In some embodiments, $R^7$ is optionally substituted $C_{4-50}$ alkynyl. In some embodiments, $R^7$ is optionally substituted $C_{4-40}$ alkynyl. In some embodiments, $R^7$ is optionally substituted $C_{4-30}$ alkynyl. In some embodiments, $R^7$ is optionally substituted $C_{4-20}$ alkynyl. In some embodiments, $R^7$ is optionally substituted $C_{4-19}$ alkynyl. In some embodiments, $R^7$ is optionally substituted $C_{4-18}$ alkynyl. In some embodiments, $R^7$ is optionally substituted $C_{4-17}$ alkynyl. In some embodiments, $R^7$ is optionally substituted $C_{4-16}$ alkynyl. In some embodiments, $R^7$ is optionally substituted $C_{4-15}$ alkynyl. In some embodiments, $R^7$ is optionally substituted $C_{4-14}$ alkynyl. In some embodiments, $R^7$ is optionally substituted $C_{4-13}$ alkynyl. In some embodiments, $R^7$ is optionally substituted $C_{4-12}$ alkynyl. In some embodiments, $R^7$ is optionally substituted $C_{4-11}$ alkynyl. In some embodiments, $R^7$ is optionally substituted $C_{4-10}$ alkynyl. In some embodiments, $R^7$ is optionally substituted $C_{4-9}$ alkynyl. In some embodiments, $R^7$ is optionally substituted $C_{4-8}$ alkynyl. In some embodiments, $R^7$ is optionally substituted $C_{4-7}$ alkynyl. In some embodiments, $R^7$ is optionally substituted $C_{4-6}$ alkynyl.

In some embodiments, $R^7$ is optionally substituted $C_{6-50}$ alkynyl. In some embodiments, $R^7$ is optionally substituted $C_{6-40}$ alkynyl. In some embodiments, $R^7$ is optionally substituted $C_{6-30}$ alkynyl. In some embodiments, $R^7$ is optionally substituted $C_{6-20}$ alkynyl. In some embodiments, $R^7$ is optionally substituted $C_{6-19}$ alkynyl. In some embodiments, $R^7$ is optionally substituted $C_{6-18}$ alkynyl. In some embodiments, $R^7$ is optionally substituted $C_{6-17}$ alkynyl. In some embodiments, $R^7$ is optionally substituted $C_{6-16}$ alkynyl. In some embodiments, $R^7$ is optionally substituted $C_{6-15}$ alkynyl. In some embodiments, $R^7$ is optionally substituted $C_{6-14}$ alkynyl. In some embodiments, $R^7$ is optionally substituted $C_{6-13}$ alkynyl. In some embodiments, $R^7$ is optionally substituted $C_{6-12}$ alkynyl. In some embodiments, $R^7$ is optionally substituted $C_{6-11}$ alkynyl. In some embodiments, $R^7$ is optionally substituted $C_{6-10}$ alkynyl. In some embodiments, $R^7$ is optionally substituted $C_{6-9}$ alkynyl. In some embodiments, $R^7$ is optionally substituted $C_{6-8}$ alkynyl. In some embodiments, $R^7$ is optionally substituted $C_{6-7}$ alkynyl.

In some embodiments, $R^7$ is optionally substituted $C_{8-50}$ alkynyl. In some embodiments, $R^7$ is optionally substituted $C_{8-40}$ alkynyl. In some embodiments, $R^7$ is optionally substituted $C_{8-30}$ alkynyl. In some embodiments, $R^7$ is optionally substituted $C_{8-20}$ alkynyl. In some embodiments, $R^7$ is optionally substituted $C_{8-19}$ alkynyl. In some embodiments, $R^7$ is optionally substituted $C_{8-18}$ alkynyl. In some embodiments, $R^7$ is optionally substituted $C_{8-17}$ alkynyl. In some embodiments, $R^7$ is optionally substituted $C_{8-16}$ alkynyl. In some embodiments, $R^7$ is optionally substituted $C_{5-15}$ alkynyl. In some embodiments, $R^7$ is optionally substituted $C_{8-14}$ alkynyl. In some embodiments, $R^7$ is optionally substituted $C_{8-13}$ alkynyl. In some embodiments, $R^7$ is optionally substituted $C_{8-12}$ alkynyl. In some embodiments, $R^7$ is optionally substituted $C_{8-11}$ alkynyl. In some embodiments, $R^7$ is optionally substituted $C_{8-10}$ alkynyl. In some embodiments, $R^7$ is optionally substituted $C_{8-9}$ alkynyl.

In some embodiments, $R^7$ is optionally substituted $C_9 50$ alkynyl. In some embodiments, $R^7$ is optionally substituted $C_{9-40}$ alkynyl. In some embodiments, $R^7$ is optionally substituted $C_{9-30}$ alkynyl. In some embodiments, $R^7$ is optionally substituted $C_{9-20}$ alkynyl. In some embodiments, $R^7$ is optionally substituted $C_{9-19}$ alkynyl. In some embodiments, $R^7$ is optionally substituted $C_{9-18}$ alkynyl. In some embodiments, $R^7$ is optionally substituted $C_{9-17}$ alkynyl. In some embodiments, $R^7$ is optionally substituted $C_{9-16}$ alkynyl. In some embodiments, $R^7$ is optionally substituted $C_{9-15}$ alkynyl. In some embodiments, $R^7$ is optionally substituted $C_{9-14}$ alkynyl. In some embodiments, $R^7$ is optionally substituted $C_{9-13}$ alkynyl. In some embodiments, $R^7$ is optionally substituted $C_{9-12}$ alkynyl. In some embodiments, $R^7$ is optionally substituted $C_{9-11}$ alkynyl. In some embodiments, $R^7$ is optionally substituted $C_{9-10}$ alkynyl.

In some embodiments, $R^7$ is optionally substituted $C_{10-50}$ alkynyl. In some embodiments, $R^7$ is optionally substituted $C_{10-40}$ alkynyl. In some embodiments, $R^7$ is optionally substituted $C_{10-30}$ alkynyl. In some embodiments, $R^7$ is optionally substituted $C_{10-20}$ alkynyl. In some embodiments, $R^7$ is optionally substituted $C_{10-19}$ alkynyl. In some embodiments, $R^7$ is optionally substituted $C_{10-18}$ alkynyl. In some embodiments, $R^7$ is optionally substituted $C_{10-17}$ alkynyl. In some embodiments, $R^7$ is optionally substituted $C_{10-16}$ alkynyl. In some embodiments, $R^7$ is optionally substituted $C_{10-15}$ alkynyl. In some embodiments, $R^7$ is optionally substituted $C_{10-14}$ alkynyl. In some embodiments, $R^7$ is optionally substituted $C_{10-13}$ alkynyl. In some embodiments, $R^7$ is optionally substituted $C_{10-12}$ alkynyl. In some embodiments, $R^7$ is optionally substituted $C_{10-11}$ alkynyl.

In some embodiments, $R^7$ is optionally substituted $C_{11-50}$ alkynyl. In some embodiments, $R^7$ is optionally substituted $C_{11-40}$ alkynyl. In some embodiments, $R^7$ is optionally substituted $C_{11-30}$ alkynyl. In some embodiments, $R^7$ is optionally substituted $C_{11-20}$ alkynyl. In some embodiments, $R^7$ is optionally substituted $C_{11-19}$ alkynyl. In some embodiments, $R^7$ is optionally substituted $C_{1-18}$ alkynyl. In some embodiments, $R^7$ is optionally substituted $C_{11-17}$ alkynyl. In some embodiments, $R^7$ is optionally substituted $C_{11-16}$ alkynyl. In some embodiments, $R^7$ is optionally substituted $C_{11-15}$ alkynyl. In some embodiments, $R^7$ is optionally substituted $C_{11-14}$ alkynyl. In some embodiments, $R^7$ is optionally substituted $C_{11-13}$ alkynyl. In some embodiments, $R^7$ is optionally substituted $C_{11-12}$ alkynyl.

In some embodiments, $R^7$ is optionally substituted $C_{12-50}$ alkynyl. In some embodiments, $R^7$ is optionally substituted $C_{12-40}$ alkynyl. In some embodiments, $R^7$ is optionally substituted $C_{12-30}$ alkynyl. In some embodiments, $R^7$ is optionally substituted $C_{12-20}$ alkynyl. In some embodiments, $R^7$ is optionally substituted $C_{12-19}$ alkynyl. In some embodiments, $R^7$ is optionally substituted $C_{12-18}$ alkynyl. In some embodiments, $R^7$ is optionally substituted $C_{12-17}$ alkynyl. In some embodiments, $R^7$ is optionally substituted $C_{12-16}$ alkynyl. In some embodiments, $R^7$ is optionally substituted $C_{12-15}$ alkynyl. In some embodiments, $R^7$ is optionally substituted $C_{12-14}$ alkynyl. In some embodiments, $R^7$ is optionally substituted $C_{12-13}$ alkynyl.

In some embodiments, $R^7$ is optionally substituted $C_6$ alkynyl. In some embodiments, $R^7$ is optionally substituted $C_7$ alkynyl. In some embodiments, $R^7$ is optionally substituted $C_8$ alkynyl. In some embodiments, $R^7$ is optionally substituted $C_9$ alkynyl. In some embodiments, $R^7$ is optionally substituted $C_{10}$ alkynyl. In some embodiments, $R^7$ is optionally substituted $C_{11}$ alkynyl. In some embodiments, $R^7$ is optionally substituted $C_{12}$ alkynyl. In some embodiments, $R^7$ is optionally substituted $C_{13}$ alkynyl. In some embodiments, $R^7$ is optionally substituted $C_{14}$ alkynyl. In some embodiments, $R^7$ is optionally substituted $C_{15}$ alkynyl. In some embodiments, $R^7$ is optionally substituted $C_{16}$ alkynyl. In some embodiments, $R^7$ is optionally substituted $C_{17}$ alkynyl. In some embodiments, $R^7$ is optionally substituted $C_{18}$ alkynyl. In some embodiments, $R^7$ is optionally substituted $C_{19}$ alkynyl. In some embodiments, $R^7$ is optionally substituted $C_{20}$ alkynyl.

In some embodiments, for example, in any of the above embodiments, $R^7$ is a substituted alkynyl group. In some embodiments, $R^7$ is an unsubstituted alkynyl group. In some embodiments, $R^7$ is an optionally substituted straight-chain alkynyl group. In some embodiments, $R^7$ is a substituted straight-chain alkynyl group. In some embodiments, $R^7$ is an unsubstituted straight-chain alkynyl group. In some embodiments, $R^7$ is an optionally substituted branched alkynyl group. In some embodiments, $R^7$ is a substituted branched alkynyl group. In some embodiments, $R^7$ is an unsubstituted branched alkynyl group.

In some embodiments, $R^7$ is optionally substituted carbocyclyl. In some embodiments, $R^7$ is optionally substituted heterocyclyl. In some embodiments, $R^7$ is optionally substituted aryl. In some embodiments, $R^7$ is optionally substituted heteroaryl. In some embodiments, $R^7$ is a nitrogen protecting group.

In some embodiments, $R^7$ is a group of formula (i). In some embodiments, $R^7$ is a $$\underset{\xi}{\overset{R^L}{\diagdown}}\!\!-\!\!\mathrm{OH}. \qquad (\text{i-a1})$$

group of formula (i-a). In some embodiments, $R^7$ is a group of formula (i-a1). In some embodiments, $R^7$ is a group of formula (i-b). In some embodiments, $R^7$ is a group of formula (ii). In some embodiments, $R^7$ is a group of formula (iii).

In some embodiments, at least one instance of $R^6$ and $R^7$ is a group of the formula (i), (ii) or (iii). In some embodiments, each instance of $R^6$ and $R^7$ is independently a group of the formula (i), (ii) or (iii). In some embodiments, each instance of $R^6$ and $R^7$ is independently a group of the formula (i). In some embodiments, each instance of $R^6$ and $R^7$ is independently a group of the formula (i-a). In some embodiments, each instance of $R^6$ and $R^7$ is independently a group of the formula (i-b). In some embodiments, each instance of $R^6$ and $R^7$ is independently a group of the formula (ii). In some embodiments, each instance of $R^6$ and $R^7$ is independently a group of the formula (iii).

In some embodiments, $R^6$ and $R^7$ are the same. In some embodiments, $R^6$ and $R^7$ are different.

In certain embodiments, both $R^6$ and $R^7$ are hydrogen. In certain embodiments, $R^6$ is hydrogen and $R^7$ is a group of the formula (i), (ii), or (iii). In certain embodiments, $R^6$ is hydrogen and $R^7$ is a group of the formula (i). In certain embodiments, $R^6$ is hydrogen and $R^7$ is a group of the formula (ii). In certain embodiments, $R^6$ is hydrogen and $R^7$ is a group of the formula (iii). In certain embodiments, each of $R^6$ and $R^7$ is independently a group of the formula (i), (ii), or (iii). In certain embodiments, each of $R^6$ and $R^7$ is independently a group of the formula (i). In certain embodiments, each of $R^6$ and $R^7$ is independently a group of the formula (ii). In certain embodiments, each of $R^6$ and $R^7$ is independently a group of the formula (iii). In certain embodiments, $R^6$ and $R^7$ are the same group, which is selected from formulas (i), (ii), and (iii). In some embodiments, $R^6$ and $R^7$ are the same group of formula (i). In some embodiments, $R^6$ and $R^7$ are the same group of formula (i-a). In some embodiments, $R^6$ and $R^7$ are the same group of formula (i-a1). In some embodiments, $R^6$ and $R^7$ are the same group of formula (i-b).

In some embodiments, $R^6$ and $R^7$ are the same group of formula

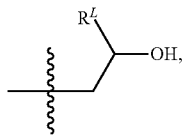
(i-a1)

wherein $R^L$ is as defined above and described herein. In some embodiments, $R^6$ and $R^7$ are the same group of formula

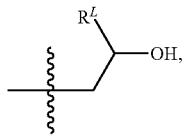
(i-a1)

wherein $R^L$ is optionally substituted $C_{1-50}$ alkyl, optionally substituted $C_{2-50}$ alkenyl, optionally substituted $C_{2-50}$ alkynyl, optionally substituted heteroC$_{1-50}$ alkyl, optionally substituted heteroC$_{2-50}$ alkenyl, or optionally substituted heteroC$_{2-50}$ alkynyl. In some embodiments, $R^6$ and $R^7$ are the same group of formula

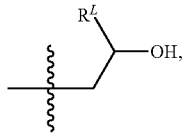
(i-a1)

wherein $R^L$ is optionally substituted $C_{5-50}$ alkyl, optionally substituted $C_{5-50}$ alkenyl, optionally substituted $C_{5-50}$ alkynyl, optionally substituted heteroC$_{5-50}$ alkyl, optionally substituted heteroC$_{5-50}$ alkenyl, or optionally substituted heteroC$_{5-50}$ alkynyl. In some embodiments, $R^6$ and $R^7$ are the same group of formula

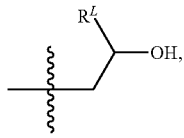
(i-a1)

wherein $R^L$ is optionally substituted $C_{5-40}$ alkyl, optionally substituted $C_{5-40}$ alkenyl, optionally substituted $C_{5-40}$ alkynyl, optionally substituted heteroC$_{5-40}$ alkyl, optionally substituted heteroC$_{5-40}$ alkenyl, or optionally substituted heteroC$_{5-40}$ alkynyl. In some embodiments, $R^6$ and $R^7$ are the same group of formula

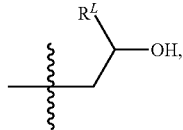
(i-a1)

wherein $R^L$ is optionally substituted $C_{5-30}$ alkyl, optionally substituted $C_{5-30}$ alkenyl, optionally substituted $C_{5-30}$ alkynyl, optionally substituted heteroC$_{5-30}$ alkyl, optionally substituted heteroC$_{5-30}$ alkenyl, or optionally substituted heteroC$_{5-30}$ alkynyl. In some embodiments, $R^6$ and $R^7$ are the same group of formula

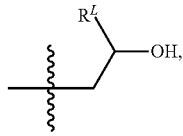
(i-a1)

wherein $R^L$ is optionally substituted $C_{5-25}$ alkyl, optionally substituted $C_{5-25}$ alkenyl, optionally substituted $C_{5-25}$ alkynyl, optionally substituted heteroC$_{5-25}$ alkyl, optionally substituted heteroC$_{5-25}$ alkenyl, or optionally substituted heteroC$_{5-25}$ alkynyl. In some embodiments, $R^6$ and $R^7$ are the same group of formula

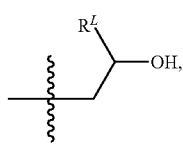
(i-a1)

wherein $R^L$ is optionally substituted $C_{5-20}$ alkyl, optionally substituted $C_{5-20}$ alkenyl, optionally substituted $C_{5-20}$ alkynyl, optionally substituted heteroC$_{5-20}$ alkyl, optionally substituted heteroC$_{5-20}$ alkenyl, or optionally substituted heteroC$_{5-20}$ alkynyl. In some embodiments, $R^6$ and $R^7$ are the same group of formula

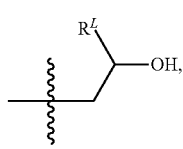
(i-a1)

wherein $R^L$ is optionally substituted $C_{5-15}$ alkyl, optionally substituted $C_{5-15}$ alkenyl, optionally substituted $C_{5-15}$ alkynyl, optionally substituted heteroC$_{5-15}$ alkyl, optionally substituted heteroC$_{5-15}$ alkenyl, or optionally substituted heteroC$_{5-15}$ alkynyl. In some embodiments, $R^6$ and $R^7$ are the same group of formula

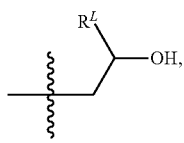

(i-a1)

wherein $R^L$ is optionally substituted $C_5$ alkyl, optionally substituted $C_5$ alkenyl, optionally substituted $C_5$ alkynyl, optionally substituted heteroC$_5$ alkyl, optionally substituted heteroC$_5$ alkenyl, or optionally substituted heteroC$_5$ alkynyl. In some embodiments, $R^6$ and $R^7$ are the same group of formula

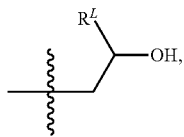

(i-a1)

wherein $R^L$ is optionally substituted $C_6$ alkyl, optionally substituted $C_6$ alkenyl, optionally substituted $C_6$ alkynyl, optionally substituted heteroC$_6$alkyl, optionally substituted heteroC$_6$alkenyl, or optionally substituted heteroC$_6$alkynyl. In some embodiments, $R^6$ and $R^7$ are the same group of formula

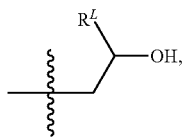

(i-a1)

wherein $R^L$ is optionally substituted $C_7$ alkyl, optionally substituted $C_7$ alkenyl, optionally substituted $C_7$ alkynyl, optionally substituted heteroC$_7$alkyl, optionally substituted heteroC$_7$alkenyl, or optionally substituted heteroC$_7$alkynyl. In some embodiments, $R^6$ and $R^7$ are the same group of formula

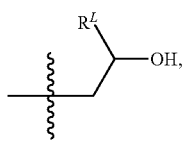

(i-a1)

wherein $R^L$ is optionally substituted $C_8$ alkyl, optionally substituted $C_8$ alkenyl, optionally substituted $C_8$ alkynyl, optionally substituted heteroC$_8$alkyl, optionally substituted heteroC$_8$alkenyl, or optionally substituted heteroC$_8$alkynyl. In some embodiments, $R^6$ and $R^7$ are the same group of formula

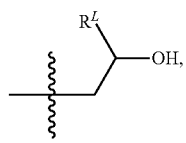

(i-a1)

wherein $R^L$ is optionally substituted $C_9$ alkyl, optionally substituted $C_9$ alkenyl, optionally substituted $C_9$ alkynyl, optionally substituted heteroC$_9$alkyl, optionally substituted heteroC$_9$alkenyl, or optionally substituted heteroC$_9$alkynyl. In some embodiments, $R^6$ and $R^7$ are the same group of formula

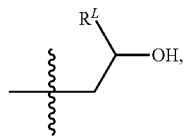

(i-a1)

wherein $R^L$ is optionally substituted $C_{10}$ alkyl, optionally substituted $C_{10}$ alkenyl, optionally substituted $C_{10}$ alkynyl, optionally substituted heteroC$_{10}$alkyl, optionally substituted heteroC$_{10}$alkenyl, or optionally substituted heteroC$_{10}$alkynyl. In some embodiments, $R^6$ and $R^7$ are the same group of formula

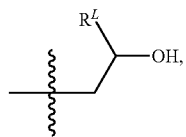

(i-a1)

wherein $R^L$ is optionally substituted $C_{11}$ alkyl, optionally substituted $C_{11}$ alkenyl, optionally substituted $C_{11}$ alkynyl, optionally substituted heteroC$_{11}$alkyl, optionally substituted heteroC$_{11}$alkenyl, or optionally substituted heteroC$_{11}$alkynyl. In some embodiments, $R^6$ and $R^7$ are the same group of formula

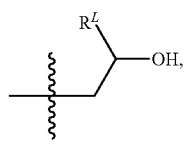

(i-a1)

wherein $R^L$ is optionally substituted $C_{12}$ alkyl, optionally substituted $C_{12}$ alkenyl, optionally substituted $C_{12}$ alkynyl, optionally substituted heteroC$_{12}$alkyl, optionally substituted heteroC$_{12}$alkenyl, or optionally substituted heteroC$_{12}$alkynyl. In some embodiments, $R^6$ and $R^7$ are the same group of formula

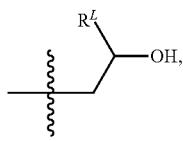
(i-a1)

wherein $R^L$ is optionally substituted $C_{13}$ alkyl, optionally substituted $C_{13}$ alkenyl, optionally substituted $C_{13}$ alkynyl, optionally substituted heteroC$_{13}$alkyl, optionally substituted heteroC$_{13}$alkenyl, or optionally substituted heteroC$_{13}$alkynyl. In some embodiments, $R^6$ and $R^7$ are the same group of formula

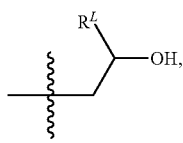
(i-a1)

wherein $R^L$ is optionally substituted $C_{14}$ alkyl, optionally substituted $C_{14}$ alkenyl, optionally substituted $C_{14}$ alkynyl, optionally substituted heteroC$_{14}$alkyl, optionally substituted heteroC$_{14}$alkenyl, or optionally substituted heteroC$_{14}$alkynyl. In some embodiments, $R^6$ and $R^7$ are the same group of formula

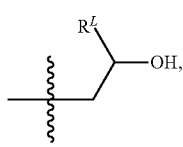
(i-a1)

wherein $R^L$ is optionally substituted $C_{15}$ alkyl, optionally substituted $C_{15}$ alkenyl, optionally substituted $C_{15}$ alkynyl, optionally substituted heteroC$_{15}$alkyl, optionally substituted heteroC$_{15}$alkenyl, or optionally substituted heteroC$_{15}$alkynyl.

In some embodiments, $R^6$ and $R^7$ are the same group of formula

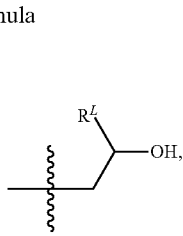
(i-a1)

wherein $R^L$ is as defined above and described herein. In some embodiments, $R^6$ and $R^7$ are the same group of formula

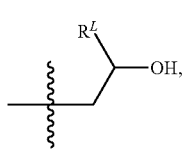
(i-a1)

wherein $R^L$ is optionally substituted $C_{1-50}$ alkyl. In some embodiments, $R^6$ and $R^7$ are the same group of formula

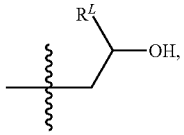
(i-a1)

wherein $R^L$ is optionally substituted $C_{5-50}$alkyl. In some embodiments, $R^6$ and $R^7$ are the same group of formula

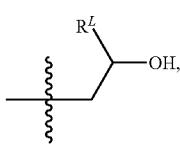
(i-a1)

wherein $R^L$ is optionally substituted $C_{5-40}$alkyl. In some embodiments, $R^6$ and $R^7$ are the same group of formula

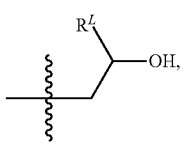
(i-a1)

wherein $R^L$ is optionally substituted $C_{5-30}$alkyl. In some embodiments, $R^6$ and $R^7$ are the same group of formula

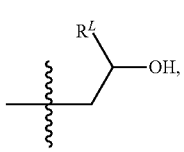
(i-a1)

wherein $R^L$ is optionally substituted $C_{5-25}$alkyl. In some embodiments, $R^6$ and $R^7$ are the same group of formula

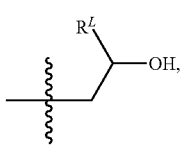
(i-a1)

wherein $R^L$ is optionally substituted $C_{5-20}$alkyl. In some embodiments, $R^6$ and $R^7$ are the same group of formula

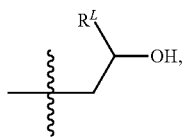
(i-a1)

wherein $R^L$ is optionally substituted $C_{5-15}$alkyl. In some embodiments, $R^6$ and $R^7$ are the same group of formula

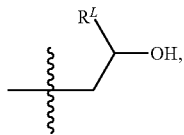
(i-a1)

wherein $R^L$ is optionally substituted $C_5$ alkyl. In some embodiments, $R^6$ and $R^7$ are the same group of formula

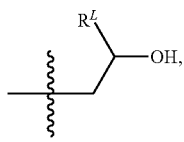
(i-a1)

wherein $R^L$ is optionally substituted $C_6$ alkyl. In some embodiments, $R^6$ and $R^7$ are the same group of formula

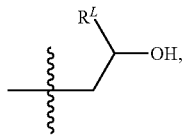
(i-a1)

wherein $R^L$ is optionally substituted $C_7$ alkyl. In some embodiments, $R^6$ and $R^7$ are the same group of formula

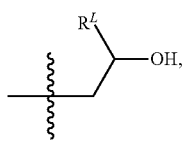
(i-a1)

wherein $R^L$ is optionally substituted $C_8$ alkyl. In some embodiments, $R^6$ and $R^7$ are the same group of formula

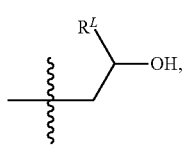
(i-a1)

wherein $R^L$ is optionally substituted $C_9$ alkyl. In some embodiments, $R^6$ and $R^7$ are the same group of formula

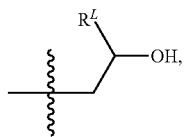
(i-a1)

wherein $R^L$ is optionally substituted $C_{10}$ alkyl. In some embodiments, $R^6$ and $R^7$ are the same group of formula

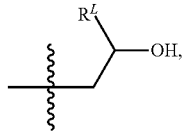
(i-a1)

wherein $R^L$ is optionally substituted $C_{11}$ alkyl. In some embodiments, $R^6$ and $R^7$ are the same group of formula

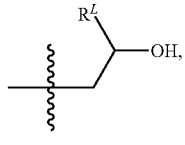
(i-a1)

wherein $R^L$ is optionally substituted $C_{12}$ alkyl. In some embodiments, $R^6$ and $R^7$ are the same group of formula

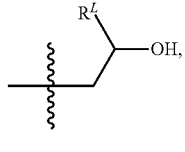
(i-a1)

wherein $R^L$ is optionally substituted $C_{13}$ alkyl. In some embodiments, $R^6$ and $R^7$ are the same group of formula

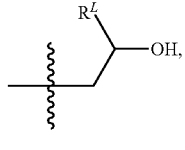
(i-a1)

wherein $R^L$ is optionally substituted $C_{14}$ alkyl. In some embodiments, $R^6$ and $R^7$ are the same group of formula

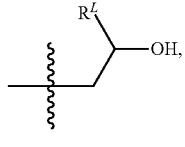
(i-a1)

wherein $R^L$ is optionally substituted $C_{15}$ alkyl.

As generally defined above, each occurrence of $R^{41}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to an sulfur atom, a nitrogen protecting group when attached to a nitrogen atom, or two $R^{41}$ groups, together with the nitrogen atom to which they are attached, are joined to form an optionally substituted heterocyclic or optionally substituted heteroaryl ring.

In some embodiments, $R^{41}$ is hydrogen. In some embodiments, $R^{41}$ is optionally substituted alkyl. In some embodiments, $R^{41}$ is optionally substituted alkenyl. In some embodiments, $R^{41}$ is optionally substituted alkynyl. In some embodiments, $R^{41}$ is optionally substituted carbocyclyl. In some embodiments, $R^{41}$ is optionally substituted heterocyclyl. In some embodiments, $R^{41}$ is optionally substituted aryl. In some embodiments, $R^{41}$ is optionally substituted heteroaryl. In some embodiments, $R^{41}$ is an oxygen protecting group when attached to an oxygen atom. In some embodiments, $R^{41}$ is a sulfur protecting group when attached to a sulfur atom. In some embodiments, $R^{41}$ is a nitrogen protecting group when attached to a nitrogen atom. In some embodiments, two $R^{41}$ groups, together with the nitrogen atom to which they are attached, are joined to form an optionally substituted heterocyclic or optionally substituted heteroaryl ring.

As generally defined above, each instance of $R^2$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of the formula (i), (ii), or (iii):

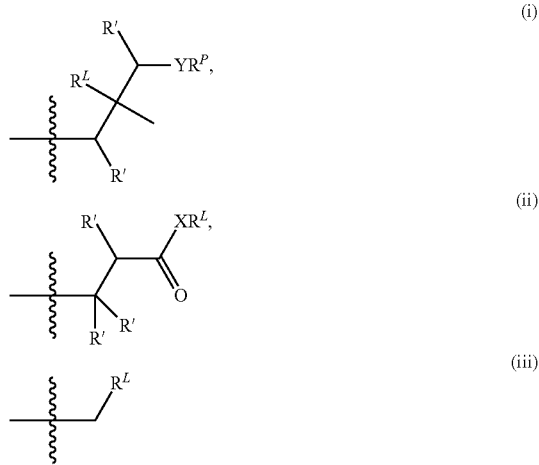

wherein each of R', Y, $R^P$, $R^L$ and X is independently as defined above and described herein.

In some embodiments, $R^2$ is hydrogen. In some embodiments, at least one instance of $R^2$ is hydrogen. In some embodiments, each instance of $R^2$ is hydrogen.

In certain embodiments, $R^2$ is optionally substituted alkyl; e.g., optionally substituted $C_{1-6}$alkyl, optionally substituted $C_{2-6}$alkyl, optionally substituted $C_{3-6}$alkyl, optionally substituted $C_{4-6}$alkyl, optionally substituted $C_{4-5}$alkyl, or optionally substituted $C_{3-4}$alkyl. In certain embodiments, at least one instance of $R^2$ is optionally substituted alkyl; e.g., optionally substituted $C_{1-6}$alkyl, optionally substituted $C_{2-6}$alkyl, optionally substituted $C_{3-6}$alkyl, optionally substituted $C_{4-6}$alkyl, optionally substituted $C_{4-5}$alkyl, or optionally substituted $C_{3-4}$alkyl.

In certain embodiments, $R^2$ is optionally substituted alkenyl, e.g., optionally substituted $C_{2-6}$alkenyl, optionally substituted $C_{3-6}$alkenyl, optionally substituted $C_{4-6}$alkenyl, optionally substituted $C_{4-5}$alkenyl, or optionally substituted $C_{3-4}$alkenyl. In certain embodiments, at least one instance of $R^2$ is optionally substituted alkenyl, e.g., optionally substituted $C_{2-6}$alkenyl, optionally substituted $C_{3-6}$alkenyl, optionally substituted $C_{4-6}$alkenyl, optionally substituted $C_{4-5}$alkenyl, or optionally substituted $C_{3-4}$alkenyl.

In certain embodiments, $R^2$ is optionally substituted alkynyl, e.g., optionally substituted $C_{2-6}$alkynyl, optionally substituted $C_{3-6}$alkynyl, optionally substituted $C_{4-6}$alkynyl, optionally substituted $C_{4-5}$alkynyl, or optionally substituted $C_{3-4}$alkynyl. In certain embodiments, at least one instance of $R^2$ is optionally substituted alkynyl, e.g., optionally substituted $C_{2-6}$alkynyl, optionally substituted $C_{3-6}$alkynyl, optionally substituted $C_{4-6}$alkynyl, optionally substituted $C_{4-5}$alkynyl, or optionally substituted $C_{3-4}$alkynyl.

In certain embodiments, $R^2$ is optionally substituted carbocyclyl, e.g., optionally substituted $C_{3-10}$carbocyclyl, optionally substituted $C_{5-8}$carbocyclyl, optionally substituted $C_{5-6}$carbocyclyl, optionally substituted $C_5$ carbocyclyl, or optionally substituted $C_6$ carbocyclyl. In certain embodiments, at least one instance of $R^2$ is optionally substituted carbocyclyl, e.g., optionally substituted $C_{3-10}$carbocyclyl, optionally substituted $C_{5-8}$carbocyclyl, optionally substituted $C_{5-6}$carbocyclyl, optionally substituted $C_5$ carbocyclyl, or optionally substituted $C_6$ carbocyclyl.

In certain embodiments, $R^2$ is optionally substituted heterocyclyl, e.g., optionally substituted 3-14 membered heterocyclyl, optionally substituted 3-10 membered heterocyclyl, optionally substituted 5-8 membered heterocyclyl, optionally substituted 5-6 membered heterocyclyl, optionally substituted 5-membered heterocyclyl, or optionally substituted 6-membered heterocyclyl. In certain embodiments, at least one instance of $R^2$ is optionally substituted heterocyclyl, e.g., optionally substituted 3-14 membered heterocyclyl, optionally substituted 3-10 membered heterocyclyl, optionally substituted 5-8 membered heterocyclyl, optionally substituted 5-6 membered heterocyclyl, optionally substituted 5-membered heterocyclyl, or optionally substituted 6-membered heterocyclyl.

In certain embodiments, $R^2$ is optionally substituted aryl, e.g., optionally substituted phenyl. In some embodiments, $R^2$ is optionally substituted phenyl. In some embodiments, $R^2$ is substituted phenyl. In some embodiments, $R^2$ is unsubstituted phenyl. In certain embodiments, at least one instance of $R^2$ is optionally substituted aryl, e.g., optionally substituted phenyl. In some embodiments, at least one instance of $R^2$ is optionally substituted phenyl. In some embodiments, at least one instance of $R^2$ is substituted phenyl. In some embodiments, at least one instance of $R^2$ is unsubstituted phenyl.

In certain embodiments, $R^2$ is optionally substituted heteroaryl, e.g., optionally substituted 5-14 membered heteroaryl, optionally substituted 5-10 membered heteroaryl, optionally substituted 5-6 membered heteroaryl, optionally substituted 5-membered heteroaryl, or optionally substituted 6-membered heteroaryl. In certain embodiments, at least one instance of $R^2$ is optionally substituted heteroaryl, e.g., optionally substituted 5-14 membered heteroaryl, optionally substituted 5-10 membered heteroaryl, optionally substituted 5-6 membered heteroaryl, optionally substituted 5-membered heteroaryl, or optionally substituted 6-membered heteroaryl.

In some embodiments, $R^2$ is a nitrogen protecting group. In some embodiments, at least one $R^2$ is a nitrogen protecting group.

In certain embodiments, $R^2$ is a group of the formula (i). In certain embodiments, $R^2$ is a group of the formula (ii). In certain embodiments, $R^2$ is a group of the formula (iii). In certain embodiments, at least one instance of $R^2$ is a group of the formula (i). In certain embodiments, at least one instance of $R^2$ is a group of the formula (ii). In certain embodiments, at least one instance of $R^2$ is a group of the formula (iii).

In certain embodiments, each instance of $R^2$ is a group other than formula (i), (ii), or (iii); in that instance, it follows that at least one $R^Q$ is a group of the formula (i), (ii), or (iii), or at least one $R^1$ is a group of formula (iv), and at least one of $R^6$ or $R^7$ encompassed by $R^1$ is a group of the formula (i), (ii), or (iii). For example, in certain embodiments, both instances of $R^2$ are hydrogen, and thus at least one $R^Q$ is a group of the formula (i), (ii), or (iii), or at least one $R^1$ is a group of formula (iv), and at least one of $R^6$ or $R^7$ encompassed by $R^1$ is a group of the formula (i), (ii), or (iii).

As generally defined above, each instance of R' is independently hydrogen or optionally substituted alkyl. In some embodiments, R' is hydrogen. In some embodiments, R' is substituted alkyl. In certain embodiments, at least one instance of R' is hydrogen. In certain embodiments, at least two instances of R' is hydrogen. In certain embodiments, each instance of R' is hydrogen. In certain embodiments, at least one instance of R' is optionally substituted alkyl, e.g., methyl. In certain embodiments, at least two instances of R' is optionally substituted alkyl, e.g., methyl. In some embodiments, at least one instance of R' is hydrogen, and at least one instance of R' is optionally substituted alkyl. In certain embodiments, one instance of R' is optionally substituted alkyl, and the rest are hydrogen.

As generally defined above, X is O, S, or $NR^X$. In some embodiments, X is O. In some embodiments, X is S. In some embodiments, X is $NR^X$, wherein $R^X$ is as defined above and described herein.

As generally defined above, $R^X$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group. In some embodiments, $R^X$ is hydrogen. In some embodiments, $R^X$ is optionally substituted alkyl. In some embodiments, $R^X$ is optionally substituted alkenyl. In some embodiments, $R^X$ is optionally substituted alkynyl. In some embodiments, $R^X$ is optionally substituted carbocyclyl. In some embodiments, $R^X$ is optionally substituted heterocyclyl. In some embodiments, $R^X$ is optionally substituted aryl. In some embodiments, $R^X$ is optionally substituted heteroaryl. In some embodiments, $R^X$ is a nitrogen protecting group.

As generally defined above, Y is O, S, or $NR^Y$. In some embodiments, Y is O. In some embodiments, Y is S. In some embodiments, Y is $NR^Y$, wherein $R^Y$ is as defined above and described herein.

As generally defined above, $R^Y$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group. In some embodiments, $R^Y$ is hydrogen. In some embodiments, $R^Y$ is optionally substituted alkyl. In some embodiments, $R^Y$ is optionally substituted alkenyl. In some embodiments, $R^Y$ is optionally substituted alkynyl. In some embodiments, $R^Y$ is is optionally substituted carbocyclyl. In some embodiments, $R^Y$ is optionally substituted heterocyclyl. In some embodiments, $R^Y$ is optionally substituted aryl. In some embodiments, $R^Y$ is is optionally substituted heteroaryl. In some embodiments, $R^Y$ is a nitrogen protecting group.

As generally defined above, $R^P$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to a sulfur atom, or a nitrogen protecting group when attached to a nitrogen atom. In some embodiments, $R^P$ is hydrogen. In some embodiments, $R^P$ is optionally substituted alkyl. In some embodiments, $R^P$ is optionally substituted alkenyl. In some embodiments, $R^P$ is optionally substituted alkynyl. In some embodiments, $R^P$ is optionally substituted carbocyclyl. In some embodiments, $R^P$ is optionally substituted heterocyclyl. In some embodiments, $R^P$ is optionally substituted aryl. In some embodiments, $R^P$ is optionally substituted heteroaryl. In some embodiments, $R^P$ is an oxygen protecting group when attached to an oxygen atom. In some embodiments, $R^1$ is a sulfur protecting group when attached to a sulfur atom. In some embodiments, $R^1$ is a nitrogen protecting group when attached to a nitrogen atom.

As generally defined above, $R^L$ is optionally substituted $C_{1-50}$ alkyl, optionally substituted $C_{2-50}$ alkenyl, optionally substituted $C_{2-50}$ alkynyl, optionally substituted heteroC$_{15-50}$ alkyl, optionally substituted heteroC$_{2-50}$ alkenyl, optionally substituted heteroC$_{2-50}$ alkynyl, or a polymer.

In some embodiments, $R^L$ is optionally substituted $C_{1-50}$ alkyl. In some embodiments, $R^L$ is optionally substituted $C_{2-50}$ alkyl. In some embodiments, $R^L$ is optionally substituted $C_{2-40}$ alkyl. In some embodiments, $R^L$ is optionally substituted $C_{2-30}$ alkyl. In some embodiments, $R^L$ is optionally substituted $C_{2-20}$ alkyl. In some embodiments, $R^L$ is optionally substituted $C_{2-19}$ alkyl. In some embodiments, $R^L$ is optionally substituted $C_{2-18}$ alkyl. In some embodiments, $R^L$ is optionally substituted $C_{2-17}$ alkyl. In some embodiments, $R^L$ is optionally substituted $C_{2-16}$ alkyl. In some embodiments, $R^L$ is optionally substituted $C_{2-15}$ alkyl. In some embodiments, $R^L$ is optionally substituted $C_{2-14}$ alkyl. In some embodiments, $R^L$ is optionally substituted $C_{2-13}$ alkyl. In some embodiments, $R^L$ is optionally substituted $C_{2-12}$ alkyl. In some embodiments, $R^L$ is optionally substituted $C_{2-11}$ alkyl. In some embodiments, $R^L$ is optionally substituted $C_{2-10}$ alkyl. In some embodiments, $R^L$ is optionally substituted $C_{2-9}$ alkyl. In some embodiments, $R^L$ is optionally substituted $C_{2-8}$ alkyl. In some embodiments, $R^L$ is optionally substituted $C_{2-7}$ alkyl. In some embodiments, $R^L$ is optionally substituted $C_{2-6}$ alkyl.

In some embodiments, $R^L$ is optionally substituted $C_{4-50}$ alkyl. In some embodiments, $R^L$ is optionally substituted $C_{4-40}$ alkyl. In some embodiments, $R^L$ is optionally substituted $C_{4-30}$ alkyl. In some embodiments, $R^L$ is optionally substituted $C_{4-20}$ alkyl. In some embodiments, $R^L$ is optionally substituted $C_{4-19}$ alkyl. In some embodiments, $R^L$ is optionally substituted $C_{4-18}$ alkyl. In some embodiments, $R^L$ is optionally substituted $C_{4-17}$ alkyl. In some embodiments, $R^L$ is optionally substituted $C_{4-16}$ alkyl. In some embodiments, $R^L$ is optionally substituted $C_{4-15}$ alkyl. In some embodiments, $R^L$ is optionally substituted $C_{4-14}$ alkyl. In some embodiments, $R^L$ is optionally substituted $C_{4-13}$ alkyl.

In some embodiments, $R^L$ is optionally substituted $C_{4-12}$ alkyl. In some embodiments, $R^L$ is optionally substituted $C_{4-10}$ alkyl. In some embodiments, $R^L$ is optionally substituted $C_{4-10}$alkyl. In some embodiments, $R^L$ is optionally substituted $C_{4-9}$ alkyl. In some embodiments, $R^L$ is optionally substituted $C_{4-8}$ alkyl. In some embodiments, $R^L$ is optionally substituted $C_{4-7}$ alkyl. In some embodiments, $R^L$ is optionally substituted $C_{4-6}$ alkyl.

In some embodiments, $R^L$ is optionally substituted $C_{6-50}$ alkyl. In some embodiments, $R^L$ is optionally substituted $C_{6-40}$ alkyl. In some embodiments, $R^L$ is optionally substituted $C_{6-30}$ alkyl. In some embodiments, $R^L$ is optionally substituted $C_{6-20}$ alkyl. In some embodiments, $R^L$ is optionally substituted $C_{6-19}$ alkyl. In some embodiments, $R^L$ is optionally substituted $C_{6-18}$ alkyl. In some embodiments, $R^L$ is optionally substituted $C_{6-17}$ alkyl. In some embodiments, $R^L$ is optionally substituted $C_{6-16}$ alkyl. In some embodiments, $R^L$ is optionally substituted $C_{6-15}$ alkyl. In some embodiments, $R^L$ is optionally substituted $C_{6-14}$ alkyl. In some embodiments, $R^L$ is optionally substituted $C_{6-13}$ alkyl. In some embodiments, $R^L$ is optionally substituted $C_{6-12}$ alkyl. In some embodiments, $R^L$ is optionally substituted $C_{6-11}$ alkyl. In some embodiments, $R^L$ is optionally substituted $C_{6-10}$ alkyl. In some embodiments, $R^L$ is optionally substituted $C_{6-9}$ alkyl. In some embodiments, $R^L$ is optionally substituted $C_{6-8}$ alkyl. In some embodiments, $R^L$ is optionally substituted $C_{6-7}$ alkyl.

In some embodiments, $R^L$ is optionally substituted $C_{8-50}$ alkyl. In some embodiments, $R^L$ is optionally substituted $C_{8-40}$ alkyl. In some embodiments, $R^L$ is optionally substituted $C_{8-30}$ alkyl. In some embodiments, $R^L$ is optionally substituted $C_{8-20}$ alkyl. In some embodiments, $R^L$ is optionally substituted $C_{8-19}$ alkyl. In some embodiments, $R^L$ is optionally substituted $C_{8-18}$ alkyl. In some embodiments, $R^L$ is optionally substituted $C_{8-17}$ alkyl. In some embodiments, $R^L$ is optionally substituted $C_{8-16}$ alkyl. In some embodiments, $R^L$ is optionally substituted $C_{8-15}$ alkyl. In some embodiments, $R^L$ is optionally substituted $C_{8-14}$ alkyl. In some embodiments, $R^L$ is optionally substituted $C_{8-13}$ alkyl. In some embodiments, $R^L$ is optionally substituted $C_{8-12}$ alkyl. In some embodiments, $R^L$ is optionally substituted $C_{8-11}$ alkyl. In some embodiments, $R^L$ is optionally substituted $C_{8-10}$ alkyl. In some embodiments, $R^L$ is optionally substituted $C_{8-9}$ alkyl.

In some embodiments, $R^L$ is optionally substituted $C_{9-50}$ alkyl. In some embodiments, $R^L$ is optionally substituted $C_{9-40}$ alkyl. In some embodiments, $R^L$ is optionally substituted $C_{9-30}$ alkyl. In some embodiments, $R^L$ is optionally substituted $C_{9-20}$ alkyl. In some embodiments, $R^L$ is optionally substituted $C_{9-19}$ alkyl. In some embodiments, $R^L$ is optionally substituted $C_{9-18}$ alkyl. In some embodiments, $R^L$ is optionally substituted $C_{9-17}$ alkyl. In some embodiments, $R^L$ is optionally substituted $C_{9-16}$ alkyl. In some embodiments, $R^L$ is optionally substituted $C_{9-15}$ alkyl. In some embodiments, $R^L$ is optionally substituted $C_{9-14}$ alkyl. In some embodiments, $R^L$ is optionally substituted $C_{9-13}$ alkyl. In some embodiments, $R^L$ is optionally substituted $C_{9-12}$ alkyl. In some embodiments, $R^L$ is optionally substituted $C_{9-11}$ alkyl. In some embodiments, $R^L$ is optionally substituted $C_{9-10}$ alkyl.

In some embodiments, $R^L$ is optionally substituted $C_{10-50}$ alkyl. In some embodiments, $R^L$ is optionally substituted $C_{10-40}$ alkyl. In some embodiments, $R^L$ is optionally substituted $C_{10-30}$ alkyl. In some embodiments, $R^L$ is optionally substituted $C_{10-20}$ alkyl. In some embodiments, $R^L$ is optionally substituted $C_{10-19}$ alkyl. In some embodiments, $R^L$ is optionally substituted $C_{10-18}$ alkyl. In some embodiments, $R^L$ is optionally substituted $C_{10-17}$ alkyl. In some embodiments, $R^L$ is optionally substituted $C_{10-16}$ alkyl. In some embodiments, $R^L$ is optionally substituted $C_{10-15}$ alkyl. In some embodiments, $R^L$ is optionally substituted $C_{10-14}$ alkyl. In some embodiments, $R^L$ is optionally substituted $C_{10-13}$ alkyl. In some embodiments, $R^L$ is optionally substituted $C_{10-12}$ alkyl. In some embodiments, $R^L$ is optionally substituted $C_{10-11}$ alkyl.

In some embodiments, $R^L$ is optionally substituted $C_{11}$-50 alkyl. In some embodiments, $R^L$ is optionally substituted $C_{11-40}$ alkyl. In some embodiments, $R^L$ is optionally substituted $C_{11-30}$ alkyl. In some embodiments, $R^L$ is optionally substituted $C_{11-20}$ alkyl. In some embodiments, $R^L$ is optionally substituted $C_{11-19}$ alkyl. In some embodiments, $R^L$ is optionally substituted $C_{11-18}$ alkyl. In some embodiments, $R^L$ is optionally substituted $C_{11-17}$ alkyl. In some embodiments, $R^L$ is optionally substituted $C_{11-16}$ alkyl. In some embodiments, $R^L$ is optionally substituted $C_{11-15}$ alkyl. In some embodiments, $R^L$ is optionally substituted $C_{11-14}$ alkyl. In some embodiments, $R^L$ is optionally substituted $C_{11-13}$ alkyl. In some embodiments, $R^L$ is optionally substituted $C_{11-12}$ alkyl.

In some embodiments, $R^L$ is optionally substituted $C_{12-50}$ alkyl. In some embodiments, $R^L$ is optionally substituted $C_{12-40}$ alkyl. In some embodiments, $R^L$ is optionally substituted $C_{12-30}$ alkyl. In some embodiments, $R^L$ is optionally substituted $C_{12-20}$ alkyl. In some embodiments, $R^L$ is optionally substituted $C_{12-19}$ alkyl. In some embodiments, $R^L$ is optionally substituted $C_{12-18}$ alkyl. In some embodiments, $R^L$ is optionally substituted $C_{12-17}$ alkyl. In some embodiments, $R^L$ is optionally substituted $C_{12-16}$ alkyl. In some embodiments, $R^L$ is optionally substituted $C_{12-15}$ alkyl. In some embodiments, $R^L$ is optionally substituted $C_{12-14}$ alkyl. In some embodiments, $R^L$ is optionally substituted $C_{12-13}$ alkyl.

In some embodiments, $R^L$ is optionally substituted $C_6$ alkyl. In some embodiments, $R^L$ is optionally substituted $C_7$ alkyl. In some embodiments, $R^L$ is optionally substituted $C_8$ alkyl. In some embodiments, $R^L$ is optionally substituted $C_9$ alkyl. In some embodiments, $R^L$ is optionally substituted $C_{10}$ alkyl. In some embodiments, $R^L$ is optionally substituted $C_{11}$ alkyl. In some embodiments, $R^L$ is optionally substituted $C_{12}$ alkyl. In some embodiments, $R^L$ is optionally substituted $C_{13}$ alkyl. In some embodiments, $R^L$ is optionally substituted $C_{14}$ alkyl. In some embodiments, $R^L$ is optionally substituted $C_{15}$ alkyl. In some embodiments, $R^L$ is optionally substituted $C_{16}$ alkyl. In some embodiments, $R^L$ is optionally substituted $C_{17}$ alkyl. In some embodiments, $R^L$ is optionally substituted $C_{18}$ alkyl. In some embodiments, $R^L$ is optionally substituted $C_{19}$ alkyl. In some embodiments, $R^L$ is optionally substituted $C_{20}$ alkyl.

In some embodiments, for example, in any of the above embodiments, $R^L$ is a substituted alkyl group. In some embodiments, $R^L$ is an unsubstituted alkyl group. In some embodiments, $R^L$ is an optionally substituted straight-chain alkyl group. In some embodiments, $R^L$ is a substituted straight-chain alkyl group. In some embodiments, $R^L$ is an unsubstituted straight-chain alkyl group. In some embodiments, $R^L$ is an optionally substituted branched alkyl group. In some embodiments, $R^L$ is a substituted branched alkyl group. In some embodiments, $R^L$ is an unsubstituted branched alkyl group.

In certain embodiments, at least one instance of $R^L$ is an unsubstituted alkyl. Exemplary unsubstituted alkyl groups include, but are not limited to, —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, —$C_{10}H_{21}$, —$C_{11}H_{23}$, —$C_{12}H_{25}$, —$C_{13}H_{27}$, —$C_{14}H_{29}$, —$C_{15}H_{31}$, —$C_{16}H_{33}$, —$C_{17}H_{35}$, —$C_{18}H_{37}$, —$C_{19}H_{39}$, —$C_{20}H_{41}$, —$C_{21}H_{43}$, —$C_{22}H_{45}$, —$C_{23}H_{47}$, —$C_{24}H_{49}$, and —$C_{25}H_{51}$.

In certain embodiments, at least one instance of $R^L$ is a substituted alkyl. For example, in certain embodimenets, at least one instance of $R^L$ is an alkyl substituted with one or more fluorine substituents. Exemplary fluorinated alkyl groups include, but are not limited to:

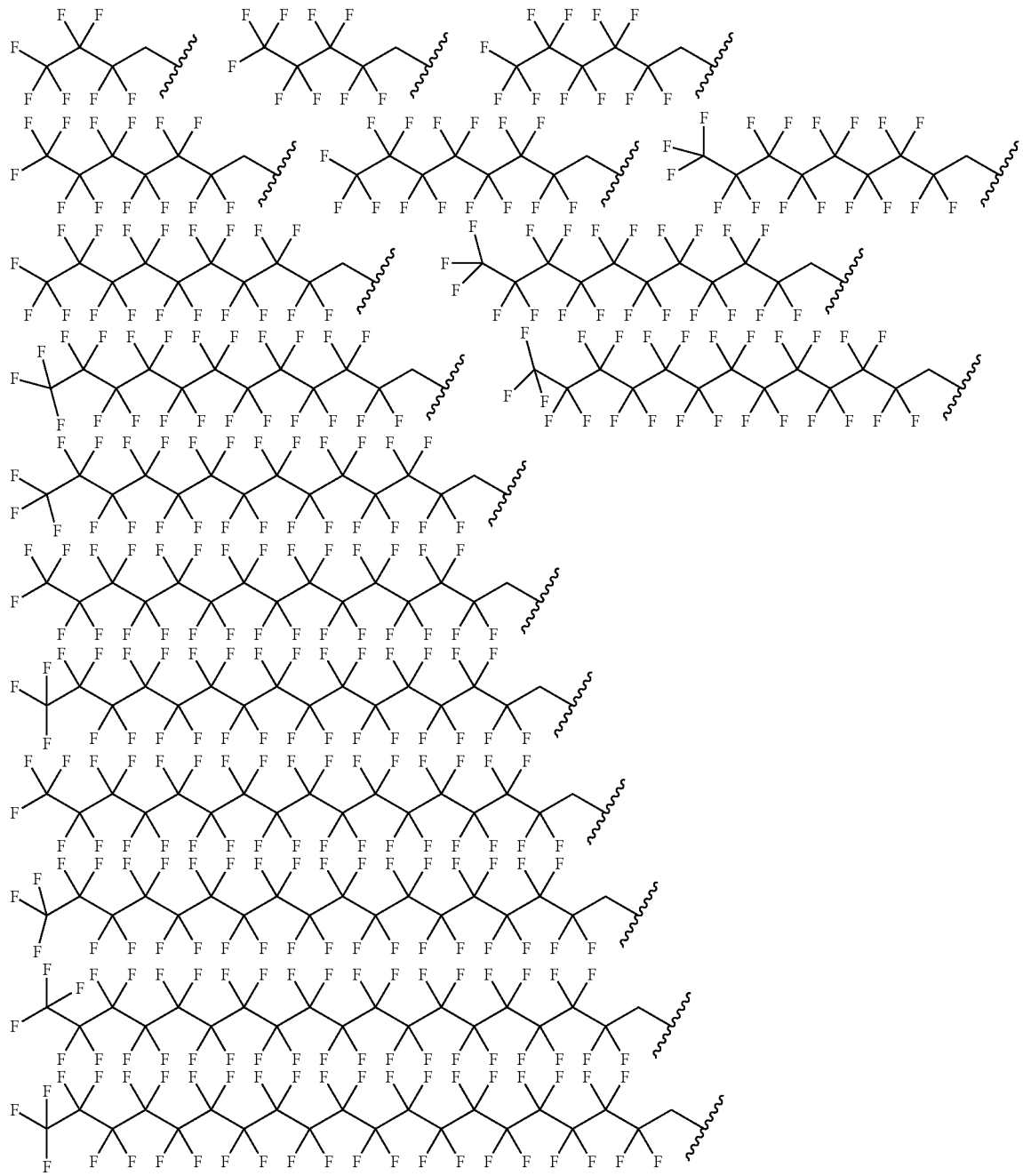

In some embodiments, $R^L$ is optionally substituted $C_{2-50}$ alkenyl. In some embodiments, $R^L$ is optionally substituted $C_{2-40}$ alkenyl. In some embodiments, $R^L$ is optionally substituted $C_{2-30}$ alkenyl. In some embodiments, $R^L$ is optionally substituted $C_{2-20}$ alkenyl. In some embodiments, $R^L$ is optionally substituted $C_{2-19}$ alkenyl. In some embodiments, $R^L$ is optionally substituted $C_{2-18}$ alkenyl. In some embodiments, $R^L$ is optionally substituted $C_{2-17}$ alkenyl. In some embodiments, $R^L$ is optionally substituted $C_{2-16}$ alkenyl. In some embodiments, $R^L$ is optionally substituted $C_{2-15}$ alkenyl. In some embodiments, $R^L$ is optionally substituted $C_{2-14}$ alkenyl. In some embodiments, $R^L$ is optionally substituted $C_{2-13}$ alkenyl. In some embodiments, $R^L$ is optionally substituted $C_{2-12}$ alkenyl. In some embodiments, $R^L$ is optionally substituted $C_{2-11}$ alkenyl. In some embodiments, $R^L$ is optionally substituted $C_{2-10}$ alkenyl. In some embodiments, $R^L$ is optionally substituted $C_{2-9}$ alkenyl. In some embodiments, $R^L$ is optionally substituted $C_{2-8}$ alkenyl. In some embodiments, $R^L$ is optionally substituted $C_{2-7}$ alkenyl. In some embodiments, $R^L$ is optionally substituted $C_{2-6}$ alkenyl.

In some embodiments, $R^L$ is optionally substituted $C_{4-40}$ alkenyl. In some embodiments, $R^L$ is optionally substituted $C_{4-40}$ alkenyl. In some embodiments, $R^L$ is optionally substituted $C_{4-30}$ alkenyl. In some embodiments, $R^L$ is optionally substituted $C_{4-20}$ alkenyl. In some embodiments, $R^L$ is optionally substituted $C_{4-19}$ alkenyl. In some embodiments, $R^L$ is optionally substituted $C_{4-18}$ alkenyl. In some embodiments, $R^L$ is optionally substituted $C_{4-17}$ alkenyl. In some embodiments, $R^L$ is optionally substituted $C_{4-16}$ alkenyl. In some embodiments, $R^L$ is optionally substituted $C_{4-15}$ alkenyl. In some embodiments, $R^L$ is optionally substituted $C_{4-14}$ alkenyl. In some embodiments, $R^L$ is optionally substituted $C_{4-13}$ alkenyl. In some embodiments, $R^L$ is optionally substituted $C_{4-12}$ alkenyl. In some embodiments, $R^L$ is optionally substituted $C_{4-11}$ alkenyl. In some embodiments, $R^L$ is optionally substituted $C_{4-10}$ alkenyl. In some embodiments, $R^L$ is optionally substituted $C_{4-9}$ alkenyl. In some embodiments, $R^L$ is optionally substituted $C_{4-8}$ alkenyl. In some embodiments, $R^L$ is optionally substituted $C_{4-7}$ alkenyl. In some embodiments, $R^L$ is optionally substituted $C_{4-6}$ alkenyl.

In some embodiments, $R^L$ is optionally substituted $C_{6-50}$ alkenyl. In some embodiments, $R^L$ is optionally substituted $C_{6-40}$ alkenyl. In some embodiments, $R^L$ is optionally substituted $C_{6-30}$ alkenyl. In some embodiments, $R^L$ is optionally substituted $C_{6-20}$ alkenyl. In some embodiments, $R^L$ is optionally substituted $C_{6-19}$ alkenyl. In some embodiments, $R^L$ is optionally substituted $C_{6-18}$ alkenyl. In some embodiments, $R^L$ is optionally substituted $C_{6-17}$ alkenyl. In some embodiments, $R^L$ is optionally substituted $C_{6-16}$ alkenyl. In some embodiments, $R^L$ is optionally substituted $C_{6-15}$ alkenyl. In some embodiments, $R^L$ is optionally substituted $C_{6-14}$ alkenyl. In some embodiments, $R^L$ is optionally substituted $C_{6-13}$ alkenyl. In some embodiments, $R^L$ is optionally substituted $C_{6-12}$ alkenyl. In some embodiments, $R^L$ is optionally substituted $C_{6-11}$ alkenyl. In some embodiments, $R^L$ is optionally substituted $C_{6-10}$ alkenyl. In some embodiments, $R^L$ is optionally substituted $C_{6-9}$ alkenyl. In some embodiments, $R^L$ is optionally substituted $C_{6-8}$ alkenyl. In some embodiments, $R^L$ is optionally substituted $C_{6-7}$ alkenyl.

In some embodiments, $R^L$ is optionally substituted $C_{8-50}$ alkenyl. In some embodiments, $R^L$ is optionally substituted $C_{8-40}$ alkenyl. In some embodiments, $R^L$ is optionally substituted $C_{8-30}$ alkenyl. In some embodiments, $R^L$ is optionally substituted $C_{8-20}$ alkenyl. In some embodiments, $R^L$ is optionally substituted $C_{8-19}$ alkenyl. In some embodiments, $R^L$ is optionally substituted $C_{8-18}$ alkenyl. In some embodiments, $R^L$ is optionally substituted $C_{8-17}$ alkenyl. In some embodiments, $R^L$ is optionally substituted $C_{8-16}$ alkenyl. In some embodiments, $R^L$ is optionally substituted $C_{8-15}$ alkenyl. In some embodiments, $R^L$ is optionally substituted $C_{8-14}$ alkenyl. In some embodiments, $R^L$ is optionally substituted $C_{8-13}$ alkenyl. In some embodiments, $R^L$ is optionally substituted $C_{8-12}$ alkenyl. In some embodiments, $R^L$ is optionally substituted $C_{8-11}$ alkenyl. In some embodiments, $R^L$ is optionally substituted $C_{8-10}$ alkenyl. In some embodiments, $R^L$ is optionally substituted $C_{8-9}$ alkenyl.

In some embodiments, $R^L$ is optionally substituted $C_{9-50}$ alkenyl. In some embodiments, $R^L$ is optionally substituted $C_{9-40}$ alkenyl. In some embodiments, $R^L$ is optionally substituted $C_{9-30}$ alkenyl. In some embodiments, $R^L$ is optionally substituted $C_{9-20}$ alkenyl. In some embodiments, $R^L$ is optionally substituted $C_{9-19}$ alkenyl. In some embodiments, $R^L$ is optionally substituted $C_{9-18}$ alkenyl. In some embodiments, $R^L$ is optionally substituted $C_{9-17}$ alkenyl. In some embodiments, $R^L$ is optionally substituted $C_{9-16}$ alkenyl. In some embodiments, $R^L$ is optionally substituted $C_{9-15}$ alkenyl. In some embodiments, $R^L$ is optionally substituted $C_{9-14}$ alkenyl. In some embodiments, $R^L$ is optionally substituted $C_{9-13}$ alkenyl. In some embodiments, $R^L$ is optionally substituted $C_{9-12}$ alkenyl. In some embodiments, $R^L$ is optionally substituted $C_{9-11}$ alkenyl. In some embodiments, $R^L$ is optionally substituted $C_{9-10}$ alkenyl.

In some embodiments, $R^L$ is optionally substituted $C_{10-50}$ alkenyl. In some embodiments, $R^L$ is optionally substituted $C_{10-40}$ alkenyl. In some embodiments, $R^L$ is optionally substituted $C_{10-30}$ alkenyl. In some embodiments, $R^L$ is optionally substituted $C_{10-20}$ alkenyl. In some embodiments, $R^L$ is optionally substituted $C_{10-19}$ alkenyl. In some embodiments, $R^L$ is optionally substituted $C_{10-18}$ alkenyl. In some embodiments, $R^L$ is optionally substituted $C_{10-17}$ alkenyl. In some embodiments, $R^L$ is optionally substituted $C_{10-16}$ alkenyl. In some embodiments, $R^L$ is optionally substituted $C_{10-15}$ alkenyl. In some embodiments, $R^L$ is optionally substituted $C_{10-14}$ alkenyl. In some embodiments, $R^L$ is optionally substituted $C_{10-13}$ alkenyl. In some embodiments, $R^L$ is optionally substituted $C_{10-12}$ alkenyl. In some embodiments, $R^L$ is optionally substituted $C_{10-11}$ alkenyl.

In some embodiments, $R^L$ is optionally substituted $C_{11-50}$ alkenyl. In some embodiments, $R^L$ is optionally substituted $C_{11-40}$ alkenyl. In some embodiments, $R^L$ is optionally substituted $C_{11-30}$ alkenyl. In some embodiments, $R^L$ is optionally substituted $C_{11-20}$ alkenyl. In some embodiments, $R^L$ is optionally substituted $C_{11-19}$ alkenyl. In some embodiments, $R^L$ is optionally substituted $C_{1-18}$ alkenyl. In some embodiments, $R^L$ is optionally substituted $C_{11-17}$ alkenyl. In some embodiments, $R^L$ is optionally substituted $C_{11-16}$ alkenyl. In some embodiments, $R^L$ is optionally substituted $C_{11-15}$ alkenyl. In some embodiments, $R^L$ is optionally substituted $C_{1-14}$ alkenyl. In some embodiments, $R^L$ is optionally substituted $C_{11-13}$ alkenyl. In some embodiments, $R^L$ is optionally substituted $C_{11-12}$ alkenyl.

In some embodiments, $R^L$ is optionally substituted $C_{12-50}$ alkenyl. In some embodiments, $R^L$ is optionally substituted $C_{12-40}$ alkenyl. In some embodiments, $R^L$ is optionally substituted $C_{12-30}$ alkenyl. In some embodiments, $R^L$ is optionally substituted $C_{12-20}$ alkenyl. In some embodiments, $R^L$ is optionally substituted $C_{12-19}$ alkenyl. In some embodiments, $R^L$ is optionally substituted $C_{12-18}$ alkenyl. In some embodiments, $R^L$ is optionally substituted $C_{12-17}$ alkenyl. In some embodiments, $R^L$ is optionally substituted $C_{12-16}$ alkenyl. In some embodiments, $R^L$ is optionally substituted $C_{12-15}$ alkenyl. In some embodiments, $R^L$ is optionally substituted $C_{12-14}$ alkenyl. In some embodiments, $R^L$ is optionally substituted $C_{12-13}$ alkenyl.

In some embodiments, $R^L$ is optionally substituted $C_6$ alkenyl. In some embodiments, $R^L$ is optionally substituted $C_7$ alkenyl. In some embodiments, $R^L$ is optionally substituted $C_8$ alkenyl. In some embodiments, $R^L$ is optionally substituted $C_9$ alkenyl. In some embodiments, $R^L$ is optionally substituted $C_{10}$ alkenyl. In some embodiments, $R^L$ is optionally substituted $C_{11}$ alkenyl. In some embodiments, $R^L$ is optionally substituted $C_{12}$ alkenyl. In some embodiments, $R^L$ is optionally substituted $C_{13}$ alkenyl. In some embodiments, $R^L$ is optionally substituted $C_{14}$ alkenyl. In some embodiments, $R^L$ is optionally substituted $C_{15}$ alkenyl. In some embodiments, $R^L$ is optionally substituted $C_{16}$ alkenyl. In some embodiments, $R^L$ is optionally substituted $C_{17}$ alkenyl. In some embodiments, $R^L$ is optionally substituted $C_{18}$ alkenyl. In some embodiments, $R^L$ is optionally substituted $C_{19}$ alkenyl. In some embodiments, $R^L$ is optionally substituted $C_{20}$ alkenyl.

In some embodiments, for example, in any of the above embodiments, $R^L$ is a substituted alkyl group. In some embodiments, $R^L$ is an unsubstituted alkyl group. In some embodiments, $R^L$ is an optionally substituted straight-chain alkenyl group. In some embodiments, $R^L$ is a substituted straight-chain alkenyl group. In some embodiments, $R^L$ is an unsubstituted straight-chain alkenyl group. In some embodiments, $R^L$ is an optionally substituted branched alkenyl group. In some embodiments, $R^L$ is a substituted branched alkenyl group. In some embodiments, $R^L$ is an unsubstituted branched alkenyl group.

Exemplary unsubstituted alkenyl group include, but are not limited to:

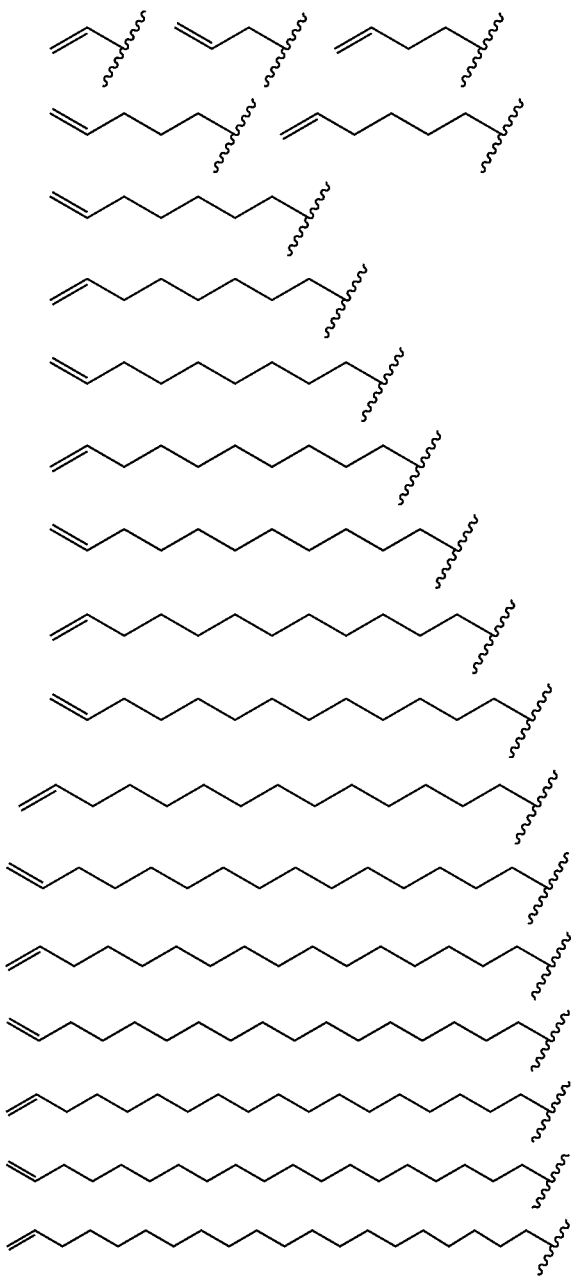

Myristoleic —$(CH_2C)_7CH=CH(CH_2)_3CH_3$,
Palmitoliec —$(CH_2)_7CH=CH(CH_2)_5CH_3$,
Sapienic —$(CH_2)_4CH=CH(CH_2)_8CH_3$,
Oleic —$(CH_2)_7CH=CH(CH_2)_7CH_3$,
Linoleic —$(CH_2)_7CH=CHCH_2CH=CH(CH_2)_4CH_3$,
α-Linolenic —$(CH_2)_7CH=CHCH_2CH=CHCH_2CH=CHCH_2CH_3$,
Arachinodonic —$(CH_2)_3CH=CHCH_2CH=CHCH_2CH=CHCH_2CH=CH(CH_2)_4CH_3$,
Eicosapentaenoic —$(CH_2)_3CH=CHCH_2CH=CHCH_2CH=CHCH_2CH=CHCH_2CH=CHCH_2CH_3$,
Erucic —$(CH_2)_{11}CH=CH(CH_2)_7CH_3$, and
Docosahexaenoic—$(CH_2)_2CH=CHCH_2CH=CHCH_2CH=CHCH_2CH=CHCH_2CH=CHCH_2CH=CH—CH_2CH_3$.

In some embodiments, wherein $R^L$ is defined as a $C_{6-50}$alkyl or $C_{6-50}$alkenyl groups, such groups are meant to encompass lipophilic groups (also referred to as a "lipid tail"). Lipophilic groups comprise a group of molecules that include fats, waxes, oils, fatty acids, and the like. Lipid tails present in these lipid groups can be saturated and unsaturated, depending on whether or not the lipid tail comprises double bonds. The lipid tail can also comprise different lengths, often categorized as medium (i.e., with tails between 7-12 carbons, e.g., $C_{7-12}$ alkyl or $C_{7-12}$ alkenyl), long (i.e., with tails greater than 12 carbons and up to 22 carbons, e.g., $C_{13-22}$alkyl or $C_{13-22}$ alkenyl), or very long (i.e., with tails greater than 22 carbons, e.g., $C_{23-30}$ alkyl or $C_{23-30}$ alkenyl).

In some embodiments, $R^L$ is optionally substituted $C_{2-50}$ alkynyl. In some embodiments, $R^L$ is optionally substituted $C_{2-40}$ alkynyl. In some embodiments, $R^L$ is optionally substituted $C_{2-30}$ alkynyl. In some embodiments, $R^L$ is optionally substituted $C_{2-20}$ alkynyl. In some embodiments, $R^L$ is optionally substituted $C_{2-19}$ alkynyl. In some embodiments, $R^L$ is optionally substituted $C_{2-18}$ alkynyl. In some embodiments, $R^L$ is optionally substituted $C_{2-17}$ alkynyl. In some embodiments, $R^L$ is optionally substituted $C_{2-16}$ alkynyl. In some embodiments, $R^L$ is optionally substituted $C_{2-15}$ alkynyl. In some embodiments, $R^L$ is optionally substituted $C_{2-14}$ alkynyl. In some embodiments, $R^L$ is optionally substituted $C_{2-13}$ alkynyl. In some embodiments, $R^L$ is optionally substituted $C_{2-12}$ alkynyl. In some embodiments, $R^L$ is optionally substituted $C_{2-11}$ alkynyl. In some embodiments, $R^L$ is optionally substituted $C_{2-10}$ alkynyl. In some embodiments, $R^L$ is optionally substituted $C_{2-9}$ alkynyl. In some embodiments, $R^L$ is optionally substituted $C_{2-8}$ alkynyl. In some embodiments, $R^L$ is optionally substituted $C_{2-7}$ alkynyl. In some embodiments, $R^L$ is optionally substituted $C_{2-6}$ alkynyl.

In some embodiments, $R^L$ is optionally substituted $C_{4-50}$ alkynyl. In some embodiments, $R^L$ is optionally substituted $C_{4-40}$ alkynyl. In some embodiments, $R^L$ is optionally substituted $C_{4-30}$ alkynyl. In some embodiments, $R^L$ is optionally substituted $C_{4-20}$ alkynyl. In some embodiments, $R^L$ is optionally substituted $C_{4-19}$ alkynyl. In some embodiments, $R^L$ is optionally substituted $C_{4-18}$ alkynyl. In some embodiments, $R^L$ is optionally substituted $C_{4-17}$ alkynyl. In some embodiments, $R^L$ is optionally substituted $C_{4-16}$ alkynyl. In some embodiments, $R^L$ is optionally substituted $C_{4-15}$ alkynyl. In some embodiments, $R^L$ is optionally substituted $C_{4-14}$ alkynyl. In some embodiments, $R^L$ is optionally substituted $C_{4-13}$ alkynyl. In some embodiments, $R^L$ is optionally substituted $C_{4-12}$ alkynyl. In some embodiments, $R^L$ is optionally substituted $C_{4-11}$ alkynyl. In some embodiments, $R^L$ is optionally substituted $C_{4-10}$ alkynyl. In some embodiments, $R^L$ is optionally substituted $C_{4-9}$ alkynyl. In some embodiments, $R^L$ is optionally substituted $C_{4-8}$ alkynyl. In some embodiments, $R^L$ is optionally substituted $C_{4-7}$ alkynyl. In some embodiments, $R^L$ is optionally substituted $C_{4-6}$ alkynyl.

In some embodiments, $R^L$ is optionally substituted $C_{6-50}$ alkynyl. In some embodiments, $R^L$ is optionally substituted $C_{6-40}$ alkynyl. In some embodiments, $R^L$ is optionally substituted $C_{6-30}$ alkynyl. In some embodiments, $R^L$ is optionally substituted $C_{6-20}$ alkynyl. In some embodiments, $R^L$ is optionally substituted $C_{6-19}$ alkynyl. In some embodiments, $R^L$ is optionally substituted $C_{6-18}$ alkynyl. In some embodiments, $R^L$ is optionally substituted $C_{6-17}$ alkynyl. In some embodiments, $R^L$ is optionally substituted $C_{6-16}$ alkynyl. In some embodiments, $R^L$ is optionally substituted $C_{6-15}$ alkynyl. In some embodiments, $R^L$ is optionally substituted $C_{6-14}$ alkynyl. In some embodiments, $R^L$ is optionally substituted $C_{6-13}$ alkynyl. In some embodiments, $R^L$ is optionally substituted $C_{6-12}$ alkynyl. In some embodiments, $R^L$ is optionally substituted $C_{6-11}$ alkynyl. In some embodiments, $R^L$ is optionally substituted $C_{6-10}$ alkynyl. In some embodiments, $R^L$ is optionally substituted $C_{6-9}$ alkynyl. In some embodiments, $R^L$ is optionally substituted $C_{6-8}$ alkynyl. In some embodiments, $R^L$ is optionally substituted $C_{6-7}$ alkynyl.

In some embodiments, $R^L$ is optionally substituted $C_{8-50}$ alkynyl. In some embodiments, $R^L$ is optionally substituted $C_{8-40}$ alkynyl. In some embodiments, $R^L$ is optionally substituted $C_{8-30}$ alkynyl. In some embodiments, $R^L$ is optionally substituted $C_{8-20}$ alkynyl. In some embodiments, $R^L$ is optionally substituted $C_{8-19}$ alkynyl. In some embodiments, $R^L$ is optionally substituted $C_{8-18}$ alkynyl. In some embodiments, $R^L$ is optionally substituted $C_{8-17}$ alkynyl. In some embodiments, $R^L$ is optionally substituted $C_{8-16}$ alkynyl. In some embodiments, $R^L$ is optionally substituted $C_{8-15}$ alkynyl. In some embodiments, $R^L$ is optionally substituted $C_{8-14}$ alkynyl. In some embodiments, $R^L$ is optionally substituted $C_{8-13}$ alkynyl. In some embodiments, $R^L$ is optionally substituted $C_{8-12}$ alkynyl. In some embodiments, $R^L$ is optionally substituted $C_{8-11}$ alkynyl. In some embodiments, $R^L$ is optionally substituted $C_{8-10}$ alkynyl. In some embodiments, $R^L$ is optionally substituted $C_{8-9}$ alkynyl.

In some embodiments, $R^L$ is optionally substituted $C_{9-50}$ alkynyl. In some embodiments, $R^L$ is optionally substituted $C_{9-40}$ alkynyl. In some embodiments, $R^L$ is optionally substituted $C_{9-30}$ alkynyl. In some embodiments, $R^L$ is optionally substituted $C_{9-20}$ alkynyl. In some embodiments, $R^L$ is optionally substituted $C_{9-19}$ alkynyl. In some embodiments, $R^L$ is optionally substituted $C_{9-18}$ alkynyl. In some embodiments, $R^L$ is optionally substituted $C_{9-17}$ alkynyl. In some embodiments, $R^L$ is optionally substituted $C_{9-16}$ alkynyl. In some embodiments, $R^L$ is optionally substituted $C_{9-15}$ alkynyl. In some embodiments, $R^L$ is optionally substituted $C_{9-14}$ alkynyl. In some embodiments, $R^L$ is optionally substituted $C_{9-13}$ alkynyl. In some embodiments, $R^L$ is optionally substituted $C_{9-12}$ alkynyl. In some embodiments, $R^L$ is optionally substituted $C_{9-11}$ alkynyl. In some embodiments, $R^L$ is optionally substituted $C_{9-10}$ alkynyl.

In some embodiments, $R^L$ is optionally substituted $C_{10-50}$ alkynyl. In some embodiments, $R^L$ is optionally substituted $C_{10-40}$ alkynyl. In some embodiments, $R^L$ is optionally substituted $C_{10-30}$ alkynyl. In some embodiments, $R^L$ is optionally substituted $C_{10-20}$ alkynyl. In some embodiments, $R^L$ is optionally substituted $C_{10-19}$ alkynyl. In some embodiments, $R^L$ is optionally substituted $C_{10-18}$ alkynyl. In some embodiments, $R^L$ is optionally substituted $C_{10-17}$ alkynyl. In some embodiments, $R^L$ is optionally substituted $C_{10-16}$ alkynyl. In some embodiments, $R^L$ is optionally substituted $C_{10-15}$ alkynyl. In some embodiments, $R^L$ is optionally substituted $C_{10-14}$ alkynyl. In some embodiments, $R^L$ is optionally substituted $C_{10-13}$ alkynyl. In some embodiments, $R^L$ is optionally substituted $C_{10-12}$ alkynyl. In some embodiments, $R^L$ is optionally substituted $C_{10-11}$ alkynyl.

In some embodiments, $R^L$ is optionally substituted $C_{11-50}$ alkynyl. In some embodiments, $R^L$ is optionally substituted $C_{11-40}$ alkynyl. In some embodiments, $R^L$ is optionally substituted $C_{11-30}$ alkynyl. In some embodiments, $R^L$ is optionally substituted $C_{11-20}$ alkynyl. In some embodiments, $R^L$ is optionally substituted $C_{11-19}$ alkynyl. In some embodiments, $R^L$ is optionally substituted $C_{11-18}$ alkynyl. In some embodiments, $R^L$ is optionally substituted $C_{11-17}$ alkynyl. In some embodiments, $R^L$ is optionally substituted $C_{11-16}$ alkynyl. In some embodiments, $R^L$ is optionally substituted $C_{11-15}$ alkynyl. In some embodiments, $R^L$ is optionally substituted $C_{11-14}$ alkynyl. In some embodiments, $R^L$ is optionally substituted $C_{11-13}$ alkynyl. In some embodiments, $R^L$ is optionally substituted $C_{11-12}$ alkynyl.

In some embodiments, $R^L$ is optionally substituted $C_{12-50}$ alkynyl. In some embodiments, $R^L$ is optionally substituted $C_{12-40}$ alkynyl. In some embodiments, $R^L$ is optionally substituted $C_{12-30}$ alkynyl. In some embodiments, $R^L$ is optionally substituted $C_{12-20}$ alkynyl. In some embodiments, $R^L$ is optionally substituted $C_{12-19}$ alkynyl. In some embodiments, $R^L$ is optionally substituted $C_{12-18}$ alkynyl. In some embodiments, $R^L$ is optionally substituted $C_{12-17}$ alkynyl. In some embodiments, $R^L$ is optionally substituted $C_{12-16}$ alkynyl. In some embodiments, $R^L$ is optionally substituted $C_{12-15}$ alkynyl. In some embodiments, $R^L$ is optionally substituted $C_{12-14}$ alkynyl. In some embodiments, $R^L$ is optionally substituted $C_{12-13}$ alkynyl.

In some embodiments, $R^L$ is optionally substituted $C_6$ alkynyl. In some embodiments, $R^L$ is optionally substituted $C_7$ alkynyl. In some embodiments, $R^L$ is optionally substituted $C_8$ alkynyl. In some embodiments, $R^L$ is optionally substituted $C_9$ alkynyl. In some embodiments, $R^L$ is optionally substituted $C_{10}$ alkynyl. In some embodiments, $R^L$ is optionally substituted $C_{11}$ alkynyl. In some embodiments, $R^L$ is optionally substituted $C_{12}$ alkynyl. In some embodiments, $R^L$ is optionally substituted $C_{13}$ alkynyl. In some embodiments, $R^L$ is optionally substituted $C_{14}$ alkynyl. In some embodiments, $R^L$ is optionally substituted $C_{15}$ alkynyl. In some embodiments, $R^L$ is optionally substituted $C_{16}$ alkynyl. In some embodiments, $R^L$ is optionally substituted $C_{17}$ alkynyl. In some embodiments, $R^L$ is optionally substituted $C_{18}$ alkynyl. In some embodiments, $R^L$ is optionally substituted $C_{19}$ alkynyl. In some embodiments, $R^L$ is optionally substituted $C_{20}$ alkynyl.

In some embodiments, for example, in any of the above embodiments, $R^L$ is a substituted alkynyl group. In some embodiments, $R^L$ is an unsubstituted alkynyl group. In some embodiments, $R^L$ is an optionally substituted straight-chain alkyl group. In some embodiments, $R^L$ is an optionally substituted straight-chain alkynyl group. In some embodiments, $R^L$ is a substituted straight-chain alkynyl group. In some embodiments, $R^L$ is an unsubstituted straight-chain alkynyl group. In some embodiments, $R^L$ is an optionally substituted branched alkynyl group. In some embodiments, $R^L$ is a substituted branched alkynyl group. In some embodiments, $R^L$ is an unsubstituted branched alkynyl group.

In some embodiments, $R^L$ is optionally substituted hetero$C_{1-50}$alkyl. In some embodiments, $R^L$ is optionally substituted hetero$C_{2-50}$alkyl. In some embodiments, $R^L$ is optionally substituted hetero$C_{2-40}$alkyl. In some embodiments, $R^L$ is optionally substituted hetero$C_{2-30}$alkyl. In some embodiments, $R^L$ is optionally substituted hetero$C_{2-20}$alkyl. In some embodiments, $R^L$ is optionally substituted hetero $C_{2-19}$alkyl. In some embodiments, $R^L$ is optionally substituted hetero$C_{2-18}$alkyl. In some embodiments, $R^L$ is optionally substituted hetero$C_{2-17}$alkyl. In some embodiments, $R^L$ is optionally substituted hetero$C_{2-16}$alkyl. In some embodiments, $R^L$ is optionally substituted hetero$C_{2-15}$alkyl. In some embodiments, $R^L$ is optionally substituted hetero$C_{2-14}$alkyl. In some embodiments, $R^L$ is optionally substituted hetero $C_{2-13}$alkyl. In some embodiments, $R^L$ is optionally substituted hetero$C_{2-12}$alkyl. In some embodiments, $R^L$ is optionally substituted hetero$C_{2-11}$alkyl. In some embodiments, $R^L$ is optionally substituted hetero$C_{2-10}$alkyl. In some embodiments, $R^L$ is optionally substituted heteroC$_{2-9}$alkyl. In some embodiments, $R^L$ is optionally substituted heteroC$_{2-8}$alkyl. In some embodiments, $R^L$ is optionally substituted hetero C$_{2-7}$alkyl. In some embodiments, $R^L$ is optionally substituted heteroC$_{2-6}$alkyl.

In some embodiments, $R^L$ is optionally substituted heteroC$_{4-50}$alkyl. In some embodiments, $R^L$ is optionally substituted heteroC$_{4-40}$alkyl. In some embodiments, $R^L$ is optionally substituted heteroC$_{4-30}$alkyl. In some embodiments, $R^L$ is optionally substituted heteroC$_{4-20}$alkyl. In some embodiments, $R^L$ is optionally substituted heteroC$_{4-19}$alkyl. In some embodiments, $R^L$ is optionally substituted hetero C$_{4-18}$alkyl. In some embodiments, $R^L$ is optionally substituted heteroC$_{4-17}$alkyl. In some embodiments, $R^L$ is optionally substituted heteroC$_{4-16}$alkyl. In some embodiments, $R^L$ is optionally substituted heteroC$_{4-15}$alkyl. In some embodiments, $R^L$ is optionally substituted heteroC$_{4-14}$alkyl. In some embodiments, $R^L$ is optionally substituted heteroC$_{4-13}$alkyl. In some embodiments, $R^L$ is optionally substituted hetero C$_{4-12}$alkyl. In some embodiments, $R^L$ is optionally substituted heteroC$_{4-11}$alkyl. In some embodiments, $R^L$ is optionally substituted heteroC$_{4-10}$alkyl. In some embodiments, $R^L$ is optionally substituted heteroC$_{4-9}$alkyl. In some embodiments, $R^L$ is optionally substituted heteroC$_{4-5}$alkyl. In some embodiments, $R^L$ is optionally substituted heteroC$_{4-7}$alkyl. In some embodiments, $R^L$ is optionally substituted hetero C$_{4-6}$alkyl.

In some embodiments, $R^L$ is optionally substituted heteroC$_{6-50}$alkyl. In some embodiments, $R^L$ is optionally substituted heteroC$_{6-40}$alkyl. In some embodiments, $R^L$ is optionally substituted heteroC$_{6-30}$alkyl. In some embodiments, $R^L$ is optionally substituted heteroC$_{6-20}$alkyl. In some embodiments, $R^L$ is optionally substituted heteroC$_{6-19}$alkyl. In some embodiments, $R^L$ is optionally substituted hetero C$_{6-18}$alkyl. In some embodiments, $R^L$ is optionally substituted heteroC$_{6-17}$alkyl. In some embodiments, $R^L$ is optionally substituted heteroC$_{6-16}$alkyl. In some embodiments, $R^L$ is optionally substituted heteroC$_{6-15}$alkyl. In some embodiments, $R^L$ is optionally substituted heteroC$_{6-14}$alkyl. In some embodiments, $R^L$ is optionally substituted heteroC$_{6-13}$alkyl. In some embodiments, $R^L$ is optionally substituted hetero C$_{6-12}$alkyl. In some embodiments, $R^L$ is optionally substituted heteroC$_{6-11}$alkyl. In some embodiments, $R^L$ is optionally substituted heteroC$_{6-10}$alkyl. In some embodiments, $R^L$ is optionally substituted heteroC$_{6-9}$alkyl. In some embodiments, $R^L$ is optionally substituted heteroC$_{6-8}$alkyl. In some embodiments, $R^L$ is optionally substituted heteroC$_{6-7}$alkyl.

In some embodiments, $R^L$ is optionally substituted heteroC$_{8-50}$alkyl. In some embodiments, $R^L$ is optionally substituted heteroC$_{8-40}$alkyl. In some embodiments, $R^L$ is optionally substituted heteroC$_{8-30}$alkyl. In some embodiments, $R^L$ is optionally substituted heteroC$_{8-20}$alkyl. In some embodiments, $R^L$ is optionally substituted heteroC$_{8-19}$alkyl. In some embodiments, $R^L$ is optionally substituted hetero C$_{8-40}$alkyl. In some embodiments, $R^L$ is optionally substituted heteroC$_{8-17}$alkyl. In some embodiments, $R^L$ is optionally substituted heteroC$_{8-16}$alkyl. In some embodiments, $R^L$ is optionally substituted heteroC$_{8-15}$alkyl. In some embodiments, $R^L$ is optionally substituted heteroC$_{8-14}$alkyl. In some embodiments, $R^L$ is optionally substituted heteroC$_{8-13}$alkyl. In some embodiments, $R^L$ is optionally substituted hetero C$_{8-12}$alkyl. In some embodiments, $R^L$ is optionally substituted heteroC$_{8-11}$alkyl. In some embodiments, $R^L$ is optionally substituted heteroC$_{8-10}$alkyl. In some embodiments, $R^L$ is optionally substituted heteroC$_{8-9}$alkyl.

In some embodiments, $R^L$ is optionally substituted heteroC$_{9-50}$alkyl. In some embodiments, $R^L$ is optionally substituted heteroC$_{9-40}$alkyl. In some embodiments, $R^L$ is optionally substituted heteroC$_{9-30}$alkyl. In some embodiments, $R^L$ is optionally substituted heteroC$_{9-20}$alkyl. In some embodiments, $R^L$ is optionally substituted heteroC$_{9-19}$alkyl. In some embodiments, $R^L$ is optionally substituted hetero C$_{9-18}$alkyl. In some embodiments, $R^L$ is optionally substituted heteroC$_{9-17}$alkyl. In some embodiments, $R^L$ is optionally substituted heteroC$_{9-16}$alkyl. In some embodiments, $R^L$ is optionally substituted heteroC$_{9-15}$alkyl. In some embodiments, $R^L$ is optionally substituted heteroC$_{9-14}$alkyl. In some embodiments, $R^L$ is optionally substituted heteroC$_{9-13}$alkyl. In some embodiments, $R^L$ is optionally substituted hetero C$_{9-12}$alkyl. In some embodiments, $R^L$ is optionally substituted heteroC$_{9-11}$alkyl. In some embodiments, $R^L$ is optionally substituted heteroC$_{9-10}$alkyl.

In some embodiments, $R^L$ is optionally substituted heteroC$_{10-50}$alkyl. In some embodiments, $R^L$ is optionally substituted heteroC$_{10-40}$alkyl. In some embodiments, $R^L$ is optionally substituted heteroC$_{10-30}$alkyl. In some embodiments, $R^L$ is optionally substituted heteroC$_{10-20}$alkyl. In some embodiments, $R^L$ is optionally substituted hetero C$_{10-19}$alkyl. In some embodiments, $R^L$ is optionally substituted heteroC$_{10-18}$alkyl. In some embodiments, $R^L$ is optionally substituted heteroC$_{10-17}$alkyl. In some embodiments, $R^L$ is optionally substituted heteroC$_{10-16}$alkyl. In some embodiments, $R^L$ is optionally substituted heteroC$_{10-15}$alkyl. In some embodiments, $R^L$ is optionally substituted hetero C$_{10-14}$alkyl. In some embodiments, $R^L$ is optionally substituted heteroC$_{10-13}$alkyl. In some embodiments, $R^L$ is optionally substituted heteroC$_{10-12}$alkyl. In some embodiments, $R^L$ is optionally substituted heteroC$_{10-11}$alkyl.

In some embodiments, $R^L$ is optionally substituted heteroC$_{11-50}$alkyl. In some embodiments, $R^L$ is optionally substituted heteroC$_{11-40}$alkyl. In some embodiments, $R^L$ is optionally substituted heteroC$_{10-30}$alkyl. In some embodiments, $R^L$ is optionally substituted heteroC$_{11-20}$alkyl. In some embodiments, $R^L$ is optionally substituted hetero C$_{11-19}$alkyl. In some embodiments, $R^L$ is optionally substituted heteroC$_{11-18}$alkyl. In some embodiments, $R^L$ is optionally substituted heteroC$_{11-17}$alkyl. In some embodiments, $R^L$ is optionally substituted heteroC$_{11-16}$alkyl. In some embodiments, $R^L$ is optionally substituted heteroC$_{11-15}$alkyl. In some embodiments, $R^L$ is optionally substituted hetero C$_{11-14}$alkyl. In some embodiments, $R^L$ is optionally substituted heteroC$_{11-13}$alkyl. In some embodiments, $R^L$ is optionally substituted heteroC$_{11-12}$alkyl.

In some embodiments, $R^L$ is optionally substituted heteroC$_{12-50}$alkyl. In some embodiments, $R^L$ is optionally substituted heteroC$_{12-40}$alkyl. In some embodiments, $R^L$ is optionally substituted heteroC$_{12-30}$alkyl. In some embodiments, $R^L$ is optionally substituted heteroC$_{12-20}$alkyl. In some embodiments, $R^L$ is optionally substituted hetero C$_{12-19}$alkyl. In some embodiments, $R^L$ is optionally substituted heteroC$_{12-18}$alkyl. In some embodiments, $R^L$ is optionally substituted heteroC$_{12-17}$alkyl. In some embodiments, $R^L$ is optionally substituted heteroC$_{12-16}$alkyl. In some embodiments, $R^L$ is optionally substituted heteroC$_{12-15}$alkyl. In some embodiments, $R^L$ is optionally substituted hetero C$_{12-14}$alkyl. In some embodiments, $R^L$ is optionally substituted heteroC$_{12-13}$alkyl.

In some embodiments, $R^L$ is optionally substituted heteroC$_6$alkyl. In some embodiments, $R^L$ is optionally substituted heteroC$_7$alkyl. In some embodiments, $R^L$ is optionally substituted heteroC$_8$alkyl. In some embodiments, $R^L$ is optionally substituted heteroC$_9$alkyl. In some embodiments, $R^L$ is optionally substituted heteroC$_{10}$alkyl. In some embodiments, $R^L$ is optionally substituted heteroC$_{11}$alkyl. In some embodiments, $R^L$ is optionally substituted heteroC$_{12}$alkyl. In some embodiments, $R^L$ is optionally substituted heteroC$_{13}$alkyl. In some embodiments, $R^L$ is optionally substituted heteroC$_{14}$alkyl. In some embodiments, $R^L$ is optionally substituted heteroC$_{15}$alkyl. In some embodiments, $R^L$ is optionally substituted heteroC$_{16}$alkyl. In some embodiments, $R^L$ is optionally substituted heteroC$_{17}$alkyl. In some embodiments, $R^L$ is optionally substituted heteroC$_{18}$alkyl. In some embodiments, $R^L$ is optionally substituted heteroC$_{19}$alkyl. In some embodiments, $R^L$ is optionally substituted heteroC$_{20}$alkyl.

In some embodiments, for example, in any of the above embodiments, $R^L$ is a substituted heteroalkyl group. In some embodiments, $R^L$ is an unsubstituted heteroalkyl group. In some embodiments, $R^L$ is an optionally substituted straight-chain heteroalkyl group. In some embodiments, $R^L$ is a substituted straight-chain heteroalkyl group. In some embodiments, $R^L$ is an unsubstituted straight-chain heteroalkyl group. In some embodiments, $R^L$ is an optionally substituted branched heteroalkyl group. In some embodiments, $R^L$ is a substituted branched heteroalkyl group. In some embodiments, $R^L$ is an unsubstituted branched heteroalkyl group.

Exemplary unsubstituted heteroalkyl groups include, but are not limited to:

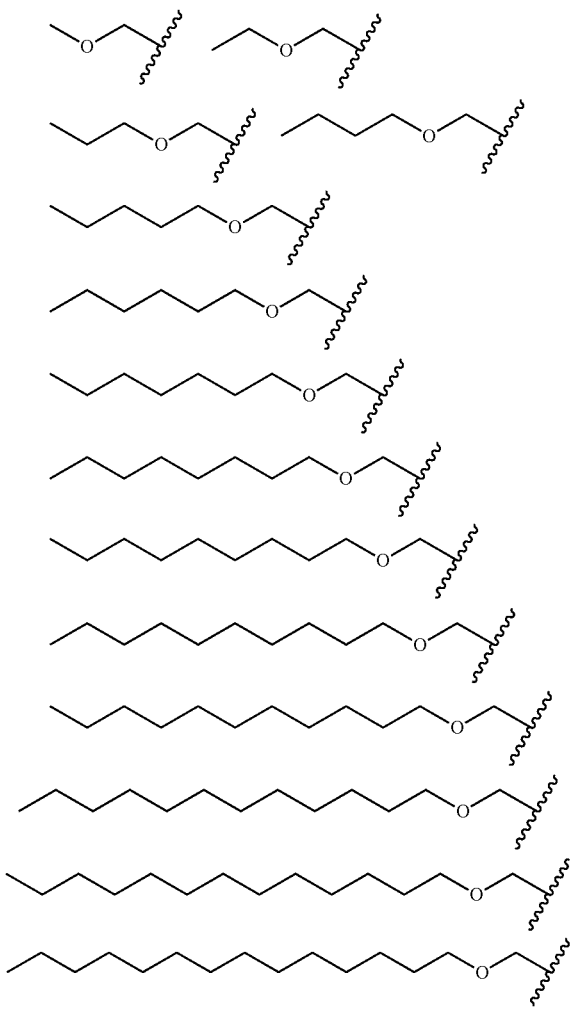

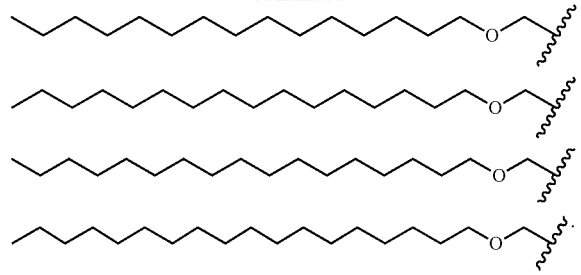

In some embodiments, $R^L$ is optionally substituted heteroC$_{25}$alkenyl. In some embodiments, $R^L$ is optionally substituted heteroC$_{2-40}$alkenyl. In some embodiments, $R^L$ is optionally substituted heteroC$_{2-30}$alkenyl. In some embodiments, $R^L$ is optionally substituted heteroC$_{2-20}$alkenyl. In some embodiments, $R^L$ is optionally substituted heteroC$_{2-19}$alkenyl. In some embodiments, $R^L$ is optionally substituted heteroC$_{2-18}$alkenyl. In some embodiments, $R^L$ is optionally substituted heteroC$_{2-17}$alkenyl. In some embodiments, $R^L$ is optionally substituted heteroC$_{2-16}$alkenyl. In some embodiments, $R^L$ is optionally substituted heteroC$_{2-15}$alkenyl. In some embodiments, $R^L$ is optionally substituted heteroC$_{2-14}$alkenyl. In some embodiments, $R^L$ is optionally substituted heteroC$_{2-13}$alkenyl. In some embodiments, $R^L$ is optionally substituted heteroC$_{2-12}$alkenyl. In some embodiments, $R^L$ is optionally substituted heteroC$_{2-11}$alkenyl. In some embodiments, $R^L$ is optionally substituted heteroC$_{2-10}$alkenyl. In some embodiments, $R^L$ is optionally substituted heteroC$_{2-9}$alkenyl. In some embodiments, $R^L$ is optionally substituted heteroC$_{2-8}$alkenyl. In some embodiments, $R^L$ is optionally substituted heteroC$_{2-7}$alkenyl. In some embodiments, $R^L$ is optionally substituted heteroC$_{2-6}$alkenyl.

In some embodiments, $R^L$ is optionally substituted heteroC$_{4-50}$alkenyl. In some embodiments, $R^L$ is optionally substituted heteroC$_{4-40}$alkenyl. In some embodiments, $R^L$ is optionally substituted heteroC$_{4-30}$alkenyl. In some embodiments, $R^L$ is optionally substituted heteroC$_{4-20}$alkenyl. In some embodiments, $R^L$ is optionally substituted heteroC$_{4-19}$alkenyl. In some embodiments, $R^L$ is optionally substituted heteroC$_{4-18}$alkenyl. In some embodiments, $R^L$ is optionally substituted heteroC$_{4-17}$alkenyl. In some embodiments, $R^L$ is optionally substituted heteroC$_{4-16}$alkenyl. In some embodiments, $R^L$ is optionally substituted heteroC$_{4-15}$alkenyl. In some embodiments, $R^L$ is optionally substituted heteroC$_{4-14}$alkenyl. In some embodiments, $R^L$ is optionally substituted heteroC$_{4-13}$alkenyl. In some embodiments, $R^L$ is optionally substituted heteroC$_{4-12}$alkenyl. In some embodiments, $R^L$ is optionally substituted heteroC$_{4-11}$alkenyl. In some embodiments, $R^L$ is optionally substituted heteroC$_{4-10}$alkenyl. In some embodiments, $R^L$ is optionally substituted heteroC$_{4-9}$alkenyl. In some embodiments, $R^L$ is optionally substituted heteroC$_{4-5}$alkenyl. In some embodiments, $R^L$ is optionally substituted heteroC$_{4-7}$alkenyl. In some embodiments, $R^L$ is optionally substituted heteroC$_{4-6}$alkenyl.

In some embodiments, $R^L$ is optionally substituted heteroC$_{6-50}$alkenyl. In some embodiments, $R^L$ is optionally substituted heteroC$_{6-40}$alkenyl. In some embodiments, $R^L$ is optionally substituted heteroC$_{6-30}$alkenyl. In some embodiments, $R^L$ is optionally substituted heteroC$_{6-20}$alkenyl. In some embodiments, $R^L$ is optionally substituted heteroC$_{6-19}$alkenyl. In some embodiments, $R^L$ is optionally substituted heteroC$_{6-18}$alkenyl. In some embodiments, $R^L$ is optionally substituted heteroC$_{6-17}$alkenyl. In some embodiments, R$^L$ is optionally substituted heteroC$_{6-16}$alkenyl. In some embodiments, R$^L$ is optionally substituted heteroC$_{6-15}$alkenyl. In some embodiments, R$^L$ is optionally substituted heteroC$_{6-14}$alkenyl. In some embodiments, R$^L$ is optionally substituted heteroC$_{6-13}$alkenyl. In some embodiments, R$^L$ is optionally substituted heteroC$_{6-12}$alkenyl. In some embodiments, R$^L$ is optionally substituted heteroC$_{6-11}$alkenyl. In some embodiments, R$^L$ is optionally substituted heteroC$_{6-10}$alkenyl. In some embodiments, R$^L$ is optionally substituted heteroC$_{6-9}$alkenyl. In some embodiments, R$^L$ is optionally substituted heteroC$_{6-8}$alkenyl. In some embodiments, R$^L$ is optionally substituted heteroC$_{6-7}$alkenyl.

In some embodiments, R$^L$ is optionally substituted heteroC$_{8-50}$alkenyl. In some embodiments, R$^L$ is optionally substituted heteroC$_{8-40}$alkenyl. In some embodiments, R$^L$ is optionally substituted heteroC$_{8-30}$alkenyl. In some embodiments, R$^L$ is optionally substituted heteroC$_{8-20}$alkenyl. In some embodiments, R$^L$ is optionally substituted heteroC$_{8-19}$alkenyl. In some embodiments, R$^L$ is optionally substituted heteroC$_{8-18}$alkenyl. In some embodiments, R$^L$ is optionally substituted heteroC$_{8-17}$alkenyl. In some embodiments, R$^L$ is optionally substituted heteroC$_{8-16}$alkenyl. In some embodiments, R$^L$ is optionally substituted heteroC$_{5-15}$alkenyl. In some embodiments, R$^L$ is optionally substituted heteroC$_{8-14}$alkenyl. In some embodiments, R$^L$ is optionally substituted heteroC$_{8-13}$alkenyl. In some embodiments, R$^L$ is optionally substituted heteroC$_{8-12}$alkenyl. In some embodiments, R$^L$ is optionally substituted heteroC$_{9-19}$alkenyl. In some embodiments, R$^L$ is optionally substituted heteroC$_{8-18}$alkenyl. In some embodiments, R$^L$ is optionally substituted heteroC$_{8-9}$alkenyl.

In some embodiments, R$^L$ is optionally substituted heteroC$_{9-50}$alkenyl. In some embodiments, R$^L$ is optionally substituted heteroC$_{9-40}$alkenyl. In some embodiments, R$^L$ is optionally substituted heteroC$_{9-30}$alkenyl. In some embodiments, R$^L$ is optionally substituted heteroC$_{9-20}$alkenyl. In some embodiments, R$^L$ is optionally substituted heteroC$_{9-19}$alkenyl. In some embodiments, R$^L$ is optionally substituted heteroC$_{9-18}$alkenyl. In some embodiments, R$^L$ is optionally substituted heteroC$_{9-17}$alkenyl. In some embodiments, R$^L$ is optionally substituted heteroC$_{9-16}$alkenyl. In some embodiments, R$^L$ is optionally substituted heteroC$_{9-15}$alkenyl. In some embodiments, R$^L$ is optionally substituted heteroC$_{9-14}$alkenyl. In some embodiments, R$^L$ is optionally substituted heteroC$_{9-13}$alkenyl. In some embodiments, R$^L$ is optionally substituted heteroC$_{9-12}$alkenyl. In some embodiments, R$^L$ is optionally substituted heteroC$_{9-11}$alkenyl. In some embodiments, R$^L$ is optionally substituted heteroC$_{9-10}$alkenyl.

In some embodiments, R$^L$ is optionally substituted heteroC$_{10-50}$alkenyl. In some embodiments, R$^L$ is optionally substituted heteroC$_{10-40}$alkenyl. In some embodiments, R$^L$ is optionally substituted heteroC$_{10-30}$alkenyl. In some embodiments, R$^L$ is optionally substituted heteroC$_{10-20}$alkenyl. In some embodiments, R$^L$ is optionally substituted heteroC$_{10-19}$alkenyl. In some embodiments, R$^L$ is optionally substituted heteroC$_{10-18}$alkenyl. In some embodiments, R$^L$ is optionally substituted heteroC$_{10-17}$alkenyl. In some embodiments, R$^L$ is optionally substituted heteroC$_{10-16}$alkenyl. In some embodiments, R$^L$ is optionally substituted heteroC$_{10-15}$alkenyl. In some embodiments, R$^L$ is optionally substituted heteroC$_{10-14}$alkenyl. In some embodiments, R$^L$ is optionally substituted heteroC$_{10-13}$alkenyl. In some embodiments, R$^L$ is optionally substituted heteroC$_{10-12}$alkenyl. In some embodiments, R$^L$ is optionally substituted heteroC$_{10-11}$ alkenyl.

In some embodiments, R$^L$ is optionally substituted heteroC$_{11-50}$alkenyl. In some embodiments, R$^L$ is optionally substituted heteroC$_{11-40}$alkenyl. In some embodiments, R$^L$ is optionally substituted heteroC$_{11-30}$alkenyl. In some embodiments, R$^L$ is optionally substituted heteroC$_{11-20}$alkenyl. In some embodiments, R$^L$ is optionally substituted heteroC$_{11-19}$alkenyl. In some embodiments, R$^L$ is optionally substituted heteroC$_{11-18}$alkenyl. In some embodiments, R$^L$ is optionally substituted heteroC$_{11-17}$alkenyl. In some embodiments, R$^L$ is optionally substituted heteroC$_{11-16}$alkenyl. In some embodiments, R$^L$ is optionally substituted heteroC$_{11-19}$alkenyl. In some embodiments, R$^L$ is optionally substituted heteroC$_{11-14}$alkenyl. In some embodiments, R$^L$ is optionally substituted heteroC$_{11-13}$alkenyl. In some embodiments, R$^L$ is optionally substituted heteroC$_{11-12}$alkenyl.

In some embodiments, R$^L$ is optionally substituted heteroC$_{12-50}$alkenyl. In some embodiments, R$^L$ is optionally substituted heteroC$_{12-40}$alkenyl. In some embodiments, R$^L$ is optionally substituted heteroC$_{12-30}$alkenyl. In some embodiments, R$^L$ is optionally substituted heteroC$_{12-20}$alkenyl. In some embodiments, R$^L$ is optionally substituted heteroC$_{12-19}$alkenyl. In some embodiments, R$^L$ is optionally substituted heteroC$_{12-18}$alkenyl. In some embodiments, R$^L$ is optionally substituted heteroC$_{12-17}$alkenyl. In some embodiments, R$^L$ is optionally substituted heteroC$_{12-16}$alkenyl. In some embodiments, R$^L$ is optionally substituted heteroC$_{12-15}$alkenyl. In some embodiments, R$^L$ is optionally substituted heteroC$_{12-14}$alkenyl. In some embodiments, R$^L$ is optionally substituted heteroC$_{12-13}$alkenyl.

In some embodiments, R$^L$ is optionally substituted heteroC$_6$alkenyl. In some embodiments, R$^L$ is optionally substituted heteroC$_7$alkenyl. In some embodiments, R$^L$ is optionally substituted heteroC$_8$alkenyl. In some embodiments, R$^L$ is optionally substituted heteroC$_9$alkenyl. In some embodiments, R$^L$ is optionally substituted heteroC$_{10}$alkenyl. In some embodiments, R$^L$ is optionally substituted heteroC$_{11}$alkenyl. In some embodiments, R$^L$ is optionally substituted heteroC$_{12}$alkenyl. In some embodiments, R$^L$ is optionally substituted heteroC$_{13}$alkenyl. In some embodiments, R$^L$ is optionally substituted heteroC$_{14}$alkenyl. In some embodiments, R$^L$ is optionally substituted heteroC$_{15}$alkenyl. In some embodiments, R$^L$ is optionally substituted heteroC$_{16}$alkenyl. In some embodiments, R$^L$ is optionally substituted heteroC$_{17}$alkenyl. In some embodiments, R$^L$ is optionally substituted heteroC$_{18}$alkenyl. In some embodiments, R$^L$ is optionally substituted heteroC$_{19}$alkenyl. In some embodiments, R$^L$ is optionally substituted heteroC$_{20}$alkenyl.

In some embodiments, for example, in any of the above embodiments, R$^L$ is a substituted heteroalkenyl group. In some embodiments, R$^L$ is an unsubstituted heteroalkenyl group. In some embodiments, R$^L$ is an optionally substituted straight-chain heteroalkenyl group. In some embodiments, R$^L$ is a substituted straight-chain heteroalkenyl group. In some embodiments, R$^L$ is an unsubstituted straight-chain heteroalkenyl group. In some embodiments, R$^L$ is an optionally substituted branched heteroalkenyl group. In some embodiments, R$^L$ is a substituted branched heteroalkenyl group. In some embodiments, R$^L$ is an unsubstituted branched heteroalkenyl group.

In some embodiments, R$^L$ is optionally substituted heteroC$_{2-50}$alkynyl. In some embodiments, R$^L$ is optionally substituted heteroC$_{2-40}$alkynyl. In some embodiments, R$^L$ is optionally substituted heteroC$_{2-30}$alkynyl. In some embodiments, $R^L$ is optionally substituted heteroC$_{2-20}$alkynyl. In some embodiments, $R^L$ is optionally substituted heteroC$_{2-19}$alkynyl. In some embodiments, $R^L$ is optionally substituted heteroC$_{2-18}$alkynyl. In some embodiments, $R^L$ is optionally substituted heteroC$_{2-17}$alkynyl. In some embodiments, $R^L$ is optionally substituted heteroC$_{2-16}$alkynyl. In some embodiments, $R^L$ is optionally substituted heteroC$_{2-15}$alkynyl. In some embodiments, $R^L$ is optionally substituted heteroC$_{2-14}$alkynyl. In some embodiments, $R^L$ is optionally substituted heteroC$_{2-13}$alkynyl. In some embodiments, $R^L$ is optionally substituted heteroC$_{2-12}$alkynyl. In some embodiments, $R^L$ is optionally substituted heteroC$_{2-11}$alkynyl. In some embodiments, $R^L$ is optionally substituted heteroC$_{2-10}$alkynyl. In some embodiments, $R^L$ is optionally substituted heteroC$_{2-9}$alkynyl. In some embodiments, $R^L$ is optionally substituted heteroC$_{2-8}$alkynyl. In some embodiments, $R^L$ is optionally substituted heteroC$_{2-7}$alkynyl. In some embodiments, $R^L$ is optionally substituted heteroC$_{2-6}$alkynyl.

In some embodiments, $R^L$ is optionally substituted heteroC$_{4-50}$alkynyl. In some embodiments, $R^L$ is optionally substituted heteroC$_{4-40}$alkynyl. In some embodiments, $R^L$ is optionally substituted heteroC$_{4-30}$alkynyl. In some embodiments, $R^L$ is optionally substituted heteroC$_{4-20}$alkynyl. In some embodiments, $R^L$ is optionally substituted heteroC$_{4-19}$alkynyl. In some embodiments, $R^L$ is optionally substituted heteroC$_{4-18}$alkynyl. In some embodiments, $R^L$ is optionally substituted heteroC$_{4-17}$alkynyl. In some embodiments, $R^L$ is optionally substituted heteroC$_{4-16}$alkynyl. In some embodiments, $R^L$ is optionally substituted heteroC$_{4-15}$alkynyl. In some embodiments, $R^L$ is optionally substituted heteroC$_{4-14}$alkynyl. In some embodiments, $R^L$ is optionally substituted heteroC$_{4-13}$alkynyl. In some embodiments, $R^L$ is optionally substituted heteroC$_{4-12}$alkynyl. In some embodiments, $R^L$ is optionally substituted heteroC$_{4-11}$alkynyl. In some embodiments, $R^L$ is optionally substituted heteroC$_{4-10}$alkynyl. In some embodiments, $R^L$ is optionally substituted heteroC$_{4-9}$alkynyl. In some embodiments, $R^L$ is optionally substituted heteroC$_{4-8}$alkynyl. In some embodiments, $R^L$ is optionally substituted heteroC$_{4-7}$alkynyl. In some embodiments, $R^L$ is optionally substituted heteroC$_{4-6}$alkynyl.

In some embodiments, $R^L$ is optionally substituted heteroC$_{6-50}$alkynyl. In some embodiments, $R^L$ is optionally substituted heteroC$_{6-40}$alkynyl. In some embodiments, $R^L$ is optionally substituted heteroC$_{6-30}$alkynyl. In some embodiments, $R^L$ is optionally substituted heteroC$_{6-20}$alkynyl. In some embodiments, $R^L$ is optionally substituted heteroC$_{6-19}$alkynyl. In some embodiments, $R^L$ is optionally substituted heteroC$_{6-18}$alkynyl. In some embodiments, $R^L$ is optionally substituted heteroC$_{6-17}$alkynyl. In some embodiments, $R^L$ is optionally substituted heteroC$_{6-16}$alkynyl. In some embodiments, $R^L$ is optionally substituted heteroC$_{6-15}$alkynyl. In some embodiments, $R^L$ is optionally substituted heteroC$_{6-14}$alkynyl. In some embodiments, $R^L$ is optionally substituted heteroC$_{6-13}$alkynyl. In some embodiments, $R^L$ is optionally substituted heteroC$_{6-12}$alkynyl. In some embodiments, $R^L$ is optionally substituted heteroC$_{6-11}$alkynyl. In some embodiments, $R^L$ is optionally substituted heteroC$_{6-10}$alkynyl. In some embodiments, $R^L$ is optionally substituted heteroC$_{6-9}$alkynyl. In some embodiments, $R^L$ is optionally substituted heteroC$_{6-8}$alkynyl. In some embodiments, $R^L$ is optionally substituted heteroC$_{6-7}$alkynyl.

In some embodiments, $R^L$ is optionally substituted heteroC$_{8-50}$alkynyl. In some embodiments, $R^L$ is optionally substituted heteroC$_{8-40}$alkynyl. In some embodiments, $R^L$ is optionally substituted heteroC$_{8-30}$alkynyl. In some embodiments, $R^L$ is optionally substituted heteroC$_{8-20}$alkynyl. In some embodiments, $R^L$ is optionally substituted heteroC$_{8-19}$alkynyl. In some embodiments, $R^L$ is optionally substituted heteroC$_{8-18}$alkynyl. In some embodiments, $R^L$ is optionally substituted heteroC$_{8-17}$alkynyl. In some embodiments, $R^L$ is optionally substituted heteroC$_{8-16}$alkynyl. In some embodiments, $R^L$ is optionally substituted heteroC$_{8-15}$alkynyl. In some embodiments, $R^L$ is optionally substituted heteroC$_{8-14}$alkynyl. In some embodiments, $R^L$ is optionally substituted heteroC$_{8-13}$alkynyl. In some embodiments, $R^L$ is optionally substituted heteroC$_{8-12}$alkynyl. In some embodiments, $R^L$ is optionally substituted heteroC$_{8-11}$alkynyl. In some embodiments, $R^L$ is optionally substituted heteroC$_{8-10}$alkynyl. In some embodiments, $R^L$ is optionally substituted heteroC$_{8-9}$alkynyl.

In some embodiments, $R^L$ is optionally substituted heteroC$_{9-50}$alkynyl. In some embodiments, $R^L$ is optionally substituted heteroC$_{9-40}$alkynyl. In some embodiments, $R^L$ is optionally substituted heteroC$_{9-30}$alkynyl. In some embodiments, $R^L$ is optionally substituted heteroC$_{9-20}$alkynyl. In some embodiments, $R^L$ is optionally substituted heteroC$_{9-19}$alkynyl. In some embodiments, $R^L$ is optionally substituted heteroC$_{9-18}$alkynyl. In some embodiments, $R^L$ is optionally substituted heteroC$_{9-17}$alkynyl. In some embodiments, $R^L$ is optionally substituted heteroC$_{9-16}$alkynyl. In some embodiments, $R^L$ is optionally substituted heteroC$_{9-15}$alkynyl. In some embodiments, $R^L$ is optionally substituted heteroC$_{9-14}$alkynyl. In some embodiments, $R^L$ is optionally substituted heteroC$_{9-13}$alkynyl. In some embodiments, $R^L$ is optionally substituted heteroC$_{9-12}$alkynyl. In some embodiments, $R^L$ is optionally substituted heteroC$_{9-11}$alkynyl. In some embodiments, $R^L$ is optionally substituted heteroC$_{9-10}$alkynyl.

In some embodiments, $R^L$ is optionally substituted heteroC$_{10-50}$alkynyl. In some embodiments, $R^L$ is optionally substituted heteroC$_{10-40}$alkynyl. In some embodiments, $R^L$ is optionally substituted heteroC$_{10-30}$alkynyl. In some embodiments, $R^L$ is optionally substituted heteroC$_{10-20}$alkynyl. In some embodiments, $R^L$ is optionally substituted heteroC$_{10-19}$alkynyl. In some embodiments, $R^L$ is optionally substituted heteroC$_{10-18}$alkynyl. In some embodiments, $R^L$ is optionally substituted heteroC$_{10-17}$alkynyl. In some embodiments, $R^L$ is optionally substituted heteroC$_{10-16}$alkynyl. In some embodiments, $R^L$ is optionally substituted heteroC$_{10-15}$alkynyl. In some embodiments, $R^L$ is optionally substituted heteroC$_{10-14}$alkynyl. In some embodiments, $R^L$ is optionally substituted heteroC$_{10-13}$alkynyl. In some embodiments, $R^L$ is optionally substituted heteroC$_{10-12}$alkynyl. In some embodiments, $R^L$ is optionally substituted heteroC$_{10-11}$alkynyl.

In some embodiments, $R^L$ is optionally substituted heteroC$_{11-50}$alkynyl. In some embodiments, $R^L$ is optionally substituted heteroC$_{11-40}$alkynyl. In some embodiments, $R^L$ is optionally substituted heteroC$_{11-30}$alkynyl. In some embodiments, $R^L$ is optionally substituted heteroC$_{11-20}$alkynyl. In some embodiments, $R^L$ is optionally substituted heteroC$_{11-19}$alkynyl. In some embodiments, $R^L$ is optionally substituted heteroC$_{11-18}$alkynyl. In some embodiments, $R^L$ is optionally substituted heteroC$_{1-17}$alkynyl. In some embodiments, $R^L$ is optionally substituted heteroC$_{11-16}$alkynyl. In some embodiments, $R^L$ is optionally substituted heteroC$_{11-15}$alkynyl. In some embodiments, $R^L$ is optionally substituted heteroC$_{11-14}$alkynyl. In some embodiments, $R^L$ is optionally substituted heteroC$_{11-13}$alkynyl. In some embodiments, $R^L$ is optionally substituted heteroC$_{11-12}$alkynyl.

In some embodiments, $R^L$ is optionally substituted heteroC$_{12-50}$alkynyl. In some embodiments, $R^L$ is optionally substituted heteroC$_{12-40}$alkynyl. In some embodiments, $R^L$ is optionally substituted heteroC$_{12-30}$alkynyl. In some embodiments, $R^L$ is optionally substituted heteroC$_{12-20}$alkynyl. In some embodiments, $R^L$ is optionally substituted heteroC$_{12-19}$alkynyl. In some embodiments, $R^L$ is optionally substituted heteroC$_{12-18}$alkynyl. In some embodiments, $R^L$ is optionally substituted heteroC$_{12-17}$alkynyl. In some embodiments, $R^L$ is optionally substituted heteroC$_{12-16}$alkynyl. In some embodiments, $R^L$ is optionally substituted heteroC$_{12-15}$alkynyl. In some embodiments, $R^L$ is optionally substituted heteroC$_{12-14}$alkynyl. In some embodiments, $R^L$ is optionally substituted heteroC$_{12-13}$alkynyl.

In some embodiments, $R^L$ is optionally substituted heteroC$_6$alkynyl. In some embodiments, $R^L$ is optionally substituted heteroC$_7$alkynyl. In some embodiments, $R^L$ is optionally substituted heteroC$_8$alkynyl. In some embodiments, $R^L$ is optionally substituted heteroC$_9$alkynyl. In some embodiments, $R^L$ is optionally substituted heteroC$_{10}$alkynyl. In some embodiments, $R^L$ is optionally substituted heteroC$_{11}$alkynyl. In some embodiments, $R^L$ is optionally substituted heteroC$_{12}$alkynyl. In some embodiments, $R^L$ is optionally substituted heteroC$_{13}$alkynyl. In some embodiments, $R^L$ is optionally substituted heteroC$_{14}$alkynyl. In some embodiments, $R^L$ is optionally substituted heteroC$_{15}$alkynyl. In some embodiments, $R^L$ is optionally substituted heteroC$_{16}$alkynyl. In some embodiments, $R^L$ is optionally substituted heteroC$_{17}$alkynyl. In some embodiments, $R^L$ is optionally substituted heteroC$_{18}$alkynyl. In some embodiments, $R^L$ is optionally substituted heteroC$_{19}$alkynyl. In some embodiments, $R^L$ is optionally substituted heteroC$_{20}$alkynyl.

In some embodiments, for example, in any of the above embodiments, $R^L$ is a substituted heteroalkynyl group. In some embodiments, $R^L$ is an unsubstituted heteroalkynyl group. In some embodiments, $R^L$ is an optionally substituted straight-chain heteroalkynyl group. In some embodiments, $R^L$ is a substituted straight-chain heteroalkynyl group. In some embodiments, $R^L$ is an unsubstituted straight-chain heteroalkynyl group. In some embodiments, $R^L$ is an optionally substituted branched heteroalkynyl group. In some embodiments, $R^L$ is a substituted branched heteroalkynyl group. In some embodiments, $R^L$ is an unsubstituted branched heteroalkynyl group.

In some embodiments, $R^L$ is a polymer. As used herein, a "polymer", in some embodiments, refers to a compound comprised of at least 3 (e.g., at least 10, 20, 30, 40, 50, 60, 70, 80, 90, 100, etc.) repeating covalently bound structural units. The polymer is in certain embodiments biocompatible (i.e., non-toxic). Exemplary polymers include, but are not limited to, cellulose polymers (e.g., hydroxyethylcellulose, ethylcellulose, carboxymethylcellulose, methylc cellulose, hydroxypropylmethylcellulose (HPMC)), dextran polymers, polymaleic acid polymers, poly(acrylic acid) polymers, poly(vinylalcohol) polymers, polyvinylpyrrolidone (PVP) polymers, and polyethyleneglycol (PEG) polymers, and combinations thereof.

In some embodiments, $R^L$ is a lipophilic, hydrophobic and/or non-polar group. In some embodiments, $R^L$ is a lipophilic group. In some embodiments, $R^L$ is a hydrophobic group. In some embodiments, $R^L$ is a non-polar group.

In some embodiments, when an $R^L$ group is depicted as bisecting a carbon-carbon bond, e.g., of the formula (i), it is understood that $R^L$ may be bonded to either carbon.

In some embodiments, at least one instance of $R^Q$, $R^2$, $R^6$, or $R^7$ is a group of the formula (i), (ii), or (iii). In some embodiments, at least one instance of $R^6$ or $R^7$ of $R^1$ is a group of formula (i), (ii) or (iii). In some embodiments, at least one instance of $R^6$ or $R^7$ of $R^1$ is a group of formula (i). In some embodiments, at least one instance of $R^6$ or $R^7$ of $R^1$ is a group of formula (i-a). In some embodiments, at least one instance of $R^6$ or $R^7$ of $R^1$ is a group of formula (i-a1). In some embodiments, at least one instance of $R^6$ or $R^7$ of $R^1$ is a group of formula (i-b). In some embodiments, at least one instance of $R^6$ or $R^7$ of $R^1$ is a group of formula (ii). In some embodiments, at least one instance of $R^6$ or $R^7$ of $R^1$ is a group of formula (iii).

Various combinations of the above embodiments of Formula I are contemplated herein.

In some embodiments, wherein each instance of Q is O, the compound of formula I is a compound of formula I-a:

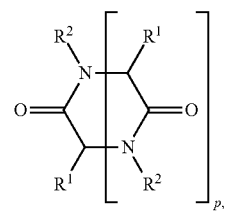

I-a or a pharmaceutically acceptable salt thereof, wherein each variable is independently as defined above and described herein.

In certain embodiments, at least one $R^1$ is a group of formula (iv). In certain embodiments, each instance of $R^1$ is a group of formula (iv). In certain embodiments, each instance of $R^2$ is independently hydrogen or optionally substituted C$_{1-6}$alkyl. In certain embodiments, each instance of $R^2$ is hydrogen. In certain embodiments, at least one instance of $R^2$ is a group of formula (i). In certain embodiments, at least one instance of $R^2$ is a group of formula (ii). In certain embodiments, at least one instance of $R^2$ is a group of formula (iii). In certain embodiments, p is 1. In certain embodiments, p is 2. In certain embodiments, p is 3.

In some embodiments, wherein at least one $R^1$ is a group of formula (iv), a compound of formula I is a compound of formula I-b:

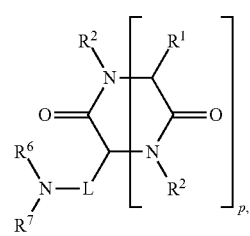

I-b or a pharmaceutically acceptable salt thereof, wherein each variable is independently as defined above and described herein.

In certain embodiments, each instance of $R^1$ is a group of formula (iv). In certain embodiments, each instance of $R^2$ is independently hydrogen or optionally substituted C$_{1-6}$alkyl. In certain embodiments, each instance of $R^2$ is hydrogen. In certain embodiments, at least one instance of $R^2$ is a group of formula (i). In certain embodiments, at least one instance of $R^2$ is a group of formula (ii). In certain embodiments, at least one instance of $R^2$ is a group of formula (iii). In certain embodiments, p is 1. In certain embodiments, p is 2. In certain embodiments, p is 3. In certain embodiments, L is an optionally substituted alkylene. In certain embodiments, $R^6$ is a group of formula (i). In certain embodiments, $R^6$ is a group of formula (ii). In certain embodiments, $R^6$ is a group of formula (iii). In certain embodiments, $R^7$ is a group of formula (i). In certain embodiments, $R^7$ is a group of formula (ii). In certain embodiments, $R^7$ is a group of formula (iii). In certain embodiments, both $R^6$ and $R^7$ are independently groups of formula (i), (ii), or (iii).

In some embodiments, wherein each instance of $R^1$ is a group the formula (iv), a compound of Formula I is a compound of formula I-c:

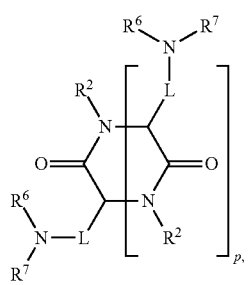

I-c or a pharmaceutically acceptable salt thereof, wherein each variable is independently as defined above and described herein.

In certain embodiments, each instance of $R^2$ is independently hydrogen or optionally substituted $C_{1-6}$alkyl. In certain embodiments, each instance of $R^2$ is hydrogen. In certain embodiments, at least one instance of $R^2$ is a group of formula (i). In certain embodiments, at least one instance of $R^2$ is a group of formula (ii). In certain embodiments, at least one instance of $R^2$ is a group of formula (iii). In certain embodiments, p is 1. In certain embodiments, p is 2. In certain embodiments, p is 3. In certain embodiments, L is an optionally substituted alkylene. In certain embodiments, $R^6$ is a group of formula (i). In certain embodiments, $R^6$ is a group of formula (ii). In certain embodiments, $R^6$ is a group of formula (iii). In certain embodiments, $R^7$ is a group of formula (i). In certain embodiments, $R^7$ is a group of formula (ii). In certain embodiments, $R^7$ is a group of formula (iii). In certain embodiments, both $R^6$ and $R^7$ are independently groups of formula (i), (ii), or (iii).

In some embodiments, p=1. In some embodiments, a compound of formula I-c is a compound of formula I-c1:

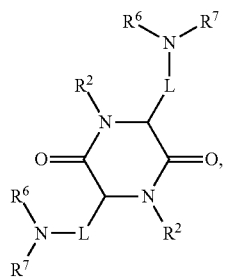

I-c1 or a pharmaceutically acceptable salt thereof, wherein each variable is independently as defined above and described herein.

In certain embodiments, each instance of $R^2$ is independently hydrogen or optionally substituted $C_{1-6}$alkyl. In certain embodiments, each instance of $R^2$ is hydrogen. In certain embodiments, at least one instance of $R^2$ is a group of formula (i). In certain embodiments, at least one instance of $R^2$ is a group of formula (ii). In certain embodiments, at least one instance of $R^2$ is a group of formula (iii). In certain embodiments, L is an optionally substituted alkylene. In certain embodiments, $R^6$ is a group of formula (i). In certain embodiments, $R^6$ is a group of formula (ii). In certain embodiments, $R^6$ is a group of formula (iii). In certain embodiments, $R^7$ is a group of formula (i). In certain embodiments, $R^7$ is a group of formula (ii). In certain embodiments, $R^7$ is a group of formula (iii). In certain embodiments, both $R^6$ and $R^7$ are independently groups of formula (i), (ii), or (iii). In some embodiments, $R^6$ and $R^7$ are the same group of formula (i). In some embodiments, $R^6$ and $R^7$ are the same group of formula (i-a). In some embodiments, $R^6$ and $R^7$ are the same group of formula (i-a1). In some embodiments, $R^6$ and $R^7$ are the same group of formula (i-b). In some embodiments, $R^6$ and $R^7$ are the same group of formula (ii). In some embodiments, $R^6$ and $R^7$ are the same group of formula (iii).

In some embodiments, each instance of $R^2$ is hydrogen. In some embodiments, a compound of formula I-c is a compound of formula I-c2:

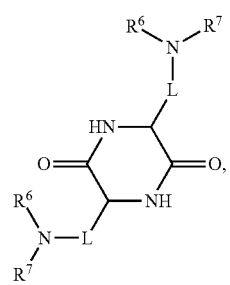

I-c2 or a pharmaceutically acceptable salt thereof, wherein each variable is independently as defined above and described herein.

In certain embodiments, L is an optionally substituted alkylene. In certain embodiments, $R^6$ is a group of formula (i). In certain embodiments, $R^6$ is a group of formula (ii). In certain embodiments, $R^6$ is a group of formula (iii). In certain embodiments, $R^7$ is a group of formula (i). In certain embodiments, $R^7$ is a group of formula (ii). In certain embodiments, $R^7$ is a group of formula (iii). In certain embodiments, both $R^6$ and $R^7$ are independently groups of formula (i), (ii), or (iii). In some embodiments, $R^6$ and $R^7$ are the same group of formula (i). In some embodiments, $R^6$ and $R^7$ are the same group of formula (i-a). In some embodiments, $R^6$ and $R^7$ are the same group of formula (i-a1). In some embodiments, $R^6$ and $R^7$ are the same group of formula (i-b). In some embodiments, $R^6$ and $R^7$ are the same group of formula (ii). In some embodiments, $R^6$ and $R^7$ are the same group of formula (iii).

In some embodiments, L is an optionally substituted alkylene. In some embodiments, a compound of formula I-c is a compound of formula I-c3:

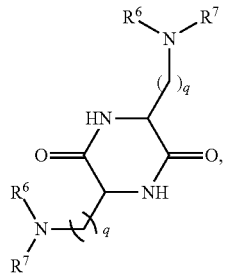

I-c3 or a pharmaceutically acceptable salt thereof, wherein each variable is independently as defined above and described herein.

In some embodiments, q is an integer between 1 and 10, inclusive. In certain embodiments, $R^6$ is a group of formula (i). In certain embodiments, $R^6$ is a group of formula (ii). In certain embodiments, $R^6$ is a group of formula (iii). In certain embodiments, $R^7$ is a group of formula (i). In certain embodiments, $R^7$ is a group of formula (ii). In certain embodiments, $R^7$ is a group of formula (iii). In certain embodiments, both $R^6$ and $R^7$ are independently groups of formula (i), (ii), or (iii). In some embodiments, $R^6$ and $R^7$ are the same group of formula (i). In some embodiments, $R^6$ and $R^7$ are the same group of formula (i-a). In some embodiments, $R^6$ and $R^7$ are the same group of formula (i-a1). In some embodiments, $R^6$ and $R^7$ are the same group of formula (i-b). In some embodiments, $R^6$ and $R^7$ are the same group of formula (ii). In some embodiments, $R^6$ and $R^7$ are the same group of formula (iii).

In some embodiments, a compound of formula I is a compound of formula I-d:

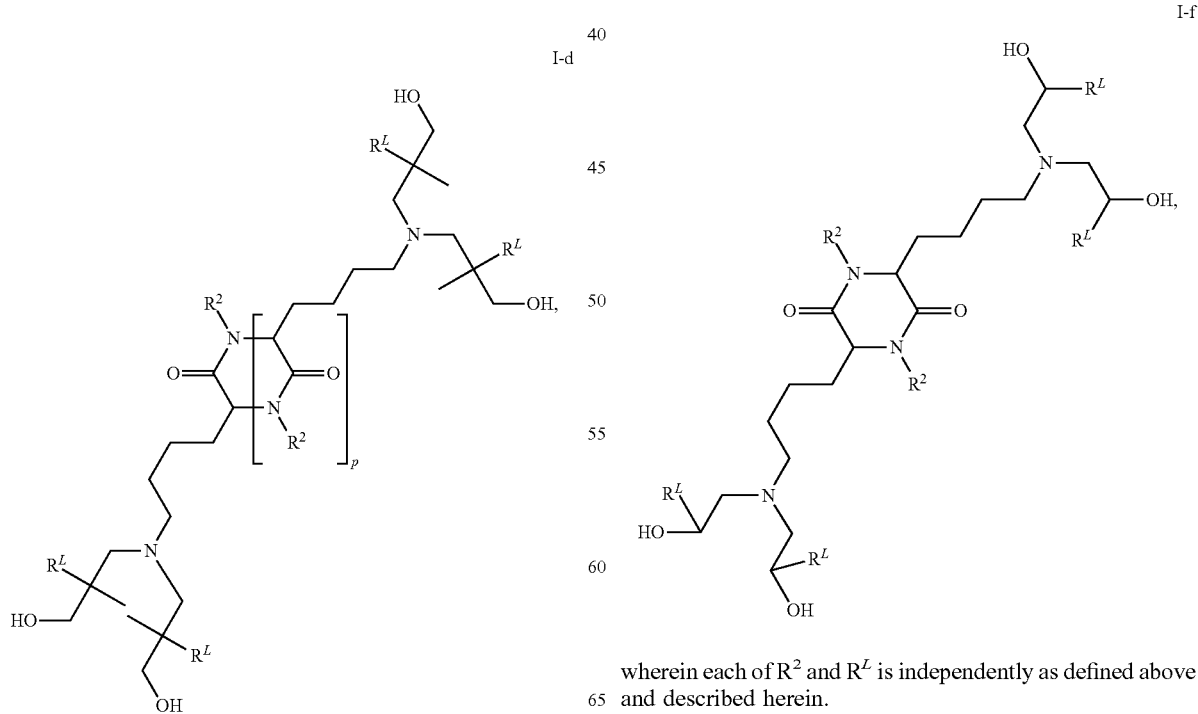

I-d wherein each of p, $R^2$ and $R^L$ is independently as defined above and described herein.

In some embodiments, a compound of formula I is a compound of formula I-e:

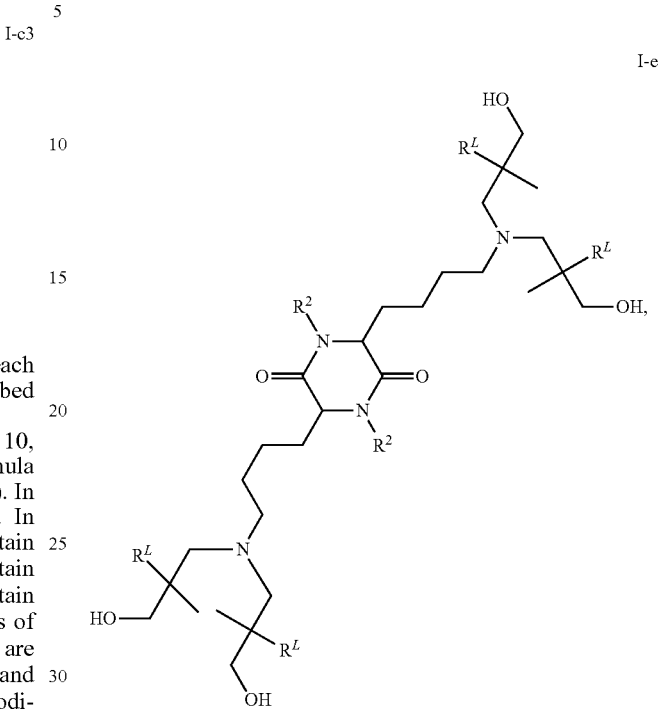

I-e wherein each of $R^2$ and $R^L$ is independently as defined above and described herein.

In some embodiments, a compound of formula I is a compound of formula I-f:

I-f wherein each of $R^2$ and $R^L$ is independently as defined above and described herein.

In some embodiments, provided liposomes include a cationic lipid described in WO 2013063468 and in U.S.

provisional application entitled "Lipid Formulations for Delivery of Messenger RNA" filed concurrently with the present application on even date, both of which are incorporated by reference herein. In some embodiments, a compound of formula I is a compound of formula I-c1-a:

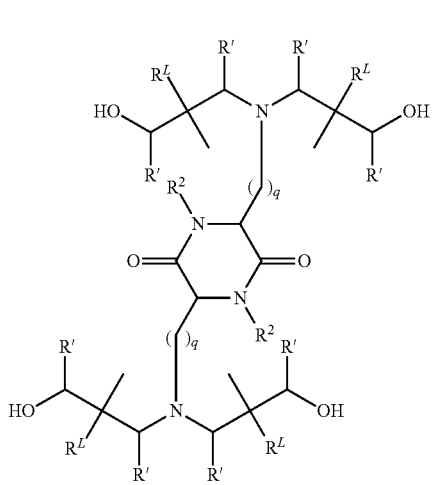

or a pharmaceutically acceptable salt thereof, wherein:
each $R^2$ independently is hydrogen or $C_{1-3}$ alkyl;
each q independently is 2 to 6;
each R' independently is hydrogen or $C_{1-3}$ alkyl;
and each $R^L$ independently is $C_{8-12}$ alkyl.

In some embodiments, each $R^2$ independently is hydrogen, methyl or ethyl. In some embodiments, each $R^2$ independently is hydrogen or methyl. In some embodiments, each $R^2$ is hydrogen.

In some embodiments, each q independently is 3 to 6. In some embodiments, each q independently is 3 to 5. In some embodiments, each q is 4.

In some embodiments, each R' independently is hydrogen, methyl or ethyl. In some embodiments, each R' independently is hydrogen or methyl. In some embodiments, each R' independently is hydrogen.

In some embodiments, each $R^L$ independently is $C_{8-12}$ alkyl. In some embodiments, each $R^L$ independently is n-$C_{8-12}$ alkyl. In some embodiments, each $R^L$ independently is $C_{9-11}$ alkyl. In some embodiments, each $R^L$ independently is n-$C_{9-11}$ alkyl. In some embodiments, each $R^L$ independently is $C_{10}$ alkyl. In some embodiments, each $R^L$ independently is n-$C_{10}$ alkyl.

In some embodiments, each $R^2$ independently is hydrogen or methyl; each q independently is 3 to 5; each R' independently is hydrogen or methyl; and each $R^L$ independently is $C_{8-12}$ alkyl.

In some embodiments, each $R^2$ is hydrogen; each q independently is 3 to 5; each R' is hydrogen; and each $R^L$ independently is $C_{8-12}$ alkyl.

In some embodiments, each $R^2$ is hydrogen; each q is 4; each R' is hydrogen; and each $R^L$ independently is $C_{8-12}$ alkyl.

In some embodiments, a compound of formula I is a compound of formula I-g:

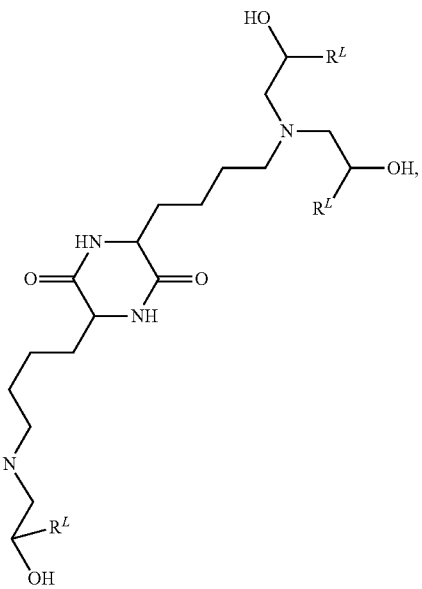

wherein each of $R^L$ is independently as defined above and described herein.

In some embodiments, a compound of formula I is a compound of formula X:

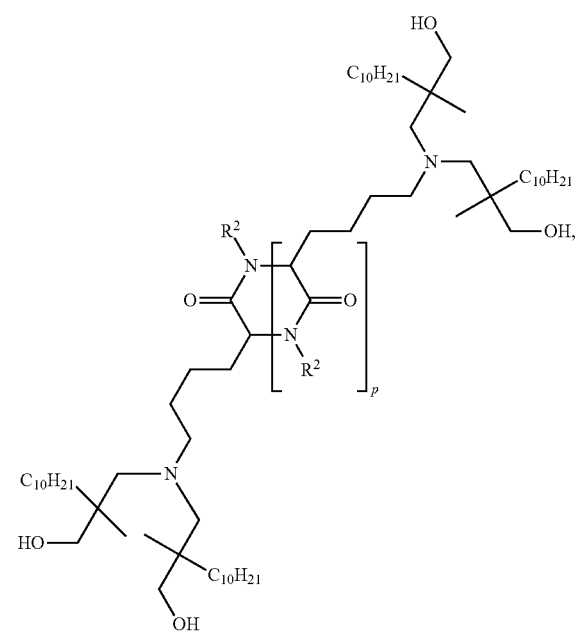

or a pharmaceutically acceptable salt thereof, wherein each variable is independently as defined above and described herein.

In some embodiments, a compound of formula I is a compound of formula X-1:

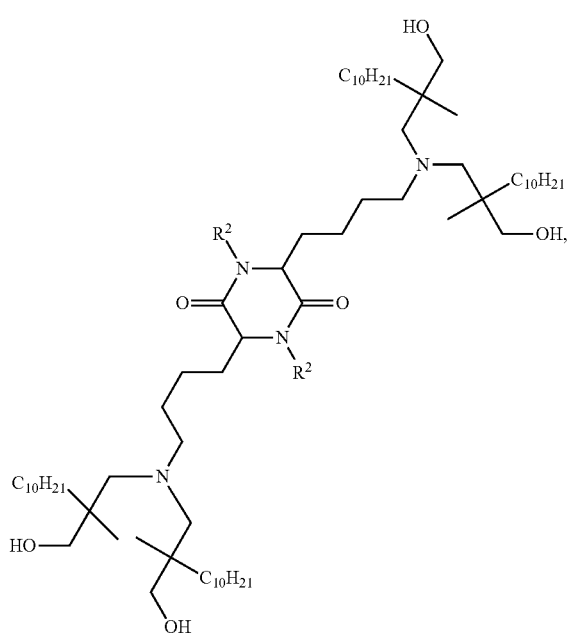

or a pharmaceutically acceptable salt thereof, wherein each $R^2$ is independently as defined above and described herein.

In some embodiments, a compound of formula I is

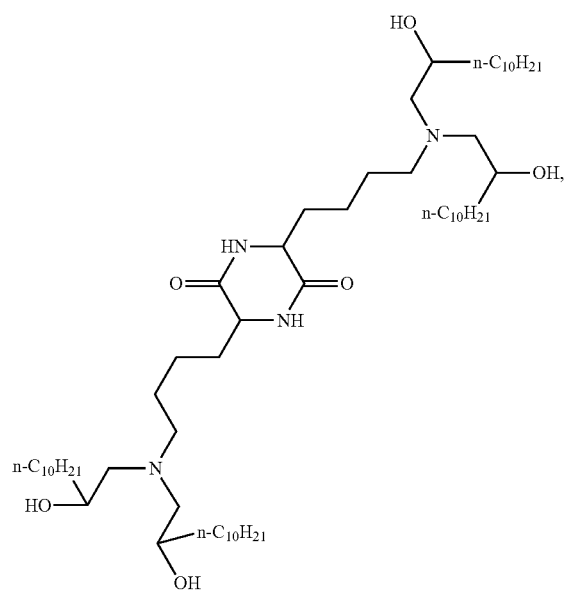

or a pharmaceutically acceptable salt thereof.

Additional examples of cationic lipids suitable for the present invention are described in WO 2013063468, which is incorporated by reference herein in its entirety.

Chemical Definitions

Definitions of specific functional groups and chemical terms are described in more detail below. The chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high performance liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally contemplates compounds as individual isomers substantially free of other isomers, and alternatively, as mixtures of various isomers.

When a range of values is listed, it is intended to encompass each value and sub-range within the range. For example "C1-6 alkyl" is intended to encompass, C1, C2, C3, C4, C5, C6, C1-6, C1-5, C1-4, C1-3, C1-2, C2-6, C2-5, C2-4, C2-3, C3-6, C3-5, C3-4, C4-6, C4-5, and C5-6 alkyl.

As used herein, "alkyl" refers to a radical of a straight-chain or branched saturated hydrocarbon group having from 1 to 50 carbon atoms ("C1-50 alkyl"). In some embodiments, an alkyl group has 1 to 40 carbon atoms ("C1-40 alkyl"). In some embodiments, an alkyl group has 1 to 30 carbon atoms ("C1-30 alkyl"). In some embodiments, an alkyl group has 1 to 20 carbon atoms ("C1-20 alkyl"). In some embodiments, an alkyl group has 1 to 10 carbon atoms ("C1-10 alkyl"). In some embodiments, an alkyl group has 1 to 9 carbon atoms ("C1-9 alkyl"). In some embodiments, an alkyl group has 1 to 8 carbon atoms ("C1-8 alkyl"). In some embodiments, an alkyl group has 1 to 7 carbon atoms ("C1-7 alkyl"). In some embodiments, an alkyl group has 1 to 6 carbon atoms ("C1-6 alkyl"). In some embodiments, an alkyl group has 1 to 5 carbon atoms ("C1-5 alkyl"). In some embodiments, an alkyl group has 1 to 4 carbon atoms ("C1-4 alkyl"). In some embodiments, an alkyl group has 1 to 3 carbon atoms ("C1-3 alkyl"). In some embodiments, an alkyl group has 1 to 2 carbon atoms ("C1-2 alkyl"). In some embodiments, an alkyl group has 1 carbon atom ("C1 alkyl"). In some embodiments, an alkyl group has 2 to 6 carbon atoms ("C2-6 alkyl"). Examples of C1-6 alkyl groups include, without limitation, methyl (C1), ethyl (C2), n-propyl (C3), isopropyl (C3), n-butyl (C4), tert-butyl (C4), sec-butyl (C4), iso-butyl (C4), n-pentyl (C5), 3-pentanyl (C5), amyl (C5), neopentyl (C5), 3-methyl-2-butanyl (C5), tertiary amyl (C5), and n-hexyl (C6). Additional examples of alkyl groups include n-heptyl (C7), n-octyl (C8) and the like.

Unless otherwise specified, each instance of an alkyl group is independently unsubstituted (an "unsubstituted alkyl") or substituted (a "substituted alkyl") with one or more substituents. In certain embodiments, the alkyl group is an unsubstituted C1-50 alkyl. In certain embodiments, the alkyl group is a substituted C1-50 alkyl.

As used herein, "heteroalkyl" refers to an alkyl group as defined herein which further includes at least one heteroatom (e.g., 1 to 25, e.g., 1, 2, 3, or 4 heteroatoms) selected from oxygen, sulfur, nitrogen, boron, silicon, and phosphorus within (i.e., inserted between adjacent carbon atoms of) and/or placed at one or more terminal position(s) of the parent chain. In certain embodiments, a heteroalkyl group refers to a saturated group having from 1 to 50 carbon atoms and 1 or more heteroatoms within the parent chain ("heteroC1-50 alkyl"). In certain embodiments, a heteroalkyl group refers to a saturated group having from 1 to 40 carbon atoms and 1 or more heteroatoms within the parent chain ("heteroC1-40 alkyl"). In certain embodiments, a heteroalkyl group refers to a saturated group having from 1 to 30 carbon atoms and 1 or more heteroatoms within the parent chain ("heteroC1-30 alkyl"). In certain embodiments, a heteroalkyl group refers to a saturated group having from 1 to 20 carbon atoms and 1 or more heteroatoms within the parent chain ("heteroC1-20 alkyl"). In certain embodiments, a heteroalkyl group refers to a saturated group having from 1 to 10 carbon atoms and 1 or more heteroatoms within the parent chain ("heteroC1-10 alkyl"). In some embodiments, a heteroalkyl group is a saturated group having 1 to 9 carbon atoms and 1 or more heteroatoms within the parent chain ("heteroC1-9 alkyl"). In some embodiments, a heteroalkyl group is a saturated group having 1 to 8 carbon atoms and 1 or more heteroatoms within the parent chain ("heteroC1-8 alkyl"). In some embodiments, a heteroalkyl group is a saturated group having 1 to 7 carbon atoms and 1 or more heteroatoms within the parent chain ("heteroC1-7 alkyl"). In some embodiments, a heteroalkyl group is a saturated group having 1 to 6 carbon atoms and 1 or more heteroatoms within the parent chain ("heteroC1-6 alkyl"). In some embodiments, a heteroalkyl group is a saturated group having 1 to 5 carbon atoms and 1 or 2 heteroatoms within the parent chain ("heteroC1-5 alkyl"). In some embodiments, a heteroalkyl group is a saturated group having 1 to 4 carbon atoms and 1 or 2 heteroatoms within the parent chain ("heteroC1-4 alkyl"). In some embodiments, a heteroalkyl group is a saturated group having 1 to 3 carbon atoms and 1 heteroatom within the parent chain ("heteroC1-3 alkyl"). In some embodiments, a heteroalkyl group is a saturated group having 1 to 2 carbon atoms and 1 heteroatom within the parent chain ("heteroC1-2 alkyl"). In some embodiments, a heteroalkyl group is a saturated group having 1 carbon atom and 1 heteroatom ("heteroC1 alkyl"). In some embodiments, a heteroalkyl group is a saturated group having 2 to 6 carbon atoms and 1 or 2 heteroatoms within the parent chain ("heteroC2-6 alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC1-50 alkyl. In certain embodiments, the heteroalkyl group is a substituted heteroC1-50 alkyl.

As used herein, "alkenyl" refers to a radical of a straight-chain or branched hydrocarbon group having from 2 to 50 carbon atoms and one or more carbon-carbon double bonds (e.g., 1, 2, 3, or 4 double bonds) ("C2-50 alkenyl"). In some embodiments, an alkenyl group has 2 to 40 carbon atoms ("C2-40 alkenyl"). In some embodiments, an alkenyl group has 2 to 30 carbon atoms ("C2-30 alkenyl"). In some embodiments, an alkenyl group has 2 to 20 carbon atoms ("C2-20 alkenyl"). In some embodiments, an alkenyl group has 2 to 10 carbon atoms ("C2-10 alkenyl"). In some embodiments, an alkenyl group has 2 to 9 carbon atoms ("C2-9 alkenyl"). In some embodiments, an alkenyl group has 2 to 8 carbon atoms ("C2-8 alkenyl"). In some embodiments, an alkenyl group has 2 to 7 carbon atoms ("C2-7 alkenyl"). In some embodiments, an alkenyl group has 2 to 6 carbon atoms ("C2-6 alkenyl"). In some embodiments, an alkenyl group has 2 to 5 carbon atoms ("C2-5 alkenyl"). In some embodiments, an alkenyl group has 2 to 4 carbon atoms ("C2-4 alkenyl"). In some embodiments, an alkenyl group has 2 to 3 carbon atoms ("C2-3 alkenyl"). In some embodiments, an alkenyl group has 2 carbon atoms ("C2 alkenyl"). The one or more carbon-carbon double bonds can be internal (such as in 2-butenyl) or terminal (such as in 1-butenyl). Examples of C2-4 alkenyl groups include, without limitation, ethenyl (C2), 1-propenyl (C3), 2-propenyl (C3), 1-butenyl (C4), 2-butenyl (C4), butadienyl (C4), and the like. Examples of C2-6 alkenyl groups include the aforementioned C2-4 alkenyl groups as well as pentenyl (C5), pentadienyl (C5), hexenyl (C6), and the like. Additional examples of alkenyl include heptenyl (C7), octenyl (C8), octatrienyl (C8), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C2-50 alkenyl. In certain embodiments, the alkenyl group is a substituted C2-50 alkenyl.

As used herein, "heteroalkenyl" refers to an alkenyl group as defined herein which further includes at least one heteroatom (e.g., 1 to 25, e.g., 1, 2, 3, or 4 heteroatoms) selected from oxygen, sulfur, nitrogen, boron, silicon, and phosphorus within (i.e., inserted between adjacent carbon atoms of) and/or placed at one or more terminal position(s) of the parent chain. In certain embodiments, a heteroalkenyl group refers to a group having from 2 to 50 carbon atoms, at least one double bond, and 1 or more heteroatoms within the parent chain ("heteroC2-50 alkenyl"). In certain embodiments, a heteroalkenyl group refers to a group having from 2 to 40 carbon atoms, at least one double bond, and 1 or more heteroatoms within the parent chain ("heteroC2-40 alkenyl"). In certain embodiments, a heteroalkenyl group refers to a group having from 2 to 30 carbon atoms, at least one double bond, and 1 or more heteroatoms within the parent chain ("heteroC2-30 alkenyl"). In certain embodiments, a heteroalkenyl group refers to a group having from 2 to 20 carbon atoms, at least one double bond, and 1 or more heteroatoms within the parent chain ("heteroC2-20 alkenyl"). In certain embodiments, a heteroalkenyl group refers to a group having from 2 to 10 carbon atoms, at least one double bond, and 1 or more heteroatoms within the parent chain ("heteroC2-10 alkenyl"). In some embodiments, a heteroalkenyl group has 2 to 9 carbon atoms at least one double bond, and 1 or more heteroatoms within the parent chain ("heteroC2-9 alkenyl"). In some embodiments, a heteroalkenyl group has 2 to 8 carbon atoms, at least one double bond, and 1 or more heteroatoms within the parent chain ("heteroC2-8 alkenyl"). In some embodiments, a heteroalkenyl group has 2 to 7 carbon atoms, at least one double bond, and 1 or more heteroatoms within the parent chain ("heteroC2-7 alkenyl"). In some embodiments, a heteroalkenyl group has 2 to 6 carbon atoms, at least one double bond, and 1 or more heteroatoms within the parent chain ("heteroC2-6 alkenyl"). In some embodiments, a heteroalkenyl group has 2 to 5 carbon atoms, at least one double bond, and 1 or 2 heteroatoms within the parent chain ("heteroC2-5 alkenyl"). In some embodiments, a heteroalkenyl group has 2 to 4 carbon atoms. at least one double bond, and for 2 heteroatoms within the parent chain ("heteroC2-4 alkenyl"). In some embodiments, a heteroalkenyl group has 2 to 3 carbon atoms, at least one double bond, and 1 heteroatom within the parent chain ("heteroC2-3 alkenyl"). In some embodiments, a heteroalkenyl group has 2 to 6 carbon atoms, at least one double, bond, and 1 or 2 heteroatoms within the parent chain ("heteroC2-6 alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC2-50 alkenyl. In certain embodiments, the heteroalkenyl group is a substituted heteroC2-50 alkenyl.

As used herein, "alkynyl" refers to a radical of a straight-chain or branched hydrocarbon group having from 2 to 50 carbon atoms and one or more carbon-carbon triple bonds (e.g., 1, 2, 3, or 4 triple bonds) and optionally one or more double bonds (e.g., 1, 2, 3, or 4 double bonds) ("C2-50 alkynyl"). An alkynyl group that has one or more triple bonds and one or more double bonds is also referred to as an "ene-yne". In some embodiments, an alkynyl group has 2 to 40 carbon atoms ("C2-40 alkynyl"). In some embodiments, an alkynyl group has 2 to 30 carbon atoms ("C2-30 alkynyl"). In some embodiments, an alkynyl group has 2 to 20 carbon atoms ("C2-20 alkynyl"). In some embodiments, an alkynyl group has 2 to 10 carbon atoms ("C2-10 alkynyl"). In some embodiments, an alkynyl group has 2 to 9 carbon atoms ("C2-9 alkynyl"). In some embodiments, an alkynyl group has 2 to 8 carbon atoms ("C2-8 alkynyl"). In some embodiments, an alkynyl group has 2 to 7 carbon atoms ("C2-7 alkynyl"). In some embodiments, an alkynyl group has 2 to 6 carbon atoms ("C2-6 alkynyl"). In some embodiments, an alkynyl group has 2 to 5 carbon atoms ("C2-5 alkynyl"). In some embodiments, an alkynyl group has 2 to 4 carbon atoms ("C2-4 alkynyl"). In some embodiments, an alkynyl group has 2 to 3 carbon atoms ("C2-3 alkynyl"). In some embodiments, an alkynyl group has 2 carbon atoms ("C2 alkynyl"). The one or more carbon-carbon triple bonds can be internal (such as in 2-butynyl) or terminal (such as in 1-butynyl). Examples of C2-4 alkynyl groups include, without limitation, ethynyl (C2), 1-propynyl (C3), 2-propynyl (C3), 1-butynyl (C4), 2-butynyl (C4), and the like. Examples of C2-6 alkenyl groups include the aforementioned C2-4 alkynyl groups as well as pentynyl (C5), hexynyl (C6), and the like. Additional examples of alkynyl include heptynyl (C7), octynyl (C8), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C2-50 alkynyl. In certain embodiments, the alkynyl group is a substituted C2-50 alkynyl.

As used herein, "heteroalkynyl" refers to an alkynyl group as defined herein which further includes at least one heteroatom (e.g., 1 to 25, e.g., 1, 2, 3, or 4 heteroatoms) selected from oxygen, sulfur, nitrogen, boron, silicon, and phosphorus within (i.e., inserted between adjacent carbon atoms of) and/or placed at one or more terminal position(s) of the parent chain. In certain embodiments, a heteroalkynyl group refers to a group having from 2 to 50 carbon atoms, at least one triple bond, and 1 or more heteroatoms within the parent chain ("heteroC2-50 alkynyl"). In certain embodiments, a heteroalkynyl group refers to a group having from 2 to 40 carbon atoms, at least one triple bond, and 1 or more heteroatoms within the parent chain ("heteroC2-40 alkynyl"). In certain embodiments, a heteroalkynyl group refers to a group having from 2 to 30 carbon atoms, at least one triple bond, and 1 or more heteroatoms within the parent chain ("heteroC2-30 alkynyl"). In certain embodiments, a heteroalkynyl group refers to a group having from 2 to 20 carbon atoms, at least one triple bond, and 1 or more heteroatoms within the parent chain ("heteroC2-20 alkynyl"). In certain embodiments, a heteroalkynyl group refers to a group having from 2 to 10 carbon atoms, at least one triple bond, and 1 or more heteroatoms within the parent chain ("heteroC2-10 alkynyl"). In some embodiments, a heteroalkynyl group has 2 to 9 carbon atoms, at least one triple bond, and 1 or more heteroatoms within the parent chain ("heteroC2-9 alkynyl"). In some embodiments, a heteroalkynyl group has 2 to 8 carbon atoms, at least one triple bond, and 1 or more heteroatoms within the parent chain ("heteroC2-8 alkynyl"). In some embodiments, a heteroalkynyl group has 2 to 7 carbon atoms, at least one triple bond, and 1 or more heteroatoms within the parent chain ("heteroC2-7 alkynyl"). In some embodiments, a heteroalkynyl group has 2 to 6 carbon atoms, at least one triple bond, and 1 or more heteroatoms within the parent chain ("heteroC2-6 alkynyl"). In some embodiments, a heteroalkynyl group has 2 to 5 carbon atoms, at least one triple bond, and 1 or 2 heteroatoms within the parent chain ("heteroC2-5 alkynyl"). In some embodiments, a heteroalkynyl group has 2 to 4 carbon atoms, at least one triple bond, and for 2 heteroatoms within the parent chain ("heteroC2-4 alkynyl"). In some embodiments, a heteroalkynyl group has 2 to 3 carbon atoms, at least one triple bond, and 1 heteroatom within the parent chain ("heteroC2-3 alkynyl"). In some embodiments, a heteroalkynyl group has 2 to 6 carbon atoms, at least one triple bond. and 1 or 2 heteroatoms within the parent chain ("heteroC2-6 alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC2-50 alkynyl. In certain embodiments, the heteroalkynyl group is a substituted heteroC2-50 alkynyl.

As used herein, "carbocyclyl" or "carbocyclic" refers to a radical of a non-aromatic cyclic hydrocarbon group having from 3 to 10 ring carbon atoms ("C3-10 carbocyclyl") and zero heteroatoms in the non-aromatic ring system. In some embodiments, a carbocyclyl group has 3 to 8 ring carbon atoms ("C3-8 carbocyclyl"). In some embodiments, a carbocyclyl group has 3 to 7 ring carbon atoms ("C3-7 carbocyclyl"). In some embodiments, a carbocyclyl group has 3 to 6 ring carbon atoms ("C3-6 carbocyclyl"). In some embodiments, a carbocyclyl group has 4 to 6 ring carbon atoms ("C4-6 carbocyclyl"). In some embodiments, a carbocyclyl group has 5 to 6 ring carbon atoms ("C5-6 carbocyclyl"). In some embodiments, a carbocyclyl group has 5 to 10 ring carbon atoms ("C5-10 carbocyclyl"). Exemplary C3-6 carbocyclyl groups include, without limitation, cyclopropyl (C3), cyclopropenyl (C3), cyclobutyl (C4), cyclobutenyl (C4), cyclopentyl (C5), cyclopentenyl (C5), cyclohexyl (C6), cyclohexenyl (C6), cyclohexadienyl (C6), and the like. Exemplary C3-8 carbocyclyl groups include, without limitation, the aforementioned C3-6 carbocyclyl groups as well as cycloheptyl (C7), cycloheptenyl (C7), cycloheptadienyl (C7), cycloheptatrienyl (C7), cyclooctyl (C8), cyclooctenyl (C8), bicyclo[2.2.1]heptanyl (C7), bicyclo[2.2.2]octanyl (C8), and the like. Exemplary C3-10 carbocyclyl groups include, without limitation, the aforementioned C3-8 carbocyclyl groups as well as cyclononyl (C9), cyclononenyl (C9), cyclodecyl (C10), cyclodecenyl (C10), octahydro-1H-indenyl (C9), decahydronaphthalenyl (C10), spiro[4.5]decanyl (C10), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C3-10 carbocyclyl. In certain embodiments, the carbocyclyl group is a substituted C3-10 carbocyclyl.

In some embodiments, "carbocyclyl" or "carbocyclic" is referred to as a "cycloalkyl", i.e., a monocyclic, saturated carbocyclyl group having from 3 to 10 ring carbon atoms ("C3-10 cycloalkyl"). In some embodiments, a cycloalkyl group has 3 to 8 ring carbon atoms ("C3-8 cycloalkyl"). In some embodiments, a cycloalkyl group has 3 to 6 ring carbon atoms ("C3-6, cycloalkyl"). In some embodiments, a cycloalkyl group has 4 to 6 ring carbon atoms ("C4-6 cycloalkyl"). In some embodiments, a cycloalkyl group has 5 to 6 ring carbon atoms ("C5-6 cycloalkyl"). In some embodiments, a cycloalkyl group has 5 to 10 ring carbon atoms ("C5-10 cycloalkyl"). Examples of C5-6 cycloalkyl groups include cyclopentyl (C5) and cyclohexyl (C5). Examples of C3-6 cycloalkyl groups include the aforementioned C5-6 cycloalkyl groups as well as cyclopropyl (C3) and cyclobutyl (C4). Examples of C3-8 cycloalkyl groups include the aforementioned C3-6 cycloalkyl groups as well as cycloheptyl (C7) and cyclooctyl (C8). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C3-10 cycloalkyl. In certain embodiments, the cycloalkyl group is a substituted C3-10 cycloalkyl.

As used herein, "heterocyclyl" or "heterocyclic" refers to a radical of a 3- to 14-membered non-aromatic ring system having ring carbon atoms and 1 or more (e.g., 1, 2, 3, or 4) ring heteroatoms, wherein each heteroatom is independently selected from oxygen, sulfur, nitrogen, boron, silicon, and phosphorus ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")). and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance ofheterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1 or more (e.g., 1, 2, 3, or 4) ring heteroatoms, wherein each heteroatom is independently selected from oxygen, sulfur, nitrogen, boron, silicon, and phosphorus ("5-10 membered heterocyclyl"). In some embodiments, a heterocyclyl group is a 5-8 membered non-aromatic ring system having ring carbon atoms and 1 or more (e.g., 1, 2, 3, or 4) ring heteroatoms, wherein each heteroatom is independently selected from oxygen, sulfur, nitrogen, boron, silicon, and phosphorus ("5-8 membered heterocyclyl"). In some embodiments, a heterocyclyl group is a 5-6 membered non-aromatic ring system having ring carbon atoms and 1 or more (e.g., 1, 2, 3, or 4) ring heteroatoms, wherein each heteroatom is independently selected from oxygen, sulfur, nitrogen, boron, silicon, and phosphorus ("5-6 membered heterocyclyl"). In some embodiments, the 5-6 membered heterocyclyl has 1 or more (e.g., 1, 2, or 3) ring heteroatoms selected from oxygen, sulfur, nitrogen, boron, silicon, and phosphorus. In some embodiments, the 5-6 membered heterocyclyl has 1 or 2 ring heteroatoms selected from oxygen, sulfur, nitrogen, boron, silicon, and phosphorus. In some embodiments, the 5-6 membered heterocyclyl has 1 ring heteroatom selected from oxygen, sulfur, nitrogen, boron, silicon, and phosphorus.

Exemplary 3-membered heterocyclyl groups containing 1 heteroatom include, without limitation, azirdinyl, oxiranyl, thiorenyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation. tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo-[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("C6-14 aryl"). In some embodiments, an aryl group has 6 ring carbon atoms ("C6 aryl"; e.g., phenyl). In some embodiments, an aryl group has 10 ring carbon atoms ("C10 aryl"; e.g., naphthyl such as 1-naphthyl and 2-naphthyl). In some embodiments, an aryl group has 14 ring carbon atoms ("C14 aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted C6-14 aryl. In certain embodiments, the aryl group is a substituted C6-14 aryl.

As used herein, "heteroaryl" refers to a radical of a 5-14 membered monocyclic or polycyclic (e.g., bicyclic or tricyclic) 4n+2 aromatic ring system (e.g., having 6, 10, or 14 π electrons shared in a cyclic array) having ring carbon atoms and 1 or more (e.g., 1, 2, 3, or 4 ring heteroatoms) ring heteroatoms provided in the aromatic ring system, wherein each heteroatom is independently selected from oxygen, sulfur, nitrogen, boron, silicon, and phosphorus ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1 or more (e.g., 1, 2, 3, or 4) ring heteroatoms provided in the aromatic ring system, wherein each heteroatom is independently selected from oxygen, sulfur, nitrogen, boron, silicon, and phosphorus ("5-10 membered heteroaryl"). In some embodiments, a heteroaryl group is a 5-8 membered aromatic ring system having ring carbon atoms and 1 or more (e.g., 1, 2, 3, or 4) ring heteroatoms provided in the aromatic ring system, wherein each heteroatom is independently selected from oxygen, sulfur, nitrogen, boron, silicon, and phosphorus ("5-8 membered heteroaryl"). In some embodiments, a heteroaryl group is a 5-6 membered aromatic ring system having ring carbon atoms and 1 or more (e.g., 1, 2, 3, or 4) ring heteroatoms provided in the aromatic ring system, wherein each heteroatom is independently selected from oxygen, sulfur, nitrogen, boron, silicon, and phosphorus ("5-6 membered heteroaryl"). In some embodiments, the 5-6 membered heteroaryl has 1 or more (e.g., 1, 2, or 3) ring heteroatoms selected from oxygen, sulfur, nitrogen, boron, silicon, and phosphorus. In some embodiments, the 5-6 membered heteroaryl has 1 or 2 ring heteroatoms selected from oxygen, sulfur, nitrogen, boron, silicon, and phosphorus. In some embodiments, the 5-6 membered heteroaryl has 1 ring heteroatom selected from oxygen, sulfur, nitrogen, boron, silicon, and phosphorus. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, the term "saturated" refers to a ring moiety that does not contain a double or triple bond, i.e., the ring contains all single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteralkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

As understood from the above, alkyl, alkenyl, alkynyl, heteroalkyl, heteroalkenyl, heteroalkynyl, carbocyclyl, heterocyclyl, aryl, and heteroaryl groups, as defined herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or. "unsubstituted" heteroalkynyl. "substituted" or "unsubstituted" carbocyclyl. "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO2, —N3, —SO2H, —SO3H, —OH, —ORaa, —ON(Rbb)2, —N(Rbb)2, —N(Rbb)3+X—, —N(ORcc)Rbb, —SeH, —SeRaa, —SH, —SRaa, —SSRcc, —C(=O)Raa, —CO2H, —CHO, —C(ORcc)2, —CO2Raa, —OC(=O)Raa, —OCO2Raa, —C(=O)N(Rbb)2, —OC(=O)N(Rbb)2, —NRbbC(=O) Raa, —NRbbCO2Raa, —NRbbC(=O)N(Rbb)2, —C(=NRbb)Raa, —C(=NRbb)ORaa, —OC(=NRbb) Raa, —OC(=NRbb)ORaa, —C(=NRbb)N(Rbb)2, —OC(=NRbb)N(Rbb)2, —NRbbC(=NRbb)N(Rbb)2, —C(=O)NRbbSO2Raa, —NRbbSO2Raa, —SO2N(Rbb)2, —SO2Raa, —SO2ORaa, —OSO2Raa, —S(=O)Raa, —OS(=O)Raa, —Si(Raa)3 —OSi(Raa)3 —C(=S)N(Rbb)2, —C(=O)SRaa, —C(=S)SRaa, —SC(=S)SRaa, —SC(=O)SRaa, —OC(=O)SRaa, —SC(=O)ORaa, —SC(=O)Raa, —P(=O)2Raa, —OP(=O)2Raa, —P(=O)(Raa)2, —OP(=O)(Raa)2, —OP(=O)(ORcc)2, —P(=O)2N(Rbb)2, —OP(=O)2N(Rbb)2, —P(=O)(NRbb)2, —OP(=O)(NRbb)2, —NRbbP(=O)(ORcc)2, —NRbbP(=O)(NRbb)2, —P(Rcc)2, —P(Rcc)3, —OP(Rcc)2, —OP(Rcc)$_3$, —B(Raa)2, —B(ORcc)2, —BRaa(ORcc), C1-50 alkyl, C2-50 alkenyl, C2-50 alkynyl, C3-14 carbocyclyl, 3-14 membered heterocyclyl, C6-14 aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 Rdd groups;

or two geminal hydrogens on a carbon atom are replaced with the group =O, =S, =NN(Rbb)$_2$, =NNRbbC(=O) Raa, =NNRbbC(=O)ORaa, =NNRbbS(=O)$_2$Raa, =NRbb, or =NORcc;

each instance of Raa is, independently, selected from C1-50 alkyl, C2-50 alkenyl, C2-50 alkynyl, C3-10 carbocyclyl, 3-14 membered heterocyclyl, C6-14 aryl, and 5-14 membered heteroaryl, or two Raa groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rdd groups;

each instance of Rbb is, independently, selected from hydrogen, —OH, —ORaa, —N(Rcc)$_2$, —CN, —C(=O) Raa, —C(=O)N(Rcc)$_2$, —CO2Raa, —SO2Raa, —C(=NRcc)ORaa, —C(=NRcc)N(Rcc)$_2$, —SO2N (Rcc)$_2$, —SO2Rcc, —SO2ORcc, —SORaa, —C(=S)N (Rcc)$_2$, —C(=O)SRcc, —C(=S)SRcc, —P(=O)$_2$Raa, —P(=O)(Raa)$_2$, —P(=O)$_2$N(Rcc)$_2$, —P(=O)(NRcc)$_2$, C1-50 alkyl, C2-50 alkenyl, C2-50 alkynyl, C3-10 carbocyclyl, 3-14 membered heterocyclyl, C6-14 aryl, and 5-14 membered heteroaryl, or two Rbb groups, together with the heteroatom to which they are attached, form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rdd groups;

each instance of Rcc is, independently, selected from hydrogen, C1-50 alkyl, C2-50 alkenyl, C2-50 alkynyl, C3-10 carbocyclyl, 3-14 membered heterocyclyl, C6-14 aryl, and 5-14 membered heteroaryl, or two Rcc groups, together with the heteroatom to which they are attached, form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rdd groups;

each instance of Rdd is, independently, selected from halogen, —CN, —NO2, —N3, —SO2H, —SO3H, —OH, —ORee, —ON(Rff)$_2$, —N(Rff)$_2$, —N(Rff)$_3$+X—, —N(ORee)Rff, —SH, —SRee, —SSRee, —C(=O)Ree, —CO2H, —CO2Ree, —OC(=O)Ree, —OCO2Ree, —C(=O)N(Rff)$_2$, —OC(=O)N(Rff)$_2$, —NRffC(=O)Ree, —NRffCO2Ree, —NRffC(=O)N(Rff)$_2$, —C(=NRff) ORee, —OC(=NRff)Ree, —OC(=NRff)ORee, —C(=NRff)N(Rff)$_2$, —OC(=NRff)N(Rff)$_2$, —NRffC (=NRff)N(Rff)$_2$, —NRffSO2Ree, —S 02N(Rff)$_2$, —SO2Ree, —SO2ORee, —OSO2Ree, —S(=O)Ree, —Si (Ree)$_3$, —OSi(Ree)$_3$, —C(=S)N(Rff)$_2$, —C(=O)SRee, —C(=S)SRee, —SC(=S)SRee, —P(=O)$_2$Ree, —P(=O)(Ree)$_2$, —OP(=O)(Ree)$_2$, —OP(=O)(ORee)$_2$, C1-50 alkyl, C2-50 alkenyl, C2-50 alkynyl, C3-10 carbocyclyl, 3-10 membered heterocyclyl, C6-10 aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 Rgg groups, or two geminal Rdd substituents can be joined to form =O or =S;

each instance of Ree is, independently, selected from C1-50 alkyl, C2-50 alkenyl, C2-50 alkynyl, C3-10 carbocyclyl, C6-10 aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 Rgg groups;

each instance of Rff is, independently, selected from hydrogen, C1-50 alkyl, C2-50 alkenyl, C2-50 alkynyl, C3-10 carbocyclyl, 3-10 membered heterocyclyl, C6-10 aryl and 5-10 membered heteroaryl, or two Rff groups, together with the heteroatom to which they are attached, form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rgg groups; and each instance of Rgg is, independently, halogen, —CN, —NO2, —N3, —SO2H, —SO3H, —OH, —OC1-50 alkyl, —ON(C1-50 alkyl)$_2$, —N(C1-50 alkyl)$_2$, —N(C1-50 alkyl)$_3$+X—, —NH(C1-50 alkyl)$_2$+X—, —NH2(C1-50 alkyl)+X—, —NH3+X—, —N(OC1-50 alkyl)(C1-50 alkyl), —N(OH)(C1-50 alkyl), —NH(OH), —SH, —SC1-50 alkyl, —SS(C1-50 alkyl), —C(=O)(C1-50 alkyl), —CO2H, —CO2(C1-50 alkyl), —OC(=O)(C1-50 alkyl), —OCO2(C1-50 alkyl), —C(=O)NH2, —C(=O)N(C1-50 alkyl)$_2$, —OC(=O)NH(C1-50 alkyl), —NHC(=O)(C1-50 alkyl), —N(C1-50 alkyl)C(=O)(C1-50 alkyl), —NHCO2 (C1-50 alkyl), —NHC(=O)N(C1-50 alkyl)$_2$, —NHC(=O)NH(C1-50 alkyl), —NHC(=O)NH2, —C(=NH)O(C1-50 alkyl), —OC(=NH)(C1-50 alkyl), —OC(=NH)OC1-50 alkyl, —C(=NH)N(C1-50 alkyl)$_2$, —C(=NH)NH(C1-50 alkyl), —C(=NH)NH2, —OC(=NH)N(C1-50alky 1)$_2$, —OC(NH)NH(C1-50 alkyl), —OC(NH)NH2, —NHC(NH)N(C1-50 alkyl)$_2$, —NHC(=NH)NH2, —NHSO2 (C1-50 alkyl), —SO2N (C1-50 alkyl)$_2$, —SO2NH (C1-50 alkyl), —SO2NH2, —SO2C1-50 alkyl, —SO2OC1-50 alkyl, —OSO2C1-6 alkyl, —SOC1-6 alkyl, —Si(C1-50 alkyl)3, —OSi(C1-6 alkyl)3 —C(=S)N(C1-50 alkyl)2, C(=S)NH (C1-50 alkyl), C(=S)NH2, —C(=O)S(C1-6 alkyl), —C(=S)SC1-6 alkyl, —SC(=S)SC1-6 alkyl, —P(=O)2 (C1-50 alkyl), —P(=O)(C1-50 alkyl)2, —OP(=O)(C1-50 alkyl)2, —OP(=O)(OC1-50 alkyl)2, C1-50 alkyl, C2-50 alkenyl, C2-50 alkynyl, C3-10 carbocyclyl, C6-10 aryl, 3-10 membered heterocyclyl, 5-10 membered heteroaryl; or two geminal Rgg substituents can be joined to form =O or =S;

wherein X— is a counterion.

As used herein, the term "halo" or "halogen" refers to fluorine (fluoro, —F), chlorine (chloro, —Cl), bromine (bromo, —Br), or iodine (iodo, —I).

As used herein, a "counterion" is a negatively charged group associated with a positively charged quarternary amine in order to maintain electronic neutrality. Exemplary counterions include halide ions (e.g., F—, Cl—, Br—, I—), NO3-, C1O4-, OH—, H2PO4-, HSO4-, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —ORaa, —N(Rcc)2, —CN, —C(=O)Raa, —C(=O)N(Rcc)2, —CO2Raa, —SO2Raa, —C(=NRbb) Raa, —C(=NRcc)ORaa, —C(=NRcc)N(Rcc)2, —SO2N (Rcc)2, —SO2Rcc, —SO2ORcc, —SORaa, —C(=S)N (Rcc)2, —C(=O)SRcc, —C(=S)SRcc, —P(=O)2Raa, —P(=O)(Raa)2, —P(=O)2N(Rcc)2, —P(=O)(NRcc)2, C1-50 alkyl, C2-50 alkenyl, C2-50 alkynyl, C3-10 carbocyclyl, 3-14 membered heterocyclyl, C6-14 aryl, and 5-14 membered heteroaryl, or two Rcc groups, together with the N atom to which they are attached, form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rdd groups, and wherein Raa, Rbb, Rcc and Rdd are as defined above.

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —ORaa, —N(Rcc)2, —CN, —C(=O)Raa, —C(=O)N(Rcc)2, —CO2Raa, —SO2Raa, —C(=NRbb) Raa, —C(=NRcc)ORaa, —C(=NRcc)N(Rcc)2, —SO2N (Rcc)2, —SO2Rcc, —SO2ORcc, —SORaa, —C(=S)N (Rcc)2, —C(=O)SRcc, —C(=S)SRcc, —P(=O)2Raa, —P(=O)(Raa)2, —P(=O)2N(Rcc)2, —P(=O)(NRcc)2, C1-10 alkyl, C1-10 perhaloalkyl, C2-10 alkenyl, C2-10 alkynyl, C3-10 carbocyclyl, 3-14 membered heterocyclyl, C6-14 aryl, and 5-14 membered heteroaryl, or two Rcc groups, together with the nitrogen atom to which they are attached, form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rdd groups, and wherein Raa, Rbb, Rcc and Rdd are as defined above.

In certain embodiments, the substituent present on a nitrogen atom is a nitrogen protecting group (also referred to as an amino protecting group). Nitrogen protecting groups include, but are not limited to, —OH, —ORaa, —N(Rcc)2, —C(=O)Raa, —C(=O)N(Rcc)2, —CO2Raa, —SO2Raa, —C(=NRcc)Raa, —C(=NRcc)ORaa, —C(=NRcc)N (Rcc)2, —SO2N(Rcc)2, —SO2Rcc, —SO2ORcc, —SORaa, —C(=S)N(Rcc)2, —C(=O)SRcc, —C(=S) SRcc, C1-10 alkyl (e.g., aralkyl, heteroaralkyl), C2-10 alkenyl, C2-10 alkynyl, C3-10 carbocyclyl, 3-14 membered heterocyclyl, C6-14 aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4 or 5 Rdd groups, and wherein Raa, Rbb, Rcc and Rdd are as defined herein. Nitrogen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

For example, nitrogen protecting groups such as amide groups (e.g., —C(=O)Raa) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)ORaa) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10, 10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methyl sulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$Raa) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), j3-trimethyl silylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethyl silyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —Raa, —N(Rbb)2, —C(=O)SRaa, —C(=O)Raa, —CO2Raa, —C(=O)N (Rbb)2, —C(=NRbb)Raa, —C(=NRbb)ORaa, —C(=NRbb)N(Rbb)2, —S(=O)Raa, —SO2Raa, Si(Raa)$_3$, —P(Rcc)2, —P(Rcc)$_3$, —P(=O)2Raa, —P(=O)(Raa)2, —P(=O)(ORcc)2, —P(=O)2N(Rbb)2, and —P(=O)(NRbb)2, wherein Raa, Rbb, and Rcc are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a, 4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1- benzyloxyethyl, 1-methyl-1-benzyloxy-2-fluoroethyl, 2,2,2-trichloroethyl, 2-trimethyl silylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picoly1 N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is an sulfur protecting group (also referred to as a thiol protecting group). Sulfur protecting groups include, but are not limited to, —Raa, —N(Rbb)2, —C(=O)SRaa, —C(=O)Raa, —CO2Raa, C(=O)N(Rbb)2, —C(=NRbb)Raa, —C(=NRbb)ORaa, —C(=NRbb)N(Rbb)2, —S(=O)Raa, —SO2Raa, —Si(Raa)3, —P(Rcc)2, —P(Rcc)3, —P(=O)2Raa, —P(=O)(Raa)2, —P(=O)(ORcc)2, —P(=O)2N(Rbb)2, and —P(=O)(NRbb)2, wherein Raa, Rbb, and Rcc are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

As used herein, a "leaving group" is an art-understood term referring to a molecular fragment that departs with a pair of electrons in heterolytic bond cleavage, wherein the molecular fragment is an anion or neutral molecule. See, for example, Smith, March's Advanced Organic Chemistry 6th ed. (501-502). Exemplary leaving groups include, but are not limited to, halo (e.g., chloro, bromo, iodo) and sulfonyl substituted hydroxyl groups (e.g., tosyl, mesyl, besyl).

Other Definitions

As used herein, use of the phrase "at least one instance" refers to one instance, but also encompasses more than one instance, e.g., for example, 1, 2, 3, 4, 5, 6, 7, 8, 9, or 10 instances, and up to 100 instances.

As used herein, a "polymer" refers to a compound comprised of at least 3 (e.g., at least 10, 20, 30, 40, 50, 60, 70, 80, 90, 100, etc.) repeating covalently bound structural units.

"Attached" refers to the covalent attachment of a group.

As used herein, "lipophilic" refers to the ability of a group to dissolve in fats, oils, lipids, and lipophilic non-polar solvents such as hexane or toluene. In general, a lipophilic group refers to an unsubstituted n-alkyl or unsubstituted n-alkenyl group having 6 to 50 carbon atoms, e.g., 6 to 40, 6 to 30, 6 to 20, 8 to 20, 8 to 19, 8 to 18, 8 to 17, 8 to 16, or 8 to 15 carbon atoms.

As used herein, the term "salt" or "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or rnalonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate. digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N+(C1-4alkyl)4 salts. Representative alkali or alkaline earth metal salts include sodium, lithium, potassium, calcium, magnesium, and the like. Further pharmaceutically acceptable salts include, when appropriate, nontoxic ammonium. quaternary ammonium, and amine cations formed using counterions such as halide, hydroxide, carboxylate, sulfate, phosphate, nitrate, sulfonate and aryl sulfonate. Further pharmaceutically acceptable salts include salts formed from the quarternization of an amine using an appropriate electrophile, e.g., an alkyl halide, to form a quarternized alkylated amino salt.

Second or Additional Cationic Lipids

In some embodiments, liposomes may comprise a second or additional cationic lipid. As used herein, the phrase "cationic lipid" refers to any of a number of lipid species that have a net positive charge at a selected pH, such as physiological pH. Several cationic lipids have been described in the literature, many of which are commercially available. Particularly suitable cationic lipids for use in the compositions and methods of the invention include those described in international patent publications WO 2010/053572 (and particularly, C12-200 described at paragraph [00225]) and WO 2012/170930, both of which are incorporated herein by reference. In certain embodiments, the compositions and methods of the invention employ a lipid nanoparticles comprising an ionizable cationic lipid described in U.S. provisional patent application 61/617,468, filed Mar. 29, 2012 (incorporated herein by reference), such as, e.g, (15Z, 18Z)—N,N-dimethyl-6-(9Z, 12Z)-octadeca-9, 12-dien-1-yl) tetracosa-15,18-dien-1-amine (HGT5000), (15Z, 18Z)—N,N-dimethyl-6-((9Z, 12Z)-octadeca-9, 12-dien-1-yl)tetracosa-4,15,18-trien-1-amine (HGT5001), and (15Z,18Z)—N,N-dimethyl-6-((9Z, 12Z)-octadeca-9, 12-dien-1-yl) tetracosa-5, 15, 18-trien-1-amine (HGT5002).

In some embodiments, the second or additional cationic lipid N-[1-(2,3-dioleyloxy)propyl]-N,N,N-trimethylammonium chloride or "DOTMA" is used. (Feigner et al. (Proc. Nat'l Acad. Sci. 84, 7413 (1987); U.S. Pat. No. 4,897,355). DOTMA can be formulated alone or can be combined with the neutral lipid, dioleoylphosphatidyl-ethanolamine or "DOPE" or other cationic or non-cationic lipids into a liposomal transfer vehicle or a lipid nanoparticle, and such liposomes can be used to enhance the delivery of nucleic acids into target cells. Other suitable cationic lipids include, for example, 5-carboxyspermylglycinedioctadecylamide or "DOGS," 2,3-dioleyloxy-N-[2(spermine-carboxamido) ethyl]-N,N-dimethyl-1-propanaminium or "DOSPA" (Behr et al. Proc. Nat.'l Acad. Sci. 86, 6982 (1989); U.S. Pat. Nos. 5,171,678; 5,334,761), 1,2-Dioleoyl-3-Dimethylammonium-Propane or "DODAP", 1,2-Dioleoyl-3-Trimethylammonium-Propane or "DOTAP". Additional exemplary cationic lipids also include 1,2-distearyloxy-N,N-dimethyl-3-aminopropane or "DSDMA", 1,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N,N-dimethylammonium chloride or "DODAC", N,N-distearyl-N,N-dimethylarnrnonium bromide or "DDAB", N-(1,2-dimyristyloxyprop-3-yl)-N,N-dimethyl-N-hydroxyethyl ammonium bromide or "DMRIE", 3-dimethylamino-2-(cholest-5-en-3-beta-oxybutan-4-oxy)-1-(cis, cis-9,12-octadecadienoxy)propane or "CLinDMA", 2-[5'-(cholest-5-en-3-beta-oxy)-3'-oxapentoxy)-3-dimethy 1-1-(cis,cis-9', 1-2'-octadecadienoxy)propane or "CpLinDMA", N,N-dimethyl-3,4-dioleyloxybenzylamine or "DMOBA", 1,2-N,N'-dioleylcarbamyl-3-dimethylaminopropane or "DOcarbDAP", 2,3-Dilinoleoyloxy-N,N-dimethylpropylamine or "DLinDAP", 1,2-N,N'-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethyl-[1,3]-dioxolane or "DLin-DMA", 2,2-dilinoleyl-4-dimethylaminoethyl-[1,3]-dioxolane or "DLin-K-XTC2-DMA", and 2-(2,2-di((9Z, 12Z)-octadeca-9,12-dien-1-yl)-1,3-dioxolan-4-yl)-N,N-dimethylethanamine (DLin-KC2-DMA)) (See, WO 2010/042877; Semple et al., Nature Biotech. 28: 172-176 (2010)), or mixtures thereof. (Heyes, J., et al., J Controlled Release 107: 276-287 (2005); Morrissey, D V., et al., Nat. Biotechnol. 23(8): 1003-1007 (2005); PCT Publication WO2005/121348A1). In some embodiments, one or more of the cationic lipids comprise at least one of an imidazole, dialkylamino, or guanidinium moiety.

In some embodiments, the second or additional cationic lipid may be chosen from XTC (2,2-Dilinoley 1-4-dimethylaminoethy 1-[1,3]-dioxolane), MC3 (((6Z,9Z,28Z,31Z)-heptatriaconta-6,9,28,31-tetraen-19-yl 4-(dimethylamino) butanoate), ALNY-100 ((3 aR, 5 s,6aS)—N,N-dimethyl-2, 2-di((9Z,12Z)-octadeca-9,12-dienyl)tetrahydro-3aH-cyclopenta[d][1,3]dioxol-5-amine)), NC98-5 (4,7,13-tris(3-oxo-3-(undecylamino)propyl)-N1,N16-diundecyl-4,7,10, 13-tetraazahexadecane-1,16-diamide), DODAP (1,2-dioleyl-3-dimethylammonium propane), HGT4003 (WO 2012/170889, the teachings of which are incorporated herein by reference in their entirety), ICE (WO 2011/068810, the teachings of which are incorporated herein by reference in their entirety), HGT5000 (U.S. Provisional Patent Application No. 61/617,468, the teachings of which are incorporated herein by reference in their entirety) or HGT5001 (cis or trans) (Provisional Patent Application No. 61/617,468), aminoalcohol lipidoids such as those disclosed in WO2010/053572, DOTAP (1,2-dioleyl-3-trimethylammonium propane), DOTMA (1,2-di-O-octadecenyl-3-trimethylammonium propane), DLinDMA (Heyes, J.; Palmer, L.; Bremner, K.; MacLachlan, I. "Cationic lipid saturation influences intracellular delivery of encapsulated nucleic acids" J. Contr. Rel. 2005, 107, 276-287), DLin-KC2-DMA (Semple, S. C. et al. "Rational Design of Cationic Lipids for siRNA Delivery" Nature Biotech. 2010, 28, 172-176), C12-200 (Love, K. T. et al. "Lipid-like materials for low-dose in vivo gene silencing" PNAS 2010, 107, 1864-1869).

Non-Cationic/Helper Lipids

In some embodiments, provided liposomes contain one or more non-cationic ("helper") lipids. As used herein, the phrase "non-cationic lipid" refers to any neutral, zwitterionic or anionic lipid. As used herein, the phrase "anionic lipid" refers to any of a number of lipid species that carry a net negative charge at a selected H, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), or a mixture thereof.

In some embodiments, such non-cationic lipids may be used alone, but are preferably used in combination with other excipients, for example, cationic lipids. In some embodiments, the non-cationic lipid may comprise a molar ratio of about 5% to about 90%, or about 10% to about 70% of the total lipid present in a liposome. In some embodiments, a non-cationic lipid is a neutral lipid, i.e., a lipid that does not carry a net charge in the conditions under which the composition is formulated and/or administered. In some embodiments, the percentage of non-cationic lipid in a liposome may be greater than 5%, greater than 10%, greater than 20%, greater than 30%, or greater than 40%.

Cholesterol-Based Lipids

In some embodiments, provided liposomes comprise one or more cholesterol-based lipids. For example, suitable cholesterol-based cationic lipids include, for example, DC-Choi (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE. In some embodiments, the cholesterol-based lipid may comprise a molar ration of about 2% to about 30%, or about 5% to about 20% of the total lipid present in a liposome. In some embodiments, The percentage of cholesterol-based lipid in the lipid nanoparticle may be greater than 5, %, 10%, greater than 20%, greater than 30%, or greater than 40%.

PEGylated Lipids

In some embodiments, provided liposomes comprise one or more PEGylated lipids. For example, the use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) is also contemplated by the present invention in combination with one or more of the cationic and, in some embodiments, other lipids together which comprise the liposome. Contemplated PEG-modified lipids include, but are not limited to, a polyethylene glycol chain of up to 5 kDa in length covalently attached to a lipid with alkyl chain(s) of $C_6$-$C_{20}$ length. In some embodiments, a PEG-modified or PEGylated lipid is PEGylated cholesterol or PEG-2K. The addition of such components may prevent complex aggregation and may also provide a means for increasing circulation lifetime and increasing the delivery of the lipid-nucleic acid composition to the target cell, (Klibanov et al. (1990) FEBS Letters, 268 (1): 235-237), or they may be selected to rapidly exchange out of the formulation in vivo (see U.S. Pat. No. 5,885,613).

In some embodiments, particularly useful exchangeable lipids are PEG-ceramides having shorter acyl chains (e.g., $C_{14}$ or $C_{18}$). The PEG-modified phospholipid and derivitized lipids of the present invention may comprise a molar ratio from about 0% to about 15%, about 0.5% to about 15%, about 1% to about 15%, about 4% to about 10%, or about 2% of the total lipid present in the liposome.

According to various embodiments, the selection of second or additional cationic lipids, non-cationic lipids and/or PEG-modified lipids which comprise the lipid nanoparticle, as well as the relative molar ratio of such lipids to each other, is based upon the characteristics of the selected lipid(s), the nature of the intended target cells, the characteristics of the mRNA to be delivered. Additional considerations include, for example, the saturation of the alkyl chain, as well as the size, charge, pH, pKa, fusogenicity and toxicity of the selected lipid(s). Thus the molar ratios may be adjusted accordingly. In some embodiments, the percentage of PEG-modified lipid in a liposome may be greater than 1%, greater than 2%, greater than 5%, greater than 10%, or greater than 15%.

Polymer

In some embodiments, a suitable liposome according to the present invention further includes a polymer, in combination with one or more cationic lipids as described and, in some embodiments, other carriers including various lipids described herein. Thus, in some embodiments, liposomal delivery vehicles, as used herein, also encompass polymer containing nanoparticles. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, protamine, PEGylated protamine, PLL, PEGylated PLL and polyethylenimine (PEI). When PEI is present, it may be branched PEI of a molecular weight ranging from 10 to 40 kDA, e.g., 25 kDa branched PEI (Sigma #408727).

In some embodiments, a suitable liposome formulation contains a combination of one or more cationic lipids, one or more non-cationic lipids, one or more cholesterol-based lipids one or more PEG-modified lipids, and/or one or more polymers. As a non-limiting example, a suitable liposome comprises cKK-E12, DOPE, cholesterol and DMG-PEG2K. In some embodiments, the ratio of cationic lipid to non-cationic lipid to cholesterol-based lipid to PEGylated lipid may be between about 30-50:25-35:20-30:1-15, respectively. In some embodiments, the ratio of cationic lipid to non-cationic lipid to cholesterol-based lipid to PEGylated lipid is approximately 40:30:20:10, respectively. In some embodiments, the ratio of cationic lipid to non-cationic lipid to cholesterol-based lipid to PEGylated lipid is approximately 40:30:25:5, respectively. In some embodiments, the ratio of cationic lipid to non-cationic lipid to cholesterol-based lipid to PEGylated lipid is approximately 40:32:25:3, respectively. mRNA The present invention can be used to deliver any mRNA. mRNA is typically thought of as the type of RNA that carries information from DNA to the ribosome. The existence of mRNA is usually very brief and includes processing and translation, followed by degradation. Typically, in eukaryotic organisms, mRNA processing comprises the addition of a "cap" on the N-terminal (5') end, and a "tail" on the C-terminal (3') end. A typical cap is a 7-methylguanosine cap, which is a guanosine that is linked through a 5'-5'-triphosphate bond to the first transcribed nucleotide. The presence of the cap is important in providing resistance to nucleases found in most eukaryotic cells. The tail is typically a polyadenylation event whereby a polyadenylyl moiety is added to the 3' end of the mRNA molecule. The presence of this "tail" serves to protect the mRNA from exonuclease degradation. Messenger RNA typically is translated by the ribosomes into a series of amino acids that make up a protein.

Any mRNA capable of being translated into one or more peptides (e.g., proteins) or peptide fragments is contemplated as within the scope of the present invention. In some embodiments, an mRNA encodes one or more naturally occurring peptides. In some embodiments, an mRNA encodes one or more modified or non-natural peptides.

In some embodiments an mRNA encodes an intracellular protein. In some embodiments, an mRNA encodes a cytosolic protein. In some embodiments, an mRNA encodes a protein associated with the actin cytoskeleton. In some embodiments, an mRNA encodes a protein associated with the plasma membrane. In some specific embodiments, an mRNA encodes a transmembrane protein. In some specific embodiments an mRNA encodes an ion channel protein. In some embodiments, an mRNA encodes a perinuclear protein. In some embodiments, an mRNA encodes a nuclear protein. In some specific embodiments, an mRNA encodes a transcription factor. In some embodiments, an mRNA encodes a chaperone protein. In some embodiments, an mRNA encodes an intracellular enzyme (e.g., mRNA encoding an enzyme associated with urea cycle or lysosomal storage metabolic disorders). In some embodiments, an mRNA encodes a protein involved in cellular metabolism, DNA repair, transcription and/or translation. In some embodiments, an mRNA encodes an extracellular protein. In some embodiments, an mRNA encodes a protein associated with the extracellular matrix. In some embodiments an mRNA encodes a secreted protein. In specific embodiments, an mRNA used in the composition and methods of the invention may be used to express functional proteins or enzymes that are excreted or secreted by one or more target cells into the surrounding extracellular fluid (e.g., mRNA encoding hormones and/or neurotransmitters).

In some embodiments, the compositions and methods of the invention provide for delivery of mRNA encoding a secreted protein. In some embodiments, the compositions and methods of the invention provide for delivery of mRNA encoding one or more secreted proteins listed in Table 1; thus, compositions of the invention may comprise an mRNA encoding a protein listed in Table 1 (or a homolog thereof) along with other components set out herein, and methods of the invention may comprise preparing and/or administering a composition comprising an mRNA encoding a protein listed in Table 1 (or a homolog thereof) along with other components set out herein.

TABLE 1

Secreted Proteins

| Uniprot ID | Protein Name | Gene Name |
|---|---|---|
| A1E959 | Odontogenic ameloblast-associated protein | ODAM |
| A1KZ92 | Peroxidasin-like protein | PXDNL |
| A1L453 | Serine protease 38 | PRSS38 |
| A1L4H1 | Soluble scavenger receptor cysteine-rich domain-containing protein SSC5D | SSC5D |
| A2RUU4 | Colipase-like protein 1 | CLPSL1 |
| A2VDF0 | Fucose mutarotase | FUOM |
| A2VEC9 | SCO-spondin | SSPO |
| A3KMH1 | von Willebrand factor A domain-containing protein 8 | VWA8 |
| A4D0S4 | Laminin subunit beta-4 | LAMB4 |
| A4D1T9 | Probable inactive serine protease 37 | PRSS37 |
| A5D8T8 | C-type lectin domain family 18 member A | CLEC18A |
| A6NC86 | phospholipase A2 inhibitor and Ly6/PLAUR domain-containing protein | PINLYP |
| A6NCI4 | von Willebrand factor A domain-containing protein 3A | VWA3A |
| A6ND01 | Probable folate receptor delta | FOLR4 |
| A6NDD2 | Beta-defensin 108B-like | |
| A6NE02 | BTB/POZ domain-containing protein 17 | BTBD17 |
| A6NEF6 | Growth hormone 1 | GH1 |
| A6NF02 | NPIP-like protein LOC730153 | |
| A6NFB4 | HCG1749481, isoform CRA_k | CSH1 |
| A6NFZ4 | Protein FAM24A | FAM24A |
| A6NG13 | Glycosyltransferase 54 domain-containing protein | |
| A6NGN9 | IgLON family member 5 | IGLON5 |
| A6NHN0 | Otolin-1 | OTOL1 |
| A6NHN6 | Nuclear pore complex-interacting protein-like 2 | NPIPL2 |
| A6NI73 | Leukocyte immunoglobulin-like receptor subfamily A member 5 | LILRA5 |
| A6NIT4 | Chorionic somatomammotropin hormone 2 isoform 2 | CSH2 |
| A6NJ69 | IgA-inducing protein homolog | IGIP |
| A6NKQ9 | Choriogonadotropin subunit beta variant 1 | CGB1 |
| A6NMZ7 | Collagen alpha-6(VI) chain | COL6A6 |
| A6NNS2 | Dehydrogenase/reductase SDR family member 7C | DHRS7C |
| A6XGL2 | Insulin A chain | INS |
| A8K0G1 | Protein Wnt | WNT7B |
| A8K2U0 | Alpha-2-macroglobulin-like protein 1 | A2ML1 |
| A8K7I4 | Calcium-activated chloride channel regulator 1 | CLCA1 |
| A8MTL9 | Serpin-like protein HMSD | HMSD |
| A8MV23 | Serpin E3 | SERPINE3 |
| A8MZH6 | Oocyte-secreted protein 1 homolog | OOSP1 |
| A8TX70 | Collagen alpha-5(VI) chain | COL6A5 |
| B0ZBE8 | Natriuretic peptide | NPPA |
| B1A4G9 | Somatotropin | GH1 |
| B1A4H2 | HCG1749481, isoform CRA_d | CSH1 |
| B1A4H9 | Chorionic somatomammotropin hormone | CSH2 |
| B1AJZ6 | Protein Wnt | WNT4 |
| B1AKI9 | Isthmin-1 | ISM1 |
| B2RNN3 | Complement C1q and tumor necrosis factor-related protein 9B | C1QTNF9B |
| B2RUY7 | von Willebrand factor C domain-containing protein 2-like | VWC2L |
| B3GLJ2 | Prostate and testis expressed protein 3 | PATE3 |
| B4DI03 | SEC11-like 3 (S. cerevisiae), isoform CRA_a | SEC11L3 |
| B4DJF9 | Protein Wnt | WNT4 |
| B4DUL4 | SEC11-like 1 (S. cerevisiae), isoform CRA_d | SEC11L1 |
| B5MCC8 | Protein Wnt | WNT10B |
| B8A595 | Protein Wnt | WNT7B |

TABLE 1-continued

Secreted Proteins

| Uniprot ID | Protein Name | Gene Name |
|---|---|---|
| B8A597 | Protein Wnt | WNT7B |
| B8A598 | Protein Wnt | WNT7B |
| B9A064 | Immunoglobulin lambda-like polypeptide 5 | IGLL5 |
| C9J3H3 | Protein Wnt | WNT10B |
| C9J8I8 | Protein Wnt | WNT5A |
| C9JAF2 | Insulin-like growth factor II Ala-25 Del | IGF2 |
| C9JCI2 | Protein Wnt | WNT10B |
| C9JL84 | HERV-H LTR-associating protein 1 | HHLA1 |
| C9JNR5 | Insulin A chain | INS |
| C9JUI2 | Protein Wnt | WNT2 |
| D6RF47 | Protein Wnt | WNT8A |
| D6RF94 | Protein Wnt | WNT8A |
| E2RYF7 | Protein PBMUCL2 | HCG22 |
| E5RFR1 | PENK(114-133) | PENK |
| E7EML9 | Serine protease 44 | PRSS44 |
| E7EPC3 | Protein Wnt | WNT9B |
| E7EVP0 | Nociceptin | PNOC |
| E9PD02 | Insulin-like growth factor I | IGF1 |
| E9PH60 | Protein Wnt | WNT16 |
| E9PJL6 | Protein Wnt | WNT11 |
| F5GYM2 | Protein Wnt | WNT5B |
| F5H034 | Protein Wnt | WNT5B |
| F5H364 | Protein Wnt | WNT5B |
| F5H7Q6 | Protein Wnt | WNT5B |
| F8WCM5 | Protein INS-IGF2 | INS-IGF2 |
| F8WDR1 | Protein Wnt | WNT2 |
| H0Y663 | Protein Wnt | WNT4 |
| H0YK72 | Signal peptidase complex catalytic subunit SEC11A | SEC11A |
| H0YK83 | Signal peptidase complex catalytic subunit SEC11A | SEC11A |
| H0YM39 | Chorionic somatomammotropin hormone | CSH2 |
| H0YMT7 | Chorionic somatomammotropin hormone | CSH1 |
| H0YN17 | Chorionic somatomammotropin hormone | CSH2 |
| H0YNA5 | Signal peptidase complex catalytic subunit SEC11A | SEC11A |
| H0YNG3 | Signal peptidase complex catalytic subunit SEC11A | SEC11A |
| H0YNX5 | Signal peptidase complex catalytic subunit SEC11A | SEC11A |
| H7BZB8 | Protein Wnt | WNT10A |
| H9KV56 | Choriogonadotropin subunit beta variant 2 | CGB2 |
| I3L0L8 | Protein Wnt | WNT9B |
| J3KNZ1 | Choriogonadotropin subunit beta variant 1 | CGB1 |
| J3KP00 | Choriogonadotropin subunit beta | CGB7 |
| J3QT02 | Choriogonadotropin subunit beta variant 1 | CGB1 |
| O00175 | C-C motif chemokine 24 | CCL24 |
| O00182 | Galectin-9 | LGALS9 |
| O00187 | Mannan-binding lectin serine protease 2 | MASP2 |
| O00230 | Cortistatin | CORT |
| O00253 | Agouti-related protein | AGRP |
| O00270 | 12-(S)-hydroxy-5,8,10,14-eicosatetraenoic acid receptor | GPR31 |
| O00292 | Left-right determination factor 2 | LEFTY2 |
| O00294 | Tubby-related protein 1 | TULP1 |
| O00295 | Tubby-related protein 2 | TULP2 |
| O00300 | Tumor necrosis factor receptor superfamily member 11B | TNFRSF11B |
| O00339 | Matrilin-2 | MATN2 |
| O00391 | Sulfhydryl oxidase 1 | QSOX1 |
| O00468 | Agrin | AGRN |
| O00515 | Ladinin-1 | LAD1 |
| O00533 | Processed neural cell adhesion molecule L1-like protein | CHL1 |
| O00584 | Ribonuclease T2 | RNASET2 |
| O00585 | C-C motif chemokine 21 | CCL21 |
| O00602 | Ficolin-1 | FCN1 |
| O00622 | Protein CYR61 | CYR61 |
| O00626 | MDC(5-69) | CCL22 |
| O00634 | Netrin-3 | NTN3 |
| O00744 | Protein Wnt-10b | WNT10B |
| O00755 | Protein Wnt-7a | WNT7A |
| O14498 | Immunoglobulin superfamily containing leucine-rich repeat protein | ISLR |

TABLE 1-continued

Secreted Proteins

| Uniprot ID | Protein Name | Gene Name |
|---|---|---|
| O14511 | Pro-neuregulin-2, membrane-bound isoform | NRG2 |
| O14594 | Neurocan core protein | NCAN |
| O14625 | C-X-C motif chemokine 11 | CXCL11 |
| O14638 | Ectonucleotide pyrophosphatase/phosphodiesterase family member 3 | ENPP3 |
| O14656 | Torsin-1A | TOR1A |
| O14657 | Torsin-1B | TOR1B |
| O14786 | Neuropilin-1 | NRP1 |
| O14788 | Tumor necrosis factor ligand superfamily member 11, membrane form | TNFSF11 |
| O14791 | Apolipoprotein L1 | APOL1 |
| O14793 | Growth/differentiation factor 8 | MSTN |
| O14904 | Protein Wnt-9a | WNT9A |
| O14905 | Protein Wnt-9b | WNT9B |
| O14944 | Proepiregulin | EREG |
| O14960 | Leukocyte cell-derived chemotaxin-2 | LECT2 |
| O15018 | Processed PDZ domain-containing protein 2 | PDZD2 |
| O15041 | Semaphorin-3E | SEMA3E |
| O15072 | A disintegrin and metalloproteinase with thrombospondin motifs 3 | ADAMTS3 |
| O15123 | Angiopoietin-2 | ANGPT2 |
| O15130 | Neuropeptide FF | NPFF |
| O15197 | Ephrin type-B receptor 6 | EPHB6 |
| O15204 | ADAM DEC1 | ADAMDEC1 |
| O15230 | Laminin subunit alpha-5 | LAMA5 |
| O15232 | Matrilin-3 | MATN3 |
| O15240 | Neuroendocrine regulatory peptide-1 | VGF |
| O15263 | Beta-defensin 4A | DEFB4A |
| O15335 | Chondroadherin | CHAD |
| O15393 | Transmembrane protease serine 2 catalytic chain | TMPRSS2 |
| O15444 | C-C motif chemokine 25 | CCL25 |
| O15467 | C-C motif chemokine 16 | CCL16 |
| O15496 | Group 10 secretory phospholipase A2 | PLA2G10 |
| O15520 | Fibroblast growth factor 10 | FGF10 |
| O15537 | Retinoschisin | RS1 |
| O43157 | Plexin-B1 | PLXNB1 |
| O43184 | Disintegrin and metalloproteinase domain-containing protein 12 | ADAM12 |
| O43240 | Kallikrein-10 | KLK10 |
| O43278 | Kunitz-type protease inhibitor 1 | SPINT1 |
| O43320 | Fibroblast growth factor 16 | FGF16 |
| O43323 | Desert hedgehog protein C-product | DHH |
| O43405 | Cochlin | COCH |
| O43508 | Tumor necrosis factor ligand superfamily member 12, membrane form | TNFSF12 |
| O43555 | Progonadoliberin-2 | GNRH2 |
| O43557 | Tumor necrosis factor ligand superfamily member 14, soluble form | TNFSF14 |
| O43692 | Peptidase inhibitor 15 | PI15 |
| O43699 | Sialic acid-binding Ig-like lectin 6 | SIGLEC6 |
| O43820 | Hyaluronidase-3 | HYAL3 |
| O43827 | Angiopoietin-related protein 7 | ANGPTL7 |
| O43852 | Calumenin | CALU |
| O43854 | EGF-like repeat and discoidin I-like domain-containing protein 3 | EDIL3 |
| O43866 | CD5 antigen-like | CD5L |
| O43897 | Tolloid-like protein 1 | TLL1 |
| O43915 | Vascular endothelial growth factor D | FIGF |
| O43927 | C-X-C motif chemokine 13 | CXCL13 |
| O60218 | Aldo-keto reductase family 1 member B10 | AKR1B10 |
| O60235 | Transmembrane protease serine 11D | TMPRSS11D |
| O60258 | Fibroblast growth factor 17 | FGF17 |
| O60259 | Kallikrein-8 | KLK8 |
| O60383 | Growth/differentiation factor 9 | GDF9 |
| O60469 | Down syndrome cell adhesion molecule | DSCAM |
| O60542 | Persephin | PSPN |
| O60565 | Gremlin-1 | GREM1 |
| O60575 | Serine protease inhibitor Kazal-type 4 | SPINK4 |
| O60676 | Cystatin-8 | CST8 |
| O60687 | Sushi repeat-containing protein SRPX2 | SRPX2 |
| O60844 | Zymogen granule membrane protein 16 | ZG16 |
| O60882 | Matrix metalloproteinase-20 | MMP20 |
| O60938 | Keratocan | KERA |
| O75015 | Low affinity immunoglobulin gamma Fc region receptor III-B | FCGR3B |

TABLE 1-continued

Secreted Proteins

| Uniprot ID | Protein Name | Gene Name |
| --- | --- | --- |
| O75077 | Disintegrin and metalloproteinase domain-containing protein 23 | ADAM23 |
| O75093 | Slit homolog 1 protein | SLIT1 |
| O75094 | Slit homolog 3 protein | SLIT3 |
| O75095 | Multiple epidermal growth factor-like domains protein 6 | MEGF6 |
| O75173 | A disintegrin and metalloproteinase with thrombospondin motifs 4 | ADAMTS4 |
| O75200 | Nuclear pore complex-interacting protein-like 1 | NPIPL1 |
| O75339 | Cartilage intermediate layer protein 1 C1 | CILP |
| O75354 | Ectonucleoside triphosphate diphosphohydrolase 6 | ENTPD6 |
| O75386 | Tubby-related protein 3 | TULP3 |
| O75398 | Deformed epidermal autoregulatory factor 1 homolog | DEAF1 |
| O75443 | Alpha-tectorin | TECTA |
| O75445 | Usherin | USH2A |
| O75462 | Cytokine receptor-like factor 1 | CRLF1 |
| O75487 | Glypican-4 | GPC4 |
| O75493 | Carbonic anhydrase-related protein 11 | CA11 |
| O75594 | Peptidoglycan recognition protein 1 | PGLYRP1 |
| O75596 | C-type lectin domain family 3 member A | CLEC3A |
| O75610 | Left-right determination factor 1 | LEFTY1 |
| O75629 | Protein CREG1 | CREG1 |
| O75636 | Ficolin-3 | FCN3 |
| O75711 | Scrapie-responsive protein 1 | SCRG1 |
| O75715 | Epididymal secretory glutathione peroxidase | GPX5 |
| O75718 | Cartilage-associated protein | CRTAP |
| O75829 | Chondrosurfactant protein | LECT1 |
| O75830 | Serpin I2 | SERPINI2 |
| O75882 | Attractin | ATRN |
| O75888 | Tumor necrosis factor ligand superfamily member 13 | TNFSF13 |
| O75900 | Matrix metalloproteinase-23 | MMP23A |
| O75951 | Lysozyme-like protein 6 | LYZL6 |
| O75973 | C1q-related factor | C1QL1 |
| O76038 | Secretagogin | SCGN |
| O76061 | Stanniocalcin-2 | STC2 |
| O76076 | WNT1-inducible-signaling pathway protein 2 | WISP2 |
| O76093 | Fibroblast growth factor 18 | FGF18 |
| O76096 | Cystatin-F | CST7 |
| O94769 | Extracellular matrix protein 2 | ECM2 |
| O94813 | Slit homolog 2 protein C-product | SLIT2 |
| O94907 | Dickkopf-related protein 1 | DKK1 |
| O94919 | Endonuclease domain-containing 1 protein | ENDOD1 |
| O94964 | N-terminal form | SOGA1 |
| O95025 | Semaphorin-3D | SEMA3D |
| O95084 | Serine protease 23 | PRSS23 |
| O95150 | Tumor necrosis factor ligand superfamily member 15 | TNFSF15 |
| O95156 | Neurexophilin-2 | NXPH2 |
| O95157 | Neurexophilin-3 | NXPH3 |
| O95158 | Neurexophilin-4 | NXPH4 |
| O95388 | WNT1-inducible-signaling pathway protein 1 | WISP1 |
| O95389 | WNT1-inducible-signaling pathway protein 3 | WISP3 |
| O95390 | Growth/differentiation factor 11 | GDF11 |
| O95393 | Bone morphogenetic protein 10 | BMP10 |
| O95399 | Urotensin-2 | UTS2 |
| O95407 | Tumor necrosis factor receptor superfamily member 6B | TNFRSF6B |
| O95428 | Papilin | PAPLN |
| O95445 | Apolipoprotein M | APOM |
| O95450 | A disintegrin and metalloproteinase with thrombospondin motifs 2 | ADAMTS2 |
| O95460 | Matrilin-4 | MATN4 |
| O95467 | LHAL tetrapeptide | GNAS |
| O95631 | Netrin-1 | NTN1 |
| O95633 | Follistatin-related protein 3 | FSTL3 |
| O95711 | Lymphocyte antigen 86 | LY86 |
| O95715 | C-X-C motif chemokine 14 | CXCL14 |
| O95750 | Fibroblast growth factor 19 | FGF19 |
| O95760 | Interleukin-33 | IL33 |
| O95813 | Cerberus | CER1 |
| O95841 | Angiopoietin-related protein 1 | ANGPTL1 |
| O95897 | Noelin-2 | OLFM2 |
| O95925 | Eppin | EPPIN |

TABLE 1-continued

Secreted Proteins

| Uniprot ID | Protein Name | Gene Name |
| --- | --- | --- |
| O95965 | Integrin beta-like protein 1 | ITGBL1 |
| O95967 | EGF-containing fibulin-like extracellular matrix protein 2 | EFEMP2 |
| O95968 | Secretoglobin family 1D member 1 | SCGB1D1 |
| O95969 | Secretoglobin family 1D member 2 | SCGB1D2 |
| O95970 | Leucine-rich glioma-inactivated protein 1 | LGI1 |
| O95972 | Bone morphogenetic protein 15 | BMP15 |
| O95994 | Anterior gradient protein 2 homolog | AGR2 |
| O95998 | Interleukin-18-binding protein | IL18BP |
| O96009 | Napsin-A | NAPSA |
| O96014 | Protein Wnt-11 | WNT11 |
| P00450 | Ceruloplasmin | CP |
| P00451 | Factor VIIIa light chain | F8 |
| P00488 | Coagulation factor XIII A chain | F13A1 |
| P00533 | Epidermal growth factor receptor | EGFR |
| P00709 | Alpha-lactalbumin | LALBA |
| P00734 | Prothrombin | F2 |
| P00738 | Haptoglobin beta chain | HP |
| P00739 | Haptoglobin-related protein | HPR |
| P00740 | Coagulation factor IXa heavy chain | F9 |
| P00742 | Factor X heavy chain | F10 |
| P00746 | Complement factor D | CFD |
| P00747 | Plasmin light chain B | PLG |
| P00748 | Coagulation factor XIIa light chain | F12 |
| P00749 | Urokinase-type plasminogen activator long chain A | PLAU |
| P00750 | Tissue-type plasminogen activator | PLAT |
| P00751 | Complement factor B Ba fragment | CFB |
| P00797 | Renin | REN |
| P00973 | 2'-5'-oligoadenylate synthase 1 | OAS1 |
| P00995 | Pancreatic secretory trypsin inhibitor | SPINK1 |
| P01008 | Antithrombin-III | SERPINC1 |
| P01009 | Alpha-1-antitrypsin | SERPINA1 |
| P01011 | Alpha-1-antichymotrypsin His-Pro-less | SERPINA3 |
| P01019 | Angiotensin-1 | AGT |
| P01023 | Alpha-2-macroglobulin | A2M |
| P01024 | Acylation stimulating protein | C3 |
| P01031 | Complement C5 beta chain | C5 |
| P01033 | Metalloproteinase inhibitor 1 | TIMP1 |
| P01034 | Cystatin-C | CST3 |
| P01036 | Cystatin-S | CST4 |
| P01037 | Cystatin-SN | CST1 |
| P01042 | Kininogen-1 light chain | KNG1 |
| P01127 | Platelet-derived growth factor subunit B | PDGFB |
| P01135 | Transforming growth factor alpha | TGFA |
| P01137 | Transforming growth factor beta-1 | TGFB1 |
| P01138 | Beta-nerve growth factor | NGF |
| P01148 | Gonadoliberin-1 | GNRH1 |
| P01160 | Atrial natriuretic factor | NPPA |
| P01178 | Oxytocin | OXT |
| P01185 | Vasopressin-neurophysin 2-copeptin | AVP |
| P01189 | Corticotropin | POMC |
| P01210 | PENK(237-258) | PENK |
| P01213 | Alpha-neoendorphin | PDYN |
| P01215 | Glycoprotein hormones alpha chain | CGA |
| P01222 | Thyrotropin subunit beta | TSHB |
| P01225 | Follitropin subunit beta | FSHB |
| P01229 | Lutropin subunit beta | LHB |
| P01233 | Choriogonadotropin subunit beta | CGB8 |
| P01236 | Prolactin | PRL |
| P01241 | Somatotropin | GH1 |
| P01242 | Growth hormone variant | GH2 |
| P01243 | Chorionic somatomammotropin hormone | CSH2 |
| P01258 | Katacalcin | CALCA |
| P01266 | Thyroglobulin | TG |
| P01270 | Parathyroid hormone | PTH |
| P01275 | Glucagon | GCG |
| P01282 | Intestinal peptide PHM-27 | VIP |
| P01286 | Somatoliberin | GHRH |
| P01298 | Pancreatic prohormone | PPY |
| P01303 | C-flanking peptide of NPY | NPY |
| P01308 | Insulin | INS |
| P01344 | Insulin-like growth factor II | IGF2 |
| P01350 | Big gastrin | GAST |
| P01374 | Lymphotoxin-alpha | LTA |

TABLE 1-continued

Secreted Proteins

| Uniprot ID | Protein Name | Gene Name |
|---|---|---|
| P01375 | C-domain 1 | TNF |
| P01562 | Interferon alpha-1/13 | IFNA1 |
| P01563 | Interferon alpha-2 | IFNA2 |
| P01566 | Interferon alpha-10 | IFNA10 |
| P01567 | Interferon alpha-7 | IFNA7 |
| P01568 | Interferon alpha-21 | IFNA21 |
| P01569 | Interferon alpha-5 | IFNA5 |
| P01570 | Interferon alpha-14 | IFNA14 |
| P01571 | Interferon alpha-17 | IFNA17 |
| P01574 | Interferon beta | IFNB1 |
| P01579 | Interferon gamma | IFNG |
| P01583 | Interleukin-1 alpha | IL1A |
| P01584 | Interleukin-1 beta | IL1B |
| P01588 | Erythropoietin | EPO |
| P01591 | Immunoglobulin J chain | IGJ |
| P01732 | T-cell surface glycoprotein CD8 alpha chain | CD8A |
| P01833 | Polymeric immunoglobulin receptor | PIGR |
| P01857 | Ig gamma-1 chain C region | IGHG1 |
| P01859 | Ig gamma-2 chain C region | IGHG2 |
| P01860 | Ig gamma-3 chain C region | IGHG3 |
| P01861 | Ig gamma-4 chain C region | IGHG4 |
| P01871 | Ig mu chain C region | IGHM |
| P01880 | Ig delta chain C region | IGHD |
| P02452 | Collagen alpha-1(I) chain | COL1A1 |
| P02458 | Chondrocalcin | COL2A1 |
| P02461 | Collagen alpha-1(III) chain | COL3A1 |
| P02462 | Collagen alpha-1(IV) chain | COL4A1 |
| P02647 | Apolipoprotein A-I | APOA1 |
| P02649 | Apolipoprotein E | APOE |
| P02652 | Apolipoprotein A-II | APOA2 |
| P02654 | Apolipoprotein C-I | APOC1 |
| P02655 | Apolipoprotein C-II | APOC2 |
| P02656 | Apolipoprotein C-III | APOC3 |
| P02671 | Fibrinogen alpha chain | FGA |
| P02675 | Fibrinopeptide B | FGB |
| P02679 | Fibrinogen gamma chain | FGG |
| P02741 | C-reactive protein | CRP |
| P02743 | Serum amyloid P-component(1-203) | APCS |
| P02745 | Complement C1q subcomponent subunit A | C1QA |
| P02746 | Complement C1q subcomponent subunit B | C1QB |
| P02747 | Complement C1q subcomponent subunit C | C1QC |
| P02748 | Complement component C9b | C9 |
| P02749 | Beta-2-glycoprotein 1 | APOH |
| P02750 | Leucine-rich alpha-2-glycoprotein | LRG1 |
| P02751 | Ugl-Y2 | FN1 |
| P02753 | Retinol-binding protein 4 | RBP4 |
| P02760 | Trypstatin | AMBP |
| P02763 | Alpha-1-acid glycoprotein 1 | ORM1 |
| P02765 | Alpha-2-HS-glycoprotein chain A | AHSG |
| P02766 | Transthyretin | TTR |
| P02768 | Serum albumin | ALB |
| P02771 | Alpha-fetoprotein | AFP |
| P02774 | Vitamin D-binding protein | GC |
| P02775 | Connective tissue-activating peptide III | PPBP |
| P02776 | Platelet factor 4 | PF4 |
| P02778 | CXCL10(1-73) | CXCL10 |
| P02786 | Transferrin receptor protein 1 | TFRC |
| P02787 | Serotransferrin | TF |
| P02788 | Lactoferroxin-C | LTF |
| P02790 | Hemopexin | HPX |
| P02808 | Statherin | STATH |
| P02810 | Salivary acidic proline-rich phosphoprotein 1/2 | PRH2 |
| P02812 | Basic salivary proline-rich protein 2 | PRB2 |
| P02814 | Peptide D1A | SMR3B |
| P02818 | Osteocalcin | BGLAP |
| P03950 | Angiogenin | ANG |
| P03951 | Coagulation factor XIa heavy chain | F11 |
| P03952 | Plasma kallikrein | KLKB1 |
| P03956 | 27 kDa interstitial collagenase | MMP1 |
| P03971 | Muellerian-inhibiting factor | AMH |
| P03973 | Antileukoproteinase | SLPI |
| P04003 | C4b-binding protein alpha chain | C4BPA |
| P04004 | Somatomedin-B | VTN |
| P04054 | Phospholipase A2 | PLA2G1B |
| P04085 | Platelet-derived growth factor subunit A | PDGFA |

TABLE 1-continued

Secreted Proteins

| Uniprot ID | Protein Name | Gene Name |
|---|---|---|
| P04090 | Relaxin A chain | RLN2 |
| P04114 | Apolipoprotein B-100 | APOB |
| P04118 | Colipase | CLPS |
| P04141 | Granulocyte-macrophage colony-stimulating factor | CSF2 |
| P04155 | Trefoil factor 1 | TFF1 |
| P04180 | Phosphatidylcholine-sterol acyltransferase | LCAT |
| P04196 | Histidine-rich glycoprotein | HRG |
| P04217 | Alpha-1B-glycoprotein | A1BG |
| P04275 | von Willebrand antigen 2 | VWF |
| P04278 | Sex hormone-binding globulin | SHBG |
| P04279 | Alpha-inhibin-31 | SEMG1 |
| P04280 | Basic salivary proline-rich protein 1 | PRB1 |
| P04628 | Proto-oncogene Wnt-1 | WNT1 |
| P04745 | Alpha-amylase 1 | AMY1A |
| P04746 | Pancreatic alpha-amylase | AMY2A |
| P04808 | Prorelaxin H1 | RLN1 |
| P05000 | Interferon omega-1 | IFNW1 |
| P05013 | Interferon alpha-6 | IFNA6 |
| P05014 | Interferon alpha-4 | IFNA4 |
| P05015 | Interferon alpha-16 | IFNA16 |
| P05019 | Insulin-like growth factor I | IGF1 |
| P05060 | GAWK peptide | CHGB |
| P05090 | Apolipoprotein D | APOD |
| P05109 | Protein S100-A8 | S100A8 |
| P05111 | Inhibin alpha chain | INHA |
| P05112 | Interleukin-4 | IL4 |
| P05113 | Interleukin-5 | IL5 |
| P05120 | Plasminogen activator inhibitor 2 | SERPINB2 |
| P05121 | Plasminogen activator inhibitor 1 | SERPINE1 |
| P05154 | Plasma serine protease inhibitor | SERPINA5 |
| P05155 | Plasma protease C1 inhibitor | SERPING1 |
| P05156 | Complement factor I heavy chain | CFI |
| P05160 | Coagulation factor XIII B chain | F13B |
| P05161 | Ubiquitin-like protein ISG15 | ISG15 |
| P05230 | Fibroblast growth factor 1 | FGF1 |
| P05231 | Interleukin-6 | IL6 |
| P05305 | Big endothelin-1 | EDN1 |
| P05408 | C-terminal peptide | SCG5 |
| P05451 | Lithostathine-1-alpha | REG1A |
| P05452 | Tetranectin | CLEC3B |
| P05543 | Thyroxine-binding globulin | SERPINA7 |
| P05814 | Beta-casein | CSN2 |
| P05997 | Collagen alpha-2(V) chain | COL5A2 |
| P06276 | Cholinesterase | BCHE |
| P06307 | Cholecystokinin-12 | CCK |
| P06396 | Gelsolin | GSN |
| P06681 | Complement C2 | C2 |
| P06702 | Protein S100-A9 | S100A9 |
| P06727 | Apolipoprotein A-IV | APOA4 |
| P06734 | Low affinity immunoglobulin epsilon Fc receptor soluble form | FCER2 |
| P06744 | Glucose-6-phosphate isomerase | GPI |
| P06850 | Corticoliberin | CRH |
| P06858 | Lipoprotein lipase | LPL |
| P06881 | Calcitonin gene-related peptide 1 | CALCA |
| P07093 | Glia-derived nexin | SERPINE2 |
| P07098 | Gastric triacylglycerol lipase | LIPF |
| P07225 | Vitamin K-dependent protein S | PROS1 |
| P07237 | Protein disulfide-isomerase | P4HB |
| P07288 | Prostate-specific antigen | KLK3 |
| P07306 | Asialoglycoprotein receptor 1 | ASGR1 |
| P07355 | Annexin A2 | ANXA2 |
| P07357 | Complement component C8 alpha chain | C8A |
| P07358 | Complement component C8 beta chain | C8B |
| P07360 | Complement component C8 gamma chain | C8G |
| P07477 | Alpha-trypsin chain 2 | PRSS1 |
| P07478 | Trypsin-2 | PRSS2 |
| P07492 | Neuromedin-C | GRP |
| P07498 | Kappa-casein | CSN3 |
| P07585 | Decorin | DCN |
| P07911 | Uromodulin | UMOD |
| P07942 | Laminin subunit beta-1 | LAMB1 |
| P07988 | Pulmonary surfactant-associated protein B | SFTPB |
| P07998 | Ribonuclease pancreatic | RNASE1 |

TABLE 1-continued

Secreted Proteins

| Uniprot ID | Protein Name | Gene Name |
|---|---|---|
| P08118 | Beta-microseminoprotein | MSMB |
| P08123 | Collagen alpha-2(I) chain | COL1A2 |
| P08185 | Corticosteroid-binding globulin | SERPINA6 |
| P08217 | Chymotrypsin-like elastase family member 2A | CELA2A |
| P08218 | Chymotrypsin-like elastase family member 2B | CELA2B |
| P08253 | 72 kDa type IV collagenase | MMP2 |
| P08254 | Stromelysin-1 | MMP3 |
| P08294 | Extracellular superoxide dismutase [Cu—Zn] | SOD3 |
| P08476 | Inhibin beta A chain | INHBA |
| P08493 | Matrix Gla protein | MGP |
| P08572 | Collagen alpha-2(IV) chain | COL4A2 |
| P08581 | Hepatocyte growth factor receptor | MET |
| P08603 | Complement factor H | CFH |
| P08620 | Fibroblast growth factor 4 | FGF4 |
| P08637 | Low affinity immunoglobulin gamma Fc region receptor III-A | FCGR3A |
| P08697 | Alpha-2-antiplasmin | SERPINF2 |
| P08700 | Interleukin-3 | IL3 |
| P08709 | Coagulation factor VII | F7 |
| P08833 | Insulin-like growth factor-binding protein 1 | IGFBP1 |
| P08887 | Interleukin-6 receptor subunit alpha | IL6R |
| P08949 | Neuromedin-B-32 | NMB |
| P08F94 | Fibrocystin | PKHD1 |
| P09038 | Fibroblast growth factor 2 | FGF2 |
| P09228 | Cystatin-SA | CST2 |
| P09237 | Matrilysin | MMP7 |
| P09238 | Stromelysin-2 | MMP10 |
| P09341 | Growth-regulated alpha protein | CXCL1 |
| P09382 | Galectin-1 | LGALS1 |
| P09466 | Glycodelin | PAEP |
| P09486 | SPARC | SPARC |
| P09529 | Inhibin beta B chain | INHBB |
| P09544 | Protein Wnt-2 | WNT2 |
| P09603 | Processed macrophage colony-stimulating factor 1 | CSF1 |
| P09681 | Gastric inhibitory polypeptide | GIP |
| P09683 | Secretin | SCT |
| P09919 | Granulocyte colony-stimulating factor | CSF3 |
| P0C091 | FRAS1-related extracellular matrix protein 3 | FREM3 |
| P0C0L4 | C4d-A | C4A |
| P0C0L5 | Complement C4-B alpha chain | C4B |
| P0C0P6 | Neuropeptide S | NPS |
| P0C7L1 | Serine protease inhibitor Kazal-type 8 | SPINK8 |
| P0C862 | Complement C1q and tumor necrosis factor-related protein 9A | C1QTNF9 |
| P0C8F1 | Prostate and testis expressed protein 4 | PATE4 |
| P0CG01 | Gastrokine-3 | GKN3P |
| P0CG36 | Cryptic family protein 1B | CFC1B |
| P0CG37 | Cryptic protein | CFC1 |
| P0CJ68 | Humanin-like protein 1 | MTRNR2L1 |
| P0CJ69 | Humanin-like protein 2 | MTRNR2L2 |
| P0CJ70 | Humanin-like protein 3 | MTRNR2L3 |
| P0CJ71 | Humanin-like protein 4 | MTRNR2L4 |
| P0CJ72 | Humanin-like protein 5 | MTRNR2L5 |
| P0CJ73 | Humanin-like protein 6 | MTRNR2L6 |
| P0CJ74 | Humanin-like protein 7 | MTRNR2L7 |
| P0CJ75 | Humanin-like protein 8 | MTRNR2L8 |
| P0CJ76 | Humanin-like protein 9 | MTRNR2L9 |
| P0CJ77 | Humanin-like protein 10 | MTRNR2L10 |
| P0DJD7 | Pepsin A-4 | PGA4 |
| P0DJD8 | Pepsin A-3 | PGA3 |
| P0DJD9 | Pepsin A-5 | PGA5 |
| P0DJI8 | Amyloid protein A | SAA1 |
| P0DJI9 | Serum amyloid A-2 protein | SAA2 |
| P10082 | Peptide YY(3-36) | PYY |
| P10092 | Calcitonin gene-related peptide 2 | CALCB |
| P10124 | Serglycin | SRGN |
| P10145 | MDNCF-a | IL8 |
| P10147 | MIP-1-alpha(4-69) | CCL3 |
| P10163 | Peptide P-D | PRB4 |
| P10451 | Osteopontin | SPP1 |
| P10599 | Thioredoxin | TXN |
| P10600 | Transforming growth factor beta-3 | TGFB3 |
| P10643 | Complement component C7 | C7 |
| P10645 | Vasostatin-2 | CHGA |
| P10646 | Tissue factor pathway inhibitor | TFPI |

TABLE 1-continued

Secreted Proteins

| Uniprot ID | Protein Name | Gene Name |
|---|---|---|
| P10720 | Platelet factor 4 variant(4-74) | PF4V1 |
| P10745 | Retinol-binding protein 3 | RBP3 |
| P10767 | Fibroblast growth factor 6 | FGF6 |
| P10909 | Clusterin alpha chain | CLU |
| P10912 | Growth hormone receptor | GHR |
| P10915 | Hyaluronan and proteoglycan link protein 1 | HAPLN1 |
| P10966 | T-cell surface glycoprotein CD8 beta chain | CD8B |
| P10997 | Islet amyloid polypeptide | IAPP |
| P11047 | Laminin subunit gamma-1 | LAMC1 |
| P11150 | Hepatic triacylglycerol lipase | LIPC |
| P11226 | Mannose-binding protein C | MBL2 |
| P11464 | Pregnancy-specific beta-1-glycoprotein 1 | PSG1 |
| P11465 | Pregnancy-specific beta-1-glycoprotein 2 | PSG2 |
| P11487 | Fibroblast growth factor 3 | FGF3 |
| P11597 | Cholesteryl ester transfer protein | CETP |
| P11684 | Uteroglobin | SCGB1A1 |
| P11686 | Pulmonary surfactant-associated protein C | SFTPC |
| P12034 | Fibroblast growth factor 5 | FGF5 |
| P12107 | Collagen alpha-1(XI) chain | COL11A1 |
| P12109 | Collagen alpha-1(VI) chain | COL6A1 |
| P12110 | Collagen alpha-2(VI) chain | COL6A2 |
| P12111 | Collagen alpha-3(VI) chain | COL6A3 |
| P12259 | Coagulation factor V | F5 |
| P12272 | PTHrP[1-36] | PTHLH |
| P12273 | Prolactin-inducible protein | PIP |
| P12544 | Granzyme A | GZMA |
| P12643 | Bone morphogenetic protein 2 | BMP2 |
| P12644 | Bone morphogenetic protein 4 | BMP4 |
| P12645 | Bone morphogenetic protein 3 | BMP3 |
| P12724 | Eosinophil cationic protein | RNASE3 |
| P12821 | Angiotensin-converting enzyme, soluble form | ACE |
| P12838 | Neutrophil defensin 4 | DEFA4 |
| P12872 | Motilin | MLN |
| P13232 | Interleukin-7 | IL7 |
| P13236 | C-C motif chemokine 4 | CCL4 |
| P13284 | Gamma-interferon-inducible lysosomal thiol reductase | IFI30 |
| P13500 | C-C motif chemokine 2 | CCL2 |
| P13501 | C-C motif chemokine 5 | CCL5 |
| P13521 | Secretogranin-2 | SCG2 |
| P13591 | Neural cell adhesion molecule 1 | NCAM1 |
| P13611 | Versican core protein | VCAN |
| P13671 | Complement component C6 | C6 |
| P13688 | Carcinoembryonic antigen-related cell adhesion molecule 1 | CEACAM1 |
| P13725 | Oncostatin-M | OSM |
| P13726 | Tissue factor | F3 |
| P13727 | Eosinophil granule major basic protein | PRG2 |
| P13942 | Collagen alpha-2(XI) chain | COL11A2 |
| P13987 | CD59 glycoprotein | CD59 |
| P14138 | Endothelin-3 | EDN3 |
| P14174 | Macrophage migration inhibitory factor | MIF |
| P14207 | Folate receptor beta | FOLR2 |
| P14222 | Perforin-1 | PRF1 |
| P14543 | Nidogen-1 | NID1 |
| P14555 | Phospholipase A2, membrane associated | PLA2G2A |
| P14625 | Endoplasmin | HSP90B1 |
| P14735 | Insulin-degrading enzyme | IDE |
| P14778 | Interleukin-1 receptor type 1, soluble form | IL1R1 |
| P14780 | 82 kDa matrix metalloproteinase-9 | MMP9 |
| P15018 | Leukemia inhibitory factor | LIF |
| P15085 | Carboxypeptidase A1 | CPA1 |
| P15086 | Carboxypeptidase B | CPB1 |
| P15151 | Poliovirus receptor | PVR |
| P15169 | Carboxypeptidase N catalytic chain | CPN1 |
| P15248 | Interleukin-9 | IL9 |
| P15291 | N-acetyllactosamine synthase | B4GALT1 |
| P15309 | PAPf39 | ACPP |
| P15328 | Folate receptor alpha | FOLR1 |
| P15374 | Ubiquitin carboxyl-terminal hydrolase isozyme L3 | UCHL3 |
| P15502 | Elastin | ELN |
| P15509 | Granulocyte-macrophage colony-stimulating factor receptor subunit alpha | CSF2RA |
| P15515 | Histatin-1 | HTN1 |
| P15516 | His3-(31-51)-peptide | HTN3 |

TABLE 1-continued

Secreted Proteins

| Uniprot ID | Protein Name | Gene Name |
|---|---|---|
| P15692 | Vascular endothelial growth factor A | VEGFA |
| P15814 | Immunoglobulin lambda-like polypeptide 1 | IGLL1 |
| P15907 | Beta-galactoside alpha-2,6-sialyltransferase 1 | ST6GAL1 |
| P15941 | Mucin-1 subunit beta | MUC1 |
| P16035 | Metalloproteinase inhibitor 2 | TIMP2 |
| P16112 | Aggrecan core protein 2 | ACAN |
| P16233 | Pancreatic triacylglycerol lipase | PNLIP |
| P16442 | Histo-blood group ABO system transferase | ABO |
| P16471 | Prolactin receptor | PRLR |
| P16562 | Cysteine-rich secretory protein 2 | CRISP2 |
| P16619 | C-C motif chemokine 3-like 1 | CCL3L1 |
| P16860 | BNP(3-29) | NPPB |
| P16870 | Carboxypeptidase E | CPE |
| P16871 | Interleukin-7 receptor subunit alpha | IL7R |
| P17213 | Bactericidal permeability-increasing protein | BPI |
| P17538 | Chymotrypsinogen B | CTRB1 |
| P17931 | Galectin-3 | LGALS3 |
| P17936 | Insulin-like growth factor-binding protein 3 | IGFBP3 |
| P17948 | Vascular endothelial growth factor receptor 1 | FLT1 |
| P18065 | Insulin-like growth factor-binding protein 2 | IGFBP2 |
| P18075 | Bone morphogenetic protein 7 | BMP7 |
| P18428 | Lipopolysaccharide-binding protein | LBP |
| P18509 | PACAP-related peptide | ADCYAP1 |
| P18510 | Interleukin-1 receptor antagonist protein | IL1RN |
| P18827 | Syndecan-1 | SDC1 |
| P19021 | Peptidylglycine alpha-hydroxylating monooxygenase | PAM |
| P19235 | Erythropoietin receptor | EPOR |
| P19438 | Tumor necrosis factor-binding protein 1 | TNFRSF1A |
| P19652 | Alpha-1-acid glycoprotein 2 | ORM2 |
| P19801 | Amiloride-sensitive amine oxidase [copper-containing] | ABP1 |
| P19823 | Inter-alpha-trypsin inhibitor heavy chain H2 | ITIH2 |
| P19827 | Inter-alpha-trypsin inhibitor heavy chain H1 | ITIH1 |
| P19835 | Bile salt-activated lipase | CEL |
| P19875 | C-X-C motif chemokine 2 | CXCL2 |
| P19876 | C-X-C motif chemokine 3 | CXCL3 |
| P19883 | Follistatin | FST |
| P19957 | Elafin | PI3 |
| P19961 | Alpha-amylase 2B | AMY2B |
| P20061 | Transcobalamin-1 | TCN1 |
| P20062 | Transcobalamin-2 | TCN2 |
| P20142 | Gastricsin | PGC |
| P20155 | Serine protease inhibitor Kazal-type 2 | SPINK2 |
| P20231 | Tryptase beta-2 | TPSB2 |
| P20333 | Tumor necrosis factor receptor superfamily member 1B | TNFRSF1B |
| P20366 | Substance P | TAC1 |
| P20382 | Melanin-concentrating hormone | PMCH |
| P20396 | Thyroliberin | TRH |
| P20742 | Pregnancy zone protein | PZP |
| P20774 | Mimecan | OGN |
| P20783 | Neurotrophin-3 | NTF3 |
| P20800 | Endothelin-2 | EDN2 |
| P20809 | Interleukin-11 | IL11 |
| P20827 | Ephrin-A1 | EFNA1 |
| P20849 | Collagen alpha-1(IX) chain | COL9A1 |
| P20851 | C4b-binding protein beta chain | C4BPB |
| P20908 | Collagen alpha-1(V) chain | COL5A1 |
| P21128 | Poly(U)-specific endoribonuclease | ENDOU |
| P21246 | Pleiotrophin | PTN |
| P21583 | Kit ligand | KITLG |
| P21741 | Midkine | MDK |
| P21754 | Zona pellucida sperm-binding protein 3 | ZP3 |
| P21781 | Fibroblast growth factor 7 | FGF7 |
| P21802 | Fibroblast growth factor receptor 2 | FGFR2 |
| P21810 | Biglycan | BGN |
| P21815 | Bone sialoprotein 2 | IBSP |
| P21860 | Receptor tyrosine-protein kinase erbB-3 | ERBB3 |
| P21941 | Cartilage matrix protein | MATN1 |
| P22003 | Bone morphogenetic protein 5 | BMP5 |
| P22004 | Bone morphogenetic protein 6 | BMP6 |
| P22079 | Lactoperoxidase | LPO |
| P22105 | Tenascin-X | TNXB |
| P22301 | Interleukin-10 | IL10 |

TABLE 1-continued

Secreted Proteins

| Uniprot ID | Protein Name | Gene Name |
|---|---|---|
| P22303 | Acetylcholinesterase | ACHE |
| P22352 | Glutathione peroxidase 3 | GPX3 |
| P22362 | C-C motif chemokine 1 | CCL1 |
| P22455 | Fibroblast growth factor receptor 4 | FGFR4 |
| P22466 | Galanin message-associated peptide | GAL |
| P22692 | Insulin-like growth factor-binding protein 4 | IGFBP4 |
| P22749 | Granulysin | GNLY |
| P22792 | Carboxypeptidase N subunit 2 | CPN2 |
| P22891 | Vitamin K-dependent protein Z | PROZ |
| P22894 | Neutrophil collagenase | MMP8 |
| P23142 | Fibulin-1 | FBLN1 |
| P23280 | Carbonic anhydrase 6 | CA6 |
| P23352 | Anosmin-1 | KAL1 |
| P23435 | Cerebellin-1 | CBLN1 |
| P23560 | Brain-derived neurotrophic factor | BDNF |
| P23582 | C-type natriuretic peptide | NPPC |
| P23946 | Chymase | CMA1 |
| P24043 | Laminin subunit alpha-2 | LAMA2 |
| P24071 | Immunoglobulin alpha Fc receptor | FCAR |
| P24347 | Stromelysin-3 | MMP11 |
| P24387 | Corticotropin-releasing factor-binding protein | CRHBP |
| P24592 | Insulin-like growth factor-binding protein 6 | IGFBP6 |
| P24593 | Insulin-like growth factor-binding protein 5 | IGFBP5 |
| P24821 | Tenascin | TNC |
| P24855 | Deoxyribonuclease-1 | DNASE1 |
| P25067 | Collagen alpha-2(VIII) chain | COL8A2 |
| P25311 | Zinc-alpha-2-glycoprotein | AZGP1 |
| P25391 | Laminin subunit alpha-1 | LAMA1 |
| P25445 | Tumor necrosis factor receptor superfamily member 6 | FAS |
| P25940 | Collagen alpha-3(V) chain | COL5A3 |
| P25942 | Tumor necrosis factor receptor superfamily member 5 | CD40 |
| P26022 | Pentraxin-related protein PTX3 | PTX3 |
| P26927 | Hepatocyte growth factor-like protein beta chain | MST1 |
| P27169 | Serum paraoxonase/arylesterase 1 | PON1 |
| P27352 | Gastric intrinsic factor | GIF |
| P27487 | Dipeptidyl peptidase 4 membrane form | DPP4 |
| P27539 | Embryonic growth/differentiation factor 1 | GDF1 |
| P27658 | Vastatin | COL8A1 |
| P27797 | Calreticulin | CALR |
| P27918 | Properdin | CFP |
| P28039 | Acyloxyacyl hydrolase | AOAH |
| P28300 | Protein-lysine 6-oxidase | LOX |
| P28325 | Cystatin-D | CST5 |
| P28799 | Granulin-1 | GRN |
| P29122 | Proprotein convertase subtilisin/kexin type 6 | PCSK6 |
| P29279 | Connective tissue growth factor | CTGF |
| P29320 | Ephrin type-A receptor 3 | EPHA3 |
| P29400 | Collagen alpha-5(IV) chain | COL4A5 |
| P29459 | Interleukin-12 subunit alpha | IL12A |
| P29460 | Interleukin-12 subunit beta | IL12B |
| P29508 | Serpin B3 | SERPINB3 |
| P29622 | Kallistatin | SERPINA4 |
| P29965 | CD40 ligand, soluble form | CD40LG |
| P30990 | Neurotensin/neuromedin N | NTS |
| P31025 | Lipocalin-1 | LCN1 |
| P31151 | Protein S100-A7 | S100A7 |
| P31371 | Fibroblast growth factor 9 | FGF9 |
| P31431 | Syndecan-4 | SDC4 |
| P31947 | 14-3-3 protein sigma | SFN |
| P32455 | Interferon-induced guanylate-binding protein 1 | GBP1 |
| P32881 | Interferon alpha-8 | IFNA8 |
| P34096 | Ribonuclease 4 | RNASE4 |
| P34130 | Neurotrophin-4 | NTF4 |
| P34820 | Bone morphogenetic protein 8B | BMP8B |
| P35030 | Trypsin-3 | PRSS3 |
| P35052 | Secreted glypican-1 | GPC1 |
| P35070 | Betacellulin | BTC |
| P35225 | Interleukin-13 | IL13 |
| P35247 | Pulmonary surfactant-associated protein D | SFTPD |
| P35318 | ADM | ADM |
| P35542 | Serum amyloid A-4 protein | SAA4 |
| P35555 | Fibrillin-1 | FBN1 |
| P35556 | Fibrillin-2 | FBN2 |

TABLE 1-continued

Secreted Proteins

| Uniprot ID | Protein Name | Gene Name |
|---|---|---|
| P35625 | Metalloproteinase inhibitor 3 | TIMP3 |
| P35858 | Insulin-like growth factor-binding protein complex acid labile subunit | IGFALS |
| P35916 | Vascular endothelial growth factor receptor 3 | FLT4 |
| P35968 | Vascular endothelial growth factor receptor 2 | KDR |
| P36222 | Chitinase-3-like protein 1 | CHI3L1 |
| P36952 | Serpin B5 | SERPINB5 |
| P36955 | Pigment epithelium-derived factor | SERPINF1 |
| P36980 | Complement factor H-related protein 2 | CFHR2 |
| P39059 | Collagen alpha-1(XV) chain | COL15A1 |
| P39060 | Collagen alpha-1(XVIII) chain | COL18A1 |
| P39877 | Calcium-dependent phospholipase A2 | PLA2G5 |
| P39900 | Macrophage metalloelastase | MMP12 |
| P39905 | Glial cell line-derived neurotrophic factor | GDNF |
| P40225 | Thrombopoietin | THPO |
| P40967 | M-alpha | PMEL |
| P41159 | Leptin | LEP |
| P41221 | Protein Wnt-5a | WNT5A |
| P41222 | Prostaglandin-H2 D-isomerase | PTGDS |
| P41271 | Neuroblastoma suppressor of tumorigenicity 1 | NBL1 |
| P41439 | Folate receptor gamma | FOLR3 |
| P42127 | Agouti-signaling protein | ASIP |
| P42702 | Leukemia inhibitory factor receptor | LIFR |
| P42830 | ENA-78(9-78) | CXCL5 |
| P43026 | Growth/differentiation factor 5 | GDF5 |
| P43251 | Biotinidase | BTD |
| P43652 | Afamin | AFM |
| P45452 | Collagenase 3 | MMP13 |
| P47710 | Casoxin-D | CSN1S1 |
| P47929 | Galectin-7 | LGALS7B |
| P47972 | Neuronal pentraxin-2 | NPTX2 |
| P47989 | Xanthine oxidase | XDH |
| P47992 | Lymphotactin | XCL1 |
| P48023 | Tumor necrosis factor ligand superfamily member 6, membrane form | FASLG |
| P48052 | Carboxypeptidase A2 | CPA2 |
| P48061 | Stromal cell-derived factor 1 | CXCL12 |
| P48304 | Lithostathine-1-beta | REG1B |
| P48307 | Tissue factor pathway inhibitor 2 | TFPI2 |
| P48357 | Leptin receptor | LEPR |
| P48594 | Serpin B4 | SERPINB4 |
| P48645 | Neuromedin-U-25 | NMU |
| P48740 | Mannan-binding lectin serine protease 1 | MASP1 |
| P48745 | Protein NOV homolog | NOV |
| P48960 | CD97 antigen subunit beta | CD97 |
| P49223 | Kunitz-type protease inhibitor 3 | SPINT3 |
| P49747 | Cartilage oligomeric matrix protein | COMP |
| P49763 | Placenta growth factor | PGF |
| P49765 | Vascular endothelial growth factor B | VEGFB |
| P49767 | Vascular endothelial growth factor C | VEGFC |
| P49771 | Fms-related tyrosine kinase 3 ligand | FLT3LG |
| P49862 | Kallikrein-7 | KLK7 |
| P49863 | Granzyme K | GZMK |
| P49908 | Selenoprotein P | SEPP1 |
| P49913 | Antibacterial protein FALL-39 | CAMP |
| P50607 | Tubby protein homolog | TUB |
| P51124 | Granzyme M | GZMM |
| P51512 | Matrix metalloproteinase-16 | MMP16 |
| P51654 | Glypican-3 | GPC3 |
| P51671 | Eotaxin | CCL11 |
| P51884 | Lumican | LUM |
| P51888 | Prolargin | PRELP |
| P52798 | Ephrin-A4 | EFNA4 |
| P52823 | Stanniocalcin-1 | STC1 |
| P53420 | Collagen alpha-4(IV) chain | COL4A4 |
| P53621 | Coatomer subunit alpha | COPA |
| P54108 | Cysteine-rich secretory protein 3 | CRISP3 |
| P54315 | Pancreatic lipase-related protein 1 | PNLIPRP1 |
| P54317 | Pancreatic lipase-related protein 2 | PNLIPRP2 |
| P54793 | Arylsulfatase F | ARSF |
| P55000 | Secreted Ly-6/uPAR-related protein 1 | SLURP1 |
| P55001 | Microfibrillar-associated protein 2 | MFAP2 |
| P55056 | Apolipoprotein C-IV | APOC4 |
| P55058 | Phospholipid transfer protein | PLTP |
| P55075 | Fibroblast growth factor 8 | FGF8 |

TABLE 1-continued

Secreted Proteins

| Uniprot ID | Protein Name | Gene Name |
|---|---|---|
| P55081 | Microfibrillar-associated protein 1 | MFAP1 |
| P55083 | Microfibril-associated glycoprotein 4 | MFAP4 |
| P55107 | Bone morphogenetic protein 3B | GDF10 |
| P55145 | Mesencephalic astrocyte-derived neurotrophic factor | MANF |
| P55259 | Pancreatic secretory granule membrane major glycoprotein GP2 | GP2 |
| P55268 | Laminin subunit beta-2 | LAMB2 |
| P55773 | CCL23(30-99) | CCL23 |
| P55774 | C-C motif chemokine 18 | CCL18 |
| P55789 | FAD-linked sulfhydryl oxidase ALR | GFER |
| P56703 | Proto-oncogene Wnt-3 | WNT3 |
| P56704 | Protein Wnt-3a | WNT3A |
| P56705 | Protein Wnt-4 | WNT4 |
| P56706 | Protein Wnt-7b | WNT7B |
| P56730 | Neurotrypsin | PRSS12 |
| P56851 | Epididymal secretory protein E3-beta | EDDM3B |
| P56975 | Neuregulin-3 | NRG3 |
| P58062 | Serine protease inhibitor Kazal-type 7 | SPINK7 |
| P58215 | Lysyl oxidase homolog 3 | LOXL3 |
| P58294 | Prokineticin-1 | PROK1 |
| P58335 | Anthrax toxin receptor 2 | ANTXR2 |
| P58397 | A disintegrin and metalloproteinase with thrombospondin motifs 12 | ADAMTS12 |
| P58417 | Neurexophilin-1 | NXPH1 |
| P58499 | Protein FAM3B | FAM3B |
| P59510 | A disintegrin and metalloproteinase with thrombospondin motifs 20 | ADAMTS20 |
| P59665 | Neutrophil defensin 1 | DEFA1B |
| P59666 | Neutrophil defensin 3 | DEFA3 |
| P59796 | Glutathione peroxidase 6 | GPX6 |
| P59826 | BPI fold-containing family B member 3 | BPIFB3 |
| P59827 | BPI fold-containing family B member 4 | BPIFB4 |
| P59861 | Beta-defensin 131 | DEFB131 |
| P60022 | Beta-defensin 1 | DEFB1 |
| P60153 | Inactive ribonuclease-like protein 9 | RNASE9 |
| P60827 | Complement C1q tumor necrosis factor-related protein 8 | C1QTNF8 |
| P60852 | Zona pellucida sperm-binding protein 1 | ZP1 |
| P60985 | Keratinocyte differentiation-associated protein | KRTDAP |
| P61109 | Kidney androgen-regulated protein | KAP |
| P61278 | Somatostatin-14 | SST |
| P61366 | Osteocrin | OSTN |
| P61626 | Lysozyme C | LYZ |
| P61769 | Beta-2-microglobulin | B2M |
| P61812 | Transforming growth factor beta-2 | TGFB2 |
| P61916 | Epididymal secretory protein E1 | NPC2 |
| P62502 | Epididymal-specific lipocalin-6 | LCN6 |
| P62937 | Peptidyl-prolyl cis-trans isomerase A | PPIA |
| P67809 | Nuclease-sensitive element-binding protein 1 | YBX1 |
| P67812 | Signal peptidase complex catalytic subunit SEC11A | SEC11A |
| P78310 | Coxsackievirus and adenovirus receptor | CXADR |
| P78333 | Secreted glypican-5 | GPC5 |
| P78380 | Oxidized low-density lipoprotein receptor 1 | OLR1 |
| P78423 | Processed fractalkine | CX3CL1 |
| P78509 | Reelin | RELN |
| P78556 | CCL20(2-70) | CCL20 |
| P80075 | MCP-2(6-76) | CCL8 |
| P80098 | C-C motif chemokine 7 | CCL7 |
| P80108 | Phosphatidylinositol-glycan-specific phospholipase D | GPLD1 |
| P80162 | C-X-C motif chemokine 6 | CXCL6 |
| P80188 | Neutrophil gelatinase-associated lipocalin | LCN2 |
| P80303 | Nucleobindin-2 | NUCB2 |
| P80511 | Calcitermin | S100A12 |
| P81172 | Hepcidin-25 | HAMP |
| P81277 | Prolactin-releasing peptide | PRLH |
| P81534 | Beta-defensin 103 | DEFB103A |
| P81605 | Dermcidin | DCD |
| P82279 | Protein crumbs homolog 1 | CRB1 |
| P82987 | ADAMTS-like protein 3 | ADAMTSL3 |
| P83105 | Serine protease HTRA4 | HTRA4 |
| P83110 | Serine protease HTRA3 | HTRA3 |
| P83859 | Orexigenic neuropeptide QRFP | QRFP |

TABLE 1-continued

Secreted Proteins

| Uniprot ID | Protein Name | Gene Name |
|---|---|---|
| P98088 | Mucin-5AC | MUC5AC |
| P98095 | Fibulin-2 | FBLN2 |
| P98160 | Basement membrane-specific heparan sulfate proteoglycan core protein | HSPG2 |
| P98173 | Protein FAM3A | FAM3A |
| Q00604 | Norrin | NDP |
| Q00796 | Sorbitol dehydrogenase | SORD |
| Q00887 | Pregnancy-specific beta-1-glycoprotein 9 | PSG9 |
| Q00888 | Pregnancy-specific beta-1-glycoprotein 4 | PSG4 |
| Q00889 | Pregnancy-specific beta-1-glycoprotein 6 | PSG6 |
| Q01523 | HD5(56-94) | DEFA5 |
| Q01524 | Defensin-6 | DEFA6 |
| Q01955 | Collagen alpha-3(IV) chain | COL4A3 |
| Q02297 | Pro-neuregulin-1, membrane-bound isoform | NRG1 |
| Q02325 | Plasminogen-like protein B | PLGLB1 |
| Q02383 | Semenogelin-2 | SEMG2 |
| Q02388 | Collagen alpha-1(VII) chain | COL7A1 |
| Q02505 | Mucin-3A | MUC3A |
| Q02509 | Otoconin-90 | OC90 |
| Q02747 | Guanylin | GUCA2A |
| Q02763 | Angiopoietin-1 receptor | TEK |
| Q02817 | Mucin-2 | MUC2 |
| Q02985 | Complement factor H-related protein 3 | CFHR3 |
| Q03167 | Transforming growth factor beta receptor type 3 | TGFBR3 |
| Q03403 | Trefoil factor 2 | TFF2 |
| Q03405 | Urokinase plasminogen activator surface receptor | PLAUR |
| Q03591 | Complement factor H-related protein 1 | CFHR1 |
| Q03692 | Collagen alpha-1(X) chain | COL10A1 |
| Q04118 | Basic salivary proline-rich protein 3 | PRB3 |
| Q04756 | Hepatocyte growth factor activator short chain | HGFAC |
| Q04900 | Sialomucin core protein 24 | CD164 |
| Q05315 | Eosinophil lysophospholipase | CLC |
| Q05707 | Collagen alpha-1(XIV) chain | COL14A1 |
| Q05996 | Processed zona pellucida sperm-binding protein 2 | ZP2 |
| Q06033 | Inter-alpha-trypsin inhibitor heavy chain H3 | ITIH3 |
| Q06141 | Regenerating islet-derived protein 3-alpha | REG3A |
| Q06828 | Fibromodulin | FMOD |
| Q07092 | Collagen alpha-1(XVI) chain | COL16A1 |
| Q07325 | C-X-C motif chemokine 9 | CXCL9 |
| Q07507 | Dermatopontin | DPT |
| Q075Z2 | Binder of sperm protein homolog 1 | BSPH1 |
| Q07654 | Trefoil factor 3 | TFF3 |
| Q07699 | Sodium channel subunit beta-1 | SCN1B |
| Q08345 | Epithelial discoidin domain-containing receptor 1 | DDR1 |
| Q08380 | Galectin-3-binding protein | LGALS3BP |
| Q08397 | Lysyl oxidase homolog 1 | LOXL1 |
| Q08431 | Lactadherin | MFGE8 |
| Q08629 | Testican-1 | SPOCK1 |
| Q08648 | Sperm-associated antigen 11B | SPAG11B |
| Q08830 | Fibrinogen-like protein 1 | FGL1 |
| Q10471 | Polypeptide N-acetylgalactosaminyltransferase 2 | GALNT2 |
| Q10472 | Polypeptide N-acetylgalactosaminyltransferase 1 | GALNT1 |
| Q11201 | CMP-N-acetylneuraminate-beta-galactosamide-alpha-2,3-sialyltransferase 1 | ST3GAL1 |
| Q11203 | CMP-N-acetylneuraminate-beta-1,4-galactoside alpha-2,3-sialyltransferase | ST3GAL3 |
| Q11206 | CMP-N-acetylneuraminate-beta-galactosamide-alpha-2,3-sialyltransferase 4 | ST3GAL4 |
| Q12794 | Hyaluronidase-1 | HYAL1 |
| Q12805 | EGF-containing fibulin-like extracellular matrix protein 1 | EFEMP1 |
| Q12836 | Zona pellucida sperm-binding protein 4 | ZP4 |
| Q12841 | Follistatin-related protein 1 | FSTL1 |
| Q12904 | Aminoacyl tRNA synthase complex-interacting multifunctional protein 1 | AIMP1 |
| Q13018 | Soluble secretory phospholipase A2 receptor | PLA2R1 |
| Q13072 | B melanoma antigen 1 | BAGE |
| Q13093 | Platelet-activating factor acetylhydrolase | PLA2G7 |
| Q13103 | Secreted phosphoprotein 24 | SPP2 |
| Q13162 | Peroxiredoxin-4 | PRDX4 |
| Q13201 | Platelet glycoprotein Ia* | MMRN1 |
| Q13214 | Semaphorin-3B | SEMA3B |
| Q13219 | Pappalysin-1 | PAPPA |
| Q13231 | Chitotriosidase-1 | CHIT1 |
| Q13253 | Noggin | NOG |

TABLE 1-continued

Secreted Proteins

| Uniprot ID | Protein Name | Gene Name |
|---|---|---|
| Q13261 | Interleukin-15 receptor subunit alpha | IL15RA |
| Q13275 | Semaphorin-3F | SEMA3F |
| Q13291 | Signaling lymphocytic activation molecule | SLAMF1 |
| Q13316 | Dentin matrix acidic phosphoprotein 1 | DMP1 |
| Q13361 | Microfibrillar-associated protein 5 | MFAP5 |
| Q13410 | Butyrophilin subfamily 1 member A1 | BTN1A1 |
| Q13421 | Mesothelin, cleaved form | MSLN |
| Q13429 | Insulin-like growth factor I | IGF-I |
| Q13443 | Disintegrin and metalloproteinase domain-containing protein 9 | ADAM9 |
| Q13519 | Neuropeptide 1 | PNOC |
| Q13751 | Laminin subunit beta-3 | LAMB3 |
| Q13753 | Laminin subunit gamma-2 | LAMC2 |
| Q13790 | Apolipoprotein F | APOF |
| Q13822 | Ectonucleotide pyrophosphatase/phosphodiesterase family member 2 | ENPP2 |
| Q14031 | Collagen alpha-6(IV) chain | COL4A6 |
| Q14050 | Collagen alpha-3(IX) chain | COL9A3 |
| Q14055 | Collagen alpha-2(IX) chain | COL9A2 |
| Q14112 | Nidogen-2 | NID2 |
| Q14114 | Low-density lipoprotein receptor-related protein 8 | LRP8 |
| Q14118 | Dystroglycan | DAG1 |
| Q14314 | Fibroleukin | FGL2 |
| Q14393 | Growth arrest-specific protein 6 | GAS6 |
| Q14406 | Chorionic somatomammotropin hormone-like 1 | CSHL1 |
| Q14507 | Epididymal secretory protein E3-alpha | EDDM3A |
| Q14508 | WAP four-disulfide core domain protein 2 | WFDC2 |
| Q14512 | Fibroblast growth factor-binding protein 1 | FGFBP1 |
| Q14515 | SPARC-like protein 1 | SPARCL1 |
| Q14520 | Hyaluronan-binding protein 2 27 kDa light chain | HABP2 |
| Q14563 | Semaphorin-3A | SEMA3A |
| Q14623 | Indian hedgehog protein | IHH |
| Q14624 | Inter-alpha-trypsin inhibitor heavy chain H4 | ITIH4 |
| Q14667 | UPF0378 protein KIAA0100 | KIAA0100 |
| Q14703 | Membrane-bound transcription factor site-1 protease | MBTPS1 |
| Q14766 | Latent-transforming growth factor beta-binding protein 1 | LTBP1 |
| Q14767 | Latent-transforming growth factor beta-binding protein 2 | LTBP2 |
| Q14773 | Intercellular adhesion molecule 4 | ICAM4 |
| Q14993 | Collagen alpha-1(XIX) chain | COL19A1 |
| Q14CN2 | Calcium-activated chloride channel regulator 4, 110 kDa form | CLCA4 |
| Q15046 | Lysine--tRNA ligase | KARS |
| Q15063 | Periostin | POSTN |
| Q15109 | Advanced glycosylation end product-specific receptor | AGER |
| Q15113 | Procollagen C-endopeptidase enhancer 1 | PCOLCE |
| Q15166 | Serum paraoxonase/lactonase 3 | PON3 |
| Q15195 | Plasminogen-like protein A | PLGLA |
| Q15198 | Platelet-derived growth factor receptor-like protein | PDGFRL |
| Q15223 | Poliovirus receptor-related protein 1 | PVRL1 |
| Q15238 | Pregnancy-specific beta-1-glycoprotein 5 | PSG5 |
| Q15363 | Transmembrane emp24 domain-containing protein 2 | TMED2 |
| Q15375 | Ephrin type-A receptor 7 | EPHA7 |
| Q15389 | Angiopoietin-1 | ANGPT1 |
| Q15465 | Sonic hedgehog protein | SHH |
| Q15485 | Ficolin-2 | FCN2 |
| Q15517 | Corneodesmosin | CDSN |
| Q15582 | Transforming growth factor-beta-induced protein ig-h3 | TGFBI |
| Q15661 | Tryptase alpha/beta-1 | TPSAB1 |
| Q15726 | Metastin | KISS1 |
| Q15782 | Chitinase-3-like protein 2 | CHI3L2 |
| Q15828 | Cystatin-M | CST6 |
| Q15846 | Clusterin-like protein 1 | CLUL1 |
| Q15848 | Adiponectin | ADIPOQ |
| Q16206 | Protein disulfide-thiol oxidoreductase | ENOX2 |
| Q16270 | Insulin-like growth factor-binding protein 7 | IGFBP7 |
| Q16363 | Laminin subunit alpha-4 | LAMA4 |
| Q16378 | Proline-rich protein 4 | PRR4 |
| Q16557 | Pregnancy-specific beta-1-glycoprotein 3 | PSG3 |
| Q16568 | CART(42-89) | CARTPT |
| Q16610 | Extracellular matrix protein 1 | ECM1 |
| Q16619 | Cardiotrophin-1 | CTF1 |

TABLE 1-continued

Secreted Proteins

| Uniprot ID | Protein Name | Gene Name |
|---|---|---|
| Q16623 | Syntaxin-1A | STX1A |
| Q16627 | HCC-1(9-74) | CCL14 |
| Q16651 | Prostasin light chain | PRSS8 |
| Q16661 | Guanylate cyclase C-activating peptide 2 | GUCA2B |
| Q16663 | CCL15(29-92) | CCL15 |
| Q16674 | Melanoma-derived growth regulatory protein | MIA |
| Q16769 | Glutaminyl-peptide cyclotransferase | QPCT |
| Q16787 | Laminin subunit alpha-3 | LAMA3 |
| Q16842 | CMP-N-acetylneuraminate-beta-galactosamide-alpha-2,3-sialyltransferase 2 | ST3GAL2 |
| Q17RR3 | Pancreatic lipase-related protein 3 | PNLIPRP3 |
| Q17RW2 | Collagen alpha-1(XXIV) chain | COL24A1 |
| Q17RY6 | Lymphocyte antigen 6K | LY6K |
| Q1L6U9 | Prostate-associated microseminoprotein | MSMP |
| Q1W4C9 | Serine protease inhibitor Kazal-type 13 | SPINK13 |
| Q1ZYL8 | Izumo sperm-egg fusion protein 4 | IZUMO4 |
| Q29960 | HLA class I histocompatibility antigen, Cw-16 alpha chain | HLA-C |
| Q2I0M5 | R-spondin-4 | RSPO4 |
| Q2L4Q9 | Serine protease 53 | PRSS53 |
| Q2MKA7 | R-spondin-1 | RSPO1 |
| Q2MV58 | Tectonic-1 | TCTN1 |
| Q2TAL6 | Brorin | VWC2 |
| Q2UY09 | Collagen alpha-1(XXVIII) chain | COL28A1 |
| Q2VPA4 | Complement component receptor 1-like protein | CR1L |
| Q2WEN9 | Carcinoembryonic antigen-related cell adhesion molecule 16 | CEACAM16 |
| Q30KP8 | Beta-defensin 136 | DEFB136 |
| Q30KP9 | Beta-defensin 135 | DEFB135 |
| Q30KQ1 | Beta-defensin 133 | DEFB133 |
| Q30KQ2 | Beta-defensin 130 | DEFB130 |
| Q30KQ4 | Beta-defensin 116 | DEFB116 |
| Q30KQ5 | Beta-defensin 115 | DEFB115 |
| Q30KQ6 | Beta-defensin 114 | DEFB114 |
| Q30KQ7 | Beta-defensin 113 | DEFB113 |
| Q30KQ8 | Beta-defensin 112 | DEFB112 |
| Q30KQ9 | Beta-defensin 110 | DEFB110 |
| Q30KR1 | Beta-defensin 109 | DEFB109P1 |
| Q32P28 | Prolyl 3-hydroxylase 1 | LEPRE1 |
| Q3B7J2 | Glucose-fructose oxidoreductase domain-containing protein 2 | GFOD2 |
| Q3SY79 | Protein Wnt | WNT3A |
| Q3T906 | N-acetylglucosamine-1-phosphotransferase subunits alpha/beta | GNPTAB |
| Q495T6 | Membrane metallo-endopeptidase-like 1 | MMEL1 |
| Q49AH0 | Cerebral dopamine neurotrophic factor | CDNF |
| Q4G0G5 | Secretoglobin family 2B member 2 | SCGB2B2 |
| Q4G0M1 | Protein FAM132B | FAM132B |
| Q4LDE5 | Sushi, von Willebrand factor type A, EGF and pentraxin domain-containing protein 1 | SVEP1 |
| Q4QY38 | Beta-defensin 134 | DEFB134 |
| Q4VAJ4 | Protein Wnt | WNT10B |
| Q4W5P6 | Protein TMEM155 | TMEM155 |
| Q4ZHG4 | Fibronectin type III domain-containing protein 1 | FNDC1 |
| Q53H76 | Phospholipase A1 member A | PLA1A |
| Q53RD9 | Fibulin-7 | FBLN7 |
| Q53S33 | BolA-like protein 3 | BOLA3 |
| Q5BLP8 | Neuropeptide-like protein C4orf48 | C4orf48 |
| Q5DT21 | Serine protease inhibitor Kazal-type 9 | SPINK9 |
| Q5EBL8 | PDZ domain-containing protein 11 | PDZD11 |
| Q5FYB0 | Arylsulfatase J | ARSJ |
| Q5FYB1 | Arylsulfatase I | ARSI |
| Q5GAN3 | Ribonuclease-like protein 13 | RNASE13 |
| Q5GAN4 | Ribonuclease-like protein 12 | RNASE12 |
| Q5GAN6 | Ribonuclease-like protein 10 | RNASE10 |
| Q5GFL6 | von Willebrand factor A domain-containing protein 2 | VWA2 |
| Q5H8A3 | Neuromedin-S | NMS |
| Q5H8C1 | FRAS1-related extracellular matrix protein 1 | FREM1 |
| Q5IJ48 | Protein crumbs homolog 2 | CRB2 |
| Q5J5C9 | Beta-defensin 121 | DEFB121 |
| Q5JS37 | NHL repeat-containing protein 3 | NHLRC3 |
| Q5JTB6 | Placenta-specific protein 9 | PLAC9 |
| Q5JU69 | Torsin-2A | TOR2A |
| Q5JXM2 | Methyltransferase-like protein 24 | METTL24 |

TABLE 1-continued

Secreted Proteins

| Uniprot ID | Protein Name | Gene Name |
|---|---|---|
| Q5JZY3 | Ephrin type-A receptor 10 | EPHA10 |
| Q5K4E3 | Polyserase-2 | PRSS36 |
| Q5SRR4 | Lymphocyte antigen 6 complex locus protein G5c | LY6G5C |
| Q5T1H1 | Protein eyes shut homolog | EYS |
| Q5T4F7 | Secreted frizzled-related protein 5 | SFRP5 |
| Q5T4W7 | Artemin | ARTN |
| Q5T7M4 | Protein FAM132A | FAM132A |
| Q5TEH8 | Protein Wnt | WNT2B |
| Q5TIE3 | von Willebrand factor A domain-containing protein 5B1 | VWA5B1 |
| Q5UCC4 | ER membrane protein complex subunit 10 | EMC10 |
| Q5VST6 | Abhydrolase domain-containing protein FAM108B1 | FAM108B1 |
| Q5VTL7 | Fibronectin type III domain-containing protein 7 | FNDC7 |
| Q5VUM1 | UPF0369 protein C6orf57 | C6orf57 |
| Q5VV43 | Dyslexia-associated protein KIAA0319 | KIAA0319 |
| Q5VWW1 | Complement C1q-like protein 3 | C1QL3 |
| Q5VXI9 | Lipase member N | LIPN |
| Q5VXJ0 | Lipase member K | LIPK |
| Q5VXM1 | CUB domain-containing protein 2 | CDCP2 |
| Q5VYX0 | Renalase | RNLS |
| Q5VYY2 | Lipase member M | LIPM |
| Q5W186 | Cystatin-9 | CST9 |
| Q5W5W9 | Regulated endocrine-specific protein 18 | RESP18 |
| Q5XG92 | Carboxylesterase 4A | CES4A |
| Q63HQ2 | Pikachurin | EGFLAM |
| Q641Q3 | Meteorin-like protein | METRNL |
| Q66K79 | Carboxypeptidase Z | CPZ |
| Q685J3 | Mucin-17 | MUC17 |
| Q68BL7 | Olfactomedin-like protein 2A | OLFML2A |
| Q68BL8 | Olfactomedin-like protein 2B | OLFML2B |
| Q68DV7 | E3 ubiquitin-protein ligase RNF43 | RNF43 |
| Q6B9Z1 | Insulin growth factor-like family member 4 | IGFL4 |
| Q6BAA4 | Fc receptor-like B | FCRLB |
| Q6E0U4 | Dermokine | DMKN |
| Q6EMK4 | Vasorin | VASN |
| Q6FHJ7 | Secreted frizzled-related protein 4 | SFRP4 |
| Q6GPI1 | Chymotrypsin B2 chain B | CTRB2 |
| Q6GTS8 | Probable carboxypeptidase PM20D1 | PM20D1 |
| Q6H9L7 | Isthmin-2 | ISM2 |
| Q6IE36 | Ovostatin homolog 2 | OVOS2 |
| Q6IE37 | Ovostatin homolog 1 | OVOS1 |
| Q6IE38 | Serine protease inhibitor Kazal-type 14 | SPINK14 |
| Q6ISS4 | Leukocyte-associated immunoglobulin-like receptor 2 | LAIR2 |
| Q6JVE5 | Epididymal-specific lipocalin-12 | LCN12 |
| Q6JVE6 | Epididymal-specific lipocalin-10 | LCN10 |
| Q6JVE9 | Epididymal-specific lipocalin-8 | LCN8 |
| Q6KF10 | Growth/differentiation factor 6 | GDF6 |
| Q6MZW2 | Follistatin-related protein 4 | FSTL4 |
| Q6NSX1 | Coiled-coil domain-containing protein 70 | CCDC70 |
| Q6NT32 | Carboxylesterase 5A | CES5A |
| Q6NT52 | Choriogonadotropin subunit beta variant 2 | CGB2 |
| Q6NUI6 | Chondroadherin-like protein | CHADL |
| Q6NUJ1 | Saposin A-like | PSAPL1 |
| Q6P093 | Arylacetamide deacetylase-like 2 | AADACL2 |
| Q6P4A8 | Phospholipase B-like 1 | PLBD1 |
| Q6P5S2 | UPF0762 protein C6orf58 | C6orf58 |
| Q6P988 | Protein notum homolog | NOTUM |
| Q6PCB0 | von Willebrand factor A domain-containing protein 1 | VWA1 |
| Q6PDA7 | Sperm-associated antigen 11A | SPAG11A |
| Q6PEW0 | Inactive serine protease 54 | PRSS54 |
| Q6PEZ8 | Podocan-like protein 1 | PODNL1 |
| Q6PKH6 | Dehydrogenase/reductase SDR family member 4-like 2 | DHRS4L2 |
| Q6Q788 | Apolipoprotein A-V | APOA5 |
| Q6SPF0 | Atherin | SAMD1 |
| Q6UDR6 | Kunitz-type protease inhibitor 4 | SPINT4 |
| Q6URK8 | Testis, prostate and placenta-expressed protein | TEPP |
| Q6UW01 | Cerebellin-3 | CBLN3 |
| Q6UW10 | Surfactant-associated protein 2 | SFTA2 |
| Q6UW15 | Regenerating islet-derived protein 3-gamma | REG3G |
| Q6UW32 | Insulin growth factor-like family member 1 | IGFL1 |
| Q6UW78 | UPF0723 protein C11orf83 | C11orf83 |

TABLE 1-continued

Secreted Proteins

| Uniprot ID | Protein Name | Gene Name |
| --- | --- | --- |
| Q6UW88 | Epigen | EPGN |
| Q6UWE3 | Colipase-like protein 2 | CLPSL2 |
| Q6UWF7 | NXPE family member 4 | NXPE4 |
| Q6UWF9 | Protein FAM180A | FAM180A |
| Q6UWM5 | GLIPR1-like protein 1 | GLIPR1L1 |
| Q6UWN8 | Serine protease inhibitor Kazal-type 6 | SPINK6 |
| Q6UWP2 | Dehydrogenase/reductase SDR family member 11 | DHRS11 |
| Q6UWP8 | Suprabasin | SBSN |
| Q6UWQ5 | Lysozyme-like protein 1 | LYZL1 |
| Q6UWQ7 | Insulin growth factor-like family member 2 | IGFL2 |
| Q6UWR7 | Ectonucleotide pyrophosphatase/phosphodiesterase family member 6 soluble form | ENPP6 |
| Q6UWT2 | Adropin | ENHO |
| Q6UWU2 | Beta-galactosidase-1-like protein | GLB1L |
| Q6UWW0 | Lipocalin-15 | LCN15 |
| Q6UWX4 | HHIP-like protein 2 | HHIPL2 |
| Q6UWY0 | Arylsulfatase K | ARSK |
| Q6UWY2 | Serine protease 57 | PRSS57 |
| Q6UWY5 | Olfactomedin-like protein 1 | OLFML1 |
| Q6UX06 | Olfactomedin-4 | OLFM4 |
| Q6UX07 | Dehydrogenase/reductase SDR family member 13 | DHRS13 |
| Q6UX39 | Amelotin | AMTN |
| Q6UX46 | Protein FAM150B | FAM150B |
| Q6UX73 | UPF0764 protein C16orf89 | C16orf89 |
| Q6UXB0 | Protein FAM131A | FAM131A |
| Q6UXB1 | Insulin growth factor-like family member 3 | IGFL3 |
| Q6UXB2 | VEGF co-regulated chemokine 1 | CXCL17 |
| Q6UXF7 | C-type lectin domain family 18 member B | CLEC18B |
| Q6UXH0 | Hepatocellular carcinoma-associated protein TD26 | C19orf80 |
| Q6UXH1 | Cysteine-rich with EGF-like domain protein 2 | CRELD2 |
| Q6UXH8 | Collagen and calcium-binding EGF domain-containing protein 1 | CCBE1 |
| Q6UXH9 | Inactive serine protease PAMR1 | PAMR1 |
| Q6UXI7 | Vitrin | VIT |
| Q6UXI9 | Nephronectin | NPNT |
| Q6UXN2 | Trem-like transcript 4 protein | TREML4 |
| Q6UXS0 | C-type lectin domain family 19 member A | CLEC19A |
| Q6UXT8 | Protein FAM150A | FAM150A |
| Q6UXT9 | Abhydrolase domain-containing protein 15 | ABHD15 |
| Q6UXV4 | Apolipoprotein O-like | APOOL |
| Q6UXX5 | Inter-alpha-trypsin inhibitor heavy chain H6 | ITIH6 |
| Q6UXX9 | R-spondin-2 | RSPO2 |
| Q6UY14 | ADAMTS-like protein 4 | ADAMTSL4 |
| Q6UY27 | Prostate and testis expressed protein 2 | PATE2 |
| Q6W4X9 | Mucin-6 | MUC6 |
| Q6WN34 | Chordin-like protein 2 | CHRDL2 |
| Q6WRI0 | Immunoglobulin superfamily member 10 | IGSF10 |
| Q6X4U4 | Sclerostin domain-containing protein 1 | SOSTDC1 |
| Q6X784 | Zona pellucida-binding protein 2 | ZPBP2 |
| Q6XE38 | Secretoglobin family 1D member 4 | SCGB1D4 |
| Q6XPR3 | Repetin | RPTN |
| Q6XZB0 | Lipase member I | LIPI |
| Q6ZMM2 | ADAMTS-like protein 5 | ADAMTSL5 |
| Q6ZMP0 | Thrombospondin type-1 domain-containing protein 4 | THSD4 |
| Q6ZNF0 | Iron/zinc purple acid phosphatase-like protein | PAPL |
| Q6ZRI0 | Otogelin | OTOG |
| Q6ZRP7 | Sulfhydryl oxidase 2 | QSOX2 |
| Q6ZWJ8 | Kielin/chordin-like protein | KCP |
| Q75N90 | Fibrillin-3 | FBN3 |
| Q76I50 | Urotensin-2B | UTS2D |
| Q76B58 | Protein FAM5C | FAM5C |
| Q76LX8 | A disintegrin and metalloproteinase with thrombospondin motifs 13 | ADAMTS13 |
| Q76M96 | Coiled-coil domain-containing protein 80 | CCDC80 |
| Q7L1S5 | Carbohydrate sulfotransferase 9 | CHST9 |
| Q7L513 | Fc receptor-like A | FCRLA |
| Q7L8A9 | Vasohibin-1 | VASH1 |
| Q7RTM1 | Otopetrin-1 | OTOP1 |
| Q7RTW8 | Otoancorin | OTOA |
| Q7RTY5 | Serine protease 48 | PRSS48 |
| Q7RTY7 | Ovochymase-1 | OVCH1 |
| Q7RTZ1 | Ovochymase-2 | OVCH2 |
| Q7Z304 | MAM domain-containing protein 2 | MAMDC2 |
| Q7Z3S9 | Notch homolog 2 N-terminal-like protein | NOTCH2NL |

TABLE 1-continued

Secreted Proteins

| Uniprot ID | Protein Name | Gene Name |
|---|---|---|
| Q7Z4H4 | Intermedin-short | ADM2 |
| Q7Z4P5 | Growth/differentiation factor 7 | GDF7 |
| Q7Z4R8 | UPF0669 protein C6orf120 | C6orf120 |
| Q7Z4W2 | Lysozyme-like protein 2 | LYZL2 |
| Q7Z5A4 | Serine protease 42 | PRSS42 |
| Q7Z5A7 | Protein FAM19A5 | FAM19A5 |
| Q7Z5A8 | Protein FAM19A3 | FAM19A3 |
| Q7Z5A9 | Protein FAM19A1 | FAM19A1 |
| Q7Z5J1 | Hydroxysteroid 11-beta-dehydrogenase 1-like protein | HSD11B1L |
| Q7Z5L0 | Vitelline membrane outer layer protein 1 homolog | VMO1 |
| Q7Z5L3 | Complement C1q-like protein 2 | C1QL2 |
| Q7Z5L7 | Podocan | PODN |
| Q7Z5P4 | 17-beta-hydroxysteroid dehydrogenase 13 | HSD17B13 |
| Q7Z5P9 | Mucin-19 | MUC19 |
| Q7Z5Y6 | Bone morphogenetic protein 8A | BMP8A |
| Q7Z7B7 | Beta-defensin 132 | DEFB132 |
| Q7Z7B8 | Beta-defensin 128 | DEFB128 |
| Q7Z7C8 | Transcription initiation factor TFIID subunit 8 | TAF8 |
| Q7Z7H5 | Transmembrane emp24 domain-containing protein 4 | TMED4 |
| Q86SG7 | Lysozyme g-like protein 2 | LYG2 |
| Q86SI9 | Protein CEI | C5orf38 |
| Q86TE4 | Leucine zipper protein 2 | LUZP2 |
| Q86TH1 | ADAMTS-like protein 2 | ADAMTSL2 |
| Q86U17 | Serpin A11 | SERPINA11 |
| Q86UU9 | Endokinin-A | TAC4 |
| Q86UW8 | Hyaluronan and proteoglycan link protein 4 | HAPLN4 |
| Q86UX2 | Inter-alpha-trypsin inhibitor heavy chain H5 | ITIH5 |
| Q86V24 | Adiponectin receptor protein 2 | ADIPOR2 |
| Q86VB7 | Soluble CD163 | CD163 |
| Q86VR8 | Four-jointed box protein 1 | FJX1 |
| Q86WD7 | Serpin A9 | SERPINA9 |
| Q86WN2 | Interferon epsilon | IFNE |
| Q86WS3 | Placenta-specific 1-like protein | PLAC1L |
| Q86X52 | Chondroitin sulfate synthase 1 | CHSY1 |
| Q86XP6 | Gastrokine-2 | GKN2 |
| Q86XS5 | Angiopoietin-related protein 5 | ANGPTL5 |
| Q86Y27 | B melanoma antigen 5 | BAGE5 |
| Q86Y28 | B melanoma antigen 4 | BAGE4 |
| Q86Y29 | B melanoma antigen 3 | BAGE3 |
| Q86Y30 | B melanoma antigen 2 | BAGE2 |
| Q86Y38 | Xylosyltransferase 1 | XYLT1 |
| Q86Y78 | Ly6/PLAUR domain-containing protein 6 | LYPD6 |
| Q86YD3 | Transmembrane protein 25 | TMEM25 |
| Q86YJ6 | Threonine synthase-like 2 | THNSL2 |
| Q86YW7 | Glycoprotein hormone beta-5 | GPHB5 |
| Q86Z23 | Complement C1q-like protein 4 | C1QL4 |
| Q8IU57 | Interleukin-28 receptor subunit alpha | IL28RA |
| Q8IUA0 | WAP four-disulfide core domain protein 8 | WFDC8 |
| Q8IUB2 | WAP four-disulfide core domain protein 3 | WFDC3 |
| Q8IUB3 | Protein WFDC10B | WFDC10B |
| Q8IUB5 | WAP four-disulfide core domain protein 13 | WFDC13 |
| Q8IUH2 | Protein CREG2 | CREG2 |
| Q8IUK5 | Plexin domain-containing protein 1 | PLXDC1 |
| Q8IUL8 | Cartilage intermediate layer protein 2 C2 | CILP2 |
| Q8IUX7 | Adipocyte enhancer-binding protein 1 | AEBP1 |
| Q8IUX8 | Epidermal growth factor-like protein 6 | EGFL6 |
| Q8IVL8 | Carboxypeptidase O | CPO |
| Q8IVN8 | Somatomedin-B and thrombospondin type-1 domain-containing protein | SBSPON |
| Q8IVW8 | Protein spinster homolog 2 | SPNS2 |
| Q8IW75 | Serpin A12 | SERPINA12 |
| Q8IW92 | Beta-galactosidase-1-like protein 2 | GLB1L2 |
| Q8IWL1 | Pulmonary surfactant-associated protein A2 | SFTPA2 |
| Q8IWL2 | Pulmonary surfactant-associated protein A1 | SFTPA1 |
| Q8IWV2 | Contactin-4 | CNTN4 |
| Q8IWY4 | Signal peptide, CUB and EGF-like domain-containing protein 1 | SCUBE1 |
| Q8IX30 | Signal peptide, CUB and EGF-like domain-containing protein 3 | SCUBE3 |
| Q8IXA5 | Sperm acrosome membrane-associated protein 3, membrane form | SPACA3 |
| Q8IXB1 | DnaJ homolog subfamily C member 10 | DNAJC10 |
| Q8IXL6 | Extracellular serine/threonine protein kinase Fam20C | FAM20C |

TABLE 1-continued

Secreted Proteins

| Uniprot ID | Protein Name | Gene Name |
| --- | --- | --- |
| Q8IYD9 | Lung adenoma susceptibility protein 2 | LAS2 |
| Q8IYP2 | Serine protease 58 | PRSS58 |
| Q8IYS5 | Osteoclast-associated immunoglobulin-like receptor | OSCAR |
| Q8IZC6 | Collagen alpha-1(XXVII) chain | COL27A1 |
| Q8IZJ3 | C3 and PZP-like alpha-2-macroglobulin domain-containing protein 8 | CPAMD8 |
| Q8IZN7 | Beta-defensin 107 | DEFB107B |
| Q8N0V4 | Leucine-rich repeat LGI family member 2 | LGI2 |
| Q8N104 | Beta-defensin 106 | DEFB106B |
| Q8N119 | Matrix metalloproteinase-21 | MMP21 |
| Q8N129 | Protein canopy homolog 4 | CNPY4 |
| Q8N135 | Leucine-rich repeat LGI family member 4 | LGI4 |
| Q8N145 | Leucine-rich repeat LGI family member 3 | LGI3 |
| Q8N158 | Glypican-2 | GPC2 |
| Q8N1E2 | Lysozyme g-like protein 1 | LYG1 |
| Q8N2E2 | von Willebrand factor D and EGF domain-containing protein | VWDE |
| Q8N2E6 | Prosalusin | TOR2A |
| Q8N2S1 | Latent-transforming growth factor beta-binding protein 4 | LTBP4 |
| Q8N302 | Angiogenic factor with G patch and FHA domains 1 | AGGF1 |
| Q8N307 | Mucin-20 | MUC20 |
| Q8N323 | NXPE family member 1 | NXPE1 |
| Q8N387 | Mucin-15 | MUC15 |
| Q8N3Z0 | Inactive serine protease 35 | PRSS35 |
| Q8N436 | Inactive carboxypeptidase-like protein X2 | CPXM2 |
| Q8N474 | Secreted frizzled-related protein 1 | SFRP1 |
| Q8N475 | Follistatin-related protein 5 | FSTL5 |
| Q8N4F0 | BPI fold-containing family B member 2 | BPIFB2 |
| Q8N4T0 | Carboxypeptidase A6 | CPA6 |
| Q8N5W8 | Protein FAM24B | FAM24B |
| Q8N687 | Beta-defensin 125 | DEFB125 |
| Q8N688 | Beta-defensin 123 | DEFB123 |
| Q8N690 | Beta-defensin 119 | DEFB119 |
| Q8N6C5 | Immunoglobulin superfamily member 1 | IGSF1 |
| Q8N6C8 | Leukocyte immunoglobulin-like receptor subfamily A member 3 | LILRA3 |
| Q8N6G6 | ADAMTS-like protein 1 | ADAMTSL1 |
| Q8N6Y2 | Leucine-rich repeat-containing protein 17 | LRRC17 |
| Q8N729 | Neuropeptide W-23 | NPW |
| Q8N8U9 | BMP-binding endothelial regulator protein | BMPER |
| Q8N907 | DAN domain family member 5 | DAND5 |
| Q8NAT1 | Glycosyltransferase-like domain-containing protein 2 | GTDC2 |
| Q8NAU1 | Fibronectin type III domain-containing protein 5 | FNDC5 |
| Q8NB37 | Parkinson disease 7 domain-containing protein 1 | PDDC1 |
| Q8NBI3 | Draxin | DRAXIN |
| Q8NBM8 | Prenylcysteine oxidase-like | PCYOX1L |
| Q8NBP7 | Proprotein convertase subtilisin/kexin type 9 | PCSK9 |
| Q8NBQ5 | Estradiol 17-beta-dehydrogenase 11 | HSD17B11 |
| Q8NBV8 | Synaptotagmin-8 | SYT8 |
| Q8NCC3 | Group XV phospholipase A2 | PLA2G15 |
| Q8NCF0 | C-type lectin domain family 18 member C | CLEC18C |
| Q8NCW5 | NAD(P)H-hydrate epimerase | APOA1BP |
| Q8NDA2 | Hemicentin-2 | HMCN2 |
| Q8NDX9 | Lymphocyte antigen 6 complex locus protein G5b | LY6G5B |
| Q8NDZ4 | Deleted in autism protein 1 | C3orf58 |
| Q8NEB7 | Acrosin-binding protein | ACRBP |
| Q8NES8 | Beta-defensin 124 | DEFB124 |
| Q8NET1 | Beta-defensin 108B | DEFB108B |
| Q8NEX5 | Protein WFDC9 | WFDC9 |
| Q8NEX6 | Protein WFDC11 | WFDC11 |
| Q8NF86 | Serine protease 33 | PRSS33 |
| Q8NFM7 | Interleukin-17 receptor D | IL17RD |
| Q8NFQ5 | BPI fold-containing family B member 6 | BPIFB6 |
| Q8NFQ6 | BPI fold-containing family C protein | BPIFC |
| Q8NFU4 | Follicular dendritic cell secreted peptide | FDCSP |
| Q8NFW1 | Collagen alpha-1(XXII) chain | COL22A1 |
| Q8NG35 | Beta-defensin 105 | DEFB105B |
| Q8NG41 | Neuropeptide B-23 | NPB |
| Q8NHW6 | Otospiralin | OTOS |
| Q8NI99 | Angiopoietin-related protein 6 | ANGPTL6 |
| Q8TAA1 | Probable ribonuclease 11 | RNASE11 |

TABLE 1-continued

Secreted Proteins

| Uniprot ID | Protein Name | Gene Name |
|---|---|---|
| Q8TAG5 | V-set and transmembrane domain-containing protein 2A | VSTM2A |
| Q8TAL6 | Fin bud initiation factor homolog | FIBIN |
| Q8TAT2 | Fibroblast growth factor-binding protein 3 | FGFBP3 |
| Q8TAX7 | Mucin-7 | MUC7 |
| Q8TB22 | Spermatogenesis-associated protein 20 | SPATA20 |
| Q8TB73 | Protein NDNF | NDNF |
| Q8TB96 | T-cell immunomodulatory protein | ITFG1 |
| Q8TC92 | Protein disulfide-thiol oxidoreductase | ENOX1 |
| Q8TCV5 | WAP four-disulfide core domain protein 5 | WFDC5 |
| Q8TD06 | Anterior gradient protein 3 homolog | AGR3 |
| Q8TD33 | Secretoglobin family 1C member 1 | SCGB1C1 |
| Q8TD46 | Cell surface glycoprotein CD200 receptor 1 | CD200R1 |
| Q8TDE3 | Ribonuclease 8 | RNASE8 |
| Q8TDF5 | Neuropilin and tolloid-like protein 1 | NETO1 |
| Q8TDL5 | BPI fold-containing family B member 1 | BPIFB1 |
| Q8TE56 | A disintegrin and metalloproteinase with thrombospondin motifs 17 | ADAMTS17 |
| Q8TE57 | A disintegrin and metalloproteinase with thrombospondin motifs 16 | ADAMTS16 |
| Q8TE58 | A disintegrin and metalloproteinase with thrombospondin motifs 15 | ADAMTS15 |
| Q8TE59 | A disintegrin and metalloproteinase with thrombospondin motifs 19 | ADAMTS19 |
| Q8TE60 | A disintegrin and metalloproteinase with thrombospondin motifs 18 | ADAMTS18 |
| Q8TE99 | Acid phosphatase-like protein 2 | ACPL2 |
| Q8TER0 | Sushi, nidogen and EGF-like domain-containing protein 1 | SNED1 |
| Q8TEU8 | WAP, kazal, immunoglobulin, kunitz and NTR domain-containing protein 2 | WFIKKN2 |
| Q8WTQ1 | Beta-defensin 104 | DEFB104B |
| Q8WTR8 | Netrin-5 | NTN5 |
| Q8WTU2 | Scavenger receptor cysteine-rich domain-containing group B protein | SRCRB4D |
| Q8WU66 | Protein TSPEAR | TSPEAR |
| Q8WUA8 | Tsukushin | TSKU |
| Q8WUF8 | Protein FAM172A | FAM172A |
| Q8WUJ1 | Neuferricin | CYB5D2 |
| Q8WUY1 | UPF0670 protein THEM6 | THEM6 |
| Q8WVN6 | Secreted and transmembrane protein 1 | SECTM1 |
| Q8WVQ1 | Soluble calcium-activated nucleotidase 1 | CANT1 |
| Q8WWA0 | Intelectin-1 | ITLN1 |
| Q8WWG1 | Neuregulin-4 | NRG4 |
| Q8WWQ2 | Inactive heparanase-2 | HPSE2 |
| Q8WWU7 | Intelectin-2 | ITLN2 |
| Q8WWY7 | WAP four-disulfide core domain protein 12 | WFDC12 |
| Q8WWY8 | Lipase member H | LIPH |
| Q8WWZ8 | Oncoprotein-induced transcript 3 protein | OIT3 |
| Q8WX39 | Epididymal-specific lipocalin-9 | LCN9 |
| Q8WXA2 | Prostate and testis expressed protein 1 | PATE1 |
| Q8WXD2 | Secretogranin-3 | SCG3 |
| Q8WXF3 | Relaxin-3 A chain | RLN3 |
| Q8WXI7 | Mucin-16 | MUC16 |
| Q8WXQ8 | Carboxypeptidase A5 | CPA5 |
| Q8WXS8 | A disintegrin and metalloproteinase with thrombospondin motifs 14 | ADAMTS14 |
| Q92484 | Acid sphingomyelinase-like phosphodiesterase 3a | SMPDL3A |
| Q92485 | Acid sphingomyelinase-like phosphodiesterase 3b | SMPDL3B |
| Q92496 | Complement factor H-related protein 4 | CFHR4 |
| Q92520 | Protein FAM3C | FAM3C |
| Q92563 | Testican-2 | SPOCK2 |
| Q92583 | C-C motif chemokine 17 | CCL17 |
| Q92626 | Peroxidasin homolog | PXDN |
| Q92743 | Serine protease HTRA1 | HTRA1 |
| Q92752 | Tenascin-R | TNR |
| Q92765 | Secreted frizzled-related protein 3 | FRZB |
| Q92819 | Hyaluronan synthase 2 | HAS2 |
| Q92820 | Gamma-glutamyl hydrolase | GGH |
| Q92824 | Proprotein convertase subtilisin/kexin type 5 | PCSK5 |
| Q92832 | Protein kinase C-binding protein NELL1 | NELL1 |
| Q92838 | Ectodysplasin-A, membrane form | EDA |
| Q92874 | Deoxyribonuclease-1-like 2 | DNASE1L2 |
| Q92876 | Kallikrein-6 | KLK6 |
| Q92913 | Fibroblast growth factor 13 | FGF13 |

TABLE 1-continued

Secreted Proteins

| Uniprot ID | Protein Name | Gene Name |
|---|---|---|
| Q92954 | Proteoglycan 4 C-terminal part | PRG4 |
| Q93038 | Tumor necrosis factor receptor superfamily member 25 | TNFRSF25 |
| Q93091 | Ribonuclease K6 | RNASE6 |
| Q93097 | Protein Wnt-2b | WNT2B |
| Q93098 | Protein Wnt-8b | WNT8B |
| Q95460 | Major histocompatibility complex class I-related gene protein | MR1 |
| Q969D9 | Thymic stromal lymphopoietin | TSLP |
| Q969E1 | Liver-expressed antimicrobial peptide 2 | LEAP2 |
| Q969H8 | UPF0556 protein C19orf10 | C19orf10 |
| Q969Y0 | NXPE family member 3 | NXPE3 |
| Q96A54 | Adiponectin receptor protein 1 | ADIPOR1 |
| Q96A83 | Collagen alpha-1(XXVI) chain | EMID2 |
| Q96A84 | EMI domain-containing protein 1 | EMID1 |
| Q96A98 | Tuberoinfundibular peptide of 39 residues | PTH2 |
| Q96A99 | Pentraxin-4 | PTX4 |
| Q96BH3 | Epididymal sperm-binding protein 1 | ELSPBP1 |
| Q96BQ1 | Protein FAM3D | FAM3D |
| Q96CG8 | Collagen triple helix repeat-containing protein 1 | CTHRC1 |
| Q96DA0 | Zymogen granule protein 16 homolog B | ZG16B |
| Q96DN2 | von Willebrand factor C and EGF domain-containing protein | VWCE |
| Q96DR5 | BPI fold-containing family A member 2 | BPIFA2 |
| Q96DR8 | Mucin-like protein 1 | MUCL1 |
| Q96DX4 | RING finger and SPRY domain-containing protein 1 | RSPRY1 |
| Q96EE4 | Coiled-coil domain-containing protein 126 | CCDC126 |
| Q96GS6 | Abhydrolase domain-containing protein FAM108A1 | FAM108A1 |
| Q96GW7 | Brevican core protein | BCAN |
| Q96HF1 | Secreted frizzled-related protein 2 | SFRP2 |
| Q96I82 | Kazal-type serine protease inhibitor domain-containing protein 1 | KAZALD1 |
| Q96ID5 | Immunoglobulin superfamily member 21 | IGSF21 |
| Q96II8 | Leucine-rich repeat and calponin homology domain-containing protein 3 | LRCH3 |
| Q96IY4 | Carboxypeptidase B2 | CPB2 |
| Q96JB6 | Lysyl oxidase homolog 4 | LOXL4 |
| Q96JK4 | HHIP-like protein 1 | HHIPL1 |
| Q96KN2 | Beta-Ala-His dipeptidase | CNDP1 |
| Q96KW9 | Protein SPACA7 | SPACA7 |
| Q96KX0 | Lysozyme-like protein 4 | LYZL4 |
| Q96L15 | Ecto-ADP-ribosyltransferase 5 | ART5 |
| Q96LB8 | Peptidoglycan recognition protein 4 | PGLYRP4 |
| Q96LB9 | Peptidoglycan recognition protein 3 | PGLYRP3 |
| Q96LC7 | Sialic acid-binding Ig-like lectin 10 | SIGLEC10 |
| Q96LR4 | Protein FAM19A4 | FAM19A4 |
| Q96MK3 | Protein FAM20A | FAM20A |
| Q96MS3 | Glycosyltransferase 1 domain-containing protein 1 | GLT1D1 |
| Q96NY8 | Processed poliovirus receptor-related protein 4 | PVRL4 |
| Q96NZ8 | WAP, kazal, immunoglobulin, kunitz and NTR domain-containing protein 1 | WFIKKN1 |
| Q96NZ9 | Proline-rich acidic protein 1 | PRAP1 |
| Q96P44 | Collagen alpha-1(XXI) chain | COL21A1 |
| Q96PB7 | Noelin-3 | OLFM3 |
| Q96PC5 | Melanoma inhibitory activity protein 2 | MIA2 |
| Q96PD5 | N-acetylmuramoyl-L-alanine amidase | PGLYRP2 |
| Q96PH6 | Beta-defensin 118 | DEFB118 |
| Q96PL1 | Secretoglobin family 3A member 2 | SCGB3A2 |
| Q96PL2 | Beta-tectorin | TECTB |
| Q96QH8 | Sperm acrosome-associated protein 5 | SPACA5 |
| Q96QR1 | Secretoglobin family 3A member 1 | SCGB3A1 |
| Q96QU1 | Protocadherin-15 | PCDH15 |
| Q96QV1 | Hedgehog-interacting protein | HHIP |
| Q96RW7 | Hemicentin-1 | HMCN1 |
| Q96S42 | Nodal homolog | NODAL |
| Q96S86 | Hyaluronan and proteoglycan link protein 3 | HAPLN3 |
| Q96SL4 | Glutathione peroxidase 7 | GPX7 |
| Q96SM3 | Probable carboxypeptidase X1 | CPXM1 |
| Q96T91 | Glycoprotein hormone alpha-2 | GPHA2 |
| Q99062 | Granulocyte colony-stimulating factor receptor | CSF3R |
| Q99102 | Mucin-4 alpha chain | MUC4 |
| Q99217 | Amelogenin, X isoform | AMELX |
| Q99218 | Amelogenin, Y isoform | AMELY |
| Q99435 | Protein kinase C-binding protein NELL2 | NELL2 |

TABLE 1-continued

Secreted Proteins

| Uniprot ID | Protein Name | Gene Name |
|---|---|---|
| Q99470 | Stromal cell-derived factor 2 | SDF2 |
| Q99542 | Matrix metalloproteinase-19 | MMP19 |
| Q99574 | Neuroserpin | SERPINI1 |
| Q99584 | Protein S100-A13 | S100A13 |
| Q99616 | C-C motif chemokine 13 | CCL13 |
| Q99645 | Epiphycan | EPYC |
| Q99674 | Cell growth regulator with EF hand domain protein 1 | CGREF1 |
| Q99715 | Collagen alpha-1(XII) chain | COL12A1 |
| Q99727 | Metalloproteinase inhibitor 4 | TIMP4 |
| Q99731 | C-C motif chemokine 19 | CCL19 |
| Q99748 | Neurturin | NRTN |
| Q99935 | Proline-rich protein 1 | PROL1 |
| Q99942 | E3 ubiquitin-protein ligase RNF5 | RNF5 |
| Q99944 | Epidermal growth factor-like protein 8 | EGFL8 |
| Q99954 | Submaxillary gland androgen-regulated protein 3A | SMR3A |
| Q99969 | Retinoic acid receptor responder protein 2 | RARRES2 |
| Q99972 | Myocilin | MYOC |
| Q99983 | Osteomodulin | OMD |
| Q99985 | Semaphorin-3C | SEMA3C |
| Q99988 | Growth/differentiation factor 15 | GDF15 |
| Q9BPW4 | Apolipoprotein L4 | APOL4 |
| Q9BQ08 | Resistin-like beta | RETNLB |
| Q9BQ16 | Testican-3 | SPOCK3 |
| Q9BQ51 | Programmed cell death 1 ligand 2 | PDCD1LG2 |
| Q9BQB4 | Sclerostin | SOST |
| Q9BQI4 | Coiled-coil domain-containing protein 3 | CCDC3 |
| Q9BQP9 | BPI fold-containing family A member 3 | BPIFA3 |
| Q9BQR3 | Serine protease 27 | PRSS27 |
| Q9BQY6 | WAP four-disulfide core domain protein 6 | WFDC6 |
| Q9BRR6 | ADP-dependent glucokinase | ADPGK |
| Q9BS86 | Zona pellucida-binding protein 1 | ZPBP |
| Q9BSG0 | Protease-associated domain-containing protein 1 | PRADC1 |
| Q9BSG5 | Retbindin | RTBDN |
| Q9BT30 | Probable alpha-ketoglutarate-dependent dioxygenase ABH7 | ALKBH7 |
| Q9BT56 | Spexin | C12orf39 |
| Q9BT67 | NEDD4 family-interacting protein 1 | NDFIP1 |
| Q9BTY2 | Plasma alpha-L-fucosidase | FUCA2 |
| Q9BU40 | Chordin-like protein 1 | CHRDL1 |
| Q9BUD6 | Spondin-2 | SPON2 |
| Q9BUN1 | Protein MENT | MENT |
| Q9BUR5 | Apolipoprotein O | APOO |
| Q9BV94 | ER degradation-enhancing alpha-mannosidase-like 2 | EDEM2 |
| Q9BWP8 | Collectin-11 | COLEC11 |
| Q9BWS9 | Chitinase domain-containing protein 1 | CHID1 |
| Q9BX67 | Junctional adhesion molecule C | JAM3 |
| Q9BX93 | Group XIIB secretory phospholipase A2-like protein | PLA2G12B |
| Q9BXI9 | Complement C1q tumor necrosis factor-related protein 6 | C1QTNF6 |
| Q9BXJ0 | Complement C1q tumor necrosis factor-related protein 5 | C1QTNF5 |
| Q9BXJ1 | Complement C1q tumor necrosis factor-related protein 1 | C1QTNF1 |
| Q9BXJ2 | Complement C1q tumor necrosis factor-related protein 7 | C1QTNF7 |
| Q9BXJ3 | Complement C1q tumor necrosis factor-related protein 4 | C1QTNF4 |
| Q9BXJ4 | Complement C1q tumor necrosis factor-related protein 3 | C1QTNF3 |
| Q9BXJ5 | Complement C1q tumor necrosis factor-related protein 2 | C1QTNF2 |
| Q9BXN1 | Asporin | ASPN |
| Q9BXP8 | Pappalysin-2 | PAPPA2 |
| Q9BXR6 | Complement factor H-related protein 5 | CFHR5 |
| Q9BXS0 | Collagen alpha-1(XXV) chain | COL25A1 |
| Q9BXX0 | EMILIN-2 | EMILIN2 |
| Q9BXY4 | R-spondin-3 | RSPO3 |
| Q9BY15 | EGF-like module-containing mucin-like hormone receptor-like 3 subunit beta | EMR3 |
| Q9BY50 | Signal peptidase complex catalytic subunit SEC11C | SEC11C |
| Q9BY76 | Angiopoietin-related protein 4 | ANGPTL4 |
| Q9BYF1 | Processed angiotensin-converting enzyme 2 | ACE2 |

TABLE 1-continued

Secreted Proteins

| Uniprot ID | Protein Name | Gene Name |
|---|---|---|
| Q9BYJ0 | Fibroblast growth factor-binding protein 2 | FGFBP2 |
| Q9BYW3 | Beta-defensin 126 | DEFB126 |
| Q9BYX4 | Interferon-induced helicase C domain-containing protein 1 | IFIH1 |
| Q9BYZ8 | Regenerating islet-derived protein 4 | REG4 |
| Q9BZ76 | Contactin-associated protein-like 3 | CNTNAP3 |
| Q9BZG9 | Ly-6/neurotoxin-like protein 1 | LYNX1 |
| Q9BZJ3 | Tryptase delta | TPSD1 |
| Q9BZM1 | Group XIIA secretory phospholipase A2 | PLA2G12A |
| Q9BZM2 | Group IIF secretory phospholipase A2 | PLA2G2F |
| Q9BZM5 | NKG2D ligand 2 | ULBP2 |
| Q9BZP6 | Acidic mammalian chitinase | CHIA |
| Q9BZZ2 | Sialoadhesin | SIGLEC1 |
| Q9C0B6 | Protein FAM5B | FAM5B |
| Q9GZM7 | Tubulointerstitial nephritis antigen-like | TINAGL1 |
| Q9GZN4 | Brain-specific serine protease 4 | PRSS22 |
| Q9GZP0 | Platelet-derived growth factor D, receptor-binding form | PDGFD |
| Q9GZT5 | Protein Wnt-10a | WNT10A |
| Q9GZU5 | Nyctalopin | NYX |
| Q9GZV7 | Hyaluronan and proteoglycan link protein 2 | HAPLN2 |
| Q9GZV9 | Fibroblast growth factor 23 | FGF23 |
| Q9GZX9 | Twisted gastrulation protein homolog 1 | TWSG1 |
| Q9GZZ7 | GDNF family receptor alpha-4 | GFRA4 |
| Q9GZZ8 | Extracellular glycoprotein lacritin | LACRT |
| Q9H0B8 | Cysteine-rich secretory protein LCCL domain-containing 2 | CRISPLD2 |
| Q9H106 | Signal-regulatory protein delta | SIRPD |
| Q9H114 | Cystatin-like 1 | CSTL1 |
| Q9H173 | Nucleotide exchange factor SIL1 | SIL1 |
| Q9H1E1 | Ribonuclease 7 | RNASE7 |
| Q9H1F0 | WAP four-disulfide core domain protein 10A | WFDC10A |
| Q9H1J5 | Protein Wnt-8a | WNT8A |
| Q9H1J7 | Protein Wnt-5b | WNT5B |
| Q9H1M3 | Beta-defensin 129 | DEFB129 |
| Q9H1M4 | Beta-defensin 127 | DEFB127 |
| Q9H1Z8 | Augurin | C2orf40 |
| Q9H239 | Matrix metalloproteinase-28 | MMP28 |
| Q9H2A7 | C-X-C motif chemokine 16 | CXCL16 |
| Q9H2A9 | Carbohydrate sulfotransferase 8 | CHST8 |
| Q9H2R5 | Kallikrein-15 | KLK15 |
| Q9H2X0 | Chordin | CHRD |
| Q9H2X3 | C-type lectin domain family 4 member M | CLEC4M |
| Q9H306 | Matrix metalloproteinase-27 | MMP27 |
| Q9H324 | A disintegrin and metalloproteinase with thrombospondin motifs 10 | ADAMTS10 |
| Q9H336 | Cysteine-rich secretory protein LCCL domain-containing 1 | CRISPLD1 |
| Q9H3E2 | Sorting nexin-25 | SNX25 |
| Q9H3R2 | Mucin-13 | MUC13 |
| Q9H3U7 | SPARC-related modular calcium-binding protein 2 | SMOC2 |
| Q9H3Y0 | Peptidase inhibitor R3HDML | R3HDML |
| Q9H4A4 | Aminopeptidase B | RNPEP |
| Q9H4F8 | SPARC-related modular calcium-binding protein 1 | SMOC1 |
| Q9H4G1 | Cystatin-9-like | CST9L |
| Q9H5V8 | CUB domain-containing protein 1 | CDCP1 |
| Q9H6B9 | Epoxide hydrolase 3 | EPHX3 |
| Q9H6E4 | Coiled-coil domain-containing protein 134 | CCDC134 |
| Q9H741 | UPF0454 protein C12orf49 | C12orf49 |
| Q9H772 | Gremlin-2 | GREM2 |
| Q9H7Y0 | Deleted in autism-related protein 1 | CXorf36 |
| Q9H8L6 | Multimerin-2 | MMRN2 |
| Q9H9S5 | Fukutin-related protein | FKRP |
| Q9HAT2 | Sialate O-acetylesterase | SIAE |
| Q9HB40 | Retinoid-inducible serine carboxypeptidase | SCPEP1 |
| Q9HB63 | Netrin-4 | NTN4 |
| Q9HBJ0 | Placenta-specific protein 1 | PLAC1 |
| Q9HC23 | Prokineticin-2 | PROK2 |
| Q9HC57 | WAP four-disulfide core domain protein 1 | WFDC1 |
| Q9HC73 | Cytokine receptor-like factor 2 | CRLF2 |
| Q9HC84 | Mucin-5B | MUC5B |
| Q9HCB6 | Spondin-1 | SPON1 |
| Q9HCQ7 | Neuropeptide NPSF | NPVF |
| Q9HCT0 | Fibroblast growth factor 22 | FGF22 |
| Q9HD89 | Resistin | RETN |

TABLE 1-continued

Secreted Proteins

| Uniprot ID | Protein Name | Gene Name |
|---|---|---|
| Q9NNX1 | Tuftelin | TUFT1 |
| Q9NNX6 | CD209 antigen | CD209 |
| Q9NP55 | BPI fold-containing family A member 1 | BPIFA1 |
| Q9NP70 | Ameloblastin | AMBN |
| Q9NP95 | Fibroblast growth factor 20 | FGF20 |
| Q9NP99 | Triggering receptor expressed on myeloid cells 1 | TREM1 |
| Q9NPA2 | Matrix metalloproteinase-25 | MMP25 |
| Q9NPE2 | Neugrin | NGRN |
| Q9NPH0 | Lysophosphatidic acid phosphatase type 6 | ACP6 |
| Q9NPH6 | Odorant-binding protein 2b | OBP2B |
| Q9NQ30 | Endothelial cell-specific molecule 1 | ESM1 |
| Q9NQ36 | Signal peptide, CUB and EGF-like domain-containing protein 2 | SCUBE2 |
| Q9NQ38 | Serine protease inhibitor Kazal-type 5 | SPINK5 |
| Q9NQ76 | Matrix extracellular phosphoglycoprotein | MEPE |
| Q9NQ79 | Cartilage acidic protein 1 | CRTAC1 |
| Q9NR16 | Scavenger receptor cysteine-rich type 1 protein M160 | CD163L1 |
| Q9NR23 | Growth/differentiation factor 3 | GDF3 |
| Q9NR71 | Neutral ceramidase | ASAH2 |
| Q9NR99 | Matrix-remodeling-associated protein 5 | MXRA5 |
| Q9NRA1 | Platelet-derived growth factor C | PDGFC |
| Q9NRC9 | Otoraplin | OTOR |
| Q9NRE1 | Matrix metalloproteinase-26 | MMP26 |
| Q9NRJ3 | C-C motif chemokine 28 | CCL28 |
| Q9NRM1 | Enamelin | ENAM |
| Q9NRN5 | Olfactomedin-like protein 3 | OLFML3 |
| Q9NRR1 | Cytokine-like protein 1 | CYTL1 |
| Q9NS15 | Latent-transforming growth factor beta-binding protein 3 | LTBP3 |
| Q9NS62 | Thrombospondin type-1 domain-containing protein 1 | THSD1 |
| Q9NS71 | Gastrokine-1 | GKN1 |
| Q9NS98 | Semaphorin-3G | SEMA3G |
| Q9NSA1 | Fibroblast growth factor 21 | FGF21 |
| Q9NT22 | EMILIN-3 | EMILIN3 |
| Q9NTU7 | Cerebellin-4 | CBLN4 |
| Q9NVR0 | Kelch-like protein 11 | KLHL11 |
| Q9NWH7 | Spermatogenesis-associated protein 6 | SPATA6 |
| Q9NXC2 | Glucose-fructose oxidoreductase domain-containing protein 1 | GFOD1 |
| Q9NY56 | Odorant-binding protein 2a | OBP2A |
| Q9NY84 | Vascular non-inflammatory molecule 3 | VNN3 |
| Q9NZ20 | Group 3 secretory phospholipase A2 | PLA2G3 |
| Q9NZC2 | Triggering receptor expressed on myeloid cells 2 | TREM2 |
| Q9NZK5 | Adenosine deaminase CECR1 | CECR1 |
| Q9NZK7 | Group IIE secretory phospholipase A2 | PLA2G2E |
| Q9NZP8 | Complement C1r subcomponent-like protein | C1RL |
| Q9NZV1 | Cysteine-rich motor neuron 1 protein | CRIM1 |
| Q9NZW4 | Dentin sialoprotein | DSPP |
| Q9P0G3 | Kallikrein-14 | KLK14 |
| Q9P0W0 | Interferon kappa | IFNK |
| Q9P218 | Collagen alpha-1(XX) chain | COL20A1 |
| Q9P2C4 | Transmembrane protein 181 | TMEM181 |
| Q9P2K2 | Thioredoxin domain-containing protein 16 | TXNDC16 |
| Q9P2N4 | A disintegrin and metalloproteinase with thrombospondin motifs 9 | ADAMTS9 |
| Q9UBC7 | Galanin-like peptide | GALP |
| Q9UBD3 | Cytokine SCM-1 beta | XCL2 |
| Q9UBD9 | Cardiotrophin-like cytokine factor 1 | CLCF1 |
| Q9UBM4 | Opticin | OPTC |
| Q9UBP4 | Dickkopf-related protein 3 | DKK3 |
| Q9UBQ6 | Exostosin-like 2 | EXTL2 |
| Q9UBR5 | Chemokine-like factor | CKLF |
| Q9UBS5 | Gamma-aminobutyric acid type B receptor subunit 1 | GABBR1 |
| Q9UBT3 | Dickkopf-related protein 4 short form | DKK4 |
| Q9UBU2 | Dickkopf-related protein 2 | DKK2 |
| Q9UBU3 | Ghrelin-28 | GHRL |
| Q9UBV4 | Protein Wnt-16 | WNT16 |
| Q9UBX5 | Fibulin-5 | FBLN5 |
| Q9UBX7 | Kallikrein-11 | KLK11 |
| Q9UEF7 | Klotho | KL |
| Q9UFP1 | Protein FAM198A | FAM198A |
| Q9UGM3 | Deleted in malignant brain tumors 1 protein | DMBT1 |
| Q9UGM5 | Fetuin-B | FETUB |

TABLE 1-continued

Secreted Proteins

| Uniprot ID | Protein Name | Gene Name |
| --- | --- | --- |
| Q9UGP8 | Translocation protein SEC63 homolog | SEC63 |
| Q9UHF0 | Neurokinin-B | TAC3 |
| Q9UHF1 | Epidermal growth factor-like protein 7 | EGFL7 |
| Q9UHG2 | ProSAAS | PCSK1N |
| Q9UHI8 | A disintegrin and metalloproteinase with thrombospondin motifs 1 | ADAMTS1 |
| Q9UHL4 | Dipeptidyl peptidase 2 | DPP7 |
| Q9UI42 | Carboxypeptidase A4 | CPA4 |
| Q9UIG4 | Psoriasis susceptibility 1 candidate gene 2 protein | PSORS1C2 |
| Q9UIK5 | Tomoregulin-2 | TMEFF2 |
| Q9UIQ6 | Leucyl-cystinyl aminopeptidase, pregnancy serum form | LNPEP |
| Q9UJA9 | Ectonucleotide pyrophosphatase/phosphodiesterase family member 5 | ENPP5 |
| Q9UJH8 | Meteorin | METRN |
| Q9UJJ9 | N-acetylglucosamine-1-phosphotransferase subunit gamma | GNPTG |
| Q9UJW2 | Tubulointerstitial nephritis antigen | TINAG |
| Q9UK05 | Growth/differentiation factor 2 | GDF2 |
| Q9UK55 | Protein Z-dependent protease inhibitor | SERPINA10 |
| Q9UK85 | Dickkopf-like protein 1 | DKKL1 |
| Q9UKJ1 | Paired immunoglobulin-like type 2 receptor alpha | PILRA |
| Q9UKP4 | A disintegrin and metalloproteinase with thrombospondin motifs 7 | ADAMTS7 |
| Q9UKP5 | A disintegrin and metalloproteinase with thrombospondin motifs 6 | ADAMTS6 |
| Q9UKQ2 | Disintegrin and metalloproteinase domain-containing protein 28 | ADAM28 |
| Q9UKQ9 | Kallikrein-9 | KLK9 |
| Q9UKR0 | Kallikrein-12 | KLK12 |
| Q9UKR3 | Kallikrein-13 | KLK13 |
| Q9UKU9 | Angiopoietin-related protein 2 | ANGPTL2 |
| Q9UKZ9 | Procollagen C-endopeptidase enhancer 2 | PCOLCE2 |
| Q9UL52 | Transmembrane protease serine 11E non-catalytic chain | TMPRSS11E |
| Q9ULC0 | Endomucin | EMCN |
| Q9ULI3 | Protein HEG homolog 1 | HEG1 |
| Q9ULZ1 | Apelin-13 | APLN |
| Q9ULZ9 | Matrix metalloproteinase-17 | MMP17 |
| Q9UM21 | Alpha-1,3-mannosyl-glycoprotein 4-beta-N-acetylglucosaminyltransferase A soluble form | MGAT4A |
| Q9UM22 | Mammalian ependymin-related protein 1 | EPDR1 |
| Q9UM73 | ALK tyrosine kinase receptor | ALK |
| Q9UMD9 | 97 kDa linear IgA disease antigen | COL17A1 |
| Q9UMX5 | Neudesin | NENF |
| Q9UN73 | Protocadherin alpha-6 | PCDHA6 |
| Q9UNA0 | A disintegrin and metalloproteinase with thrombospondin motifs 5 | ADAMTS5 |
| Q9UNI1 | Chymotrypsin-like elastase family member 1 | CELA1 |
| Q9UNK4 | Group IID secretory phospholipase A2 | PLA2G2D |
| Q9UP79 | A disintegrin and metalloproteinase with thrombospondin motifs 8 | ADAMTS8 |
| Q9UPZ6 | Thrombospondin type-1 domain-containing protein 7A | THSD7A |
| Q9UQ72 | Pregnancy-specific beta-1-glycoprotein 11 | PSG11 |
| Q9UQ74 | Pregnancy-specific beta-1-glycoprotein 8 | PSG8 |
| Q9UQC9 | Calcium-activated chloride channel regulator 2 | CLCA2 |
| Q9UQE7 | Structural maintenance of chromosomes protein 3 | SMC3 |
| Q9UQP3 | Tenascin-N | TNN |
| Q9Y223 | UDP-N-acetylglucosamine 2-epimerase | GNE |
| Q9Y240 | C-type lectin domain family 11 member A | CLEC11A |
| Q9Y251 | Heparanase 8 kDa subunit | HPSE |
| Q9Y258 | C-C motif chemokine 26 | CCL26 |
| Q9Y264 | Angiopoietin-4 | ANGPT4 |
| Q9Y275 | Tumor necrosis factor ligand superfamily member 13b, membrane form | TNFSF13B |
| Q9Y287 | BRI2 intracellular domain | ITM2B |
| Q9Y2E5 | Epididymis-specific alpha-mannosidase | MAN2B2 |
| Q9Y334 | von Willebrand factor A domain-containing protein 7 | VWA7 |
| Q9Y337 | Kallikrein-5 | KLK5 |
| Q9Y3B3 | Transmembrane emp24 domain-containing protein 7 | TMED7 |
| Q9Y3E2 | BolA-like protein 1 | BOLA1 |
| Q9Y426 | C2 domain-containing protein 2 | C2CD2 |
| Q9Y4K0 | Lysyl oxidase homolog 2 | LOXL2 |

TABLE 1-continued

Secreted Proteins

| Uniprot ID | Protein Name | Gene Name |
|---|---|---|
| Q9Y4X3 | C-C motif chemokine 27 | CCL27 |
| Q9Y5C1 | Angiopoietin-related protein 3 | ANGPTL3 |
| Q9Y5I2 | Protocadherin alpha-10 | PCDHA10 |
| Q9Y5I3 | Protocadherin alpha-1 | PCDHA1 |
| Q9Y5K2 | Kallikrein-4 | KLK4 |
| Q9Y5L2 | Hypoxia-inducible lipid droplet-associated protein | HILPDA |
| Q9Y5Q5 | Atrial natriuretic peptide-converting enzyme | CORIN |
| Q9Y5R2 | Matrix metalloproteinase-24 | MMP24 |
| Q9Y5U5 | Tumor necrosis factor receptor superfamily member 18 | TNFRSF18 |
| Q9Y5W5 | Wnt inhibitory factor 1 | WIF1 |
| Q9Y5X9 | Endothelial lipase | LIPG |
| Q9Y625 | Secreted glypican-6 | GPC6 |
| Q9Y646 | Carboxypeptidase Q | CPQ |
| Q9Y6C2 | EMILIN-1 | EMILIN1 |
| Q9Y6F9 | Protein Wnt-6 | WNT6 |
| Q9Y6I9 | Testis-expressed sequence 264 protein | TEX264 |
| Q9Y6L7 | Tolloid-like protein 2 | TLL2 |
| Q9Y6N3 | Calcium-activated chloride channel regulator family member 3 | CLCA3P |
| Q9Y6N6 | Laminin subunit gamma-3 | LAMC3 |
| Q9Y6R7 | IgGFc-binding protein | FCGBP |
| Q9Y6Y9 | Lymphocyte antigen 96 | LY96 |
| Q9Y6Z7 | Collectin-10 | COLEC10 |

In some embodiments, the compositions and methods of the invention provide for the delivery of one or more mRNAs encoding one or more additional exemplary proteins listed in Table 2; thus, compositions of the invention may comprise an mRNA encoding a protein listed in Table 2 (or a homolog thereof) along with other components set out herein, and methods of the invention may comprise preparing and/or administering a composition comprising an mRNA encoding a protein chosen from the proteins listed in Table 2 (or a homolog thereof) along with other components set out herein.

TABLE 2

Additional Exemplary Proteins

| Uniprot ID | Protein Name | Gene Name |
|---|---|---|
| A6NGW2 | Putative stereocilin-like protein | STRCP1 |
| A6NIE9 | Putative serine protease 29 | PRSS29P |
| A6NJ16 | Putative V-set and immunoglobulin domain-containing-like protein IGHV4OR15-8 | IGHV4OR15-8 |
| A6NJS3 | Putative V-set and immunoglobulin domain-containing-like protein IGHV1OR21-1 | IGHV1OR21-1 |
| A6NMY6 | Putative annexin A2-like protein | ANXA2P2 |
| A8MT79 | Putative zinc-alpha-2-glycoprotein-like 1 | |
| A8MWS1 | Putative killer cell immunoglobulin-like receptor like protein KIR3DP1 | KIR3DP1 |
| A8MXU0 | Putative beta-defensin 108A | DEFB108P1 |
| C9JUS6 | Putative adrenomedullin-5-like protein | ADM5 |
| P0C7V7 | Putative signal peptidase complex catalytic subunit SEC11B | SEC11B |
| P0C854 | Putative cat eye syndrome critical region protein 9 | CECR9 |
| Q13046 | Putative pregnancy-specific beta-1-glycoprotein 7 | PSG7 |
| Q16609 | Putative apolipoprotein(a)-like protein 2 | LPAL2 |
| Q2TV78 | Putative macrophage-stimulating protein MSTP9 | MST1P9 |
| Q5JQD4 | Putative peptide YY-3 | PYY3 |
| Q5R387 | Putative inactive group IIC secretory phospholipase A2 | PLA2G2C |

TABLE 2-continued

Additional Exemplary Proteins

| Uniprot ID | Protein Name | Gene Name |
|---|---|---|
| Q5VSP4 | Putative lipocalin 1-like protein 1 | LCN1P1 |
| Q5W188 | Putative cystatin-9-like protein CST9LP1 | CST9LP1 |
| Q6UXR4 | Putative serpin A13 | SERPINA13P |
| Q86SH4 | Putative testis-specific prion protein | PRNT |
| Q86YQ2 | Putative latherin | LATH |
| Q8IVG9 | Putative humanin peptide | MT-RNR2 |
| Q8NHM4 | Putative trypsin-6 | TRY6 |
| Q8NHW4 | C-C motif chemokine 4-like | CCL4L2 |
| Q9H7L2 | Putative killer cell immunoglobulin-like receptor-like protein KIR3DX1 | KIR3DX1 |
| Q9NRI6 | Putative peptide YY-2 | PYY2 |
| Q9UF72 | Putative TP73 antisense gene protein 1 | TP73-AS1 |
| Q9UKY3 | Putative inactive carboxylesterase 4 | CES1P1 |

The Uniprot IDs set forth in Table 1 and Table 2 refer to the human versions the listed proteins and the sequences of each are available from the Uniprot database. Sequences of the listed proteins are also generally available for various animals, including various mammals and animals of veterinary or industrial interest. Accordingly, in some embodiments, compositions and methods of the invention provide for the delivery of one or more mRNAs encoding one or more proteins chosen from mammalian homologs or homologs from an animal of veterinary or industrial interest of the secreted proteins listed in Table 1 or Table 2; thus, compositions of the invention may comprise an mRNA encoding a protein chosen from mammalian homologs or homologs from an animal of veterinary or industrial interest of a protein listed in Table 1 or Table 2 along with other components set out herein, and methods of the invention may comprise preparing and/or administering a composition comprising an mRNA encoding a protein chosen from mammalian homologs or homologs from an animal of veterinary or industrial interest of a protein listed in Table 1 or Table 2 along with other components set out herein. In some embodiments, mammalian homologs are chosen from mouse, rat, hamster, gerbil, horse, pig, cow, llama, alpaca, mink, dog, cat, ferret, sheep, goat, or camel homologs. In some embodiments, the animal of veterinary or industrial interest is chosen from the mammals listed above and/or chicken, duck, turkey, salmon, catfish, or tilapia.

In embodiments, the compositions and methods of the invention provide for the delivery of mRNA encoding a lysosomal protein chosen from Table 3. In some embodiments, the compositions and methods of the invention provide for the delivery of one or more mRNAs encoding one or more lysosomal and/or related proteins listed in Table 3; thus, compositions of the invention may comprise an mRNA encoding a protein listed in Table 3 (or a homolog thereof) along with other components set out herein, and methods of the invention may comprise preparing and/or administering a composition comprising an mRNA encoding a protein chosen from the proteins listed in Table 3 (or a homolog thereof) along with other components set out herein.

TABLE 3

Lysosomal and Related Proteins

α-fucosidase
α-galactosidase
α-glucosidase
α-Iduronidase
α-mannosidase
α-N-acetylgalactosaminidase (α-galactosidase B)
β-galactosidase
β-glucuronidase
β-hexosaminidase
β-mannosidase
3-hydroxy-3-methylglutaryl-CoA (HMG-CoA) lyase
3-methylcrotonyl-CoA carboxylase
3-O-sulfogalactosyl cerebroside sulfatase (arylsulfatase A)
acetyl-CoA transferase
acid alpha-glucosidase
acid ceramidase
acid lipase
acid phosphatase
acid sphingomyelinase
alpha-galactosidase A
arylsulfatase A
beta-galactosidase
beta-glucocerebrosidase
beta-hexosaminidase
biotinidase
cathepsin A
cathepsin K
CLN3
CLN5
CLN6
CLN8
CLN9
cystine transporter (cystinosin)
cytosolic protein beta3A subunit of the adaptor protein-3 complex, AP3
formyl-Glycine generating enzyme (FGE)
galactocerebrosidase
galactose-1-phosphate uridyltransferase (GALT)
galactose 6-sulfate sulfatase
(also known as N-acetylgalactosamine-6-sulfatase)
glucocerebrosidase
glucuronate sulfatase TABLE 3-continued Lysosomal and Related Proteins glucuronidase
glycoprotein cleaving enzymes
glycosaminoglycan cleaving enzymes
glycosylasparaginase (aspartylglucosaminidase)
GM2-AP
Heparan-alpha-glucosaminide N-acetyltransferase (HGSNAT, TMEM76)
Heparan sulfatase
hexosaminidase A lysosomal proteases methylmalonyl-CoA mutase
hyaluronidase
Iduronate sulfatase
LAMP-2
lysosomal α-mannosidase
Lysosomal p40 (C2orf18)
Major facilitator superfamily domain containing 8 protein (MFSD8 or CLN7)
N-acetylgalactosamine 4-sulfatase
N-acetyl glucosamine 6-sulfatase
N-acetyl glucosaminidase
N-acetylglucosamine-1-phosphate transferase
NPC1
NPC2
palmitoyl-protein thioesterase
palmitoyl-protein thioesterase (CLN1)
Saposin A (Sphingolipid activator protein A)
Saposin B (Sphingolipid activator protein B)
Saposin C (Sphingolipid activator protein C)
Saposin D (Sphingolipid activator protein D)
sialic acid transporter (sialin)
sialidase
Sialin
sulfatase
Transmembrane protein 74 (TMEM74)
tripeptidyl-peptidase
tripeptidyl-peptidase I (CLN2)
UDP-N-acetylglucosamine-phosphotransferase Information regarding lysosomal proteins is available from Lubke et al., "Proteomics of the Lysosome," *Biochim Biophys Acta*. (2009) 1793: 625-635. In some embodiments, the protein listed in Table 3 and encoded by mRNA in the compositions and methods of the invention is a human protein. Sequences of the listed proteins are also available for various animals, including various mammals and animals of veterinary or industrial interest as described above.

In some embodiments, the compositions and methods of the invention provide for the delivery of mRNA encoding a therapeutic protein (e.g., cytosolic, transmembrane or secreted) such as those listed in Table 4. In some embodiments, the compositions and methods of the invention provide for the delivery of an mRNA encoding a therapeutic protein useful in treating a disease or disorder (i.e., indication) listed in Table 4; thus, compositions of the invention may comprise an mRNA encoding a therapeutic protein listed or not listed in Table 4 (or a homolog thereof, as discussed below) along with other components set out herein for treating a disease or disorder (i.e., indication) listed in Table 4, and methods of the invention may comprise preparing and/or administering a composition comprising an mRNA encoding a such a protein (or a homolog thereof, as discussed below) along with other components set out herein for treatment of a disease or disorder listed in Table 4.

TABLE 4

Exemplary Indications and Related Proteins

| Indication | Therapeutic Protein |
| --- | --- |
| 3-Methylcrotonyl-CoA carboxylase deficiency | Methylcrotonoyl-CoA carboxylase |
| 3-Methylglutaconic aciduria | Methylglutaconyl-CoA hydratase |
| Actinic keratosis | |

TABLE 4-continued

Exemplary Indications and Related Proteins

| Indication | Therapeutic Protein |
| --- | --- |
| Acute intermittent porphyria | Porphobilinogen deaminase |
| Acute lymphocytic leukemia | |
| Acute myeloid leukemia | |
| Addison's disease | |
| Adenosine deaminase deficiency | Adenosine deaminase |
| Adrenoleukodystrophy | ABCD1 |
| Adrenomyeloneuropathy | |
| AIDS/HIV | |
| Alcohol use disorders | |
| Alkaptonuria | Homogentisate 1,2-dioxygenase |
| Allergic asthma | Anti-IgE mAb |
| Allergies (dermatitis, rhinitis) | |
| Alopecia areata | |
| Alpers' disease | POLG |
| Alpers-Huttenlocher syndrome | |
| Alpha 1-antitrypsin deficiency | Alpha 1 protease inhibitor |
| Alpha-mannosidosis | Alpha-D-mannosidase |
| Alport syndrome | |
| Alzheimer's disease | |
| Amyloid light-chain amyloidosis | |
| Amyotrophic lateral sclerosis (ALS) | |
| Anemia | Erythropoietin |
| Aortic valve stenosis | |
| Argininemia | Arginase |
| Argininosuccinic acidemia | Argininosuccinate lyase |
| Arrhythmogenic right ventricular dysplasia | |
| Autism | |
| Autosomal dominant and recessive progressive external ophthalmoplegia with mitochondrial DNA deletions | |
| Autosomal recessive polycystic kidney disease | ARPKD |
| Bacterial infections | |
| Basal cell carcinoma | |
| Batten disease | Battenin + others |
| B-cell chronic lymphocytic leukemia | |
| Becker muscular dystrophy | Dystrophin |
| Beta-thalassemia | Beta globin |
| Binge eating disorder | |
| Bipolar disorder | |
| Bladder cancer | |
| Blepharospasm, Cervical dystonia, Chronic migraine, more | Botulinum toxin |
| Bronchiolitis obliterans | |
| Brugada syndrome | |
| Buerger's disease | |
| CACNA1A | |
| CACNB4-related Episodic Ataxia Type 2 | |
| Cancer and depression | |
| Cancer and sexual dysfunction | |
| Cancer in pregnancy | |
| Carbamylphosphate synthetase deficiency | Carbamylphosphate synthetase |
| Carcinoma of the gallbladder | |
| Cardiomyopathy (diabetic) | |
| Cardiomyopathy (hypertrophic) | |
| Carnitine uptake defect | SLC22A5 |
| Catecholaminergic polymorphic ventricular tachycardia | |
| CDKL5-related Atypical Rett Syndrome | |
| Celiac disease | |
| Cellulitis | |
| Cerebrovascular disease | |
| Cervix uteri cancer | |
| Chronic fatigue syndrome | |
| Chronic graft versus host disease | |
| Chronic idiopathic urticaria | |
| Chronic immune thrombocytopenia | Thrombopoietin |
| Chronic kidney kisease | |
| Chronic liver disease | |
| Chronic lymphocytic leukemia | |
| Chronic myeloid leukemia | |
| Chronic pancreatitis | |
| Cirrhosis of the liver | |
| Citrullinemia, type I | Argininosuccinate synthase |
| Classic Rett Syndrome | |
| Classical galactosemia | Galactose-1-phosphate uridylyltransferase |
| *Clostridium difficile* associated diarrhea | |

TABLE 4-continued

Exemplary Indications and Related Proteins

| Indication | Therapeutic Protein |
|---|---|
| Clotting disorders | |
| COAD/COPD | |
| Cocaine addiction | |
| COL4A5-related disorders | |
| Cold contact urticaria | |
| Contraception, female | |
| Coronary artery diseases | |
| Corpus uteri cancer | |
| Corticobasal degeneration | |
| Crigler-Najjar syndrome | UDP-glucuronosyltransferase |
| Critical limb ischemia | |
| CTNS-related cystinosis | |
| Cutaneous lupus erythematosus | |
| Cutaneous neuroendocrine carcinoma (Merkel Cell) | |
| Cystic fibrosis | CFTR |
| Cystic fibrosis | Deoxyribonuclease I |
| Cystinosis | Cystinosin |
| Cystinuria | SLC7A9 |
| Dementia (Lewy body) | |
| Depression | |
| Diabetic foot infections | |
| Diabetic foot ulcer | |
| Diabetic peripheral neuropathy | |
| Diabetic ulcers | |
| Diarrhoeal diseases | |
| Diffuse large B-cell lymphoma | |
| DiGeorge syndrome | |
| Diverticulitis | |
| Drug use disorders | |
| Duchenne muscular dystrophy | Dystrophin |
| Dysarthria | |
| Dyskinesia (levodopa-induced) | |
| Early-onset autosomal dominant Alzheimer's disease | |
| Eczema | |
| Ehlers-Danlos syndrome, type 1 | |
| EIF2B1 | |
| EIF2B2 | |
| EIF2B3 | |
| EIF2B4 | |
| EIF2B5-related childhood ataxia with central nervous system hypomyelination/vanishing white matter | |
| Eosinophilic esophagitis | |
| Epilepsy | |
| Erectile dysfunction | |
| Erythropoietic protoporphyria | Ferrochelatase |
| Esophageal carcinoma | |
| Essential tremor | |
| Fabry disease | Alpha galactosidase |
| Familial adenomatous polyposis | APC |
| Familial chylomicronemia | Lipoprotein lipase |
| Familial dysbetalipoproteinemia | Apolipoprotein E |
| Familial isolated dilated cardiomyopathy | |
| Familial mediterranean fever | Pyrin (MEFV) |
| Familial melanoma | |
| Female infertility | Follicle stimulating hormone |
| Female sexual dysfunction | |
| Fibromyalgia | |
| FMR1-related disorders | |
| Fracture healing | |
| Fragile X Premature Ovarian Failure Syndrome | |
| Fragile X syndrome | FMRP |
| Fragile X-Associated Tremor/Ataxia Syndrome | |
| Friedreich's ataxia | |
| Frontotemporal dementia | |
| Fryns syndrome | |
| Galactocerebrosidase deficiencies | |
| GALE deficiency | Galactose epimerase |
| GALK deficiency | Galactokinase |
| GALT-related galactosemia | |
| Gastric cancer | |
| Gastroesophageal reflux disease | |
| Gaucher disease | Glucocerebrosidase |
| Gilbert syndrome | UDP-glucuronosyltransferase |
| Glioblastoma multiforme | |
| Glomerulonephritis | |

TABLE 4-continued

Exemplary Indications and Related Proteins

| Indication | Therapeutic Protein |
|---|---|
| Glutaric acidemia, type I | Glutaryl-CoA dehydrogenase |
| GM2 gangliosidosis | HEXA, HEXB |
| Gout | Urate oxidase |
| Graft versus host disease | |
| Growth hormone deficiency | Growth hormone 1/Growth hormone 2 |
| Head and neck cancer, Metastatic colorectal cancer | Anti-EGFr mAb |
| Hearing loss, adult onset | |
| Heart failure | |
| Hemachromatosis | HFE protein |
| Hemifacial spasm | |
| Hemolytic uremic syndrome | Anti-complement factor C5 mAb |
| Hemophilia A | Factor VIII |
| Hemophilia A, Hemophilia B | Factor VII |
| Hemophilia B | Factor IX |
| Hepatitis B, Hepatitis C | Interferon alpha |
| HER2+ breast cancer, gastric cancer | Anti-HER2 mAb |
| Hereditary angioedema | C1 esterase inhibitor |
| Hereditary hemorrhagic telangiectasia | |
| Hereditary hemorrhagic telangiectasia (AT) | |
| Hereditary spherocytosis | |
| Hidradenitis suppurativa | |
| Homocystinuria | Cystathionine beta-synthase |
| Homozygous familial hypercholesterolemia | LDL receptor |
| Hunter syndrome (MPS II) | Iduronate-2-sulfatase |
| Huntington disease | Huntingtin |
| Hurler syndrome (MPS I) | Alpha-L iduronidase |
| Hydrolethalus | |
| Hyperalgesia | |
| Hyperbilirubinemia | |
| Hyperhidrosis | |
| Hyperlipidemia | |
| Hypermethioninemia | Methionine adenosyltransferase |
| Hyperoxaluria, type I | Serine-pyruvate aminotransferase |
| Hypertension | |
| Hyperuricemia | |
| Hyponatremia | |
| Hypoparathyroidism | Parathyroid hormone |
| Hypophosphatasia | TNSALP |
| Idiopathic pulmonary fibrosis | |
| Iminoglycinuria | |
| Immunoglobulin deficiency | Immunoglobulin |
| Infection (adenovirus) | |
| Infection (anthrax prophylaxis) | |
| Infection (BK virus) | |
| Infection (*Clostridium difficile* prophylaxis) | |
| Infection (Dengue fever prophylaxis) | |
| Infection (Epstein-Barr virus) | |
| Infection (Hepatitis-D) | |
| Infection (Lyme disease prophylaxis) | |
| Infection (Smallpox virus) | |
| Infectious diseases vaccines | Infectious antigen |
| Inflammatory heart diseases | |
| Insomnia | |
| Interstitial cystitis | |
| Iron-deficiency anaemia | |
| Irritable bowel disease | |
| Ischaemic heart disease | |
| Isovaleric aciduria | Isovaleric acid CoA dehydrogenase deficiency |
| Jansky-Bielschowsky disease | |
| Juvenile Batten disease | |
| Juvenile Neuronal Ceroid Lipofuscinosis (JNCL) | |
| Juvenile rheumatoid arthritis | TNF-alpha inhibitors |
| Kennedy's disease (SBMA) | |
| Keratoconus | |
| Krabbe disease | Galactocerebrosidase |
| Leber's hereditary optic neuropathy | NADH dehydrogenase |
| Leiomyosarcoma | |
| Lennox-Gastaut syndrome | |
| Lesch-Nyhan syndrome | Hypoxanthine phosphoribosyltransferase 1 |
| Leukaemia | |
| Li-Fraumeni syndrome | TP53 |
| Lipoma | |
| Liposarcoma | |
| Liver cancer | |
| Long-chain 3-OH acyl-CoA dehydrogenase deficiency | Long-chain-3-hydroxyacyl-CoA dehydrogenase |
| Lower respiratory infections | |

TABLE 4-continued

Exemplary Indications and Related Proteins

| Indication | Therapeutic Protein |
|---|---|
| Lysosomal acid lipase deficiency | Lysosomal acid lipase |
| Macular degeneration | |
| Major depressive disorder | |
| Malignant fibrous histiocytoma | |
| Mantle cell lymphoma | |
| Maple syrup urine disease | 3-methyl-2-oxobutanoate dehydrogenase |
| Marfan syndrome | FBN1 |
| Maroteaux-Lamy syndrome (MPS VI) | N-acetylgalactosamine 4-sulfatase |
| Mastocytosis | |
| McArdle disease | Muscle glycogen phosphorylase |
| MECP2-related disorders | |
| MECP2-related Severe Neonatal Encephalopathy | |
| Medium-chain acyl-CoA dehydrogenase deficiency | Acyl-CoA dehydrogenase |
| Melanoma | Anti-CTLA4 mAb |
| Metachromatic leukodystrophy | Arylsulfatase A |
| Metastatic colorectal cancer, NSCLC, others | Anti-VEGF mAb |
| Methylmalonyl-CoA mutase deficiency | Methylmalonyl-CoA mutase |
| Migraine | |
| Mitochondrial oxidative phosphorylation disorders | |
| Morquio syndrome, type A (MPS IVA) | Galactose 6-sulfate sulfatase |
| Morquio syndrome, type B (MPS IVB) | Beta-galactosidase |
| Mouth and oropharynx cancers | |
| Multiple carboxylase deficiency | Biotin-methylcrotonoyl-CoA-carboxylase ligase |
| Multiple myeloma | |
| Multiple sclerosis | Anti-VLA-4 mAb |
| Multiple sclerosis | Interferon beta |
| Multiple system atrophy | |
| Myasthenia gravis | |
| Myelofibrosis | |
| Narcolepsy | |
| Neonatal bronchopulmonary dysplasia | |
| Neonatal infections | |
| Nephritis and nephrosis | |
| Neurofibromatosis, type 1 | NF-1 |
| Neuronal ceroid lipofuscinoses-related diseases | |
| Neutropenia | G-CSF |
| Niemann Pick disease, type A/B | SMPD1 |
| Niemann Pick disease, type C | NPC1 |
| Niemann-Pick disease Type C1 | |
| Nocturia | |
| Non-alcoholic fatty liver disease | |
| Non-Hodgkin lymphoma | Anti-CD20 mAb |
| Non-small cell lung cancer | |
| Notch-3 related cerebral autosomal dominant arteriopathy with subcortical infarcts and leukoencephalopathy (CADASIL) | |
| Obesity | |
| Ophthalmoparesis | |
| Opioid induced constipation | |
| Ornithine transcarbamylase deficiency | Ornithine transcarbamylase |
| Osteoarthritis | |
| Osteopetrosis | |
| Osteoporosis | Anti-RANKL mAb |
| Ovarian cancer | |
| Paget disease of bone | Sequestosome 1 |
| Pain | |
| Pancreatic carcinoma | |
| Panic disorder | |
| Parkinson disease | |
| Paroxysmal nocturnal hemoglobinuria | Anti-complement factor C5 Mab |
| *Pediculosis capitis* (head lice) | |
| Pelizaeus-Merzbacher disease | |
| Pemphigus vulgaris | |
| Peptic ulcer disease | |
| Peripheral neuropathy | |
| Peyronie's disease | |
| Phenylketonuria | Phenylalanine hydroxylase |
| Pneumococcal infection prophylaxis | |
| POLG-related sensory ataxic neuropathy | |
| Polycystic kidney disease | |
| Polycystic ovary syndrome | |
| Polycythaemia vera | |
| Polymerase G-related disorders | |
| Polymorphous light eruption | |

TABLE 4-continued

Exemplary Indications and Related Proteins

| Indication | Therapeutic Protein |
| --- | --- |
| Pompe disease | Alpha glucosidase |
| Porphyria cutanea tarda | Uroporphyrinogen decarboxylase |
| Post herpetic neuralgia | |
| Post-organ transplant | |
| Pouchitis | |
| PPM-X Syndrome | |
| Prader-Willi syndrome | |
| Preeclampsia | |
| Premature ejaculation | |
| Prematurity and low birth weight | |
| Primary ciliary dyskinesia | |
| Primary glomerular diseases | |
| Primary humoral immune deficiencies (e.g., CVID) | Immunoglobulin |
| Proctitis | |
| Progressive multifocal leukoencephalopathy | |
| Progressive supranuclear palsy | |
| Propionic acidemia | Propionyl-CoA carboxylase |
| Prostate cancer | |
| Psoriasis | Anti-IL-12 & IL-23 mAb |
| Psoriatic arthritis | TNF-alpha inhibitors |
| PTT-1 | |
| Pulmonary arterial hypertension | |
| Pulmonary arterial hypertension | |
| Raynaud's phenomenon | |
| Refractive errors | |
| Renal cell carcinoma | |
| Restless leg syndrome | |
| Retinitis pigmentosa | |
| Rheumatic heart disease | |
| Rheumatoid arthritis | Anti-interleukin-6 (IL-6) mAb |
| Rheumatoid arthritis | T-cell costimulation blocker |
| Rheumatoid arthritis | TNF-alpha inhibitor |
| Romano-Ward syndrome | |
| Rosacea | |
| Sanfilippo syndrome, type A (MPS IIIA) | Heparan N-sulfatase |
| Sanfilippo syndrome, type B (MPS IIIB) | N-acetyl-alpha-D-glucosaminidase |
| Santavuori-Haltia disease | |
| Schizophrenia | |
| Schnitzler syndrome | |
| Scleroderma | |
| SCN1A | |
| SCN1B-related seizure disorders | |
| Short-chain acyl-CoA dehydrogenase deficiency | Butyryl-CoA dehydrogenase |
| Sickle cell disease | Hemoglobin |
| SLC3A1-related disorders | |
| Small cell lung cancer | |
| SMN-1-related spinal muscular atrophy (SMA) | |
| Spinal muscular atrophy | Survival motor neuron protein |
| Squamous cell carcinoma of head and neck | |
| Stickler syndrome | |
| Stomach cancer | |
| Stroke prophylaxis | |
| Synovial sarcoma | |
| Systemic lupus erythematosus | Anti-BAFF |
| Systemic sclerosis | |
| Tetrahydrobiopterin-deficient hyperphenylalaninemia | Tetrahydrobiopterin |
| Thromboangiitis obliterans | |
| Thrombotic disorders | |
| Thyroid cancer | |
| TPP1 deficiencies | |
| Trachea, bronchus, lung cancers | |
| Tricuspid atresia | |
| TSC1 | |
| TSC2-related tuberous sclerosis | |
| Type 2 diabetes mellitus | Glucagon-like peptide 1 (GLP-1) agonist |
| Type 2 diabetes mellitus | Insulin |
| Tyrosinemia, type I | Fumarylacetoacetase |
| Ulcerative colitis | |
| Uterine fibroids | |
| Varicose veins | |
| Venous thromboembolism | |
| Very long-chain acyl-CoA dehydrogenase deficiency | Long-chain-acyl-CoA dehydrogenase |
| von Gierke's disease | Glucose-6-phosphatase |
| Von Hippel-Lindau disease | pVHL |
| Wegener granulomatosis | |

TABLE 4-continued

Exemplary Indications and Related Proteins

| Indication | Therapeutic Protein |
|---|---|
| Wilson disease | Wilson disease protein |
| X-Linked adrenal hypoplasia | |
| X-linked adrenoleukodystrophy | |
| X-linked agammaglobulinemia | Bruton's tyrosine kinase |

In some embodiments, the present invention is used to prevent, treat and/or cure a subject affected with a disease or disorder listed or associated with the proteins listed in Tables 1, 2, 3 or 4. In some embodiments, an mRNA encodes one or more of argininosuccinate synthetase (ASS1), Factor IX, survival motor neuron 1 (SMN1), or phenylalanine hydroxylase Synthesis of mRNA mRNAs according to the present invention may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application.

In some embodiments, for the preparation of mRNA according to the invention, a DNA template is transcribed in vitro. A suitable DNA template typically has a promoter, for example a T3, T7 or SP6 promoter, for in vitro transcription, followed by desired nucleotide sequence for desired mRNA and a termination signal.

Desired mRNA sequence(s) according to the invention may be determined and incorporated into a DNA template using standard methods. For example, starting from a desired amino acid sequence (e.g., an enzyme sequence), a virtual reverse translation is carried out based on the degenerated genetic code. Optimization algorithms may then be used for selection of suitable codons. Typically, the G/C content can be optimized to achieve the highest possible G/C content on one hand, taking into the best possible account the frequency of the tRNAs according to codon usage on the other hand. The optimized RNA sequence can be established and displayed, for example, with the aid of an appropriate display device and compared with the original (wild-type) sequence. A secondary structure can also be analyzed to calculate stabilizing and destabilizing properties or, respectively, regions of the RNA.

Modified mRNA

In some embodiments, mRNA according to the present invention may be synthesized as unmodified or modified mRNA. Typically, mRNAs are modified to enhance stability. Modifications of mRNA can include, for example, modifications of the nucleotides of the RNA. An modified mRNA according to the invention can thus include, for example, backbone modifications, sugar modifications or base modifications. In some embodiments, mRNAs may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thiouracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thiouracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, . beta.-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g. from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosures of which are incorporated by reference in their entirety.

In some embodiments, mRNAs (e.g., enzyme encoding mRNAs) may contain RNA backbone modifications. Typically, a backbone modification is a modification in which the phosphates of the backbone of the nucleotides contained in the RNA are modified chemically. Exemplary backbone modifications typically include, but are not limited to, modifications from the group consisting of methylphosphonates, methylphosphoramidates, phosphoramidates, phosphorothioates (e.g. cytidine 5'-O-(1-thiophosphate)), boranophosphates, positively charged guanidinium groups etc., which means by replacing the phosphodiester linkage by other anionic, cationic or neutral groups.

In some embodiments, mRNAs (e.g., enzyme encoding mRNAs) may contain sugar modifications. A typical sugar modification is a chemical modification of the sugar of the nucleotides it contains including, but not limited to, sugar modifications chosen from the group consisting of 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-aracytidine 5'-triphosphate, 2'-arauridine 5'-triphosphate), or azidotriphosphates (2'-azido-2'-deoxycytidine 5'-triphosphate, 2'-azido-2'-deoxyuridine 5'-triphosphate).

In some embodiments, mRNAs (e.g., enzyme encoding mRNAs) may contain modifications of the bases of the nucleotides (base modifications). A modified nucleotide which contains a base modification is also called a base-modified nucleotide. Examples of such base-modified nucleotides include, but are not limited to, 2-amino-6- chloropurine riboside 5'-triphosphate, 2-aminoadenosine 5'-triphosphate, 2-thiocytidine 5'-triphosphate, 2-thiouridine 5'-triphosphate, 4-thiouridine 5'-triphosphate, 5-aminoallyl-cytidine 5'-triphosphate, 5-aminoallyluridine 5'-triphosphate, 5-bromocytidine 5'-triphosphate, 5-bromouridine 5'-triphosphate, 5-iodocytidine 5'-triphosphate, 5-iodouridine 5'-triphosphate, 5-methylcytidine 5'-triphosphate, 5-methyluridine 5'-triphosphate, 6-azacytidine 5'-triphosphate, 6-azauridine 5'-triphosphate, 6-chloropurine riboside 5'-triphosphate, 7-deazaadenosine 5'-triphosphate, 7-deazaguanosine 5'-triphosphate, 8-azaadenosine 5'-triphosphate, 8-azidoadenosine 5'-triphosphate, benzimidazole riboside 5'-triphosphate, N1-methyladenosine 5'-triphosphate, N1-methylguanosine 5'-triphosphate, N6-methyladenosine 5'-triphosphate, O6-methylguanosine 5'-triphosphate, pseudouridine 5'-triphosphate, puromycin 5'-triphosphate or xanthosine 5'-triphosphate.

Cap Structure

Typically, mRNA synthesis includes the addition of a "cap" on the N-terminal (5') end, and a "tail" on the C-terminal (3') end. The presence of the cap is important in providing resistance to nucleases found in most eukaryotic cells. The presence of a "tail" serves to protect the mRNA from exonuclease degradation.

Thus, in some embodiments, mRNAs (e.g., enzyme encoding mRNAs) include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G (5')ppp(5')A and G(5')ppp(5')G.

In some embodiments, naturally occurring cap structures comprise a 7-methyl guanosine that is linked via a triphosphate bridge to the 5'-end of the first transcribed nucleotide, resulting in a dinucleotide cap of m$^7$G(5')ppp(5')N, where N is any nucleoside. In vivo, the cap is added enzymatically. The cap is added in the nucleus and is catalyzed by the enzyme guanylyl transferase. The addition of the cap to the 5' terminal end of RNA occurs immediately after initiation of transcription. The terminal nucleoside is typically a guanosine, and is in the reverse orientation to all the other nucleotides, i.e., G(5')ppp(5')GpNpNp.

A common cap for mRNA produced by in vitro transcription is m$^7$G(5')ppp(5')G, which has been used as the dinucleotide cap in transcription with T7 or SP6 RNA polymerase in vitro to obtain RNAs having a cap structure in their 5'-termini. The prevailing method for the in vitro synthesis of capped mRNA employs a pre-formed dinucleotide of the form m$^7$G(5')ppp(5')G ("m$^7$GpppG") as an initiator of transcription.

To date, a usual form of a synthetic dinucleotide cap used in in vitro translation experiments is the Anti-Reverse Cap Analog ("ARCA") or modified ARCA, which is generally a modified cap analog in which the 2' or 3' OH group is replaced with —OCH$_3$.

Additional cap analogs include, but are not limited to, chemical structures selected from the group consisting of m$^7$GpppG, m$^7$GpppA, m$^7$GpppC; unmethylated cap analogs (e.g., GpppG); dimethylated cap analog (e.g., m$^{2,7}$GpppG), trimethylated cap analog (e.g., m$^{2,2,7}$GpppG), dimethylated symmetrical cap analogs (e.g., m$^7$Gpppm$^7$G), or anti reverse cap analogs (e.g., ARCA; m$^{7,2'Ome}$GpppG, m$^{72'd}$GpppG, m$^{7,3'Ome}$GpppG, m$^{7,3'd}$GpppG and their tetraphosphate derivatives) (see, e.g., Jemielity, J. et al., "Novel 'anti-reverse' cap analogs with superior translational properties", RNA, 9: 1108-1122 (2003)).

In some embodiments, a suitable cap is a 7-methyl guanylate ("m$^7$G") linked via a triphosphate bridge to the 5'-end of the first transcribed nucleotide, resulting in m$^7$G (5')ppp(5')N, where N is any nucleoside. A preferred embodiment of a m$^7$G cap utilized in embodiments of the invention is m$^7$G(5')ppp(5')G.

In some embodiments, the cap is a Cap0 structure. Cap0 structures lack a 2'-O-methyl residue of the ribose attached to bases 1 and 2. In some embodiments, the cap is a Cap1 structure. Cap1 structures have a 2'-O-methyl residue at base 2. In some embodiments, the cap is a Cap2 structure. Cap2 structures have a 2'-O-methyl residue attached to both bases 2 and 3.

A variety of m$^7$G cap analogs are known in the art, many of which are commercially available. These include the m$^7$GpppG described above, as well as the ARCA 3'-OCH$_3$ and 2'-OCH$_3$ cap analogs (Jemielity, J. et al., RNA, 9: 1108-1122 (2003)). Additional cap analogs for use in embodiments of the invention include N7-benzylated dinucleoside tetraphosphate analogs (described in Grudzien, E. et al., RNA, 10: 1479-1487 (2004)), phosphorothioate cap analogs (described in Grudzien-Nogalska, E., et al., RNA, 13: 1745-1755 (2007)), and cap analogs (including biotinylated cap analogs) described in U.S. Pat. Nos. 8,093,367 and 8,304,529, incorporated by reference herein.

Tail Structure

Typically, the presence of a "tail" serves to protect the mRNA from exonuclease degradation. The poly A tail is thought to stabilize natural messengers and synthetic sense RNA. Therefore, in certain embodiments a long poly A tail can be added to an mRNA molecule thus rendering the RNA more stable. Poly A tails can be added using a variety of art-recognized techniques. For example, long poly A tails can be added to synthetic or in vitro transcribed RNA using poly A polymerase (Yokoe, et al. Nature Biotechnology. 1996; 14: 1252-1256). A transcription vector can also encode long poly A tails. In addition, poly A tails can be added by transcription directly from PCR products. Poly A may also be ligated to the 3' end of a sense RNA with RNA ligase (see, e.g., Molecular Cloning A Laboratory Manual, 2nd Ed., ed. by Sambrook, Fritsch and Maniatis (Cold Spring Harbor Laboratory Press: 1991 edition)).

In some embodiments, mRNAs (e.g., enzyme encoding mRNAs) include a 3' poly(A) tail structure. Typically, the length of the poly A tail can be at least about 10, 50, 100, 200, 300, 400 at least 500 nucleotides (SEQ ID NO: 12). In some embodiments, a poly-A tail on the 3' terminus of mRNA typically includes about 10 to 300 adenosine nucleotides (SEQ ID NO: 13) (e.g., about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). In some embodiments, mRNAs include a 3' poly(C) tail structure. A suitable poly-C tail on the 3' terminus of mRNA typically include about 10 to 200 cytosine nucleotides (SEQ ID NO: 14) (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, the length of the poly A or poly C tail is adjusted to control the stability of a modified sense mRNA molecule of the invention and, thus, the transcription of protein. For example, since the length of the poly A tail can influence the half-life of a sense mRNA molecule, the length of the poly A tail can be adjusted to modify the level of resistance of the mRNA to nucleases and thereby control the time course of polynucleotide expression and/or polypeptide production in a target cell.

' and 3' Untranslated Region

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Exemplary 3' and/or 5' UTR sequences can be derived from mRNA molecules which are stable (e.g., globin, actin, GAPDH, tubulin, histone, or citric acid cycle enzymes) to increase the stability of the sense mRNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of the polynucleotide (e.g., mRNA) to further stabilize the polynucleotide. Generally, these modifications improve the stability and/or pharmacokinetic properties (e.g., half-life) of the polynucleotide relative to their unmodified counterparts, and include, for example modifications made to improve such polynucleotides' resistance to in vivo nuclease digestion.

According to various embodiments, any size mRNA may be encapsulated by provided liposomes. In some embodiments, the provided liposomes may encapsulate mRNA of greater than about 0.5 kb, 1 kb, 1.5 kb, 2 kb, 2.5 kb, 3 kb, 3.5 kb, 4 kb, 4.5 kb, or 5 kb in length.

Formation of Liposomes

The liposomes for use in provided compositions can be prepared by various techniques which are presently known in the art. For example, multilamellar vesicles (MLV) may be prepared according to conventional techniques, such as by depositing a selected lipid on the inside wall of a suitable container or vessel by dissolving the lipid in an appropriate solvent, and then evaporating the solvent to leave a thin film on the inside of the vessel or by spray drying. An aqueous phase may then added to the vessel with a vortexing motion which results in the formation of MLVs. Uni-lamellar vesicles (ULV) can then be formed by homogenization, sonication or extrusion of the multi-lamellar vesicles. In addition, unilamellar vesicles can be formed by detergent removal techniques.

In certain embodiments, provided compositions comprise a liposome wherein the mRNA is associated on both the surface of the liposome and encapsulated within the same liposome. For example, during preparation of the compositions of the present invention, cationic liposomes may associate with the mRNA through electrostatic interactions. For example, during preparation of the compositions of the present invention, cationic liposomes may associate with the mRNA through electrostatic interactions.

In some embodiments, the compositions and methods of the invention comprise mRNA encapsulated in a liposome. In some embodiments, the one or more mRNA species may be encapsulated in the same liposome. In some embodiments, the one or more mRNA species may be encapsulated in different liposomes. In some embodiments, the mRNA is encapsulated in one or more liposomes, which differ in their lipid composition, molar ratio of lipid components, size, charge (Zeta potential), targeting ligands and/or combinations thereof. In some embodiments, the one or more liposome may have a different composition of cationic lipids, neutral lipid, PEG-modified lipid and/or combinations thereof. In some embodiments the one or more lipisomes may have a different molar ratio of cationic lipid, neutral lipid, cholesterol and PEG-modified lipid used to create the liposome.

The process of incorporation of a desired mRNA into a liposome is often referred to as "loading". Exemplary methods are described in Lasic, et al., FEBS Lett., 312: 255-258, 1992, which is incorporated herein by reference. The liposome-incorporated nucleic acids may be completely or partially located in the interior space of the liposome, within the bilayer membrane of the liposome, or associated with the exterior surface of the liposome membrane. The incorporation of a nucleic acid into liposomes is also referred to herein as "encapsulation" wherein the nucleic acid is entirely contained within the interior space of the liposome. The purpose of incorporating a mRNA into a transfer vehicle, such as a liposome, is often to protect the nucleic acid from an environment which may contain enzymes or chemicals that degrade nucleic acids and/or systems or receptors that cause the rapid excretion of the nucleic acids. Accordingly, in some embodiments, a suitable delivery vehicle is capable of enhancing the stability of the mRNA contained therein and/or facilitate the delivery of mRNA to the target cell or tissue.

Liposome Size

Suitable liposomes in accordance with the present invention may be made in various sizes. In some embodiments, provided liposomes may be made smaller than previously known mRNA encapsulating liposomes. In some embodiments, decreased size of liposomes is associated with more efficient delivery of mRNA. Selection of an appropriate liposome size may take into consideration the site of the target cell or tissue and to some extent the application for which the liposome is being made.

In some embodiments, an appropriate size of liposome is selected to facilitate systemic distribution of antibody encoded by the mRNA. In some embodiments, it may be desirable to limit transfection of the mRNA to certain cells or tissues. For example, to target hepatocytes a liposome may be sized such that its dimensions are smaller than the fenestrations of the endothelial layer lining hepatic sinusoids in the liver; in such cases the liposome could readily penetrate such endothelial fenestrations to reach the target hepatocytes.

Alternatively or additionally, a liposome may be sized such that the dimensions of the liposome are of a sufficient diameter to limit or expressly avoid distribution into certain cells or tissues. For example, a liposome may be sized such that its dimensions are larger than the fenestrations of the endothelial layer lining hepatic sinusoids to thereby limit distribution of the liposomes to hepatocytes.

In some embodiments, the size of a liposome is determined by the length of the largest diameter of the liposome particle. In some embodiments, a suitable liposome has a size of or less than about 500 nm, 450 nm, 400 nm, 350 nm, 300 nm, 250 nm, 200 nm, 150 nm, 125 nm, 110 nm, 100 nm, 95 nm, 90 nm, 85 nm, 80 nm, 75 nm, 70 nm, 65 nm, 60 nm, 55 nm, or 50 nm. In some embodiments, a suitable liposome has a size no greater than about 250 nm (e.g., no greater than about 225 nm, 200 nm, 175 nm, 150 nm, 125 nm, 100 nm, 75 nm, or 50 nm). In some embodiments, a suitable liposome has a size ranging from about 10-250 nm (e.g., ranging from about 10-225 nm, 10-200 nm, 10-175 nm, 10-150 nm, 10-125 nm, 10-100 nm, 10-75 nm, or 10-50 nm). In some embodiments, a suitable liposome has a size ranging from about 100-250 nm (e.g., ranging from about 100-225 nm, 100-200 nm, 100-175 nm, 100-150 nm). In some embodiments, a suitable liposome has a size ranging from about 10-100 nm (e.g., ranging from about 10-90 nm, 10-80 nm, 10-70 nm, 10-60 nm, or 10-50 nm).

A variety of alternative methods known in the art are available for sizing of a population of liposomes. One such sizing method is described in U.S. Pat. No. 4,737,323, incorporated herein by reference. Sonicating a liposome suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the liposomes may be determined by quasi-electric light scattering (QELS) as described in Bloomfield, Ann. Rev. Biophys. Bioeng., 10:421-150 (1981), incorporated herein by reference. Average liposome diameter may be reduced by sonication of formed liposomes. Intermittent sonication cycles may be alternated with QELS assessment to guide efficient liposome synthesis.

Pharmaceutical Compositions

To facilitate expression of mRNA in vivo, delivery vehicles such as liposomes can be formulated in combination with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition.

Provided liposomally-encapsulated or associated mRNAs, and compositions containing the same, may be administered and dosed in accordance with current medical practice, taking into account the clinical condition of the subject, the site and method of administration, the scheduling of administration, the subject's age, sex, body weight and other factors relevant to clinicians of ordinary skill in the art. The "effective amount" for the purposes herein may be determined by such relevant considerations as are known to those of ordinary skill in experimental clinical research, pharmacological, clinical and medical arts. In some embodiments, the amount administered is effective to achieve at least some stabilization, improvement or elimination of symptoms and other indicators as are selected as appropriate measures of disease progress, regression or improvement by those of skill in the art. For example, a suitable amount and dosing regimen is one that causes at least transient protein (e.g., enzyme) production.

Suitable routes of administration include, for example, oral, rectal, vaginal, transmucosal, pulmonary including intratracheal or inhaled, or intestinal administration; parenteral delivery, including intradermal, transdermal (topical), intramuscular, subcutaneous, intramedullary injections, as well as intrathecal, direct intraventricular, intravenous, intraperitoneal, and/or intranasal administration.

Alternately or additionally, liposomally encapsulated mRNAs and compositions of the invention may be administered in a local rather than systemic manner, for example, via injection of the pharmaceutical composition directly into a targeted tissue, preferably in a sustained release formulation. Local delivery can be affected in various ways, depending on the tissue to be targeted. For example, aerosols containing compositions of the present invention can be inhaled (for nasal, tracheal, or bronchial delivery); compositions of the present invention can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection. Formulations containing provided compositions complexed with therapeutic molecules or ligands can even be surgically administered, for example in association with a polymer or other structure or substance that can allow the compositions to diffuse from the site of implantation to surrounding cells. Alternatively, they can be applied surgically without the use of polymers or supports.

In some embodiments, provided liposomes and/or compositions are formulated such that they are suitable for extended-release of the mRNA contained therein. Such extended-release compositions may be conveniently administered to a subject at extended dosing intervals. For example, in one embodiment, the compositions of the present invention are administered to a subject twice day, daily or every other day. In a preferred embodiment, the compositions of the present invention are administered to a subject twice a week, once a week, every ten days, every two weeks, every three weeks, or more preferably every four weeks, once a month, every six weeks, every eight weeks, every other month, every three months, every four months, every six months, every eight months, every nine months or annually. Also contemplated are compositions and liposomes which are formulated for depot administration (e.g., intramuscularly, subcutaneously, intravitreally) to either deliver or release a mRNA over extended periods of time. Preferably, the extended-release means employed are combined with modifications made to the mRNA to enhance stability.

Also contemplated herein are lyophilized pharmaceutical compositions comprising one or more of the liposomes disclosed herein and related methods for the use of such compositions as disclosed for example, in U.S. Provisional Application No. 61/494,882, filed Jun. 8, 2011, the teachings of which are incorporated herein by reference in their entirety. For example, lyophilized pharmaceutical compositions according to the invention may be reconstituted prior to administration or can be reconstituted in vivo. For example, a lyophilized pharmaceutical composition can be formulated in an appropriate dosage form (e.g., an intradermal dosage form such as a disk, rod or membrane) and administered such that the dosage form is rehydrated over time in vivo by the individual's bodily fluids.

Provided liposomes and compositions may be administered to any desired tissue. In some embodiments, the mRNA delivered by provided liposomes or compositions is expressed in the tissue in which the liposomes and/or compositions were administered. In some embodiments, the mRNA delivered is expressed in a tissue different from the tissue in which the liposomes and/or compositions were administered Exemplary tissues in which delivered mRNA may be delivered and/or expressed include, but are not limited to the liver, kidney, heart, spleen, serum, brain, skeletal muscle, lymph nodes, skin, and/or cerebrospinal fluid.

According to various embodiments, the timing of expression of delivered mRNAs can be tuned to suit a particular medical need. In some embodiments, the expression of the protein encoded by delivered mRNA is detectable 1, 2, 3, 6, 12, 18, 24, 30, 36, 42, 48, 54, 60, 66, and/or 72 hours in serum or target tissues after a single administration of provided liposomes or compositions. In some embodiments, the expression of the protein encoded by the mRNA is detectable 1 day, 2 days, 3 days, 4 days, 5 days, 6 days, and/or 7 days in serum or target tissues after a single administration of provided liposomes or compositions. In some embodiments, the expression of the protein encoded by the mRNA is detectable 1 week, 2 weeks, 3 weeks, and/or 4 weeks in serum or target tissues after a single administration of provided liposomes or compositions. In some embodiments, the expression of the protein encoded by the mRNA is detectable after a month or longer after a single administration of provided liposomes or compositions.

The present invention can be used to deliver mRNA at various doses. In some embodiments, an mRNA is administered at a dose ranging from about 0.1-5.0 mg/kg body weight, for example about 0.1-4.5, 0.1-4.0, 0.1-3.5, 0.1-3.0, 0.1-2.5, 0.1-2.0, 0.1-1.5, 0.1-1.0, 0.1-0.5, 0.1-0.3, 0.3-5.0, 0.3-4.5, 0.3-4.0, 0.3-3.5, 0.3-3.0, 0.3-2.5, 0.3-2.0, 0.3-1.5, 0.3-1.0, 0.3-0.5, 0.5-5.0, 0.5-4.5, 0.5-4.0, 0.5-3.5, 0.5-3.0, 0.5-2.5, 0.5-2.0, 0.5-1.5, or 0.5-1.0 mg/kg body weight. In some embodiments, an mRNA is administered at a dose of or less than about 5.0, 4.5, 4.0, 3.5, 3.0, 2.5, 2.0, 1.5, 1.0, 0.8, 0.6, 0.5, 0.4, 0.3, 0.2, or 0.1 mg/kg body weight.

EXAMPLES

While certain compounds, compositions and methods of the present invention have been described with specificity in accordance with certain embodiments, the following examples serve only to illustrate the compounds of the invention and are not intended to limit the same.

Example 1. Exemplary Liposome Formulations for mRNA Delivery and Expression

This example provides exemplary liposome formulations incorporating the cationic lipids described in this application, for example, cKK-E12, for effective delivery and expression of mRNA encoding therapeutic proteins in vivo.

Lipid Materials

In general, the formulations described herein are based on a multi-component lipid mixture of varying ratios employing one or more cationic lipids, one or more helper lipids (e.g., non-cationic lipids and/or cholesterol-based lipids), and one or more PEGylated lipids designed to encapsulate various nucleic acid-based materials. As a non-limiting example, cKK-E12 (3,6-bis(4-(bis(2-hydroxydodecyl) amino)butyl)piperazine-2,5-dione) is used in various formulations described herein. Exemplary helper lipids include one or more of DSPC (1,2-di stearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyri stoyl-sn-glycero-3-phosphoethanolamine), DOPG (2-dioleoyl-sn-glycero-3-phospho-(1'-rac-glycerol)), cholesterol, etc. Exemplary PEGylated lipids include a poly(ethylene) glycol chain of up to 5 kDa in length covalently attached to a lipid with alkyl chain(s) of $C_6$-$C_{20}$ length, for example, PEG-2K. As non-limiting examples, liposome formulations used in various examples described herein include cKK-E12, DOPE, cholesterol and DMG-PEG2K at various ratios. For example, in some cases, the ratio of cKK-E12:DOPE:cholesterol:DMG-PEG2K is approximately 40:30:20:10 by weight. In other cases, the ratio of cKK-E12:DOPE:cholesterol:DMG-PEG2K is approximately 40:32:25:3 by weight. Unless otherwise specified, the below Examples include a mixture in the ratio of cKK-E 12:DOPE:cholesterol:DMG-PEG2K of approximately 40:30:25:5 by weight.

Messenger RNA Material

The formulations described herein may be used to deliver any mRNA, in particular, therapeutic mRNA. As used herein, a therapeutic mRNA refers to an mRNA that encodes a therapeutic protein. The formulations described herein can also be used to deliver any modified or unmodified mRNA, or mRNA with naturally occurring sequences or codon-optimized.

As non-limiting examples, human Factor IX (FIX), codon-optimized Firefly Luciferase (FFL), codon-optimized human argininosuccinate synthetase (ASS1) messenger RNA, codon-optimized human Survival of Motor Neuron 1(SMN) mRNA were synthesized by in vitro transcription from a plasmid DNA template encoding the gene, which was followed by the addition of a 5' cap structure (Cap 1) (Fechter, P.; Brownlee, G. G. "Recognition of mRNA cap structures by viral and cellular proteins" *J. Gen. Virology* 2005, 86, 1239-1249) and a 3' poly(A) tail of, e.g., approximately 250 nucleotides in length (SEQ ID NO: 15) as determined by gel electrophoresis. Typically, 5' and 3' untranslated regions (UTR) are present in each mRNA product and are represented as X and Y, respectively. Example 5' and 3' UTR sequences are described below. The exemplary sequences of FIX, ASS1, and FFL mRNA used in the examples herein are listed below. Also shown are the 5' and 3' UTR sequences.

```
Human Factor IX (FIX) mRNA:
                                    (SEQ ID NO.: 1)
XAUGCAGCGCGUGAACAUGAUCAUGGCAGAAUCACCAGGCCUCAUCACCA

UCUGCCUUUUAGGAUAUCUACUCAGUGCUGAAUGUACAGUUUUUCUUGAU

CAUGAAAACGCCAACAAAAUUCUGAGGCGGAGAAGGAGGUAUAAUUCAGG

UAAAUUGGAAGAGUUUGUUCAAGGGAACCUUGAGAGAGAAUGUAUGGAAG

AAAAGUGUAGUUUUGAAGAAGCACGAGAAGUUUUUGAAAACACUGAAAGA

ACAACUGAAUUUUGGAAGCAGUAUGUUGAUGGAGAUCAGUGUGAGUCCAA

UCCAUGUUUAAAUGGCGGCAGUUGCAAGGAUGACAUUAAUUCCUAUGAAU

GUUGGUGUCCCUUUGGAUUUGAAGGAAAGAACUGUGAAUUAGAUGUAACA

UGUAACAUUAAGAAUGGCAGAUGCGAGCAGUUUUGUAAAAAUAGUGCUGA

UAACAAGGUGGUUUGCUCCUGUACUGAGGGAUAUCGACUUGCAGAAAACC

AGAAGUCCUGUGAACCAGCAGUGCCAUUUCCAUGUGGAAGAGUUUCUGUU

UCACAAACUUCUAAGCUCACCCGUGCUGAGGCUGUUUUUCCUGAUGUGGA

CUAUGUAAAUUCUACUGAAGCUGAAACCAUUUUGGAUAACAUCACUCAAA

GCACCCAAUCAUUUAAUGACUUCACUCGGGUUGUUGGUGGAGAAGAUGCC

AAACCAGGUCAAUUCCCUUGGCAGGUUGUUUUGAAUGGUAAAGUUGAUGC
```

-continued

AUUCUGUGGAGGCUCUAUCGUUAAUGAAAAAUGGAUUGUAACUGCUGCCC

ACUGUGUUGAAACUGGUGUUAAAAUUACAGUUGUCGCAGGUGAACAUAAU

AUUGAGGAGACAGAACAUACAGAGCAAAAGCGAAAUGUGAUUCGAAUUAU

UCCUCACCACAACUACAAUGCAGCUAUUAAUAAGUACAACCAUGACAUUG

CCCUUCUGGAACUGGACGAACCCUUAGUGCUAAACAGCUACGUUACACCU

AUUUGCAUUGCUGACAAGGAAUACACGAACAUCUUCCUCAAAUUUGGAUC

UGGCUAUGUAAGUGGCUGGGGAAGAGUCUUCCACAAAGGGAGAUCAGCUU

UAGUUCUUCAGUACCUUAGAGUUCCACUUGUUGACCGAGCCACAUGUCUU

CGAUCUACAAAGUUCACCAUCUAUAACAACAUGUUCUGUGCUGGCUUCCA

UGAAGGAGGUAGAGAUUCAUGUCAAGGAGAUAGUGGGGGACCCCAUGUUA

CUGAAGUGGAAGGGACCAGUUUCUUAACUGGAAUUAUUAGCUGGGGUGAA

GAGUGUGCAAUGAAAGGCAAAUAUGGAAUAUAUACCAAGGUAUCCCGGUA

UGUCAACUGGAUUAAGGAAAAAACAAAGCUCACUUAAY

Codon-Optimized Human Argininosuccinate
Synthetase (ASS1) mRNA:
(SEQ ID NO.: 2)
XAUGAGCAGCAAGGGCAGCGUGGUGCUGGCCUACAGCGGCGGCCUGGACA

CCAGCUGCAUCCUGGUGUGGCUGAAGGAGCAGGGCUACGACGUGAUCGCC

UACCUGGCCAACAUCGGCCAGAAGGAGGACUUCGAGGAGGCCCGCAAGAA

GGCCCUGAAGCUGGGCGCCAAGAAGGUGUUCAUCGAGGACGUGAGCCGCG

AGUUCGUGGAGGAGUUCAUCUGGCCCGCCAUCCAGAGCAGCGCCCUGUAC

GAGGACCGCUACCUGCUGGGCACCAGCCUGGCCCGCCCCUGCAUCGCCCG

CAAGCAGGUGGAGAUCGCCCAGCGCGAGGGCGCCAAGUACGUGAGCCACG

GCGCCACCGGCAAGGGCAACGACCAGGUGCGCUUCGAGCUGAGCUGCUAC

AGCCUGGCCCCCCAGAUCAAGGUGAUCGCCCCCUGGCGCAUGCCCGAGUU

CUACAACCGCUUCAAGGGCCGCAACGACCUGAUGGAGUACGCCAAGCAGC

ACGGCAUCCCCAUCCCCGUGACCCCCAAGAACCCCUGGAGCAUGGACGAG

AACCUGAUGCACAUCAGCUACGAGGCCGGCAUCCUGGAGAACCCCAAGAA

CCAGGCCCCCCCGGCCUGUACACCAAGACCCAGGACCCCGCCAAGGCCC

CCAACACCCCCGACAUCCUGGAGAUCGAGUUCAAGAAGGGCGUGCCCGUG

AAGGUGACCAACGUGAAGGACGGCACCACCCACCAGACCAGCCUGGAGCU

GUUCAUGUACCUGAACGAGGUGGCCGGCAAGCACGGCGUGGGCCGCAUCG

ACAUCGUGGAGAACCGCUUCAUCGGCAUGAAGAGCCGCGGCAUCUACGAG

ACCCCCGCCGGCACCAUCCUGUACCACGCCCACCUGGACAUCGAGGCCUU

CACCAUGGACCGCGAGGUGCGCAAGAUCAAGCAGGGCCUGGGCCUGAAGU

UCGCCGAGCUGGUGUACACCGGCUUCUGGCACAGCCCCGAGUGCGAGUUC

GUGCGCCACUGCAUCGCCAAGAGCCAGGAGCGCGUGGAGGGCAAGGUGCA

GGUGAGCGUGCUGAAGGGCCAGGUGUACAUCCUGGGCCGCGAGAGCCCCC

UGAGCCUGUACAACGAGGAGCUGGUGAGCAUGAACGUGCAGGGCGACUAC

GAGCCCACCGACGCCACCGGCUUCAUCAACAUCAACAGCCUGCGCCUGAA

GGAGUACCACCGCCUGCAGAGCAAGGUGACCGCCAAGUGAY

-continued

Codon-Optimized Firefly Luciferase (FFL) mRNA:
(SEQ ID NO.: 3)
XAUGGAAGAUGCCAAAAACAUUAAGAAGGGCCCAGCGCCAUUCUACCCAC

UCGAAGACGGGACCGCCGGCGAGCAGCUGCACAAAGCCAUGAAGCGCUAC

GCCCUGGUGCCCGGCACCAUCGCCUUUACCGACGCACAUAUCGAGGUGGA

CAUUACCUACGCCGAGUACUUCGAGAUGAGCGUUCGGCUGGCAGAAGCUA

UGAAGCGCUAUGGGCUGAAUACAAACCAUCGGAUCGUGGUGUGCAGCGAG

AAUAGCUUGCAGUUCUUCAUGCCCGUGUUGGGUGCCCUGUUCAUCGGUGU

GGCUGUGGCCCCAGCUAACGACAUCUACAACGAGCGCGAGCUGCUGAACA

GCAUGGGCAUCAGCCAGCCCACCGUCGUAUUCGUGAGCAAGAAAGGGCUG

CAAAAGAUCCUCAACGUGCAAAAGAAGCUACCGAUCAUACAAAAGAUCAU

CAUCAUGGAUAGCAAGACCGACUACCAGGGCUUCCAAAGCAUGUACACCU

UCGUGACUUCCCAUUUGCCACCCGGCUUCAACGAGUACGACUUCGUGCCC

GAGAGCUUCGACCGGGACAAAACCAUCGCCCUGAUCAUGAACAGUAGUGG

CAGUACCGGAUUGCCCAAGGGCGUAGCCCUACCGCACCGCACCGCUUGUG

UCCGAUUCAGUCAUGCCCGCGACCCCAUCUUCGGCAACCAGAUCAUCCCC

GACACCGCUAUCCUCAGCGUGGUGCCAUUUCACCACGGCUUCGGCAUGUU

CACCACGCUGGGCUACUUGAUCUGCGGCUUUCGGGUCGUGCUCAUGUACC

GCUUCGAGGAGGAGCUAUUCUUGCGCAGCUUGCAAGACUAUAAGAUUCAA

UCUGCCCUGCUGGUGCCCACACUAUUUAGCUUCUUCGCUAAGAGCACUCU

CAUCGACAAGUACGACCUAAGCAACUUGCACGAGAUCGCCAGCGGCGGGG

CGCCGCUCAGCAAGGAGGUAGGUGAGGCCGUGGCCAAACGCUUCCACCUA

CCAGGCAUCCGCCAGGGCUACGGCCUGACAGAAACAACCAGCGCCAUUCU

GAUCACCCCCGAAGGGGACGACAAGCCUGGCGCAGUAGGCAAGGUGGUGC

CCUUCUUCGAGGCUAAGGUGGUGGACUUGGACACCGGUAAGACACUGGGU

GUGAACCAGCGCGGCGAGCUGUGCGUCCGUGGCCCCAUGAUCAUGAGCGG

CUACGUUAACAACCCCGAGGCUACAAACGCUCUCAUCGACAAGGACGGCU

GGCUGCACAGCGGCGACAUCGCCUACUGGGACGAGGACGAGCACUUCUUC

AUCGUGGACCGGCUGAAGAGCCUGAUCAAAUACAAGGGCUACCAGGUAGC

CCCAGCCGAACUGGAGAGCAUCCUGCUGCAACACCCCAACAUCUUCGACG

CCGGGGUCGCCGGCCUGCCCGACGACGAUGCCGGCGAGCUGCCCGCCGCA

GUCGUCGUGCUGGAACACGGUAAAACCAUGACCGAGAAGGAGAUCGUGGA

CUAUGUGGCCAGCCAGGUUACAACCGCCAAGAAGCUGCGCGGUGGUGUUG

UGUUCGUGGACGAGGUGCCUAAAGGACUGACCGGCAAGUUGGACGCCCGC

AAGAUCCGCGAGAUUCUCAUUAAGGCCAAGAAGGGCGGCAAGAUCGCCGU

GUAAY

Codon-Optimized Human Survival of Motor
Neuron 1 (SMN) mRNA:
(SEQ ID NO: 4)
XAUGGCCAUGAGCAGCGGAGGCAGCGGCGGAGGAGUGCCCGAGCAGGAGG

ACAGCGUGCUGUUCAGGAGAGGCACCGGCCAGAGCGAUGACAGCGAUAUC

UGGGACGAUACCGCUCUGAUCAAGGCCUACGACAAGGCCGUGGCCAGCUU

CAAGCACGCCCUGAAAAACGGCGACAUCUGCGAGACCAGCGGCAAGCCCA

-continued

AGACAACCCCCAAGAGAAAGCCCGCCAAGAAGAAUAAGAGCCAGAAAAAG

AACACCGCCGCCAGCCUGCAGCAGUGGAAGGUGGGCGACAAGUGCAGCGC

CAUCUGGAGCGAGGACGGCUGCAUCUACCCCGCCACCAUCGCCAGCAUCG

ACUUCAAGAGAGAGACCUGCGUGGUCGUGUACACCGGCUACGGCAACAGA

GAGGAGCAGAACCUGAGCGACCUGCUGAGCCCCAUUUGUGAGGUGGCCAA

UAACAUCGAACAGAACGCCCAGGAGAACGAGAAUGAAAGCCAGGUGAGCA

CCGACGAGAGCGAGAACAGCAGAUCUCCUGGCAACAAGAGCGACAACAUC

AAGCCUAAGUCUGCCCCUUGGAACAGCUUCCUGCCCCUCCUCCACCCAU

GCCCGGACCCAGACUGGGACCCGGAAAACCUGGCCUGAAGUUCAACGGAC

CACCUCCCCUCCACCUCCUCCCCACCUCAUCUCCUGAGCUGCUGGCUG

CCACCCUUCCCCAGCGGACCCCCUAUCAUCCCACCACCCCCUCCCAUCUG

CCCCGACAGCCUGGACGACGCCGAUGCCCUGGGCAGCAUGCUGAUCAGCU

GGUACAUGAGCGGCUACCACACAGGAUACUACAUGGGCUUCAGACAGAAC

CAGAAGGAGGGCAGAUGCUCCCACUCCCUGAACUGAY

5' and 3' UTR Sequences
X (5' UTR Sequence) =
(SEQ ID NO.: 5)
GGACAGAUCGCCUGGAGACGCCAUCCACGCUGUUUUGACCUUCCAUAGAAG

ACACCGGGACCGAUCCAGCCUCCGCGGCCGGGAACGGUGCAUUGGAACGC

GGAUUCCCCGUGCCAAGAGUGACUCACCGUCCUUGACACG

Y (3' UTR Sequence) =
(SEQ ID NO.: 6)
CGGGUGGCAUCCCUGUGACCCCUCCCCAGUGCCUCUCCUGGCCCUGGAAG

UUGCCACUCCAGUGCCCACCAGCCUUGUCCUAAUAAAAUUAAGUUGCAUC

AAGCU
or
(SEQ ID NO.: 7)
GGGUGGCAUCCCUGUGACCCCUCCCCAGUGCCUCUCCUGGCCCUGGAAGU

UGCCACUCCAGUGCCCACCAGCCUUGUCCUAAUAAAAUUAAGUUGCAUCA

AGCU

C-terminal His₁₀ Codon-Optimized Human
CFTR mRNA ("His₁₀" disclosed
as SEQ ID NO: 11):
(SEQ ID NO.: 8)
XAUGCAGCGGUCCCCGCUCGAAAAGGCCAGUGUCGUGUCCAAACUCUUCU

UCUCAUGGACUCGGCCUAUCCUUAGAAAGGGGUAUCGGCAGAGGCUUGAG

UUGUCUGACAUCUACCAGAUCCCCUCGGUAGAUUCGCGGAUAACCUCUC

GGAGAAGCUCGAACGGGAAUGGGACCGCGAACUCGCGUCUAAGAAAAACC

CGAAGCUCAUCAACGCACUGAGAAGGUGCUUCUUCUGGCGGUUCAUGUUC

UACGGUAUCUUCUUGUAUCUCGGGGAGGUCACAAAAGCAGUCCAACCCCU

GUUGUUGGGUCGCAUUAUCGCCUCGUACGACCCCGAUAACAAAGAAGAAC

GGAGCAUCGCGAUCUACCUCGGGAUCGGACUGUGUUUGCUUUUCAUCGUC

AGAACACUUUUGUUGCAUCCAGCAAUCUUCGGCCUCCAUCACAUCGGUAU

GCAGAUGCGAAUCGCUAUGUUUAGCUUGAUCUACAAAAAGACACUGAAAC

UCUCGUCGCGGGUGUUGGAUAAGAUUUCCAUCGGUCAGUGGUGUCCCUG

CUUAGUAAUAACCUCAACAAAUUCGAUGAGGGACUGGCGCUGGCACAUUU

CGUGUGGAUUGCCCCGUUGCAAGUCGCCCUUUUGAUGGGCCUUAUUUGGG

AGCUGUUGCAGGCAUCUGCCUUUUGUGGCCUGGGAUUUCUGAUUGUGUUG

GCAUUGUUUCAGGCUGGGCUUGGGCGGAUGAUGAUGAAGUAUCGCGACCA

GAGAGCGGGUAAAAUCUCGGAAAGACUCGUCAUCACUUCGGAAAUGAUCG

AAAACAUCCAGUCGGUCAAAGCCUAUUGCUGGGAAGAAGCUAUGGAGAAG

AUGAUUGAAAACCUCCGCCAAACUGAGCUGAAACUGACCCGCAAGGCGGC

GUAUGUCCGGUAUUUCAAUUCGUCAGCGUUCUUCUUUUCCGGGUUCUUCG

UUGUCUUUCUCUCGGUUUUGCCUUAUGCCUUGAUUAAGGGGAUUAUCCUC

CGCAAGAUUUUCACCACGAUUUCGUUCUGCAUUGUAUUGCGCAUGGCAGU

GACACGGCAAUUUCCGUGGGCCGUGCAGACAUGGUAUGACUCGCUUGGAG

CGAUCAACAAAAUCCAAGACUUCUUGCAAAAGCAAGAGUACAAGACCCUG

GAGUACAAUCUUACUACUACGGAGGUAGUAAUGGAGAAUGUGACGGCUUU

UUGGGAAGAGGGUUUUGGAGAACUGUUUGAGAAAGCAAAGCAGAAUAACA

ACAACCGCAAGACCUCAAAUGGGGACGAUUCCCUGUUUUUCUCGAACUUC

UCCCUGCUCGGAACACCCGUGUUGAAGGACAUCAAUUUCAAGAUUGAGAG

GGACAGCUUCUCGCGGUAGCGGGAAGCACGGUGCGGGAAAAACUAGCC

UCUUGAUGGUGAUUAUGGGGGAGCUUGAGCCCAGCGAGGGGAAGAUUAAA

CACUCCGGGCGUAUCUCAUUCUGUAGCCAGUUUUCAUGGAUCAUGCCCGG

AACCAUUAAAGAGAACAUCAUUUUCGGAGUAUCCUAUGAUGAGUACCGAU

ACAGAUCGGUCAUUAAGGCGUGCCAGUUGGAAGAGGACAUUUCUAAGUUC

GCCGAGAAGGAUAACAUCGUCUUUGGGAGAAGGGGUAUUACAUUGUCGGG

AGGGCAGCGAGCGCGGAUCAGCCUCGCGAGAGCGGUAUACAAAGAUGCAG

AUUUGUAUCUGCUUGAUUCACCGUUUGGAUACCUCGACGUAUUGACAGAA

AAAGAAAUCUUCGAGUCGUGCGUGUGUAAACUUAUGGCUAAUAAGACGAG

AAUCCUGGUGACAUCAAAAAUGGAACACCUUAAGAAGGCGGACAAGAUCC

UGAUCCUCCACGAAGGAUCGUCCUACUUUUACGGCACUUUCUCAGAGUUG

CAAAACUUGCAGCCGGACUUCUCAAGCAAACUCAUGGGGUGUGACUCAUU

CGACCAGUUCAGCGCGGAACGGCGGAACUCGAUCUUGACGGAAACGCUGC

ACCGAUUCUCGCUUGAGGGUGAUGCCCCGGUAUCGUGGACCGAGACAAAG

AAGCAGUCGUUUAAGCAGACAGGAGAAUUGGUGAGAAAAGAAAGAACAG

UAUCUUGAAUCCUAUUAACUCAAUUCGCAAGUUCUCAAUCGUCCAGAAAA

CUCCACUGCAGAUGAAUGGAAUUGAAGAGGAUUCGGACGAACCCCUGGAG

CGCAGGCUUAGCCUCGUGCCGGAUUCAGAGCAAGGGGAGGCCAUUCUUCC

CCGGAUUUCGGUGAUUUCAACCGGACCUACACUUCAGGCGAGGCGAAGGC

AAUCCGUGCUCAACCUCAUGACGCAUUCGGUAAACCAGGGGCAAAACAUU

CACCGCAAAACGACGGCCUCAACGAGAAAAGUGUCACUUGCACCCCAGGC

GAAUUUGACUGAACUCGACAUCUACAGCCGUAGGCUUUCGCAAGAAACCG

GACUUGAGAUCAGCGAAGAAAUCAAUGAAGAAGAUUUGAAAGAGUGUUUC

UUUGAUGACAUGGAAUCAAUCCCAGCGGUGACAACGUGGAACACAUACUU

GCGUUACAUCACGGUGCACAAGUCCUUGAUUUUCGUCCUCAUCUGGUGUC

UCGUGAUCUUUCUCGCUGAGGUCGCAGCGUCACUUGUGGUCCUCUGGCUG

-continued

CUUGGUAAUACGCCCUUGCAAGACAAAGGCAAUUCUACACACUCAAGAAA
CAAUUCCUAUGCCGUGAUUAUCACUUCUACAAGCUCGUAUUACGUGUUUU
ACAUCUACGUAGGAGUGGCCGACACUCUGCUCGCGAUGGGUUUCUUCCGA
GGACUCCCACUCGUUCACACGCUUAUCACUGUCUCCAAGAUUCUCCACCA
UAAGAUGCUUCAUAGCGUACUGCAGGCUCCCAUGUCCACCUUGAAUACGC
UCAAGGCGGGAGGUAUUUUGAAUCGCUUCUCAAAAGAUAUUGCAAUUUUG
GAUGACCUUCUGCCCCUGACGAUCUUCGACUUCAUCCAGUUGUUGCUGAU
CGUGAUUGGGGCUAUUGCAGUAGUCGCUGUCCUCCAGCCUUACAUUUUUG
UCGCGACCGUUCCGGUGAUCGUGGCGUUUAUCAUGCUGCGGGCCUAUUUC
UUGCAGACGUCACAGCAGCUUAAGCAACUGGAGUCUGAAGGGAGGUCGCC
UAUCUUUACGCAUCUUGUGACCAGUUUGAAGGGAUUGUGGACGUUGCGCG
CCUUUGGCAGGCAGCCCUACUUUGAAACACUGUUCCACAAAGCGCUGAAU
CUCCAUACGGCAAAUUGGUUUUUGUAUUUGAGUACCCUCCGAUGGUUUCA
GAUGCGCAUUGAGAUGAUUUUUGUGAUCUUCUUUAUCGCGGUGACUUUUA
UCUCCAUCUUGACCACGGGAGAGGGCGAGGGACGGGUCGGUAUUAUCCUG
ACACUCGCCAUGAACAUUAUGAGCACUUUGCAGUGGGCAGUGAACAGCUC
GAUUGAUGUGGAUAGCCUGAUGAGGUCCGUUUCGAGGGUCUUUAAGUUCA
UCGACAUGCCGACGGAGGGAAAGCCCACAAAAAGUACGAAACCCUAUAAG
AAUGGGCAAUUGAGUAAGGUAAUGAUCAUCGAGAACAGUCACGUGAAGAA
GGAUGACAUCUGGCCUAGCGGGGGUCAGAUGACCGUGAAGGACCUGACGG
CAAAAUACACCGAGGGAGGGAACGCAAUCCUUGAAAACAUCUCGUUCAGC
AUUAGCCCCGGUCAGCGUGUGGGGUUGCUCGGGAGGACCGGGUCAGGAAA
AUCGACGUUGCUGUCGGCCUUCUUGAGACUUCUGAAUACAGAGGGUGAGA
UCCAGAUCGACGGCGUUUCGUGGGAUAGCAUCACCUUGCAGCAGUGGCGG
AAAGCGUUUGGAGUAAUCCCCAAAAGGUCUUUAUCUUUAGCGGAACCUU
CCGAAAGAAUCUCGAUCCUUAUGAACAGUGGUCAGAUCAAGAGAUUUGGA
AAGUCGCGGACGAGGUUGGCCUUCGGAGUGUAAUCGAGCAGUUUCCGGGA
AAACUCGACUUUGUCCUUGUAGAUGGGGAUGCGUCCUGUCGCAUGGGCA
CAAGCAGCUCAUGUGCCUGGCGCGAUCCGUCCUCUCUAAAGCGAAAAUUC
UUCUCUUGGAUGAACCUUCGGCCCAUCUGGACCCGGUAACGUAUCAGAUC
AUCAGAAGGACACUUAAGCAGGCGUUUGCCGACUGCACGUGAUUCUCUG
UGAGCAUCGUAUCGAGGCCAUGCUCGAAUGCCAGCAAUUUCUUGUCAUCG
AAGAGAAUAAGGUCCGCCAGUACGACUCCAUCCAGAAGCUGCUUAAUGAG
AGAUCAUUGUUCCGGCAGGCGAUUUCACCAUCCGAUAGGGUGAAACUUUU
UCCACACAGAAAUUCGUCGAAGUGCAAGUCCAAACCGCAGAUCGCGGCCU
UGAAAGAAGAGACUGAAGAAGAAGUUCAAGACACGCGUCUUCACCAUCAC
CAUCACCAUCACCAUCACCAUUAAY

Codon-Optimized Human CFTR mRNA:
(SEQ ID NO.: 9)
XAUGCAGCGGUCCCCGCUCGAAAAGGCCAGUGUCGUGUCCAAACUCUUCU
UCUCAUGGACUCGGCCUAUCCUUAGAAAGGGGUAUCGGCAGAGGCUUGAG UUGUCUGACAUCUACCAGAUCCCCUCGGUAGAUUCGGCGGAUAACCUCUC
GGAGAAGCUCGAACGGGAAUGGGACCGCGAACUCGCGUCUAAGAAAAACC
CGAAGCUCAUCAACGCACUGAGAAGGUGCUUCUUCUGGCGGUUCAUGUUC
UACGGUAUCUUCUUGUAUCUCGGGGAGGUCACAAAAGCAGUCCAACCCCU
GUUGUUGGGUCGCAUUAUCGCCUCGUACGACCCCGAUAACAAAGAAGAAC
GGAGCAUCGCGAUCUACCUCGGGAUCGGACUGUGUUUGCUUUUCAUCGUC
AGAACACUUUUGUUGCAUCCAGCAAUCUUCGGCCUCCAUCACAUCGGUAU
GCAGAUGCGAAUCGCUAUGUUUAGCUUGAUCUACAAAAAGACACUGAAAC
UCUCGUCGCGGGUGUUGGAUAAGAUUUCCAUCGGUCAGUUGGUGUCCCUG
CUUAGUAAUAACCUCAACAAAUUCGAUGAGGGACUGGCGCUGGCACAUUU
CGUGUGGAUUGCCCCGUUGCAAGUCGCCCUUUUGAUGGGCCUUAUUGGG
AGCUGUUGCAGGCAUCUGCCUUUUGUGGCCUGGGAUUUCUGAUUGUGUUG
GCAUUGUUUCAGGCUGGGCUUGGGCGGAUGAUGAUGAAGUAUCGCGACCA
GAGAGCGGGUAAAAUCUCGGAAAGACUCGUCAUCACUUCGGAAAUGAUCG
AAAACAUCCAGUCGGUCAAAGCCUAUUGCUGGGAAGAAGCUAUGGAGAAG
AUGAUUGAAAACCUCCGCCAAACUGAGCUGAAACUGACCCGCAAGGCGGC
GUAUGUCCGGUAUUUCAAUUCGUCAGCGUUCUUCUUUUCCGGGUUCUUCG
UUGUCUUUCUCUCGGUUUUGCCUUAUGCCUUGAUUAAGGGGAUUAUCCUC
CGCAAGAUUUUCACCACGAUUUCGUUCUGCAUUGUAUUGCGCAUGGCAGU
GACACGGCAAUUUCCGUGGGCCGUGCAGACAUGGUAUGACUCGCUUGGAG
CGAUCAACAAAAUCCAAGACUUCUUGCAAAAGCAAGAGUACAAGACCCUG
GAGUACAAUCUUACUACUACGGAGGUAGUAAUGGAGAAUGUGACGGCUUU
UUGGGAAGAGGGUUUUGGAGAACUGUUUGAGAAAGCAAAGCAGAAUAACA
ACAACCGCAAGACCUCAAAUGGGGACGAUUCCCUGUUUUUCUCGAACUUC
UCCCUGCUCGGAACACCCGUGUUGAAGGACAUCAAUUUCAAGAUUGAGAG
GGGACAGCUUCUCGCGGUAGCGGGAAGCACUGGUGCGGGAAAAACUAGCC
UCUUGAUGGUGAUUAUGGGGGAGCUUGAGCCCAGCGAGGGGAAGAUUAAA
CACUCCGGGCGUAUCUCAUUCUGUAGCCAGUUUUCAUGGAUCAUGCCCGG
AACCAUUAAAGAGAACAUCAUUUUCGGAGUAUCCUAUGAUGAGUACCGAU
ACAGAUCGGUCAUUAAGGCGUGCCAGUUGGAAGAGGACAUUUCUAAGUUC
GCCGAGAAGGAUAACAUCGUCUUGGGAGAAGGGGGUAUUACAUUGUCGGG
AGGGCAGCGAGCGCGGAUCAGCCUCGCGAGAGCGGUAUACAAAGAUGCAG
AUUUGUAUCUGCUUGAUUCACCGUUUGGAUACCUCGACGUAUUGACAGAA
AAAGAAAUCUUCGAGUCGUGCGUGUGUAAACUUAUGGCUAAUAAGACGAG
AAUCCUGGUGACAUCAAAAAUGGAACACCUUAAGAAGGCGGACAAGAUCC
UGAUCCUCCACGAAGGAUCGUCCUACUUUUACGGCACUUUCUCAGAGUUG
CAAAACUUGCAGCCGGACUUCUCAAGCAAACUCAUGGGGUGUGACUCAUU
CGACCAGUUCAGCGCGAACGGCGGAACUCGAUCUUGACGGAAACGCUGC
ACCGAUUCUCGCUUGAGGGUGAUGCCCCGGUAUCGUGGGACCGAGACAAAG
AAGCAGUCGUUUAAGCAGACAGGAGAAUUGGUGAGAAAAGAAAGAACAG
UAUCUUGAAUCCUAUUAACUCAAUUCGCAAGUUCUCAAUCGUCCAGAAAA -continued

CUCCACUGCAGAUGAAUGGAAUUGAAGAGGAUUCGGACGAACCCCUGGAG

CGCAGGCUUAGCCUCGUGCCGGAUUCAGAGCAAGGGGAGGCCAUUCUUCC

CCGGAUUUCGGUGAUUUCAACCGGACCUACACUUCAGGCGAGGCGAAGGC

AAUCCGUGCUCAACCUCAUGACGCAUUCGGUAAACCAGGGGCAAAACAUU

CACCGCAAAACGACGGCCUCAACGAGAAAAGUGUCACUUGCACCCCAGGC

GAAUUUGACUGAACUCGACAUCUACAGCCGUAGGCUUUCGCAAGAAACCG

GACUUGAGAUCAGCGAAGAAAUCAAUGAAGAAGAUUUGAAAGAGUGUUUC

UUUGAUGACAUGGAAUCAAUCCCAGCGGUGACAACGUGGAACACAUACUU

GCGUUACAUCACGGUGCACAAGUCCUUGAUUUUCGUCCUCAUCUGGUGUC

UCGUGAUCUUUCUCGCUGAGGUCGCAGCGUCACUUGUGGUCCUCUGGCUG

CUUGGUAAUACGCCCUUGCAAGACAAAGGCAAUUCUACACACUCAAGAAA

CAAUUCCUAUGCCGUGAUUAUCACUUCUACAAGCUCGUAUUACGUGUUUU

ACAUCUACGUAGGAGUGGCCGACACUCUGCUCGCGAUGGGUUUCUUCCGA

GGACUCCCACUCGUUCACACGCUUAUCACUGUCUCCAAGAUUCUCCACCA

UAAGAUGCUUCAUAGCGUACUGCAGGCUCCCAUGUCCACCUUGAAUACGC

UCAAGGCGGGAGGUAUUUUGAAUCGCUUCUCAAAAGAUAUUGCAAUUUUG

GAUGACCUUCUGCCCCUGACGAUCUUCGACUUCAUCCAGUUGUUGCUGAU

CGUGAUUGGGGCUAUUGCAGUAGUCGCUGUCCUCCAGCCUUACAUUUUUG

UCGCGACCGUUCCGGUGAUCGUGGCGUUUAUCAUGCUGCGGGCCUAUUUC

UUGCAGACGUCACAGCAGCUUAAGCAACUGGAGUCUGAAGGGAGGUCGCC

UAUCUUUACGCAUCUUGUGACCAGUUUGAAGGGAUUGUGGACGUUGCGCG

CCUUUGGCAGGCAGCCCUACUUUGAAACACUGUUCCACAAAGCGCUGAAU

CUCCAUACGGCAAAUGGUUUUUGUAUUUGAGUACCCUCCGUGGUUUCA

GAUGCGCAUUGAGAUGAUUUUUGUGAUCUUCUUUAUCGCGGUGACUUUA

UCUCCAUCUUGACCACGGGAGAGGGCGAGGGACGGGUCGGUAUUAUCCUG

ACACUCGCCAUGAACAUUAUGAGCACUUUGCAGUGGGCAGUGAACAGCUC

GAUUGAUGUGGAUAGCCUGAUGAGGUCCGUUCGAGGGUCUUUAAGUUCA

UCGACAUGCCGACGGAGGGAAAGCCCACAAAAAGUACGAAACCCUAUAAG

AAUGGGCAAUUGAGUAAGGUAAUGAUCAUCGAGAACAGUCACGUGAAGAA

GGAUGACAUCUGGCCUAGCGGGGGUCAGAUGACCGUGAAGGACCUGACGG

CAAAAUACACCGAGGGAGGGAACGCAAUCCUUGAAAACAUCUCGUUCAGC

AUUAGCCCCGGUCAGCGUGUGGGGUUGCUCGGGAGGACCGGGUCAGGAAA

AUCGACGUUGCUGUCGGCCUUCUUGAGACUUCUGAAUACAGAGGGUGAGA

UCCAGAUCGACGGCGUUUCGUGGGAUAGCAUCACCUUGCAGCAGUGGCGG

AAAGCGUUUGGAGUAAUCCCCCAAAAGGUCUUUAUCUUUAGCGGAACCUU

CCGAAAGAAUCUCGAUCCUUAUGAACAGUGGUCAGAUCAAGAGAUUUGGA

AAGUCGCGGACGAGGUUGGCCUUCGGAGUGUAAUCGAGCAGUUUCCGGGA

AAACUCGACUUUGUCCUUGUAGAUGGGGGAUGCGUCCUGUCGCAUGGGCA

CAAGCAGCUCAUGUGCCUGGCGCGAUCCGUCCUCUCUAAAGCGAAAAUUC

UUCUCUUGGAUGAACCUUCGGCCCAUCUGGACCCCGGUAACGUAUCAGAUC

-continued

AUCAGAAGGACACUUAAGCAGGCGUUUGCCGACUGCACGGUGAUUCUCUG

UGAGCAUCGUAUCGAGGCCAUGCUCGAAUGCCAGCAAUUUCUUGUCAUCG

AAGAGAAUAAGGUCCGCCAGUACGACUCCAUCCAGAAGCUGCUUAAUGAG

AGAUCAUUGUUCCGGCAGGCGAUUUCACCAUCCGAUAGGGUGAAACUUUU

UCCACACAGAAAUUCGUCGAAGUGCAAGUCCAAACCGCAGAUCGCGGCCU

UGAAAGAAGAGACUGAAGAAGAAGUUCAAGACACGCGUCUUUAAY

Codon Optimized Human CFTR mRNA coding sequence
with a Growth Hormone Leader Sequence
(italicized and underlined)
(SEQ ID NO: 10)

*<u>AUGGCCACUGGAUCAAGAACCUCACUGCUGCUCGCUUUUGGACUGCUUUG</u>*

*<u>CCUGCCCUGGUUGCAAGAAGGAUCGGCUUUCCCGACCAUCCCACUCUCC</u>*A

UGCAGCGGUCCCCGCUCGAAAAGGCCAGUGUCGUGUCCAAACUCUUCUUC

UCAUGGACUCGGCCUAUCCUUAGAAAGGGGUAUCGGCAGAGGCUUGAGUU

GUCUGACAUCUACCAGAUCCCCUCGGUAGAUUCGGCGGAUAACCUCUCGG

AGAAGCUCGAACGGGAAUGGGACCGCGAACUCGCGUCUAAGAAAAACCCG

AAGCUCAUCAACGCACUGAGAAGGUGCUUCUUCUGGCGGUUCAUGUUCUA

CGGUAUCUUCUUGUAUCUCGGGGAGGUCACAAAAGCAGUCCAACCCCUGU

UGUGGGGUCGCAUUAUCGCCUCGUACGACCCCGAUAACAAAGAAGAACGG

AGCAUCGCGAUCUACCUCGGGAUCGGACUGUGUUUGCUUUUCAUCGUCAG

AACACUUUUGUUGCAUCCAGCAAUCUUCGGCCUCCAUCACAUCGGUAUGC

AGAUGCGAAUCGCUAUGUUUAGCUUGAUCUACAAAAAGACACUGAAACUC

UCGUCGCGGGUGUGGAUAAGAUUUCCAUCGGUCAGUUGGUGUCCCUGCU

UAGUAAUAACCUCAACAAAUUCGAUGAGGGACUGGCGCUGGACAUUUCG

UGUGGAUUGCCCCGUUGCAAGUCGCCCUUUUGAUGGGCUUAUUUGGGAG

CUGUUGCAGGCAUCUGCCUUUUGUGGCCUGGGAUUUCUGAUUGUGUUGGC

AUUGUUUCAGGCUGGGCUUGGGCGGAUGAUGAUGAAGUAUCGCGACCAGA

GAGCGGGUAAAAUCUCGGAAAGACUCGUCAUCACUUCGGAAAUGAUCGAA

AACAUCCAGUCGGUCAAAGCCUAUUGCUGGGAAGAAGCUAUGGAGAAGAU

GAUUGAAACCUCCGCCAAACUGAGCUGAAACUGACCCGCAAGGCGGCGU

AUGUCCGGUAUUUCAAUUCGUCAGCGUUCUUCUUUCCGGGUUCUUCGUU

GUCUUUCUCUCGGUUUUGCCUUAUGCCUUGAUUAAGGGGAUUAUCCUCCG

CAAGAUUUCACCACGAUUUCGUUCUGCAUUGUAUUGCGCAUGGCAGUGA

CACGGCAAUUUCCGUGGCCGUGCAGACAUGGUAUGACUCGCUUGGAGCG

AUCAACAAAAUCCAAGACUUCUUGCAAAAGCAAGAGUACAAGACCCUGGA

GUACAAUCUUACUACUACGGAGGUAGUAAUGGAGAAUGUGACGGCUUUUU

GGGAAGAGGGUUUUGGAGAACUGUUUGAGAAAGCAAAGCAGAAUAACAAC

AACCGCAAGACCUCAAAUGGGGACGAUUCCCUGUUUUUCUCGAACUUCUC

CCUGCUCGGAACACCCGUGUUGAAGGACAUCAAUUUCAAGAUUGAGAGGG

GACAGCUUCUCGCGGUAGCGGGAAGCACUGGUGCGGGAAAAACUAGCCUC

UUGAUGGUGAUUAUGGGGGAGCUUGAGCCCAGCGAGGGGAAGAUUAAACA

CUCCGGGCGUAUCUCAUUCUGUAGCCAGUUUUCAUGGAUCAUGCCCGGAA

CCAUUAAAGAGAACAUCAUUUUCGGAGUAUCCUAUGAUGAGUACCGAUAC

-continued

AGAUCGGUCAUUAAGGCGUGCCAGUUGGAAGAGGACAUUUCUAAGUUCGC

CGAGAAGGAUAACAUCGUCUUGGGAGAAGGGGUAUUACAUUGUCGGGAG

GGCAGCGAGCGCGGAUCAGCCUCGCGAGAGCGGUAUACAAAGAUGCAGAU

UUGUAUCUGCUUGAUUCACCGUUUGGAUACCUCGACGUAUUGACAGAAA

AGAAAUCUUCGAGUCGUGCGUGUGUAAACUUAUGGCUAAUAAGACGAGAA

UCCUGGUGACAUCAAAAAUGGAACACCUUAAGAAGGCGGACAAGAUCCUG

AUCCUCCACGAAGGAUCGUCCUACUUUUACGGCACUUUCUCAGAGUUGCA

AAACUUGCAGCCGGACUUCUCAAGCAAACUCAUGGGGUGUGACUCAUUCG

ACCAGUUCAGCGCGGAACGGCGGAACUCGAUCUUGACGGAAACGCUGCAC

CGAUUCUCGCUUGAGGGUGAUGCCCCGGUAUCGUGGACCGAGACAAAGAA

GCAGUCGUUUAAGCAGACAGGAGAAUUUGGUGAGAAAAGAAAGAACAGUA

UCUUGAAUCCUAUUAACUCAAUUCGCAAGUUCUCAAUCGUCCAGAAAACU

CCACUGCAGAUGAAUGGAAUUGAAGAGGAUUCGGACGAACCCCUGGAGCG

CAGGCUUAGCCUCGUGCCGGAUUCAGAGCAAGGGGAGGCCAUUCUUCCCC

GGAUUUCGGUGAUUUCAACCGGACCUACACUUCAGGCGAGGCGAAGGCAA

UCCGUGCUCAACCUCAUGACGCAUUCGGUAAACCAGGGGCAAAACAUUCA

CCGCAAAACGACGGCCUCAACGAGAAAAGUGUCACUUGCACCCCAGGCGA

AUUUGACUGAACUCGACAUCUACAGCCGUAGGCUUUCGCAAGAAACCGGA

CUUGAGAUCAGCGAAGAAAUCAAUGAAGAAGAUUUGAAAGAGUGUUUCUU

UGAUGACAUGGAAUCAAUCCCAGCGGUGACAACGUGGAACACAUACUUGC

GUUACAUCACGGUGCACAAGUCCUUGAUUUUCGUCCUCAUCUGGUGUCUC

GUGAUCUUUCUCGCUGAGGUCGCAGCGUCACUUGUGGUCCUCUGGCUGCU

UGGUAAUACGCCCUUGCAAGACAAAGGCAAUUCUACACACUCAAGAAACA

AUUCCUAUGCCGUGAUUAUCACUUCUACAAGCUCGUAUUACGUGUUUUAC

AUCUACGUAGGAGUGGCCGACACUCUGCUCGCGAUGGGUUUCUUCCGAGG

ACUCCCACUCGUUCACACGCUUAUCACUGUCUCCAAGAUUCUCCACCAUA

AGAUGCUUCAUAGCGUACUGCAGGCUCCCAUGUCCACCUUGAAUACGCUC

AAGGCGGGAGGUAUUUUGAAUCGCUUCUCAAAAGAUAUUGCAAUUUUGGA

UGACCUUCUGCCCCUGACGAUCUUCGACUUCAUCCAGUUGUUGCUGAUCG

UGAUUGGGCUAUUGCAGUAGUCGCUGUCCUCCAGCCUUACAUUUUUGUC

GCGACCGUUCCGGUGAUCGUGGCGUUUAUCAUGCUGCGGGCCUAUUUCUU

GCAGACGUCACAGCAGCUUAAGCAACUGGAGUCUGAAGGGAGGUCGCCUA

UCUUUACGCAUCUUGUGACCAGUUUGAAGGGAUUGUGGACGUUGCGCGCC

UUUGGCAGGCAGCCCUACUUUGAAACACUGUUCCACAAAGCGCUGAAUCU

CCAUACGGCAAAUUGGUUUUUGUAUUUGAGUACCCUCCGAUGGUUUCAGA

UGCGCAUUGAGAUGAUUUUUGUGAUCUUCUUUAUCGCGGUGACUUUUAUC

UCCAUCUUGACCACGGGAGAGGGCGAGGGACGGGUCGGUAUUAUCCUGAC

ACUCGCCAUGAACAUUAUGAGCACUUUGCAGUGGGCAGUGAACAGCUCGA

UUGAUGUGGAUAGCCUGAUGAGGUCCGUUUCGAGGGUCUUUAAGUUCAUC

GACAUGCCGACGGAGGGAAAGCCCACAAAAAGUACGAAACCCUAUAAGAA

UGGGCAAUUGAGUAAGGUAAUGAUCAUCGAGAACAGUCACGUGAAGAAGG

AUGACAUCUGGCCUAGCGGGGGUCAGAUGACCGUGAAGGACCUGACGGCA

AAAUACACCGAGGGAGGGAACGCAAUCCUUGAAAACAUCUCGUUCAGCAU

UAGCCCCGGUCAGCGUGUGGGGUUGCUCGGGAGGACCGGGUCAGGAAAAU

CGACGUUGCUGUCGGCCUUCUUGAGACUUCUGAAUACAGAGGGUGAGAUC

CAGAUCGACGGCGUUUCGUGGGAUAGCAUCACCUUGCAGCAGUGGCGGAA

AGCGUUUGGAGUAAUCCCCCAAAAGGUCUUUAUCUUUAGCGGAACCUUCC

GAAAGAAUCUCGAUCCUUAUGAACAGUGGUCAGAUCAAGAGAUUUGGAAA

GUCGCGGACGAGGUUGGCCUUCGGAGUGUAAUCGAGCAGUUUCCGGGAAA

ACUCGACUUUGUCCUUGUAGAUGGGGAUGCGUCCUGUCGCAUGGGCACA

AGCAGCUCAUGUGCCUGGCGCGAUCCGUCCUCUCUAAAGCGAAAAUUCUU

CUCUUGGAUGAACCUUCGGCCCAUCUGGACCCGGUAACGUAUCAGAUCAU

CAGAAGGACACUUAAGCAGGCGUUUGCCGACUGCACGGUGAUUCUCUGUG

AGCAUCGUAUCGAGGCCAUGCUCGAAUGCCAGCAAUUUCUUGUCAUCGAA

GAGAAUAAGGUCCGCCAGUACGACUCCAUCCAGAAGCUGCUUAAUGAGAG

AUCAUUGUUCCGGCAGGCGAUUUCACCAUCCGAUAGGGUGAAACUUUUUC

CACACAGAAAUUCGUCGAAGUGCAAGUCCAAACCGCAGAUCGCGGCCUUG

AAAGAAGAGACUGAAGAAGAAGUUCAAGACACGCGUCUUUAA

Aliquots of 50 mg/mL ethanolic solutions of cKK-E12, DOPE, Chol and DMG-PEG2K were mixed in a molar ratio of 40:30:25:5 and diluted with ethanol to 3 mL final volume. Separately, an aqueous buffered solution (10 mM citrate/150 mM NaCl, pH 4.5) of FIX, ASS1, or FFL mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. The final concentration of FIX mRNA was approximately 0.77 mg/mL FIX mRNA (encapsulated), $Z_{ave}$=76 nm, PDI=0.08. The final concentration of ASS1 mRNA was approximately 0.64 mg/mL ASS1 mRNA (encapsulated), $Z_{ave}$=78 nm (Dv (50)=46 nm; Dv(90)=96 nm). The final concentration of FFL mRNA was approximately 1.31 mg/mL FFL mRNA (encapsulated), $Z_{ave}$=75 nm, PDI—0.11. The final concentration of SMN mRNA was approximately 1.85 mg/mL SMN mRNA (encapsulated). Average particle size ($Z_{ave}$)=71 nm, (particle size for 50% of particles was 44 nm or less (Dv(50))=44 nm; and the particle size for 90% of the particles was 93n or less (Dv(90)=93 nm)).

Example 2. Administration of mRNA-Loaded Liposome Nanoparticles

This example illustrates exemplary methods of administering mRNA-loaded liposome nanoparticles and methods for analyzing delivered mRNA and subsequently expressed protein in various target tissues in vivo.

All studies were performed using male CD-1 mice of approximately 6-8 weeks of age at the beginning of each experiment. Samples were introduced by a single bolus tail-vein injection of an equivalent total dose of 1.0 mg/kg (or otherwise specified) of encapsulated FIX, FFL or ASS1 mRNA. Mice were sacrificed and perfused with saline at the designated time points.

Various organ tissues such as the liver, spleen, kidney and heart of each mouse was harvested, apportioned into separate parts, and stored in either 10% neutral buffered formalin or snap-frozen and stored at −80° C. for analysis.

All animals were euthanized by $CO_2$ asphyxiation at designated time points post dose administration (±5%) followed by thoracotomy and terminal cardiac blood collection. Whole blood (maximal obtainable volume) was collected via cardiac puncture on euthanized animals into serum separator tubes, allowed to clot at room temperature for at least 30 minutes, centrifuged at 22° C.±5° C. at 9300 g for 10 minutes, and the serum extracted. For interim blood collections, approximately 40-50 µL of whole blood was collected via facial vein puncture or tail snip. Samples collected from non-treatment animals were used as a baseline ASS1 levels for comparison to study animals.

Enzyme-Linked Immunosorbent Assay (ELISA) Analysis

A. Human FIX ELISA

Quantification of FIX protein was performed following procedures reported for human FIX ELISA kit (AssayMax, Assay Pro, Catalog # EF1009-1).

B. Human ASS1 ELISA

Standard ELISA procedures were followed employing mouse anti-ASS1 2D1-2E12 IgG as the capture antibody with rabbit anti-ASS1 #3285 IgG as the secondary (detection) antibody (Shire Human Genetic Therapies). Horseradish peroxidase (HRP)-conjugated goat anti-rabbit IgG was used for activation of the 3,3',5,5'-tetramethylbenzidine (TMB) substrate solution. The reaction was quenched using 2N H2SO4 after 20 minutes. Detection was monitored via absorption (450 nm) on a Molecular Device SpectraMax instrument. Untreated mouse serum and organs and human ASS1 protein were used as negative and positive controls, respectively.

IVIS Bioluminometer Measurements

To visual luminescence in treated mice, several steps were followed. Anesthesia using isoflurane vaporizer at 1-3% (usually @2.5%) was initially employed. Using a microsprayer, 50 µL/animal of luciferin in PBS was administered at 60 mg/mL via intratracheal/intranasal. Luciferin was allowed to distribute for 5-10 minutes. Animals were placed in an isoflurane chamber until anesthetized. Anesthetized animals were placed into the IVIS imaging chamber at dorsal recumbency and positioned into the manifold. Pictures of mice were taken. In these Examples, the acquisition settings providing highest sensitivity were: camera height at D level, F/Stop at f1, binning at high resolution, and exposure time at 5 minutes. Exposures were repeated up to 3 times (5, 10 and 15 minutes post Luciferin Injection).

In Situ Hybridization (ISH) Analysis

In situ hybridization was performed using "ZZ" probe technology. Probes were generated based on codon-optimized sequence of human messenger RNA. Tissues were fixed for 24-48 hours in 10% neutral buffered formalin and embedded in paraffin. Positive detection of desired mRNA was achieved through 6 consecutive amplification steps followed by chromagenic visualization using 3,3'-diaminobenzidine (DAB). Positive signal was compared to that of untreated mouse.

Example 3. Highly Effective In Vivo Production of Therapeutic Proteins

This example demonstrates highly efficient and sustained production of proteins encoded by mRNA delivered by liposomes incorporating the cationic lipids described herein (e.g., cKK-E12) in serum and various organ tissues.

In Vivo Human FIX Protein Production Results

The production of human FIX protein via hFIX mRNA-loaded cKK-E12-based lipid nanoparticles was tested in CD-1 mice as a single, bolus intravenous injection. FIG. 1 represents the amount of human FIX protein detected via ELISA when treating mice with human FIX mRNA-loaded cKK-E12-based lipid nanoparticles as compared to a C12-200-based lipid nanoparticle encapsulating hFIX mRNA. The mice were sacrificed twenty-four hours post-injection and organs were harvested (as described above).

C12-200-based lipid nanoparticles have been shown to be an effective vehicle to deliver and express mRNA in vivo (see, PCT Application Publication NO. WO2012170930, the disclosure of which is hereby incorporated by reference). Surprisingly, as represented in FIG. 1, cKK-E12 based lipid nanoparticles are even more effective in delivering human FIX mRNA in vivo, resulting in close to 50% higher protein expression detected in the plasma of the treated mice, as compared to C12-200-based lipid nanoparticles.

Figure 2:
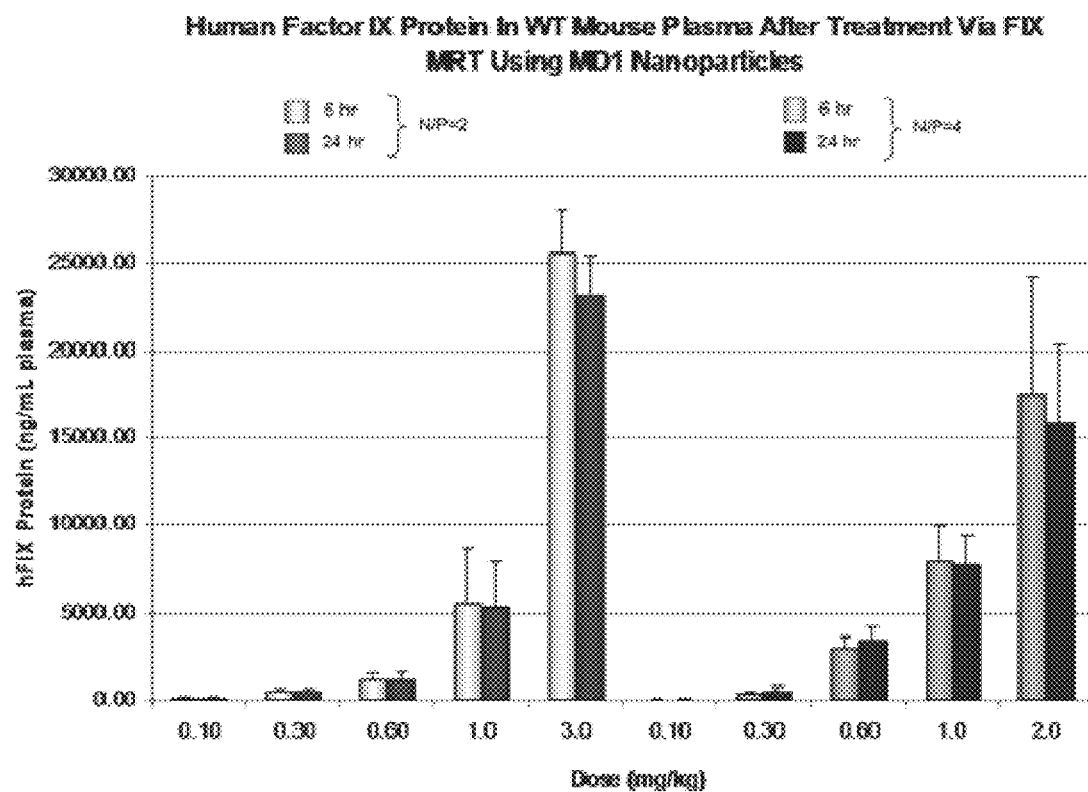
FIG. 2 shows an exemplary graph of FIX detected in the plasma of mice treated with 0.1, 0.3, 0.6, 1.0, or 3.0 mg/kg of one of two ratios of FIX mRNA containing cKK-E12 liposomes either 6 or 24 hours after administration.

FIG. 2 shows the results of a dose-response experiment as represented by the amount of human FIX protein detected via ELISA when treating mice with human FIX mRNA-loaded cKK-E12-based lipid nanoparticles at various doses. The mice were bled at 6 hours and sacrificed twenty-four hours post-injection and organs were harvested (as described above).

A clear dose response was achieved when measuring liver levels of human FIX protein. The dosing range was from 0.10-3.0 mg/kg of encapsulated human FIX mRNA. These data demonstrate the ability of the lipid nanoparticles to efficiently deliver messenger RNA, release the payload and process this exogenous mRNA via translation to produce human FIX protein, which is then subsequently secreted into the bloodstream. Levels of human FIX protein are well above therapeutic levels (>100 ng/mL plasma) and surpass normal physiological levels (~5 ug/mL plasma) when dosing at 1.0 mg/kg or greater. Further, the plasma residence time of this human protein is sustained through at least 24 hours post administration.

In Vivo Human ASS1 Protein Production Results

Figure 3:
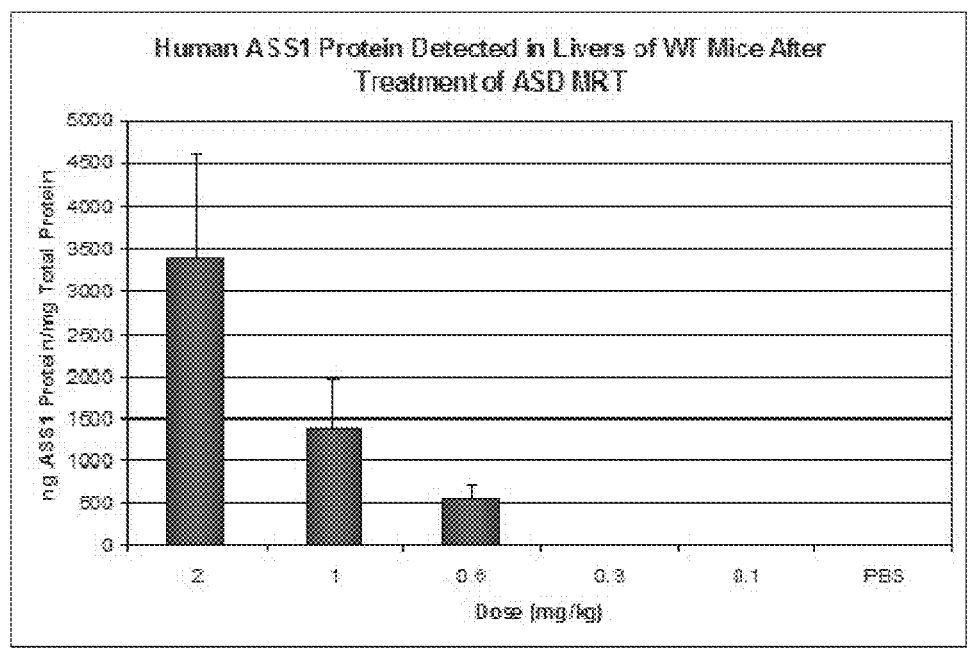
FIG. 3 shows an exemplary graph of the level of ASS1 protein detected in the livers of mice treated with 0.1, 0.3, 0.6, 1.0, or 3.0 mg/kg of ASS1 mRNA-containing cKK-E12 liposomes 24 hours after administration.

The production of human ASS1 protein via codon-optimized hASS1 mRNA-loaded cKK-E12-based lipid nanoparticles was tested in CD-1 mice as a single, bolus intravenous injection. FIG. 3 represents the amount of human ASS1 protein detected via ELISA when treating mice with human ASS1 mRNA-loaded cKK-E12-based lipid nanoparticles at various doses. The mice were sacrificed twenty-four hours post-injection and organs were harvested (as described above).

A clear dose response was achieved when measuring liver levels of human ASS1 protein. As shown in Table 5, the dosing range was from 0.10-2.0 mg/kg of encapsulated human ASS1 mRNA in cKK-E12 lipid nanoparticles. These data demonstrate the ability of the lipid nanoparticles to accumulate in the liver and release the mRNA payload and the liver to process this exogenous mRNA via translation to produce human ASS1 protein.

TABLE 5

Raw values of human ASS1 protein as measured via ELISA analysis (as depicted in FIG. 1). Codon-optimized human ASS1 mRNA was delivered via cKK-E12-based lipid nanoparticles. Doses are based on encapsulated ASS1 mRNA. Values are depicted as nanogram of human ASS1 protein per milligram total protein in liver.

| Dose Encapsulated ASS1 mRNA (mg/kg) | Human ASS1 Protein (ng/mg total protein) |
| --- | --- |
| 0.10 | BLD |
| 0.30 | BLD |
| 0.60 | 546 |
| 1.0 | 1388 |
| 2.0 | 3371 |

BLD = Below Limit of Detection for ELISA.

Figure 4:
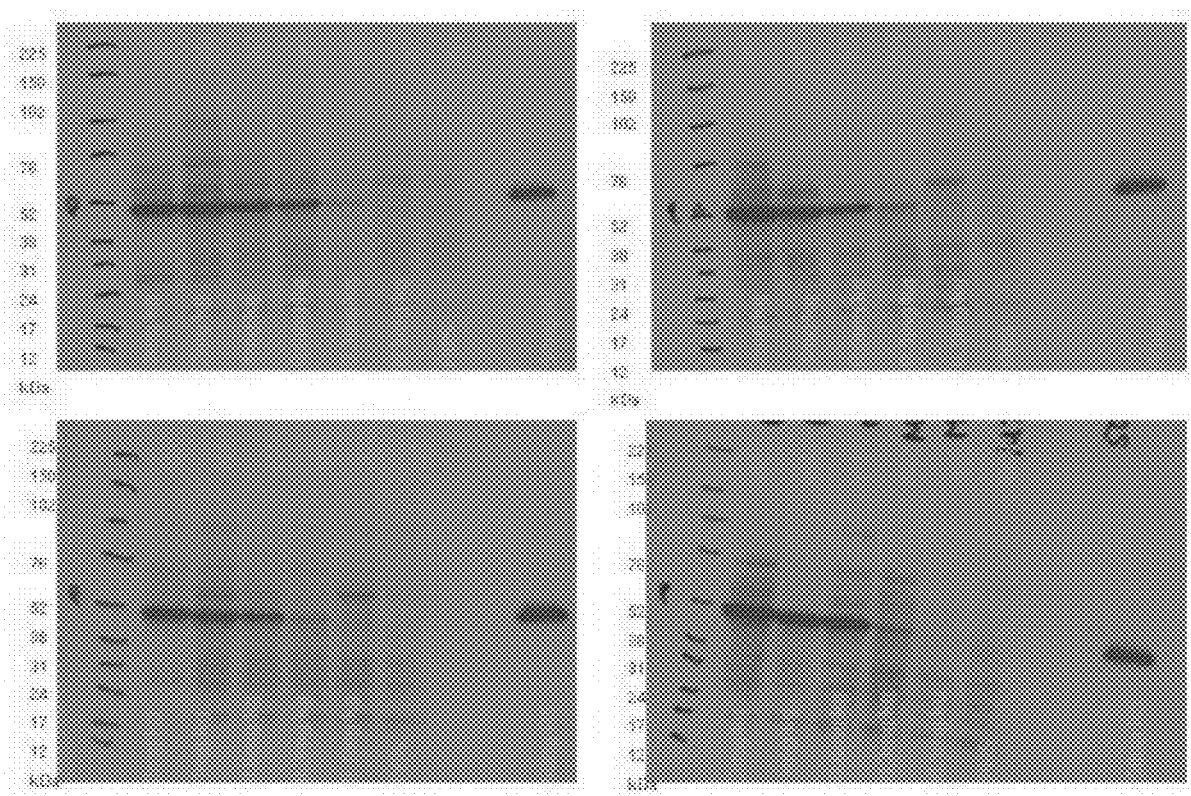
FIG. 4 shows exemplary western blot analyses of ASS1 protein levels in the liver 24 hours post administration of 0.1, 0.3, 0.6, 1.0, or 3.0 mg/kg of cKK-E12 liposomes containing ASS1 mRNA.

While the sensitivity of the ELISA has limitations at lower values, western blot analysis allows for clear visualization of the human ASS1 protein at lower doses (0.3-3.0 mg/kg) (see FIG. 4). FIG. 4 depicts a comparison of human ASS1 protein levels in liver as a function of dose via western blot analysis upon a single intravenous dose of human ASS1 mRNA-encapsulated cKK-E12 lipid nanoparticles. CD1 mice were sacrificed at 24 hours post-administration and livers were harvested and analyzed as described above.

Figure 5:
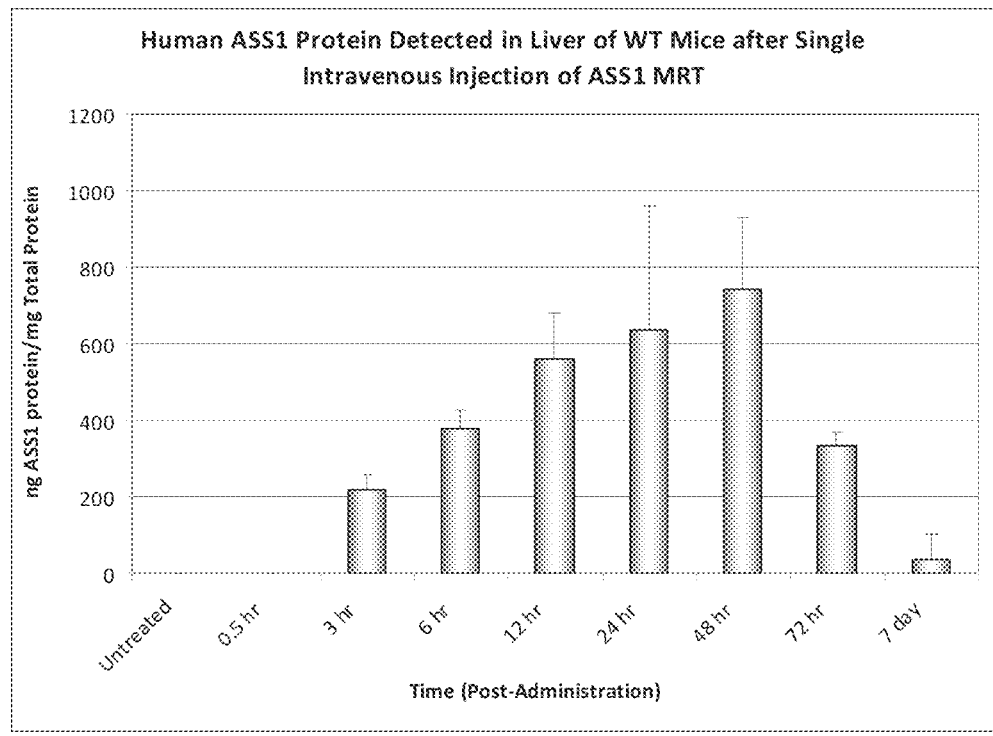
FIG. 5 shows an exemplary graph of ASS1 protein levels in the liver of mice 0.5, 3, 6, 12, 24, 48, 72 hours after a single IV injection of ASS1 mRNA containing cKK-E12 liposomes (1 mg/kg). Also shown is the level of ASS1 protein 7 days after administration.

To further understand the ability of ASS1 mRNA-encapsulated lipid nanoparticles to facilitate the delivery of mRNA to selected organs (liver), a pharmacokinetic analysis was performed, monitoring human ASS1 protein levels in the liver over a one week time period. FIG. 5 depicts the quantity of human ASS1 protein detected in the liver at various time points up to 7 days after administration of human ASS1-loaded lipid nanoparticles (cKK-E12). This was accomplished as a single dose (1.0 mg/kg encapsulated mRNA) given intravenously.

Figure 6:
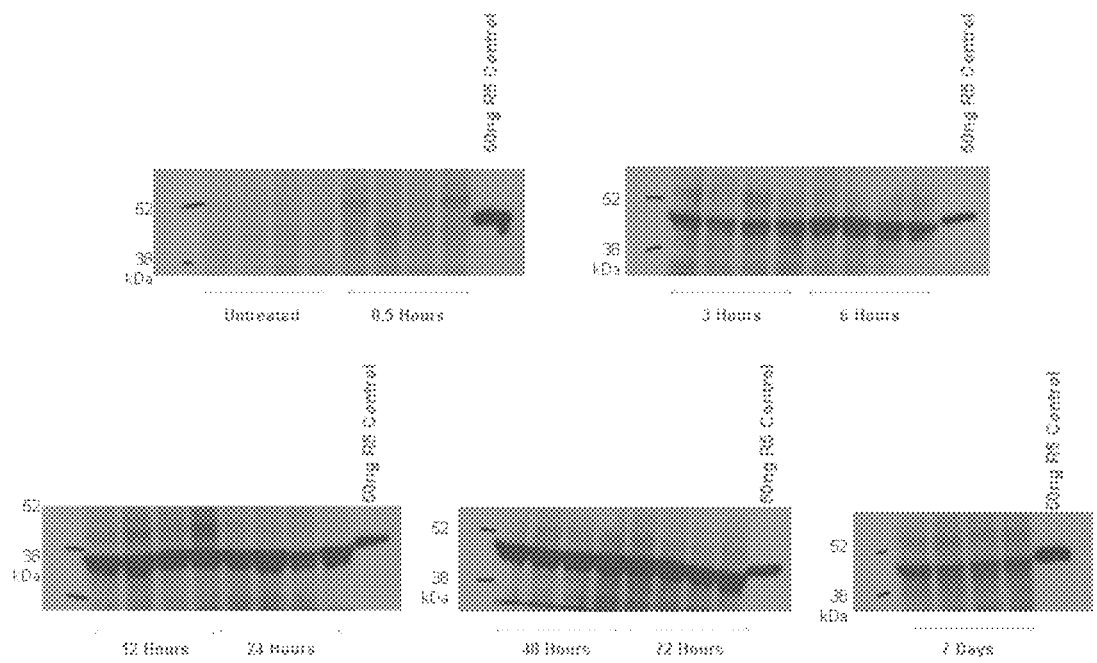
FIG. 6 shows exemplary western blot analyses of ASS1 protein levels in the liver 0.5, 3, 6, 12, 24, 48, 72 hours after a single IV injection of 1 mg/kg ASS1 mRNA containing cKK-E12 liposomes. Also shown is the level of ASS1 protein 7 days after administration.

In this case, we observed a maximum serum level of human ASS1 protein at approximately 24-48 hours post-administration. Measurable levels of protein were still observed 1 week post-administration as determined by both ELISA and western blot (FIGS. 5 and 6, respectively). FIG. 6 depicts a comparison of human ASS1 protein levels in liver over time via western blot analysis upon a single intravenous dose of human ASS1 mRNA-encapsulated lipid nanoparticles (1.0 mg/kg dose).

Figure 7:
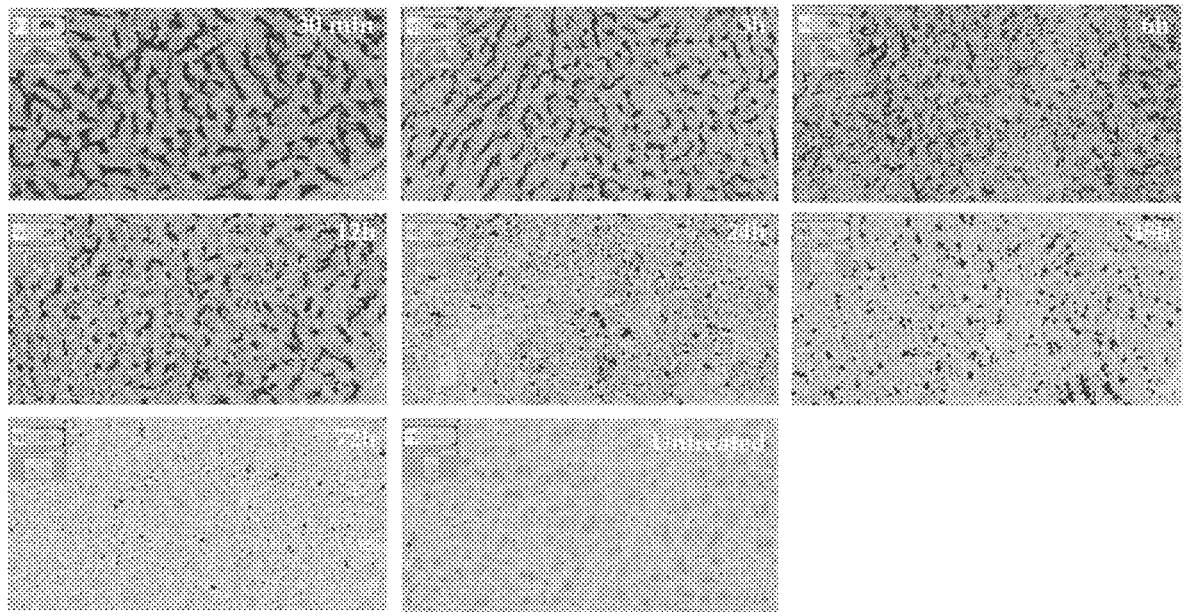
FIG. 7—shows detection of human ASS1 messenger RNA via in situ hybridization in the livers of treated mice. Exogenous mRNA is observable for at least 72 hr post-administration after a single dose (1.0 mg/kg) of ASS1 mRNA-loaded MD1-based lipid nanoparticles. Human ASS1 mRNA is detectable in sinusoidal cells as well as hepatocytes.
Figure 8:
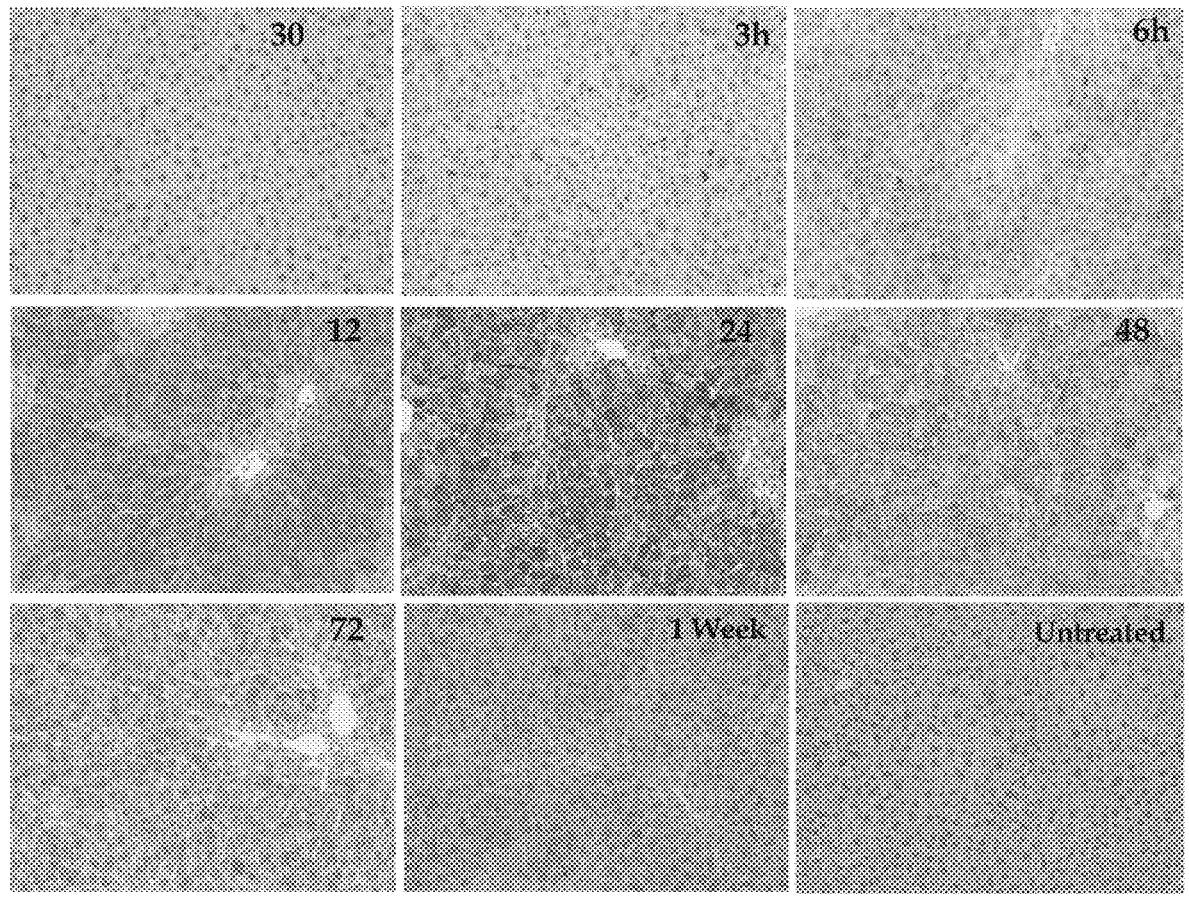
FIG. 8—shows exemplary immunohistochemical staining of ASS1 protein levels in mouse liver 24 hours after administration of 1 mg/kg ASS1 mRNA containing cKK-E12 lipid nanoparticles. Human ASS1 protein is detectable in sinusoidal cells as well as hepatocytes.

Direct detection of the active pharmaceutical ingredient (ASS1 mRNA) in the livers of the treated mice was achieved using in situ hybridization (ISH) based methods. As demonstrated in FIGS. 7 & 8, the exogenous human ASS1 messenger RNA could be detected in high levels at the earliest time point tested (30 minutes) and the signal remained strong for 48 hours after dosing. Further, human ASS1 mRNA was still detectable 72 hours post-administration.

Figure 9:
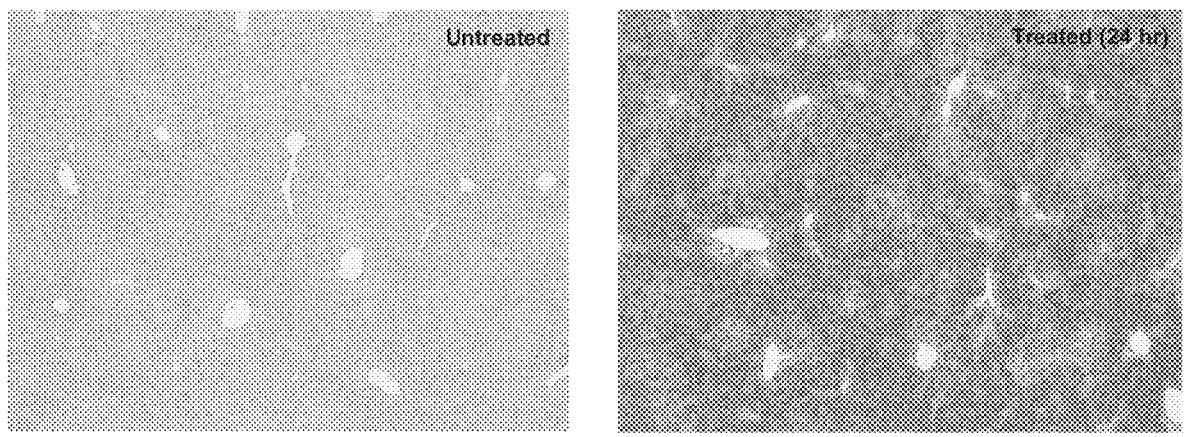
FIG. 9 shows low magnification (4×) immunohistochemical staining of ASS1 protein levels in mouse liver 24 hours after administration of 1 mg/kg ASS1 mRNA containing cKK-E12 liposomes. A comparison to untreated mouse liver (left) demonstrates the widespread distribution of human ASS1 protein throughout the liver.

In addition to ISH, detection of the resulting human ASS1 protein was achieved using immunohistochemical (IHC) means. Using a mouse monoclonal antibody (02D2-2E12) for specific binding, the presence of target human ASS1 protein in the cytoplasm of hepatocytes of treated livers can be readily observed. FIG. 9 shows the immunohistochemical staining of human ASS1 protein in treated mouse livers 24 hours after administration.

In Vivo Delivery of FFL mRNA Via Nebulization

Figure 10:
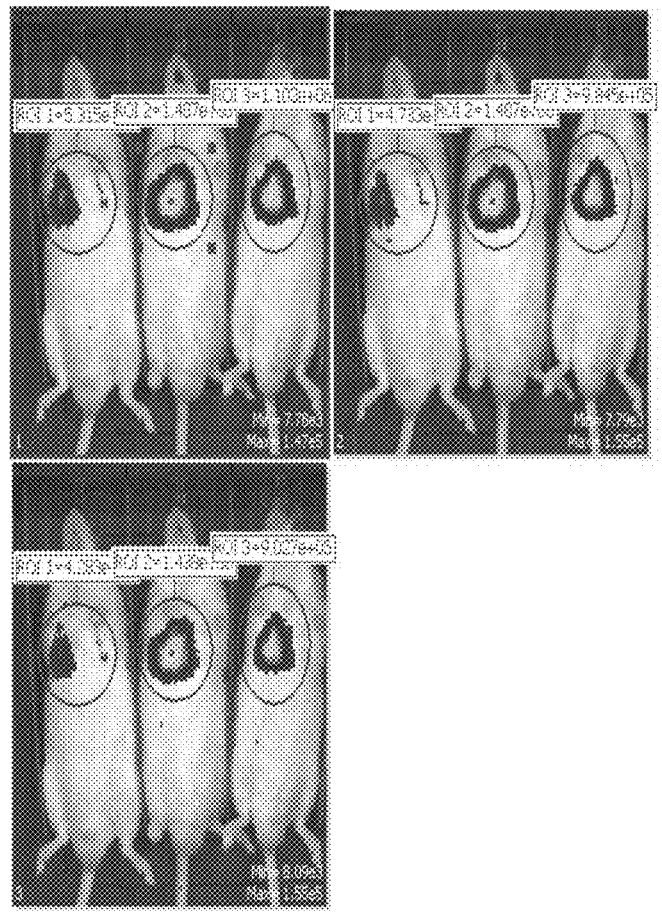
FIG. 10 shows exemplary results illustrating that cKK-E12 lipid nanoparticles efficiently delivered FL mRNA via nebulization. Mice were exposed to milligram of encapsulated FL mRNA and analysis was performed 24 hours post-exposure.

To assess whether additional routes of delivery were feasible, FFL mRNA was encapsulated in cKK-E12 liposomes and those liposomes were nebulized. As shown in FIG. 10, it is possible to efficiently nebulize cKK-E12 based lipid nanoparticles encapsulating mRNA. FIG. 10 represents mice treated with luciferin 24 hours after exposure to nebulized FFL mRNA loaded cKK-E12 lipid nanoparticles.

Example 4. CNS Delivery of hSMN-1 mRNA

This example provides an exemplary cKK-E12 liposome formulations for effective delivery and expression of mRNA in the CNS. Specifically, the example demonstrates that delivery of human survival of motor neuron-1 (hSMN-1) mRNA into various tissues of the brain and spinal cord.

Messenger RNA Material

Codon-optimized human Survival of Motor Neuron-1 (hSMN-1) messenger RNA (see SEQ ID NO: 4) was synthesized by in vitro transcription from a plasmid DNA template encoding the gene, which was followed by the addition of a 5' cap structure (Cap 1) (Fechter, P.; Brownlee, G. G. "Recognition of mRNA cap structures by viral and cellular proteins" J. Gen. Virology 2005, 86, 1239-1249) and a 3' poly(A) tail of approximately 250 nucleotides in length (SEQ ID NO: 15) as determined by gel electrophoresis. The 5' and 3' untranslated regions present in each mRNA product are represented as X and Y, respectively and defined as stated in Example 1.

Formulation Protocol

Lipid nanoparticles (LNP) were formed via standard ethanol injection methods (Ponsa, M.; Foradada, M.; Estelrich, J. "Liposomes obtained by the ethanol injection method" Int. J. Pharm. 1993, 95, 51-56). For the various lipid components, a 50 mg/ml ethanolic stock solutions was prepared and stored at −20° C. In preparation of the cKK-E12 lipid nanoparticle formulation listed in Table 6, each indicated lipid component was added to an ethanol solution to achieve a predetermined final concentration and molar ratio, and scaled to a 3 ml final volume of ethanol. Separately, an aqueous buffered solution (10 mM citrate/150 mM NaCl, pH 4.5) of hSMN-1 mRNA was prepared from a 1 mg/ml stock. The lipid solution was injected rapidly into the aqueous mRNA solution and shaken to yield a final suspension in 20% ethanol. The resulting nanoparticle suspension was filtered and dialysed against 1×PBS (pH 7.4), concentrated and stored between 2-8° C. SMN-1 mRNA concentration was determined via the Ribogreen assay (Invitrogen). Encapsulation of mRNA was calculated by performing the Ribogreen assay with and without the presence of 0.1% Triton-X 100. Particle sizes (dynamic light scattering (DLS)) and zeta potentials were determined using a Malvern Zetasizer instrument in 1×PBS and 1 mM KCl solutions, respectively.

TABLE 6

Exemplary cKK-E12 Lipid Nanoparticle formulation

| Formulations | Components | Molar Ratio of lipids | Final mRNA Concentration | Zeta Parameters |
| --- | --- | --- | --- | --- |
| 1 | cKK-E12<br>DOPE<br>Cholesterol<br>DMG-PEG-2K<br>hSMN-1 mRNA | 40:30:25:5 | 1.8 mg/ml | $Z_{ave}$ = 72 nm;<br>$Dv_{(50)}$ = 49 nm;<br>$Dv_{(90)}$ = 90 nm |

Intrathecal Administration of mRNA Loaded Liposome Nanoparticles

All in vivo studies were performed using either rats or mice of approximately 6-8 weeks of age at the beginning of each experiment. At the start of the experiment, each animal was anesthetized with isoflurane (1-3%, to effect) by inhalation. Once anesthetized, each animal was shaved at the exact injection site (L4-L5 or L5-L6). Following insertion of the needle, reflexive flick of the tail was used to indicate puncture of the dura and confirm intrathecal placement. Each animal received a single bolus intrathecal injection of the test formulation listed in Table 6. All animals were sacrificed 24 hours post injection and perfused with saline.

Isolation of Organ Tissues for Analysis

All animals had the whole brain and spinal cord harvested. The brain was cut longitudinally and placed in one histology cassette per animal. The whole spinal cord was stored ambient in a 15 ml tube containing 10% neutral buffered formalin (NBF) for at least 24 hours and no more than 72 hours before transfer into 70% histology grade alcohol solution. Each spinal cord sample was cut into cervical, thoracic and lumbar sections. Each spinal cord section cut in half and both halves were placed in individual cassettes per section (cervical, thoracic and lumbar) for processing. All three cassettes were embedded into one paraffin block per animal. When applicable, portions of brain and spinal cord were snap frozen and stored at −80° C.

hSMN-1 Western Blot Analysis

Figure 11:
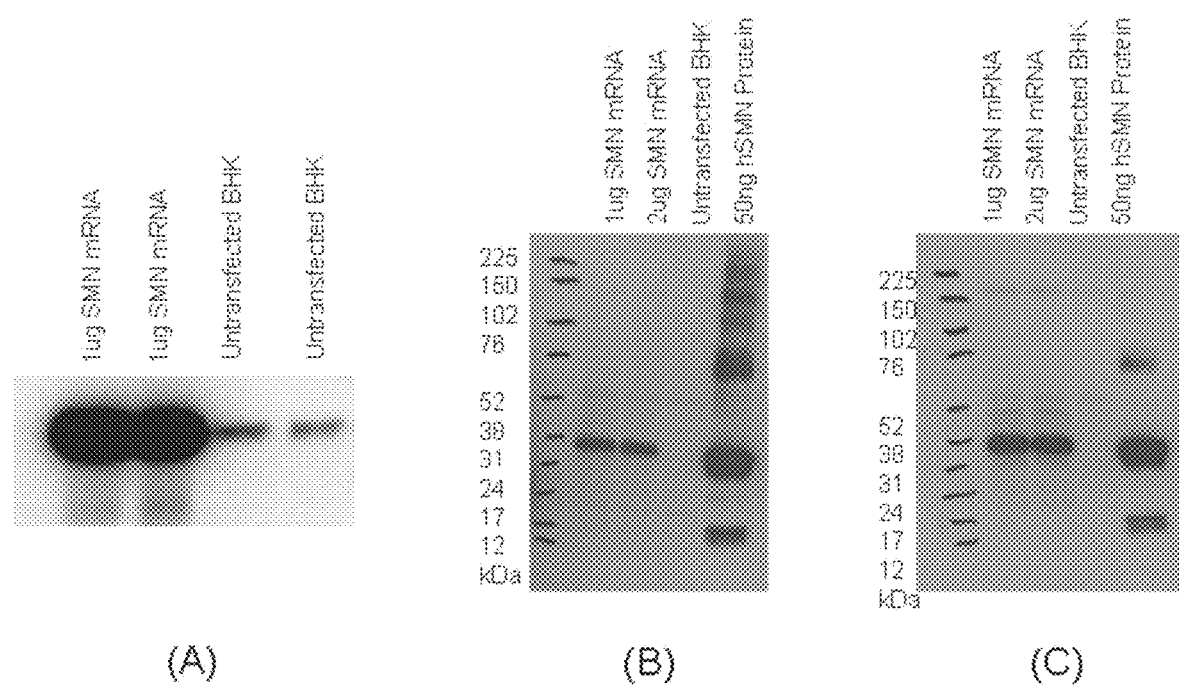
FIG. 11 illustrates detection via western blot of human SMN-1 protein derived from exogenous hSMN-1 mRNA that was transfected into BHK-21 cells. Various antibodies specific to human SMN were employed: (A) anti-SMN 4F11 antibody at 1:1,000 dilution; (B) Pierce PA5-27309 a-SMN antibody at 1:10,000 dilution; and (C) LSBio C138149 a-SMN antibody at 1:10,000 dilution.

Standard western blot procedures were followed employing various antibodies that recognizes hSMN protein, such as: (A) anti-SMN 4F11 antibody at 1:1,000 dilution; (B) Pierce PA5-27309 a-SMN antibody at 1:1,000 dilution; and (C) LSBio C138149 a-SMN antibody at 1:1,000 dilution. For each experiment one microgram of hSMN mRNA was transfected into ~1×10$^6$ BHK-21 cells using Lipofectamine 2000. Cells were treated with OptiMem and harvested 16-18 hours post-transfection. Cell lysates were harvested, processed and loaded on to an 8-16% Tris Glycine gel. The gel was transferred using a PVDF membrane and treated with the respective primary antibody. Goat anti-mouse HRP antibody was used as the secondary antibody at 1:10,000 dilution for 45 minutes at room temperature followed by washing and development. The data demonstrates that each antibody tested showed a strong signal for hSMN-1 and was specific for human SMN, as indicated by an absence in a cross-reactive signal for untreated BHK cells (FIG. 11).

In Situ Hybridzation (ISH) Analysis

Tissue from each representative sample, was assayed for hSMN-1 mRNA using a manual in situ hybridization analysis, performed using RNAscope® (Advanced Cell Diagnostic) "ZZ" probe technology. Probes were generated based on the codon-optimized sequence of human SMN messenger RNA (SEQ ID NO: 4). Briefly, the RNAscope® assay is an in situ hybridication assay designed to visualize single RNA molecules per cell in formalin-fixed, paraffin-embedded (FFPE) tissue mounted on slides. Each embedded tissue sample was pretreated according to the manufacturers protocol and incubated with a target specific hSMN-1 RNA probe. The hSMN-1 probe was shown to be specific for human SMN-1 and had little to no cross reactivity with mouse or rat SMN-1. Once bound, the hSMN-1 probe is hybridized to a cascade of signal amplification molecules, through a series of 6 consecutive rounds of amplification. The sample was then treated with an HRP-labeled probe specific to the signal amplification cassette and assayed by chromatic visualization using 3,3'-diaminobenzidine (DAB). A probe specific for Ubiquitin C was used as the positive control. Positive SMN signal was compared to that of untreated and vehicle control treated rat or mouse tissue. Stained samples were visualized under a standard bright field microscope.

Immunohistochemical Analysis

Figure 13:
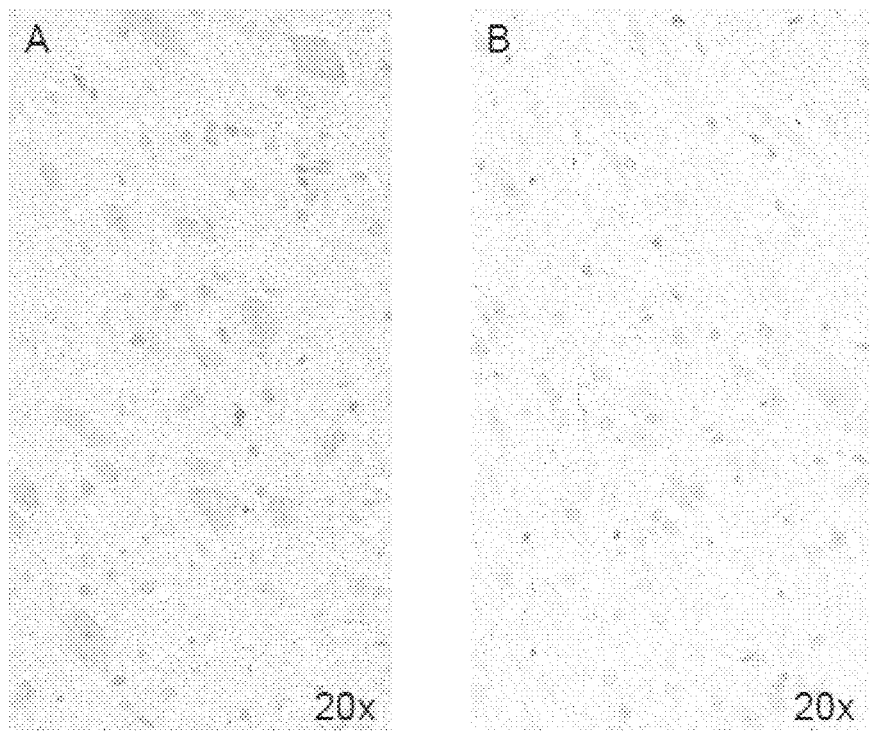
FIG. 13 illustrates positive detection of human SMN-1 protein produced in the spinal cord of a rat 24 hours post-intrathecal administration of human SMN-1 mRNA-loaded lipid nanoparticles. Anti-human SMN 4F11 antibody was employed at 1:2500 dilution. Panel A represents treated rat spinal cord tissue and panel B represents untreated rat spinal cord tissue.

Human SMN-1 mRNA-loaded lipid nanoparticles were administered to rats via intrathecal injection, and tissue samples collected and processed 24 hours post administration in accordance with the methods described above. Rat spinal tissue samples were then assayed for hSMN-1 protein expression. Briefly, fixed tissue embedded in paraffin was processed and placed on slides. The slides were dewaxed, rehydrated and antigen retrieval was performed using a pressure cooker with citrate buffer. Several blocking buffers were employed followed by primary antibody incubation overnight at 4° C., using the 4F11 antibody at a 1:2500 dilution. The resulting slides were washed and incubated at ambient temperature with the secondary antibody polymer followed by washing and subsequent chromagen development. The data demonstrates that in as little as 24 hours post intrathecal adminiatration of hSMN-1 mRNA, staining is observed for human SMN-1 protein when compared to no-treatment control (FIG. 13). This supports the previous findings which demonstrate delivery of hSMN-1 mRNA to the spinal tissue. Furthermore, the data demonstrates that once delivered to the cell hSMN-1 mRNA is effectively expressed to generate hSMN-1 protein.

Results

The data presented in this example demonstrates that intrathecal administration of hSMN-1 mRNA loaded liposomes (e.g., lipid or polymer-based nanoparticles) results in successful intracellular delivery of mRNA in neurons in the brain and spinal cord, including those difficult to treat cells, such as anterior horn cells and dorsal root ganglia.

Figure 12A:
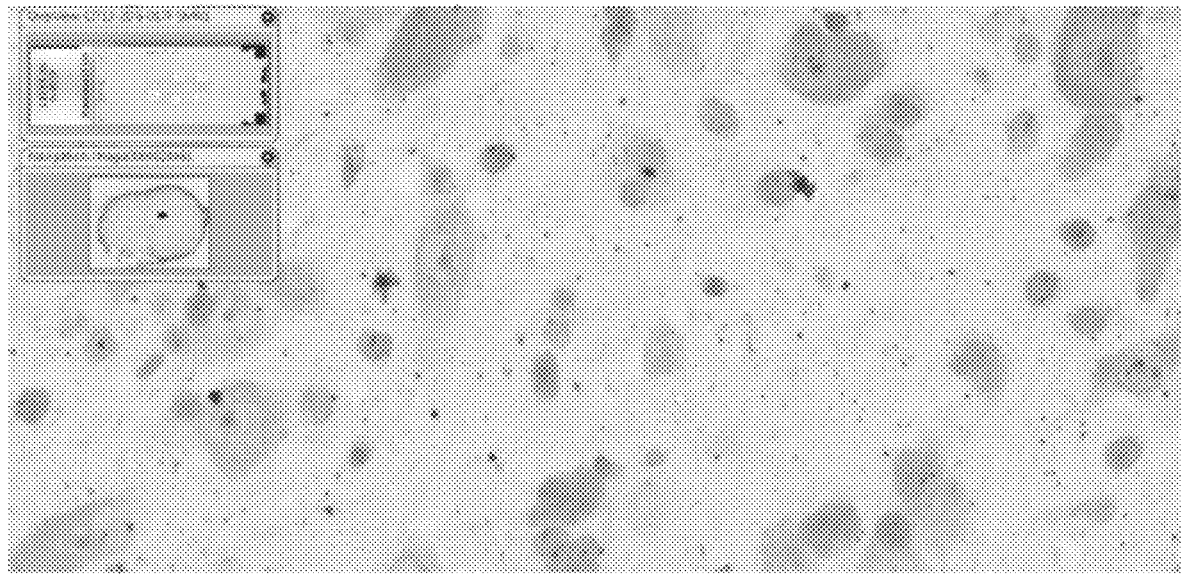
FIG. 12A-C illustrates multiplex nucleic acid in situ detection of human Survival of Motor Neuron (hSMN-1) mRNA in (A) Cervical, (B) Thoracic and (C) Lumbar spinal tissue, 24 hours post intrathecal delivery.
Figure 12B:
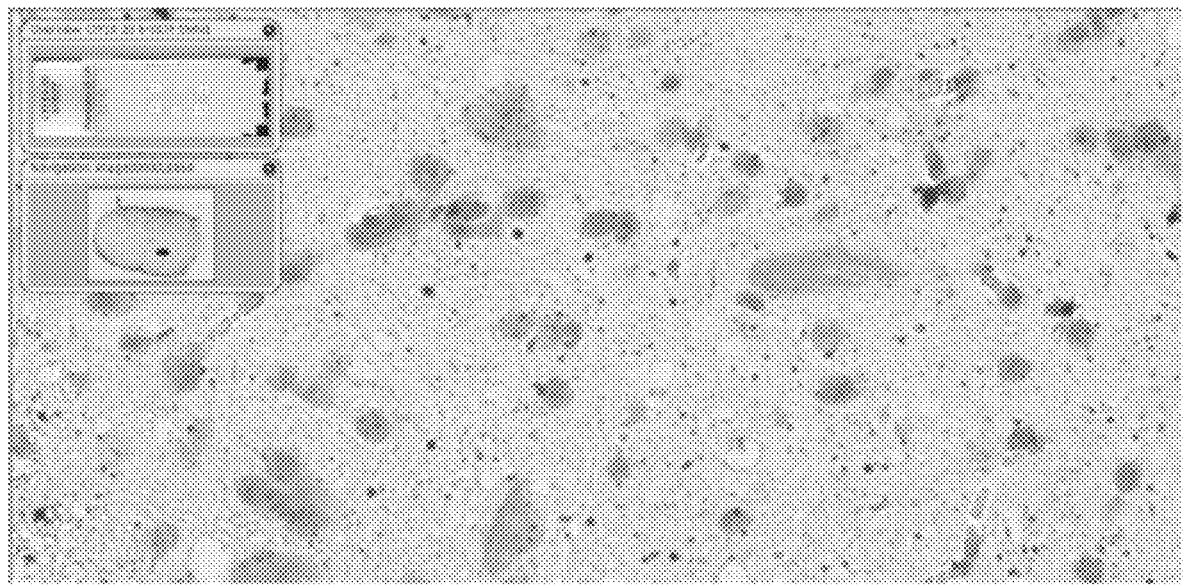
Figure 12C:
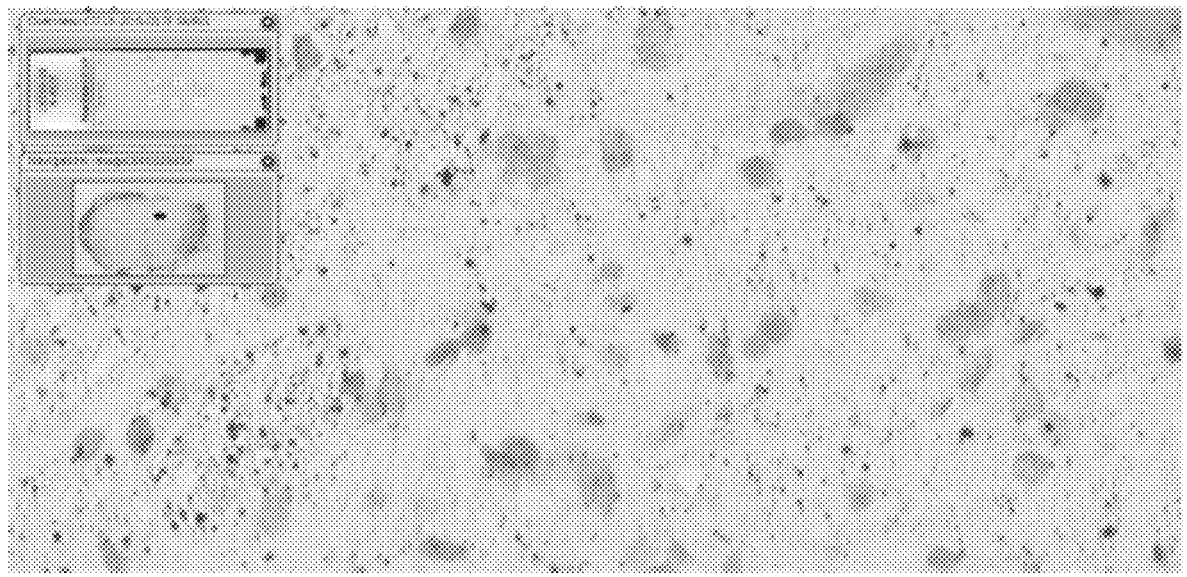

The results have shown that mRNA encapsulated within a lipid nanoparticle (e.g., lipid nanoparticle comprising cKK-E12) can be effectively delivered to various tissues of the CNS following intrathecal administrations. Using the exemplary formulation disclosed in Table 6, mRNA was effectively delivered and internalized within various neurons of the spinal cord (FIGS. 12A-12C), as verified by in situ hybridization assay. Surprisingly, intracellular mRNA delivery was demonstrated in the difficult to reach neuronal cells of the anterior horn, located deep within the tissues of the spinal column (FIGS. 12A-12C). Little to no background was observed with mouse or rat SMN-1, indicating specificity for the human SMN-1 probe. Positive SMN signal was compared to that of untreated and vehicle control treated rat or mouse tissue. Stained samples were visualized under a standard bright field microscope.

These data demonstrates that the lipid or polymer nanoparticle based mRNA delivery approach described herein was able to successfully permeate the complex and dense cell membrane of the spinal cord neurons and deliver the mRNA payload for the production of encoded proteins inside neurons. It was particularly surprising that the mRNA delivery approach described herein was equally successful in permeating difficult to treat neurons such as anterior horn cell and dorsal root ganglia. Thus, the data presented herein demonstrates that lipid or polymer nanoparticles, such as those comprising cKK-E12, may serve as a promising option for delivering mRNA to neuronal cells in the treatment of a CNS disease. In particular, the present example demonstrates that hSMN mRNA loaded nanoparticles can be effectively delivered to neurons, including those difficult to treat motor neurons in the spinal cord, and can be used for the production of SMN protein and treatment of spinal muscular atrophy.

Example 5. In Vivo CO-CFTR—C-His$_{11}$ mRNA Delivery to CFTR Knockout Mice

Messenger RNA Synthesis. For the experiment, C-terminal His$_{10}$ tagged codon-optimized human cystic fibrosis transmembrane conductance regulator (CO-CFTR—C-His$_{10}$) (SEQ ID NO:8) ("His$_{10}$" disclosed as SEQ ID NO: 11) and non-tagged codon-optimized human CFTR (CO-CFTR) (SEQ ID NO:9) mRNA were synthesized by in vitro transcription from a plasmid DNA template using standard method. mRNAs used in this example and Example 6 were produced by IVT in which 25% of U residues were 2-thiouridine and 25% of C residues were 5-methylcytidine.

Analysis of Human CFTR Protein Produced Via Intratracheal Administered mRNA-Loaded Nanoparticles.

For the study, CFTR knockout mice were used. CFTR mRNA formulation or vehicle control was introduced using a PARI Boy jet nebulizer. Mice were sacrificed and perfused with saline, after a predetermined period of time, to allow for protein expression from the mRNA.

PEI Formulation.

PEI formulation has been used to deliver CFTR mRNA to the lung and was used as a control in this experiment. Polymeric nanoparticle formulations with 25 kDa branched PEI were prepared as follows. The required amount of mRNA was diluted just before application in water for injection (Braun, Melsungen) to a total volume of 4 ml and added quickly to 4 ml of an aqueous solution of branched PEI 25 kDa using a pipette at an N/P ratio of 10. The solution was mixed by pipetting up and down ten times and nebulized as two separate 4.0 ml fractions one after another to the mouse lungs using the indicated nebulizer.

cKK-E12 Formulation.

For the lipid-based nanoparticle experiment, a lipid formulation was created using CO-CFTR—C-His$_{10}$ RNA in a formulation of cKK-E12:DOPE:Chol:PEGDMG2K (relative amounts 50:25:20:5 (mg:mg:mg:mg)). The solution was nebulized to the mouse lungs using the indicated nebulizer.

Nebulization (Aerosol) Administration of Human CO-CFTR—C-His$_{10}$ mRNA.

CFTR test materials were administered by a single aerosol inhalation via PARI Boy jet nebulizer (nominal dose volume of up to 8 mL/group). The test material was delivered to a box containing the whole group of animals (n=4) and connected to oxygen flow and scavenger system.

Administration of Human CO-CFTR-C-His$_{10}$ mRNA.

CFTR mRNA was prepared in the manner described above. Four CFTR knockout mice were placed in an aerosol chamber box and exposed to 2 mg total codon optimized unmodified human CFTR mRNA (comprising the coding sequence of SEQ ID NO: 8) via nebulization (Pari Boy jet nebulizer) over the course of approximately one hour. Mice were sacrificed 24 hours post-exposure.

Euthanasia.

Animals were euthanized by CO$_2$ asphyxiation at representative times post-dose administration (+5%) followed by thoracotomy and exsanguinations. Whole blood (maximal obtainable volume) was collected via cardiac puncture and discarded.

Perfusion.

Following exsanguination, all animals underwent cardiac perfusion with saline. In brief, whole body intracardiac perfusion was performed by inserting 23/21 gauge needle attached to 10 mL syringe containing saline set into the lumen of the left ventricle for perfusion. The right atrium was incised to provide a drainage outlet for perfusate. Gentle and steady pressure was applied to the plunger to perfuse the animal after the needle had been positioned in the heart. Adequate flow of the flushing solution was ensured when the exiting perfusate flows clear (free of visible blood) indicating that the flushing solution has saturated the body and the procedure was complete.

Tissue Collection.

Following perfusion, all animals had their lungs (right and left) harvested. Both (right and left) lungs were snap frozen in liquid nitrogen and stored separately at nominally −70° C.

Expression of Human CFTR in CO-CFTR-C-His$_{10}$ in CFTR Knockout Mice.

Figure 14:
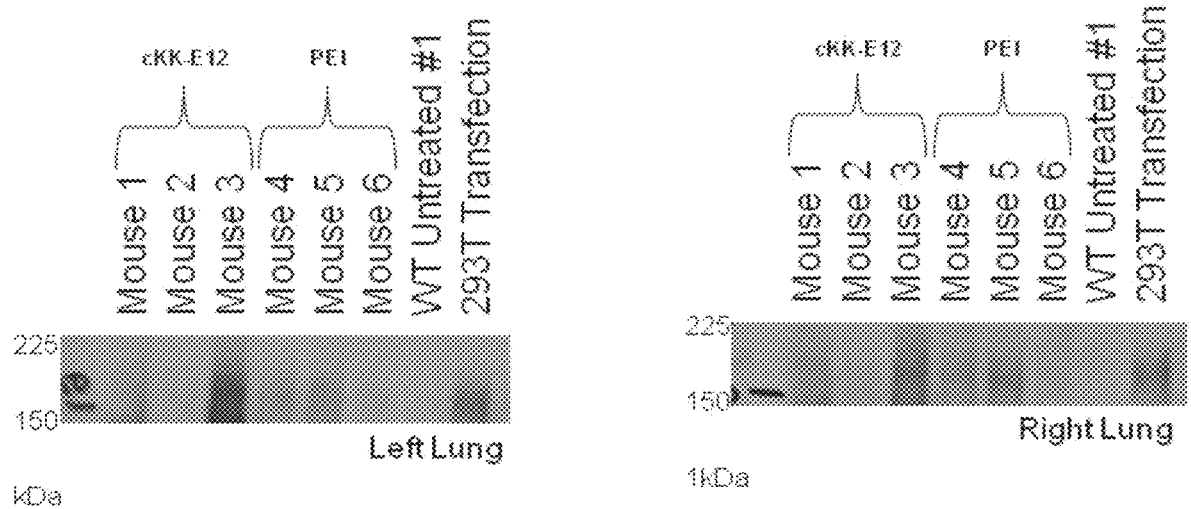
FIG. 14 In vivo transfection of CFTR knockout mice with C-terminal $His_{10}$ tagged (SEQ ID NO: 11) codon-optimized human CFTR mRNA encapsulated within either a lipid (cKK-E12) or polymeric (PEI) nanoparticle formulation. Following nebulized delivery of each respective mRNA formulation, Right and Left lung tissue lysate was collected and analyzed for CFTR expression by Western blot using anti-His antibody 1187. Control CFTR knockout lung tissue and CFTR-$His_{10}$ HEK293 lysate ("$His_{10}$" disclosed as SEQ ID NO: 11) was used as a negative and positive controls respectively.

CFTR expression was detected by Western blot analysis of tissue lysate collected from CFTR mRNA-treated mouse lungs. Mature "C" band was detected in left and right lungs of all treated mice, for both the cKK-E12-based and PEI-based formulations (FIG. 14). Expression of the mature "C" band was verified by comparison with lysate collected from HEK 293T human CO-CFTR—C-His$_{10}$ positive cells. In contrast, no detectable signal was observed in lysate collected from wild type untreated control mice (FIG. 14). Taken together, these data suggest that cKK-E12 may be used to deliver mRNA (e.g., CFTR mRNA) to the lung via, e.g., inhalation, as effectively as or even better than PEI based formulations.

Example 6: In Vivo Expression in the Lung

This example further desmonstrates successful in vivo expression in the lung following aerosol delivery of mRNA-loaded ckk-E12 based nanoparticles. All studies were performed using pigs of the German Landrace, obtained from Technical University Munich, Weihenstephan, Germany. The pigs had a body weight ranging from 35-90 kg. FFL/CO-CFTR—C-His10 mRNA formulation or vehicle control was introduced using a Pari jet nebulizer. Pigs were sacrificed and perfused with saline, after a predetermined period of time, to allow for protein expression from the mRNA.

Messenger RNA Synthesis.

In the example, codon optimized fire fly luciferase (CO-FFL) mRNA was synthesized by in vitro transcription from plasmid DNA templates.

cKK-E12 Formulation.

For the lipid-based nanoparticle experiment, a lipid formulation was created using 1 mg FFL+9 mg of CO-CFTR—C-His$_{10}$ mRNA encapsulated in a formulation of cKK-E12:DOPE:Chol:PEGDMG2K (relative amounts 40:30:25:5 (mol ratio). The solution was nebulized to the Pig lungs using the indicated nebulizer.

Aerosol Application.

The aerosol (Saline or CO-FFL cKK-E12 formulation) was nebulized and inhaled into the anaesthetized pig. Sedation in pigs was initiated by premedication with azaperone 2 mg/kg body weight, ketamine 15 mg/kg body weight, atropine 0.1 mg/kg body weight and followed by insertion of an intravenous line to the lateral auricular vein. Pigs were anesthetized by intravenous injection of propofol 3-5 mg/kg body weight as required. Anesthesia was maintained by isoflurane (2-3%) with 1% propofol bolus injection at 4 to 8 mg/kg body weight to enhance anesthesia as required. Duration of the anesthesia was approximately 1-3 hrs. Pigs were killed with bolus injection of pentobarbital (100 mg/kg body weight) and potassium chloride via the lateral ear vein. Lungs were excised and tissue specimens were collected from various lung regions followed by incubation in cell culture medium overnight. The stored samples were subjected to bioluminescence detection.

Bioluminescence Analysis.

Figure 15:
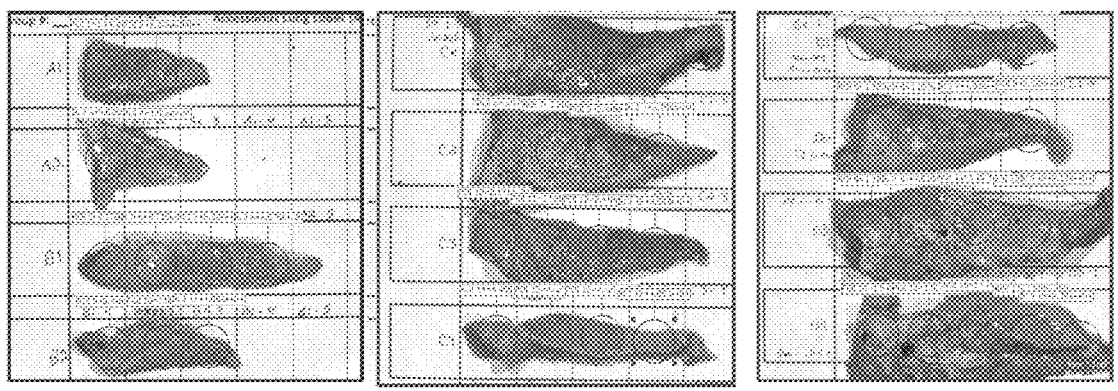
FIG. 15 illustrates positive detection of active firefly luciferase (FFL) protein in a treated pig lung via luminescence upon exposure to FFL/CO-CFTR—C-$His_{10}$ mRNA ("$His_{10}$" disclosed as SEQ ID NO: 11) encapsulated cKK-E12 lipid nanoparticles. Pigs were treated with 1 mg FFL+9 mg CO-CFTR—C-$His_{10}$ mRNA ("$His_{10}$" disclosed as SEQ ID NO: 11) encapsulated lipid nanoparticles via nebulization using a Pari jet nebulizer and sacrificed 24 hours post-treatment. FFL luminescence was visualized using an IVIS bioluminometer.
Figure 15:
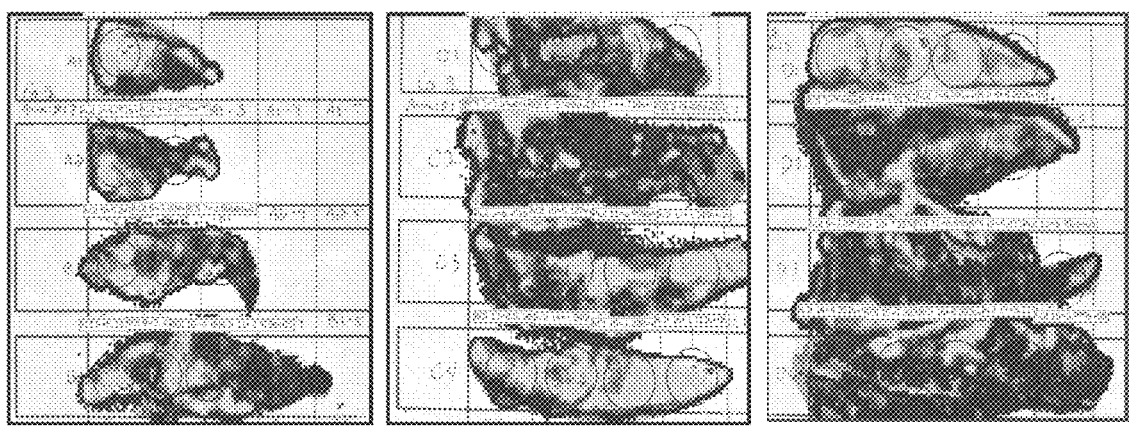

For measurement of luciferase activity, tissue specimens were either homogenized and analyzed in a tube luminometer or incubated in a medium bath comprising D-Luciferin substrate and subjected to ex vivo luciferase BLI. The data illustrate that a strong bioluminescence signal was observed for each of the (A)CO-FFL/CO-CFTR—C-His$_{10}$ mRNA treated pigs, when compared to (B) control lung tissue samples from control pigs (Saline vehicle control) (FIGS. 15 A&B).

These data illustrate that FFL/CFTR mRNA were successfully delivered to and expressed in the lung by aerosol administration of a cKK-E12 based lipid formulation.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A method of delivery of messenger RNA (mRNA) in vivo, comprising administering to a subject in need of delivery a composition comprising an mRNA encoding a protein that is argininosuccinate synthetase (ASS1), encapsulated within a liposome such that the administering of the composition results in the expression of the protein encoded by the mRNA in vivo;

wherein the liposome comprises a cationic lipid of formula I-c:

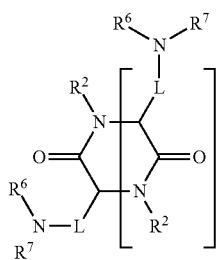

or a pharmaceutically acceptable salt thereof,
wherein:
  p is an integer of between 1 and 9, inclusive;
  each instance of $R^2$ is independently hydrogen or optionally substituted $C_{1-6}$ alkyl;
  each instance of $R^6$ and $R^7$ is independently a group of the formula (i), (ii), or (iii);
  Formulae (i), (ii), and (iii) are:

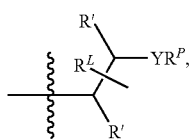

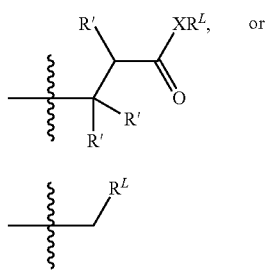

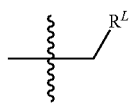

wherein:
  each instance of R' is independently hydrogen or optionally substituted alkyl;
  X is O, S, or $NR^X$, wherein $R^X$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;
  Y is O, S, or $NR^Y$, wherein R is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;
  $R^P$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to a sulfur atom, or a nitrogen protecting group when attached to a nitrogen atom; and
  $R^L$ is optionally substituted C1-50 alkyl, optionally substituted $C_{2-50}$ alkenyl, optionally substituted $C_{2-50}$ alkynyl, optionally substituted hetero$C_{1-50}$ alkyl, optionally substituted hetero$C_{2-50}$ alkenyl, optionally substituted hetero$C_{2-50}$ alkynyl, or a polymer.

2. The method of claim 1, wherein the cationic lipid is cKK-E12:

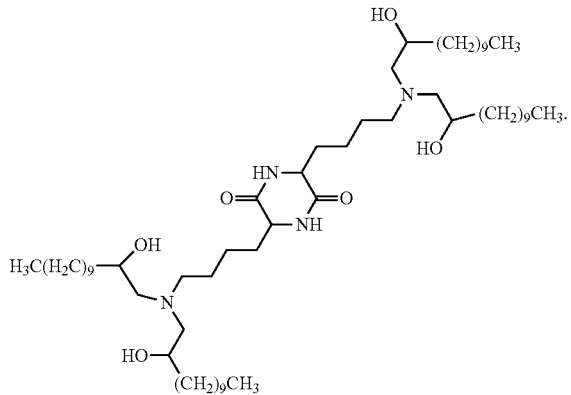

3. The method of claim 1, wherein the liposome further comprises one or more non-cationic lipids, one or more cholesterol-based lipids and/or one or more PEG-modified lipids.

4. The method of claim 3, wherein the one or more non-cationic lipids are selected from DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG-dieleeyl-(1,2-dioleoyl-sn-glycero-3-phospho-(1'-rac-glycerol)).

5. The method of claim 3, wherein the one or more cholesterol-based lipids are cholesterol and/or PEGylated cholesterol.

6. The method of a claim 3, wherein the liposome comprises cKK-E12, DOPE, cholesterol and DMG-PEG2K.

7. The method of claim 1, wherein the liposome has a size less than about 250 nm, 200 nm, 150 nm, 100 nm, 75 nm, or 50 nm.

8. The method of claim 1, wherein the composition is administered intravenously.

9. The method of claim 1, wherein the expression of the argininosuccinate synthetase (ASS1) protein encoded by the mRNA is detectable in liver.

10. The method of claim 1, wherein the mRNA comprises one or more modified nucleotides that are pseudouridine, N-1-methyl-pseudouridine, 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, and/or 2-thiocytidine.

11. The method of claim 1, wherein the mRNA is unmodified.

12. A method of treating citrullinemia, type I comprising administering to subject in need of treatment a composition comprising an mRNA encoding a therapeutic protein that is argininosuccinate synthetase (ASS1) encapsulated within a liposome such that the administering of the composition results in the expression of the ASS1 protein encoded by the mRNA in one or more tissues affected by the citrullinemia, type I;

wherein the liposome comprises a cationic lipid of formula I-c:

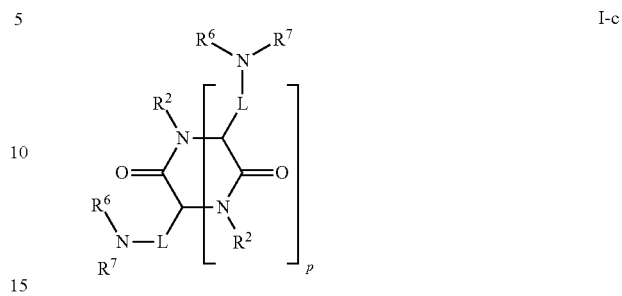

or a pharmaceutically acceptable salt thereof,
wherein:
p is an integer of between 1 and 9, inclusive;
each instance of $R^2$ is independently hydrogen or optionally substituted $C_{1-6}$ alkyl;
each instance of $R^6$ and $R^7$ is independently a group of the formula (i), (ii), or (iii);
Formulae (i), (ii), and (iii) are:

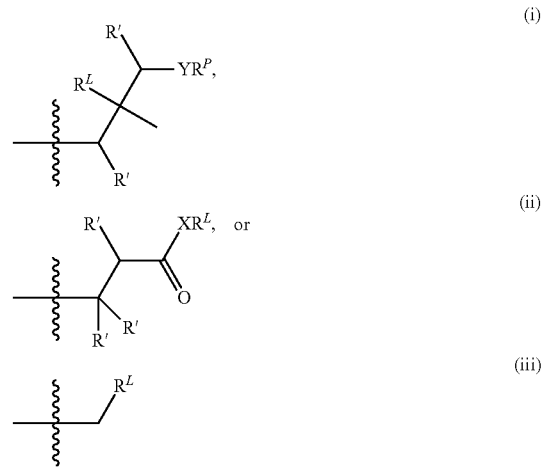

wherein:
each instance of R' is independently hydrogen or optionally substituted alkyl;
X is O, S, or $NR^X$, wherein $R^X$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;
Y is O, S, or $NR^Y$, wherein $R^Y$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;
$R^P$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to a sulfur atom, or a nitrogen protecting group when attached to a nitrogen atom; and $R^L$ is optionally substituted C1-50 alkyl, optionally substituted C2-50 alkenyl, optionally substituted $C_{2-50}$ alkynyl, optionally substituted heteroC$_{1-50}$ alkyl, optionally substituted heteroC$_{2-50}$ alkenyl, optionally substituted heteroC$_{2-50}$ alkynyl, or a polymer.

13. The method of claim 12, wherein the cationic lipid is cKK-E12:

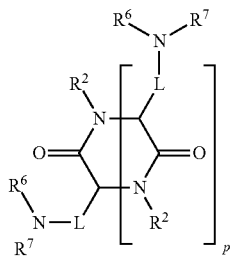

14. A composition for delivery of messenger RNA (mRNA) comprising an mRNA encoding a protein that is argininosuccinate synthetase (ASS1) encapsulated within a liposome, wherein the liposome comprises a cationic lipid of formula I-c:

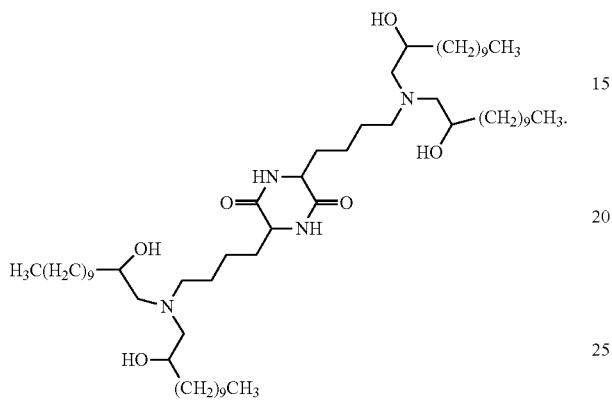

or a pharmaceutically acceptable salt thereof, wherein:
  p is an integer of between 1 and 9, inclusive;
  each instance of $R^2$ is independently hydrogen or optionally substituted $C_{1-6}$ alkyl;
  each instance of $R^6$ and $R^7$ is independently a group of the formula (i), (ii), or (iii);
  Formulae (i), (ii), and (iii) are:

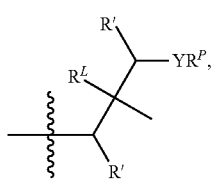

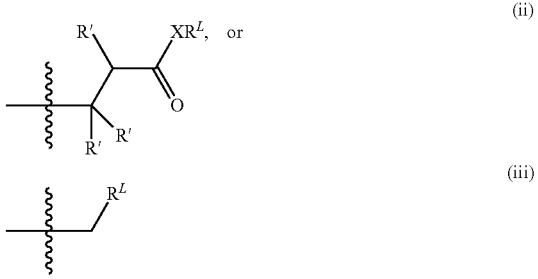

wherein:
  each instance of R' is independently hydrogen or optionally substituted alkyl;
  X is O, S, or NR$^X$, wherein R$^X$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;
  Y is O, S, or NR$^Y$, wherein R is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;
  R$^P$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to a sulfur atom, or a nitrogen protecting group when attached to a nitrogen atom; and
  R$^L$ is optionally substituted $C_{1-50}$ alkyl, optionally substituted C2-50 alkenyl, optionally substituted $C_{2-50}$ alkynyl, optionally substituted heteroC$_{1-50}$ alkyl, optionally substituted heteroC$_{2-50}$ alkenyl, optionally substituted heteroC$_{2-50}$ alkynyl, or a polymer.

15. The composition of claim 14, wherein the cationic lipid is cKK-E12:

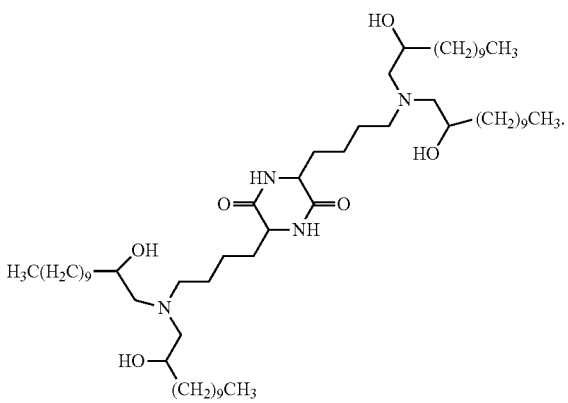

16. The composition of claim 14, wherein the liposome further comprises one or more non-cationic lipids, one or more cholesterol-based lipids and/or one or more PEG-modified lipids.

17. The composition of claim 16, wherein the one or more non-cationic lipids are selected from DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG (1,2-dioleoyl-sn-glycero-3-phospho-(1'-rac-glycerol)).

18. The composition of claim 16, wherein the liposome comprises cKK-E12, DOPE, cholesterol and DMG-PEG2K.

19. The composition of claim 16, wherein the cationic lipid constitutes about 30-50% of the liposome by molar ratio.

20. The composition of claim 14, wherein the liposome has a size less than about 250 nm, 200 nm, 150 nm, 100 nm, 75 nm, or 50 nm.

21. The composition of claim 14, wherein the composition is formulated for intravenous administration.

22. The composition of claim 16, wherein the one or more cholesterol-based lipids are cholesterol and/or PEGylated cholesterol.

23. The composition of claim 14, wherein the mRNA comprises one or more modified nucleotides comprise pseudouridine, N-1-methyl-pseudouridine, 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, and/or 2-thiocytidine.

24. The composition of claim 14, wherein the mRNA is unmodified.

* * * * *

UNITED STATES PATENT AND TRADEMARK OFFICE
CERTIFICATE OF CORRECTION

PATENT NO. : 10,959,953 B2
APPLICATION NO. : 16/685287
DATED : March 30, 2021
INVENTOR(S) : Michael Heartlein et al.

It is certified that error appears in the above-identified patent and that said Letters Patent is hereby corrected as shown below:

In the Claims

In Claim 4, Column 221, Line 33-34:
Delete "3-phosphoethanolamine), DOPG-dieleeyl-(1,2-dioleoyl-sn-glycero-3-phospho-(1'-rac-glycerol))."
Replace with --3-phosphoethanolamine), DOPG (1,2-dioleoyl-sn-glycero-3-phospho-(1'-rac-glycerol)).--

In Claim 14, Column 224, Line 24:
Delete "Y is O, S, or $NR^Y$, wherein R is hydrogen, optionally"
Replace with --Y is O, S, or $NR^Y$, wherein $R^Y$ is hydrogen, optionally--

Signed and Sealed this
Nineteenth Day of September, 2023

*Katherine Kelly Vidal*
*Director of the United States Patent and Trademark Office*